US009896440B2

(12) United States Patent
Schunk et al.

(10) Patent No.: US 9,896,440 B2
(45) Date of Patent: *Feb. 20, 2018

(54) ARYL SUBSTITUTED HETEROCYCLYL SULFONES

(71) Applicant: GRÜNENTHAL GMBH, Aachen (DE)

(72) Inventors: Stefan Schunk, Aachen (DE); Melanie Reich, Aachen (DE); Florian Jakob, Aachen (DE); René Michael Koenigs, Aachen (DE); Nils Damann, Hürth (DE); Michael Haurand, Aachen (DE); Marc Rogers, Cambridgeshire (GB); Kathy MacKenzie, Hertfordshire (GB); Richard Hamlyn, Cambridgeshire (GB)

(73) Assignee: GRÜNENTHAL GMBH, Aachen (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/685,742

(22) Filed: Apr. 14, 2015

(65) Prior Publication Data
US 2015/0291573 A1 Oct. 15, 2015

(30) Foreign Application Priority Data
Apr. 14, 2014 (EP) .................................. 14001345

(51) Int. Cl.
C07D 405/04 (2006.01)
C07D 309/02 (2006.01)
C07D 413/04 (2006.01)
C07D 307/18 (2006.01)
C07D 405/12 (2006.01)
C07D 309/08 (2006.01)
C07D 405/10 (2006.01)
C07D 407/04 (2006.01)

(52) U.S. Cl.
CPC .......... C07D 413/04 (2013.01); C07D 307/18 (2013.01); C07D 309/08 (2013.01); C07D 405/04 (2013.01); C07D 405/10 (2013.01); C07D 405/12 (2013.01); C07D 407/04 (2013.01)

(58) Field of Classification Search
CPC ........................... C07D 405/04; C07D 309/02
See application file for complete search history.

(56) References Cited

U.S. PATENT DOCUMENTS

2015/0291572 A1  10/2015  Schunk et al.
2017/0101397 A1  4/2017  Schunk et al.
2017/0101398 A1  4/2017  Schunk et al.

FOREIGN PATENT DOCUMENTS

WO  2007/125398 A2  11/2007
WO  2010-007072 A1  1/2010
WO  2011-035159 A1  3/2011

OTHER PUBLICATIONS

Maakosza et al (2009):STN International HCAPLUS database, Columbus (OH), Accession No. 2009:371746.*
Bennett et al., "A Peripheral Mononeuropathy in rat that produces disorders of pain sensation like those seen in man": Pain, Elsevier Sciences Publishers B.V., No. 33, pp. 87-107, 1998.
D'Amour et al., "A Method for Determining Loss of Pain Sensation", The Biologic Research Laboratory, University of Denver, pp. 74-79, Jan. 27, 1941.
Dubuisson et al., "The Formalin Test: A Quantitative Study of the Analgesic Effects of Morphine, Meperidine, and Brain Stem Stimulations in Rats and Cat"; Elsevier/North-Holland Biomedical Press, Pain, No. 4, pp. 161-174, 1977.
Kim et al., "An Experimental Model for Peripheral Neuropathy Produced by Segmental Spinal Nerve Ligation in the Rat", Pain, Elsevier Sciences Publishers B.V., No. 50, pp. 355-363, 1992.
Makosza et al., "γ-Diphenylphosphinoxy Carbanions: Slow Reacting Analogues of γ-Halocarbanions", Phosphorus, Sulfur, and Silicon, No. 184, pp. 857-864, 2009.
G.P. Miljanich,"Ziconotide: Neuronal Calcium Channel Blocker for Treating Severe Chronic Pain", Current Medicinal Chemistry, No. 11, pp. 3029-3040, 2004.
Rauck et al., "Intrathecal Ziconotide for Neuropathic Pain: A Review", Pain Practice, vol. 9, Issue 5, pp. 327-337, 2009.
Staats et al., "Intrathecal Ziconotide in the Treatment of Refractory Pain in Patients With Cancer or AIDS a Randomized Controlled Trial", American Medical Association, vol. 291, No. 1, pp. 63-70, 2004.
Craig "Stereoselective Synthesis of 2,5-Dialky-3-(phenylsulfonyl) Tetrahydrofurans via Cyclisation of Z-Sulfonyl- . . . ", Tetrahedron Letters, vol. 36, No. 4, pp. 7531-7534, 1995.
Craig et al., "Stereoselective Synthesis of 3-(Phenylsulphonyl)-2,5 Disubstituted Tetrahydrofurans via 5-Endo-trig Ring-Closure Reactions"; Tetrahedron Letters, vol. 33, No. 5, pp. 695-698, 1992.
Makosza et al., "New Reactions of γ-Halocarbanions: Simple Synthesis of Substituted Tetrahydrofurans"; Chem. Eur. J., vol. 8, No. 18, pp. 4234-4240, 2002.
Makosza et al., "Diastereoselective Synthesis of Tetrahydrofurans via Reaction of γ,δ-Eposycarbanions with Aldehydes", Organic Letters, vol. 7, No. 14, pp. 2945-2948, 2005.
Craig, et al., "Stereoselective Synthesis of Substituted Tetrahydrofurans Using 5-Endo-trig Cyclisation Reactions"; Tetrahedron 55, pp. 13471-13494, 1999.
Barbasiewicz, et al., "New reactions of γ-halocarbanions: underestimated reactive intermediates in organic synthesis"; Russian Chemical Bulletin, International Edition, vol. 53, No. 9, pp. 1846-1858, Sep. 2004.

(Continued)

Primary Examiner — Golam M M Shameem
(74) Attorney, Agent, or Firm — Norris McLaughlin & Marcus, P.A.

(57) ABSTRACT

The invention relates to aryl substituted heterocyclyl sulfones as voltage gated calcium channel blockers, to pharmaceutical compositions containing these compounds and also to these compounds for use in the treatment and/or prophylaxis of pain and further diseases and/or disorders.

14 Claims, No Drawings

(56) References Cited

OTHER PUBLICATIONS

Brandt, et al., "Synthesis of substituted tetrahydrofurans via intermolecular reactions of γ-chlorocarbanions of 3-substituted 3-chloropropylphenyl sulfones with aldehydes", Tetrahedron 66, pp. 3378-3385, 2010.

Yamamoto, et al; "Recent Updates of N-Type Calcium Channel Blockers with Therapeutic Potential for Neuropathic Pain . . . " Current Topics in Medicinal Chemistry, 2009, 9, 377-395.

* cited by examiner

ARYL SUBSTITUTED HETEROCYCLYL SULFONES

This application claims priority of European Patent Application No. 14001345.9, filed Apr. 14, 2014, the entire contents of which are incorporated herein by reference.

FIELD OF THE INVENTION

The invention relates to aryl-substituted heterocycl sulfones as voltage gated Ca-channel (CaV) blockers, to pharmaceutical compositions containing these compounds and also to these compounds for use in the treatment and/or prophylaxis of pain and further diseases and/or disorders.

BACKGROUND OF THE INVENTION

Ion channels are proteins that form pores in membranes of biological cells and control the flow of ions down their electrochemical gradient. They are involved in the regulation of a wide range of cellular functions in both excitable and nonexcitable cells and provide attractive therapeutic targets for the treatment of various diseases.

In the somatosensory context, CaV2.2 channels, specific cellular plasma membrane calcium channels that belong to a diverse superfamily of voltage-gated calcium channels (VGCCs), were demonstrated to play an important role in spinal nociceptive processing.

The critical role of CaV2.2 in pain processing was underlined by the clinical efficacy of the intrathecally delivered, selective CaV2.2 channel antagonist Ziconotide (SNX-111; Prialt™), a synthetic peptide derived from a ω-(omega)-conotoxin peptide (Miljanich, 2004, Curr. Med. Chem., 11(23), p. 3029-40; Staats et al., 2004, JAMA, 291(1), p. 63-70). Inthrathecal administration of Ziconotide is required in order to reach the ion channel in presynaptic terminals of sensory neurons in the spinal cord. Common side effects of Ziconotide include memory impairment, dizziness, nystagmus, speech disorder, nervousness, somnolence and abnormal gait (Rauck et al., 2009, Pain Pract., 9, p. 327-37), which have been attributed to the inhibition of CaV2.2 channels in the brain by Ziconotide.

Therefore, a demand remains for the development of orally available CaV2.2 calcium channel blockers that show the desired qualities and effectively block CaV2.2 calcium channels in the nociceptive signaling pathway.

SUMMARY OF THE INVENTION

The present invention describes small molecule CaV2.2 channel blockers. Sulfonamide based CaV2.2 channel modulators are known from WO 2007125398.

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by CaV2.2 calcium channels.

This object is achieved by the subject matter described herein.

The present invention therefore relates to a compound of general formula (I),

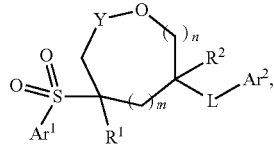

(I)

wherein
m represents 0, 1 or 2;
n denotes 0 or 1;
Y is selected from the group consisting of bond and —C(R$^3$)$_2$—,
  wherein each R$^3$ is independently selected from the group consisting of H and C$_{1-6}$-alkyl, or two R$^3$ form together with the C-atom connecting them a C$_{3-10}$-cycloalkyl or a 3 to 7 membered heterocyclyl;
L is —[C(R$^4$)$_2$]$_x$—(X)$_y$—[C(R$^4$)$_2$]$_z$—,
  wherein x is 0, 1 or 2, y is 0 or 1 and z is 0 or 1, with the proviso that x≥y (x is greater or equal to y),
  each R$^4$ is independently selected from the group consisting of H and C$_{1-6}$-alkyl,
  or two R$^4$ form together with the C-atom connecting them a C$_{3-10}$-cycloalkyl or a 3 to 7 membered heterocyclyl or two R$^4$ form together with two adjacent C-atoms connecting them a C$_{3-10}$-cycloalkyl or a 3 to 7 membered heterocyclyl and
  X is selected from the group consisting of O, S, S(O)$_2$, N(H) or N(C$_{1-6}$-alkyl);
R$^1$ is selected from the group consisting of H; F; Cl; CN; C$_{1-6}$-alkyl; C$_{1-6}$-alkyl-O(R$^5$) and C$_{1-6}$-alkyl-N(R$^5$)$_2$,
  wherein each R$^5$ is independently selected from H or C$_{1-6}$-alkyl or two R$^5$ form together with the N-atom connecting them a 3 to 7 membered heterocyclyl;
R$^2$ is selected from the group consisting of H; F; Cl; CN; C$_{1-6}$-alkyl; C$_{1-6}$-alkyl-O(R$^6$) and C$_{1-6}$-alkyl-N(R$^6$)$_2$;
  wherein each R$^6$ is independently selected from H or C$_{1-6}$-alkyl or two R$^6$ form together with the N-atom connecting them a 3 to 7 membered heterocyclyl;
Ar$^1$ represents aryl or heteroaryl, wherein said aryl or said heteroaryl is substituted by zero or one or two or three substituents R$^7$,
Ar$^2$ represents aryl or C$_{3-10}$-cycloalkyl, wherein said aryl or said C$_{3-10}$-cycloalkyl is substituted by zero or one or two or three substituents R$^8$,
  wherein each R$^7$ and each R$^8$ is independently selected from the group consisting of F; Cl; Br; I; NO$_2$; CN; C$_{1-6}$-alkyl; CF$_3$; CF$_2$H; CFH$_2$; CF$_2$Cl; CFCl$_2$; C(=O)—H; C(=O)—C$_{1-6}$-alkyl; C(=O)—OH; C(=O)—O—C$_{1-6}$-alkyl; C(=O)—N(H)(OH); C(=O)—NH$_2$; C(=O)—N(H)(C$_{1-6}$-alkyl); C(=O)—N(C$_{1-6}$-alkyl)$_2$; C(=N—OH)—H; C(=N—OH)—C$_{1-6}$-alkyl; C(=N—O—C$_{1-6}$-alkyl)-H; C(=N—O—C$_{1-6}$-alkyl)-C$_{1-6}$-alkyl; OH; OCF$_3$; OCF$_2$H; OCFH$_2$; OCF$_2$Cl; OCFCl$_2$; O—C$_{1-6}$-alkyl; 0-C(=O)—C$_{1-6}$-alkyl; 0-C(=O)—O—C$_{1-6}$-alkyl; O—(C=O)—N(H)(C$_{1-6}$-alkyl); 0-C(=O)—N(C$_{1-6}$-alkyl)$_2$; O—S(=O)$_2$—C$_{1-6}$-alkyl; O—S(=O)$_2$—OH; O—S(=O)$_2$—O—C$_{1-6}$-alkyl; O—S(=O)$_2$—NH$_2$; O—S(=O)$_2$—N(H)(C$_{1-6}$-alkyl); O—S(=O)$_2$—N(C$_{1-6}$-alkyl)$_2$; NH$_2$; N(H)(C$_{1-6}$-alkyl); N(C$_{1-6}$-alkyl)$_2$; N(H)—C(=O)—C$_{1-6}$-alkyl; N(H)—C(=O)—O—C$_{1-6}$-alkyl; N(H)—C(=O)—NH$_2$; N(H)—C(=O)—N(H)(C$_{1-6}$-alkyl); N(H)—C(=O)—N(C$_{1-6}$-alkyl)$_2$; N(C$_{1-6}$-alkyl)-C(=O)—C$_{1-6}$-alkyl; N(C$_{1-6}$-alkyl)-C(=O)—O—C$_{1-6}$-alkyl; N(C$_{1-6}$-alkyl)-C(=O)—NH$_2$;

N($C_{1-6}$-alkyl)-C(=O)—N(H)($C_{1-6}$-alkyl); N($C_{1-6}$-alkyl)$_2$-C(=O)—N($C_{1-6}$-alkyl)$_2$; N(H)—S(=O)$_2$OH; N(H)—S(=O)$_2$—$C_{1-6}$-alkyl; N(H)—S(=O)$_2$—O—$C_{1-6}$-alkyl; N(H)—S(=O)$_2$—NH$_2$; N(H)—S(=O)$_2$—N(H)($C_{1-6}$-alkyl); N(H)—S(=O)$_2$N($C_{1-6}$-alkyl)$_2$; N($C_{1-6}$-alkyl)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—NH$_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; SCF$_3$; SCF$_2$H; SCFH$_2$; SCF$_2$Cl; SCFCl$_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—NH$_2$; S(=O)$_2$—N(H)($C_{1-6}$-alkyl); S(=O)$_2$—N($C_{1-6}$-alkyl)$_2$; $C_{3-10}$-cycloalkyl; 3 to 7 membered heterocyclyl; aryl; heteroaryl; O—$C_{3-10}$-cycloalkyl; O-(3 to 7 membered heterocyclyl); O-aryl; O-heteroaryl; C(=O)—$C_{3-10}$-cycloalkyl; C(=O)-(3 to 7 membered heterocyclyl); C(=O)-aryl; C(=O)-heteroaryl; S(=O)$_2$—$C_{3-10}$-cycloalkyl; S(=O)$_2$-(3 to 7 membered heterocyclyl); S(=O)$_2$-aryl; S(=O)$_2$-heteroaryl; S(=O)(=NR$^{13}$)—$C_{3-10}$-cycloalkyl; S(=O)(=NR$^{13}$)—(3 to 7 membered heterocyclyl); S(=O)(=NR$^{13}$)-aryl and S(=O)(=NR$^{13}$)-heteroaryl, wherein R$^{13}$ represents H or $C_{1-6}$-alkyl;
wherein in each case said $C_{1-6}$-alkyl may be branched or unbranched; unsubstituted or mono- or polysubstituted; and wherein in each case said $C_{3-10}$-cycloalkyl, 3 to 7 membered heterocyclyl aryl and heteroaryl may be unsubstituted or mono- or polysubstituted;
optionally in the form of an individual stereoisomer or a mixture of stereoisomers, in the form of the free compound and/or a physiologically acceptable salt and/or a physiologically acceptable solvate thereof.

DETAILED DESCRIPTION

The term "single stereoisomer" preferably means in the sense of the present invention an individual enantiomer or diastereomer. The term "mixture of stereoisomers" means in the sense of this invention the racemate and mixtures of enantiomers and/or diastereomers in any mixing ratio.

The compounds according to general formula (I) possess at least 2 stereogenic carbon atoms: the carbon atom bearing R$^1$ and the carbon atom bearing R$^2$.

The compounds according to formula (I) may be stereochemically differentiated according to their relative structural orientation. The compounds wherein the residues R$^1$ and R$^2$ have the same relative orientation, for instance both up ("bold wedge") or both down ("broken wedge") are referred within the scope of the present invention as the "cis" diastereomer (scheme 1). The compounds wherein the residues R$^1$ and R$^2$ have a differented relative orientation, for instance R$^1$ up ("bold wedge") and R$^2$ down ("broken wedge") or vice versa are referred within the scope of the present invention as the "trans" diastereomer (scheme 2).

Diastereoisomers differ with respect to their physical and chemical properties. Methods to determine the diastereomeric ratio (dr) are well known to the person skilled in the art and include, but are not limited to, NMR-methods.

A diastereomerically pure compound or a diastereomer according to the present invention refers to a stereoisomer, having a diastereomeric ratio of >90:10, particularly >92:8, preferably >95:5, more preferably >98:2 and even more preferably >99:1.

For both diastereomers, two enantiomers are possible.

An enantiomerically pure compound or an enantiomer according to the present invention refers to a stereoisomer, having an enantiomeric excess of >90% ee, particularly >92% ee, preferably >95% ee, more preferably >98% ee and even more preferably >98% ee. A racemic mixture or a racemate refers to an equal mixture of two corresponding enantiomers.

Methods to determine the enantiomeric excess are well known to the person skilled in the art and include, but are not limited to, optical rotary dispersion, circular dichroism, NMR-methods using chiral auxiliaries ("shift reagents") or separation via chiral HPLC (high performance liquid chromatography, using a chiral stationary phase), chiral GLC (gas-liquid chromatography, using a chiral stationary phase) or chiral SFC (supercritical fluid chromatography using a chiral stationary phase).

Determination of the absolute stereochemical structure is well known to the person skilled in the art and includes, but are not limited to, x-ray diffractometry.

The stereogenic information of the compounds of the present invention is described according to their relative chemical structure as as detailed below:

1) A cis racemic compound (cis-rac) refers to a racemic mixture of two enantiomers as depicted in scheme 1.

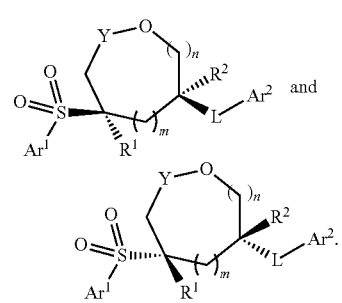

(Scheme 1)

2) A trans racemic compound (trans-rac) refers to a racemic mixture of two enantiomers as depicted in scheme 2.

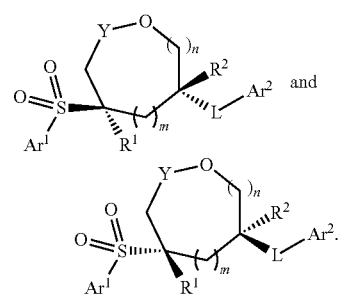

(Scheme 2)

3) A cis enantiomer 1 compound (cis-EN1) refers to one single enantiomer as depicted in scheme 3.

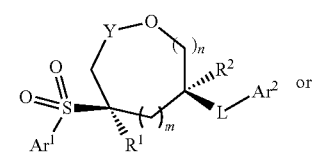

(Scheme 3)

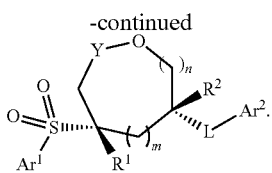

4) A cis enantiomer 2 compound (cis-EN2) refers to the other single enantiomer, which is not cis-EN1 as depicted in scheme 3.

(Scheme 3)

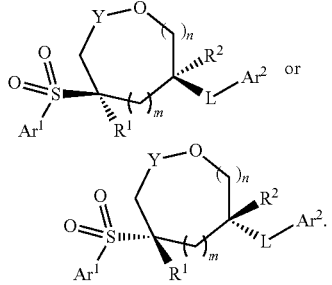

5) A trans enantiomer 1 compound (trans-EN1) refers to one single enantiomer as depicted in scheme 4.

(Scheme 4)

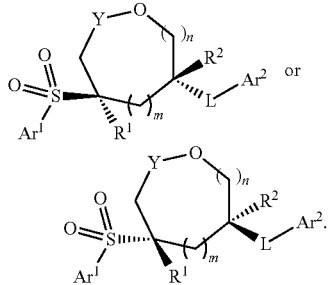

6) A trans enantiomer 2 compound (trans-EN2) refers to the other single enantiomer, which is not trans-EN1 as depicted in scheme 4.

(Scheme 4)

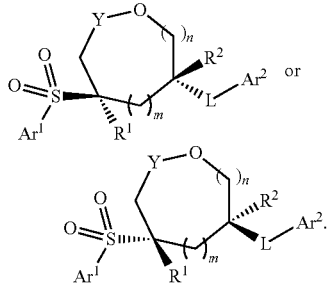

The term "physiologically acceptable salt" preferably comprises in the sense of this invention a salt of at least one compound according to the present invention and at least one physiologically acceptable acid or base.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents.

The term "$C_{1-6}$-alkyl" comprise in the sense of this invention acyclic sat. aliphatic hydrocarbon residues, which can be respectively branched or unbranched and can be unsubstituted or can be mono- or polysubstituted, e.g. mono-, di- or trisubstituted, and which contain 1 to 6 carbon atoms, i.e. 1, 2, 3, 4, 5 or 6 carbon atoms. Preferred $C_{1-6}$-alkyl groups are selected from the group consisting of methyl, ethyl, n-propyl, 2-propyl, n-butyl, isobutyl, sec.-butyl, tert.-butyl, n-pentyl, isopentyl, neopentyl, and n-hexyl.

In relation to the term "$C_{1-6}$-alkyl" the term "monosubstituted" or "polysubstituted" such as di- or tri-substituted refers in the sense of this invention, with respect to the corresponding groups, to the single substitution or multiple substitution, e.g. disubstitution or trisubstitution, of one or more hydrogen atoms each independently of one another by at least one substituent. The term "polysubstituted" such as di- or tri-substituted with respect to polysubstituted groups such as di- or tri-substituted groups includes the polysubstitution of these groups either on different or on the same atoms, for example trisubstituted on the same carbon atom, as in the case of $CF_3$ or $CH_2CF_3$ or at various points, as in the case of $CH(OH)$—$CH_2CH_2$—$CHCl_2$. The multiple substitution can be carried out using the same or using different substituents.

The term "$C_{3-10}$-cycloalkyl" mean for the purposes of this invention cyclic aliphatic hydrocarbons containing 3, 4, 5, 6, 7, 8, 9 or 10 carbon atoms, respectively, wherein the hydrocarbons in each case can be sat. or unsat. (but not aromatic), unsubstituted or mono- or polysubstituted. The cycloalkyl group can be bound to the respective superordinate general structure via any desired and possible ring member of the cycloalkyl group. The cycloalkyl group can also be condensed with further sat., (partially) unsat., (hetero)cyclic, aromatic or heteroaromatic ring systems, i.e. with cycloalkyl, heterocyclyl, aryl or heteroaryl residues, which in each case can in turn be unsubstituted or mono- or polysubstituted. $C_{3-10}$-cycloalkyls can furthermore be singly or multiply bridged such as, for example, in the case of adamantyl, bicyclo[2.2.1]heptyl or bicyclo[2.2.2]octyl. Preferred $C_{3-10}$-cycloalkyl groups are selected from the group consisting of cyclopropyl, cyclobutyl, cyclopentyl, cyclohexyl, cycloheptyl, cyclooctyl, cyclononyl, cyclodecyl, adamantly, cyclopentenyl, cyclohexenyl, cycloheptenyl, cyclooctenyl,

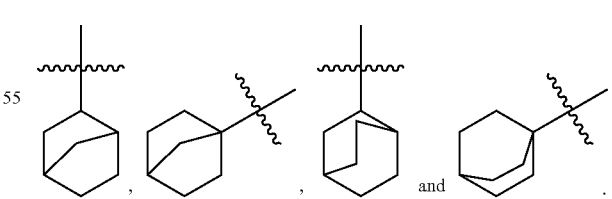

Particularly preferred $C_{3-10}$-cycloalkyl groups are $C_{3-6}$-cycloalkyl groups such as cyclopropyl, cyclobutyl, cyclopentyl, cyclohexyl, cyclopentenyl and cyclohexenyl, in particular cyclopropyl.

The terms "3 to 7-membered heterocyclyl" mean for the purposes of this invention heterocycloaliphatic sat. or unsat. (but not aromatic) residues having 3 to 7, i.e. 3, 4, 5, 6 or 7 ring members, respectively, in which in each case at least one, if appropriate also two or three carbon atoms are replaced by a heteroatom or a heteroatom group each selected independently of one another from the group consisting of O, S, S(=O), S(=O)$_2$, N, NH and N(C$_{1-6}$-alkyl) such as N(CH$_3$), wherein the ring members can be unsubstituted or mono- or polysubstituted. The cycloalkyl groups can also be condensed with further sat. or (partially) unsat. cycloalkyl or heterocyclyl, aromatic or heteroaromatic ring systems, which in each case can in turn be unsubstituted or mono- or polysubstituted. The heterocyclyl group can be bound to the superordinate general structure via any desired and possible ring member of the heterocycloaliphatic residue if not indicated otherwise.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further sat. or (partially) unsat. cycloalkyl or heterocyclyl, aromatic or heteroaromatic ring systems, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5-, 6-, 8-, 9- or 10-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 10 ring members, wherein the ring system can be formed with further sat. or (partially) unsat. cycloalkyl or heterocyclyl, aromatic or heteroaromatic ring systems, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

In relation to the terms "C$_{1-6}$-alkyl", "C$_{3-10}$-cycloalkyl", "3 to 7-membered heterocyclyl" and "3 to 10-membered heterocyclyl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; I; NO$_2$; CN; =O; =NH; =N(OH); =N(O—C$_{1-6}$-alkyl); CF$_3$; CF$_2$H; CFH$_2$; CF$_2$Cl; CFCl$_2$; C$_{1-6}$-alkyl; C(=O)—H; C(=O)—C$_{1-6}$-alkyl; C(=O)—OH; C(=O)—O—C$_{1-6}$-alkyl; C(=O)—N(H)(OH); C(=O)—NH$_2$; C(=O)—N(H)(C$_{1-6}$-alkyl); C(=O)—N(C$_{1-6}$-alkyl)$_2$; C(=N—OH)—H; C(=N—OH)—C$_{1-6}$-alkyl; C(=N—O—C$_{1-6}$-alkyl)-H; C(=N—O—C$_{1-6}$-alkyl)-C$_{1-6}$-alkyl; OH; OCF$_3$; OCF$_2$H; OCFH$_2$; OCF$_2$Cl; OCFCl$_2$; O—C$_{1-6}$-alkyl; 0-C(=O)—C$_{1-6}$-alkyl; 0-C(=O)—O—C$_{1-6}$-alkyl; O—(C=O)—N(H)(C$_{1-6}$-alkyl); 0-C(=O)—N(C$_{1-6}$-alkyl)$_2$; O—S(=O)$_2$—C$_{1-6}$-alkyl; 0-S(=O)$_2$—OH; O—S(=O)$_2$—O—C$_{1-6}$-alkyl; O—S(=O)$_2$—NH$_2$; O—S(=O)$_2$—N(H)(C$_{1-6}$-alkyl); O—S(=O)$_2$—N(C$_{1-6}$-alkyl)$_2$; NH$_2$; N(H)(C$_{1-6}$-alkyl); N(C$_{1-6}$-alkyl)$_2$; N(H)—C(=O)—C$_{1-6}$-alkyl; N(H)—C(=O)—O—C$_{1-6}$-alkyl; N(H)—C(=O)—NH$_2$; N(H)—C(=O)—N(H)(C$_{1-6}$-alkyl); N(H)—C(=O)—N(C$_{1-6}$-alkyl)$_2$; N(C$_{1-6}$-alkyl)-C(=O)—C$_{1-6}$-alkyl; N(C$_{1-6}$-alkyl)-C(=O)—O—C$_{1-6}$-alkyl; N(C$_{1-6}$-alkyl)-C(=O)—NH$_2$; N(C$_{1-6}$-alkyl)-C(=O)—N(H)(C$_{1-6}$-alkyl); N(C$_{1-6}$-alkyl)-C(=O)—N(C$_{1-6}$-alkyl)$_2$; N(H)—S(=O)$_2$—OH; N(H)—S(=O)$_2$—C$_{1-6}$-alkyl; N(H)—S(=O)$_2$—O—C$_{1-6}$-alkyl; N(H)—S(=O)$_2$—NH$_2$; N(H)—S(=O)$_2$—N(H)(C$_{1-6}$-alkyl); N(H)—S(=O)$_2$—N(C$_{1-6}$-alkyl)$_2$; N(C$_{1-6}$-alkyl)-S(=O)$_2$—OH; N(C$_{1-6}$-alkyl)-S(=O)$_2$—C$_{1-6}$-alkyl; N(C$_{1-6}$-alkyl)-S(=O)$_2$—O—C$_{1-6}$-alkyl; N(C$_{1-6}$-alkyl)-S(=O)$_2$—NH$_2$; N(C$_{1-6}$-alkyl)-S(=O)$_2$—N(H)(C$_{1-6}$-alkyl); N(C$_{1-6}$-alkyl)-S(=O)$_2$—N(C$_{1-6}$-alkyl)$_2$; SH; SCF$_3$; SCF$_2$H; SCFH$_2$; SCF$_2$Cl; SCFCl$_2$; S—C$_{1-6}$-alkyl; S(=O)—C$_{1-6}$-alkyl; S(=O)$_2$—C$_{1-6}$-alkyl; S(=O)$_2$—OH; S(=O)$_2$—O—C$_{1-6}$-alkyl; S(=O)$_2$—NH$_2$; S(=O)$_2$—N(H)(C$_{1-6}$-alkyl); S(=O)$_2$—N(C$_{1-6}$-alkyl)$_2$; C$_{3-6}$-cycloalkyl; 3 to 7 membered heterocyclyl; aryl or heteroaryl. The term "polysubstituted" with respect to polysubstituted residues and groups includes the polysubstitution of these residues and groups either on different or on the same atoms, for example trisubstituted on the same carbon atom, as in the case of CF$_3$, CH$_2$CF$_3$ or 1,1-difluorocyclohexyl, or at various points, as in the case of CH(OH)—CHCl$_2$ or 1-chloro-3-fluorocyclohexyl. A substituent can if appropriate for its part in turn be mono- or polysubstituted. The multiple substitution can be carried out using the same or using different substituents.

Preferred substituents of "C$_{1-6}$-alkyl" are selected from the group consisting of F; Cl; Br; CF$_3$; C(=O)—NH$_2$; C(=O)—N(H)(C$_{1-6}$-alkyl); C(=O)—N(C$_{1-6}$-alkyl)$_2$; C$_{3-6}$-cycloalkyl or 3 to 7 membered heterocyclyl; OH; O—C$_{1-6}$-alkyl; NH$_2$; N(H)(C$_{1-6}$-alkyl); N(C$_{1-6}$-alkyl)$_2$; N(H)—C(=O)—C$_{1-6}$-alkyl; N(H)—S(=O)$_2$—C$_{1-6}$-alkyl; N(C$_{1-6}$-alkyl)-S(=O)$_2$—C$_{1-6}$-alkyl; N(H)—S(=O)$_2$—NH$_2$; SH; S—C$_{1-6}$-alkyl; S(=O)$_2$C$_{1-6}$-alkyl and S(=O)$_2$—N(H)(C$_{1-6}$-alkyl).

Preferred substituents of "C$_{3-6}$-cycloalkyl" and "3 to 7-membered heterocyclyl" are selected from the group consisting of F; Cl; Br; CF$_3$; CN; =O; C$_{1-6}$-alkyl; C$_{3-6}$-cycloalkyl or 3 to 7 membered heterocyclyl; CHO; C(=O)—C$_{1-6}$-alkyl; CO$_2$H; C(=O)O—C$_{1-6}$-alkyl; CONH$_2$; C(=O)NH—C$_{1-6}$-alkyl; C(=O)N(C$_{1-6}$-alkyl)$_2$; OH; O—C$_{1-6}$-alkyl; OCF$_3$; O—C(=O)—C$_{1-6}$-alkyl; NH$_2$; NH—C$_{1-6}$-alkyl; N(C$_{1-6}$-alkyl)$_2$; NH—C(=O)—C$_{1-6}$-alkyl; SH; S—C$_{1-6}$-alkyl; SCF$_3$; S(=O)$_2$—C$_{1-6}$-alkyl; S(=O)$_2$OH; S(=O)$_2$O—C$_{1-6}$-alkyl and S(=O)$_2$—NH—C$_{1-6}$-alkyl.

In relation to the terms "aryl" and "heteroaryl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; $NO_2$; CN; $CF_3$; $CF_2H$; $CFH_2$; $CF_2Cl$; $CFCl_2$; $C_{1-6}$-alkyl; $C_{3-6}$-cycloalkyl; 3 to 7 membered heterocyclyl; aryl; heteroaryl; aryl, heteroaryl, $C_{3-6}$-cycloalkyl or 3 to 7 membered heterocyclyl, each connected via a $C_{1-8}$-alkylene; C(=O)H; C(=O)—($C_{1-6}$-alkyl); C(=O)—($C_{3-6}$-cycloalkyl); C(=O)-(3 to 7 membered heterocyclyl); C(=O)-(aryl); C(=O)-(heteroaryl); C(=O)OH; C(=O)—O($C_{1-6}$-alkyl); C(=O)—O($C_{3-6}$-cycloalkyl); C(=O)—O (3 to 7 membered heterocyclyl); C(=O)—O (aryl); C(=O)—O(heteroaryl); C(=O)—$NH_2$; C(=O)—N(H)($C_{1-6}$-alkyl); C(=O)—N(H)($C_{3-6}$-cycloalkyl); C(=O)—N(H)(3 to 7 membered heterocycloalkyl); C(=O)—N(H)(aryl); C(=O)—N(H)(heteroaryl); C(=O)—N($C_{1-6}$-alkyl)$_2$; C(=O)—N($C_{1-6}$-alkyl)($C_{3-6}$-cycloalkyl); C(=O)—N($C_{1-6}$-alkyl)(3 to 7 membered heterocyclyl); C(=O)—N($C_{1-6}$-alkyl)(aryl); C(=O)—N($C_{1-6}$-alkyl)(heteroaryl); OH; =O; O—($C_{1-6}$-alkyl); O—($C_{3-6}$-cycloalkyl); O-(3 to 7 membered heterocyclyl); O-(aryl); O-(heteroaryl); $OCF_3$; $OCF_2H$; $OCFH_2$; $OCF_2Cl$; $OCFCl_2$; O—C(=O)—($C_{1-6}$-alkyl); O—C(=O)—($C_{3-6}$-cycloalkyl); O—C(=O)-(3 to 7 membered heterocyclyl); O—C(=O)-(aryl); C(=O)-(heteroaryl); O—C(=O)—$NH_2$; O—C(=O)—N(H)($C_{1-6}$-alkyl); O—C(=O)—N(H)($C_{3-6}$-cycloalkyl); O—C(=O)—N(H)(3 to 7 membered heterocyclyl); O—C(=O)—N(H)(aryl); O—C(=O)—N(H)(heteroaryl); O—C(=O)—N($C_{1-6}$-alkyl)$_2$; O—C(=O)—N($C_{1-6}$-alkyl)($C_{3-6}$-cycloalkyl); O—C(=O)—N($C_{1-6}$-alkyl)(3 to 7 membered heterocyclyl); O—C(=O)—N($C_{1-6}$-alkyl)(aryl); O—C(=O)—N($C_{1-6}$-alkyl) (heteroaryl); $NH_2$; N(H)($C_{1-6}$-alkyl); N(H)($C_{3-6}$-cycloalkyl); N(H)(3 to 7 membered heterocyclyl); N(H)(aryl); N(H)(heteroaryl); N($C_{1-6}$-alkyl)$_2$; N($C_{1-6}$-alkyl)($C_{3-6}$-cycloalkyl); N($C_{1-6}$-alkyl)(3 to 7 membered heterocyclyl); N($C_{1-6}$-alkyl) (aryl); N($C_{1-6}$-alkyl)(heteroaryl); N(H)—C(=O)—($C_{1-6}$-alkyl); N(H)—C(=O)—($C_{3-6}$-cycloalkyl); N(H)—C(=O)-(3 to 7 membered heterocyclyl); N(H)—C(=O)-(aryl); N(H)—C(=O)-(heteroaryl); N($C_{1-6}$-alkyl)-C(=O)—($C_{1-6}$-alkyl); N($C_{1-6}$-alkyl)-C(=O)—($C_{3-6}$-cycloalkyl); N($C_{1-6}$-alkyl)-C(=O)-(3 to 7 membered heterocyclyl); N($C_{1-6}$-alkyl)-C(=O)-(aryl); N($C_{1-6}$-alkyl)-C(=O)-(heteroaryl); N(H)—S(=O)$_2$—($C_{1-6}$-alkyl); N(H)—S(=O)$_2$—($C_{3-6}$-cycloalkyl); N(H)—S(=O)$_2$-(3 to 7 membered heterocyclyl); N(H)—S(=O)$_2$-(aryl); N(H)—S(=O)$_2$-(heteroaryl); N($C_{1-4}$-alkyl)-S(=O)$_2$—($C_{1-6}$-alkyl); N($C_{1-6}$-alkyl)-S(=O)$_2$—($C_{3-6}$-cycloalkyl); N($C_{1-6}$-alkyl)-S(=O)$_2$-(3 to 7 membered heterocyclyl); N($C_{1-6}$-alkyl)-S(=O)$_2$-(aryl); N($C_{1-6}$-alkyl)-S(=O)$_2$-(heteroaryl); N(H)—C(=O)—O($C_{1-6}$-alkyl); N(H)—C(=O)—O($C_{3-6}$-cycloalkyl); N(H)—C(=O)—O (3 to 7 membered heterocyclyl); N(H)—C(=O)—O(aryl); N(H)—C(=O)—O(heteroaryl); N($C_{1-6}$-alkyl)-C(=O)—O($C_1$-6-alkyl); N($C_{1-6}$-alkyl)-C(=O)—O($C_{3-6}$-cycloalkyl); N($C_{1-6}$-alkyl)-C(=O)—O (3 to 7 membered heterocyclyl); N($C_{1-6}$-alkyl)-C(=O)—O(aryl); N($C_{1-6}$-alkyl)-C(=O)—O(heteroaryl); N(H)—C(=O)—$NH_2$; N(H)—C(=O)—N(H)($C_{1-6}$-alkyl); N(H)—C(=O)—N(H)($C_{3-6}$-cycloalkyl); N(H)—C(=O)—N(H)(3 to 7 membered heterocyclyl); N(H)—C(=O)—N(H)(aryl); N(H)—C(=O)—N(H)(heteroaryl); N($C_{1-6}$-alkyl)-C(=O)—$NH_2$; N($C_{1-6}$-alkyl)-C(=O)—N(H)($C_{1-6}$-alkyl); N($C_{1-6}$-alkyl)-C(=O)—N(H)($C_{3-6}$-cycloalkyl); N($C_{1-6}$-alkyl)-C(=O)—N(H)(3 to 7 membered heterocyclyl); N($C_{1-6}$-alkyl)-C(=O)—N(H)(aryl); N($C_{1-6}$-alkyl)-C(=O)—N(H)(heteroaryl); N(H)—C(=O)—N($C_{1-6}$-alkyl)$_2$; N(H)—C(=O)—N($C_{1-6}$-alkyl)($C_{3-6}$-cycloalkyl); N(H)—C(=O)—N($C_{1-6}$-alkyl)(3 to 7 membered heterocyclyl); N(H)—C(=O)—N($C_{1-6}$-alkyl)(aryl); N(H)—C(=O)—N($C_{1-6}$-alkyl) (heteroaryl); N($C_{1-6}$-alkyl)-C(=O)—N($C_{1-6}$-alkyl)$_2$; N($C_{1-6}$-alkyl)-C(=O)—N($C_{1-6}$-alkyl)($C_{3-6}$-cycloalkyl); N($C_{1-6}$-alkyl)-C(=O)—N($C_{1-6}$-alkyl)(3 to 7 membered heterocyclyl); N($C_{1-6}$-alkyl)-C(=O)—N($C_{1-6}$-alkyl)(aryl); N($C_{1-6}$-alkyl)-C(=O)—N($C_{1-6}$-alkyl) heteroaryl); SH; S—($C_{1-6}$-alkyl); S—($C_{3-6}$-cycloalkyl); S-(3 to 7 membered heterocyclyl); S-(aryl); S-(heteroaryl); $SCF_3$; S(=O)$_2$OH; S(=O)—($C_{1-6}$-alkyl); S(=O)—($C_{3-6}$-cycloalkyl); S(=O)-(3 to 7 membered heterocyclyl); S(=O)-(aryl); S(=O)-(heteroaryl); S(=O)$_2$—($C_{1-6}$-alkyl); S(=O)$_2$—($C_{3-6}$-cycloalkyl); S(=O)$_2$-(3 to 7 membered heterocyclyl); S(=O)$_2$-(aryl); S(=O)$_2$-(heteroaryl); S(=O)$_2$—O($C_{1-6}$-alkyl); S(=O)$_2$—O($C_{3-6}$-cycloalkyl); S(=O)$_2$—O (3 to 7 membered heterocyclyl); S(=O)$_2$—O (aryl); S(=O)$_2$—O(heteroaryl); S(=O)$_2$—N(H)($C_{1-6}$-alkyl); S(=O)$_2$—N(H)($C_{3-6}$-cycloalkyl); S(=O)$_2$—N(H)(3 to 7 membered heterocyclyl); S(=O)$_2$—N(H)(aryl); S(=O)$_2$—N(H)(heteroaryl); S(=O)$_2$—N($C_{1-6}$-alkyl)$_2$; S(=O)$_2$—N($C_{1-6}$-alkyl)($C_{3-6}$-cycloalkyl); S(=O)$_2$—N($C_{1-6}$-alkyl)(3 to 7 membered heterocyclyl); S(=O)$_2$—N($C_{1-6}$-alkyl)(aryl); S(=O)$_2$—N($C_{1-6}$-alkyl)(heteroaryl); S(=O) (=$NR^{13}$)—$C_{3-10}$-cycloalkyl; S(=O)(=$NR^{13}$)-(3 to 7 membered heterocyclyl); S(=O)(=$NR^{13}$)-aryl and S(=O) (=$NR^{13}$)-heteroaryl, wherein $R^{13}$ represents H or $C_{1-6}$-alkyl.

Preferred substituents of "aryl" and "heteroaryl" are selected from the group consisting of F; Cl; $CF_3$; CN; $C_{1-6}$-alkyl; C(=O)—OH; C(=O)—O—$C_{1-6}$-alkyl; CO—$NH_2$; C(=O)—N(H)$C_{1-6}$-alkyl; C(=O)—N($C_{1-6}$-alkyl)$_2$; OH; O—$C_{1-6}$-alkyl; O—C(=O)—$C_{1-6}$-alkyl; $OCF_3$; $OCHF_2$; $OCH_2F$; $NH_2$; N(H)$C_{1-6}$-alkyl; N($C_{1-6}$-alkyl)$_2$; N(H)—C(=O)—$C_{1-6}$-alkyl; N($C_{1-6}$-alkyl)-C(=O)$C_{1-6}$-alkyl; N(H)—S(=O)$_2$—$C_{1-6}$-alkyl; N($C_{1-6}$-alkyl)-S(=O)$_2$ ($C_{1-6}$-alkyl); N(H)C(=O)$NH_2$; N(H)—C(=O)—N(H)$C_{1-6}$-alkyl; N(H)—C(=O)—N($C_{1-6}$-alkyl)$_2$; N($C_{1-6}$-alkyl)-C(=O)—$NH_2$; N($C_{1-6}$-alkyl)-C(=O)—N(H)$C_{1-6}$-alkyl; N($C_{1-6}$-alkyl)-C(=O)—N($C_{1-6}$-alkyl)$_2$; S(=O)$_2C_{1-6}$-alkyl; S(=O)$_2$—$NH_2$; S(=O)$_2$—N(H)$C_{1-6}$-alkyl and S(=O)$_2$—N($C_{1-6}$-alkyl)$_2$.

The compounds according to the invention are defined by substituents, for example by $R^1$, $R^2$ and $R^3$ ($1^{st}$ generation substituents) which are for their part if appropriate themselves substituted ($2^{nd}$ generation substituents). Depending on the definition, these substituents of the substituents can for their part be resubstituted ($3^{rd}$ generation substituents). If, for example, $R^1$=a $C_{1-6}$-alkyl ($1^{st}$ generation substituent), then the $C_{1-6}$-alkyl can for its part be substituted, for example with a NH— $C_{1-6}$-alkyl ($2^{nd}$ generation substituent). This produces the functional group $R^1$=($C_{1-6}$-alkyl-NH—$C_{1-6}$-alkyl). The NH—$C_{1-6}$-alkyl can then for its part be resubstituted, for example with Cl ($3^{rd}$ generation substituent). Overall, this produces the functional group $R^1$=$C_{1-6}$-alkyl-NH—$C_{1-6}$-alkyl, wherein the $C_{1-6}$-alkyl of the NH—$C_{1-6}$-alkyl is substituted by Cl. However, in a preferred embodiment, the $3^{rd}$ generation substituents may not be resubstituted, i.e. there are then no $4^{th}$ generation substituents. If a residue occurs multiply within a molecule, then this residue can have respectively different meanings for various substituents: if, for example, both $R^1$ and $R^2$ denote a 3 to 10 membered heterocyclyl, then the 3 to 10 membered heterocyclyl can e.g. represent morpholinyl for $R^1$ and can represent piperazinyl for $R^2$.

Within the scope of the present invention, the symbols

used in the formulae denotes a link of a corresponding residue to the respective superordinate general structure.

In one embodiment of the first aspect of the invention, the compound according to general formula (I) is characterized in that m represents 0 or 1. Preferably, m represents 1.

In another embodiment of the first aspect of the invention, the compound according to general formula (I) is characterized in that n represents 0.

In yet another embodiment of the first aspect of the invention, the compound according to general formula (I) is characterized in that m represents 1 and n represents 0, so the compound is represented by general formula (II),

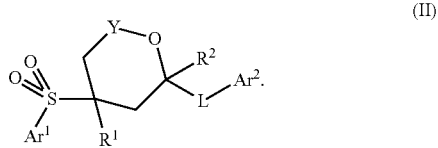
(II)

In a preferred embodiment of the of the first aspect of the invention, the compound according to general formula (I) is characterized in that m represents 1, n represents 0, and Y is bond, $CH_2$ or $C(CH_3)_2$.

In a particularly preferred embodiment of the of the first aspect of the invention, the compound according to general formula (I) is characterized in that m represents 1, n represents 0 and Y is $CH_2$, so the compound is represented by general formula (IIa),

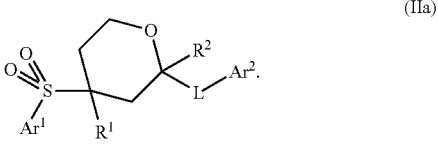
(IIa)

In another particularly preferred embodiment of the first aspect of the invention, the compound according to general formula (I) is characterized in that m represents 1, n represents 0 and Y is bond, so the compound is represented by general formula (IIb),

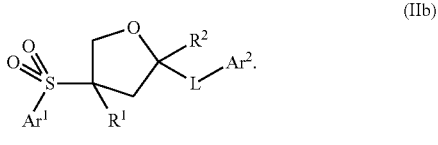
(IIb)

In another embodiment of the first aspect of the invention, the compound according to the invention is one diastereomer. Preferably, the compound according to the invention is the cis-diastereomer. Still preferably, the compound according to the invention is the trans-diastereomer.

Thus, one preferred embodiment of the first aspect of the invention is characterized in that the compound of general formula (I), (II), (IIa) or (IIb) is one diastereomer.

The cis-diastereomer or the trans-diastereomer may be in the form of a single enantiomer or in the form of an enantiomeric mixture, preferably of a racemate.

In yet another embodiment of the first aspect of the invention, the compound according to the invention is in only one enantiomeric form. Preferably, the compound according to the invention is the racemate of the cis-diastereomer (cis-rac) or a single enantiomer of the cis-diastereomer (cis-EN1 or cis-EN2). Still preferably, the compound according to the invention is the racemate of the trans-diastereomer (trans-rac) or a single enantiomer of the trans-diastereomer (trans-EN1 or trans-EN2).

Thus, one preferred embodiment of the first aspect of the invention is characterized in that the compound of general formula (I), (II), (IIa) or (IIb) is one enantiomer.

In one preferred embodiment of the first aspect of the invention is characterized in that the compound of general formula (I), (II), (IIa) or (IIb) is the enantiomer, which exhibits at room temperature and a wavelength of 589 nm (Na-D-line) a positive optical rotation in dichloromethane or methanol.

In another preferred embodiment of the first aspect of the invention is characterized in that the compound of general formula (I), (II), (IIa) or (IIb) is the enantiomer, which exhibits at room temperature and a wavelength of 589 nm (Na-D-line) a negative optical rotation in dichloromethane or methanol.

In another embodiment of the first aspect of the invention, the compound according to general formula (I) is characterized in that $R^2$ represents H, $CH_3$, $C_2H_5$, $CH_2CH_2CH_3$, $CH(CH_3)_2$, $CH_2OH$, $CH_2OCH_3$, $CH_2NH_2$, $CH_2N(H)CH_3$ or $CH_2N(CH_3)_2$.

Preferably, $R^2$ represents H, $CH_3$ or $C_2H_5$.

In a preferred embodiment, the compound according to formula (I) is characterized in that m represents 1, n represents 0, Y is $CH_2$, and $R^2$ represents H, $CH_3$ or $C_2H_5$.

In another preferred embodiment, the compound according to formula (I) is characterized in that m represents 1, n represents 0, Y is bond, and $R^2$ represents H, $CH_3$ or $C_2H_5$.

In another embodiment of the first aspect of the invention, the compound according to general formula (I) is characterized in that $R^1$ represents H, $CH_3$, $C_2H_5$, $CH_2CH_2CH_3$, $CH_2OCH_3$ or $CH_2N(CH_3)_2$.

Preferably, $R^1$ represents H, $CH_3$, $C_2H_5$ or $CH_2OCH_3$. Particularly preferred are compounds wherein $R^1$ represents $CH_3$.

In a preferred embodiment, the compound according to formula (I) is characterized in that m represents 1, n represents 0, Y is $CH_2$, and $R^1$ represents H, $CH_3$, $C_2H_5$ or $CH_2OCH_3$.

In another preferred embodiment, the compound according to formula (I) is characterized in that m represents 1, n represents 0, Y is bond, and $R^1$ represents H, $CH_3$, $C_2H_5$ or $CH_2OCH_3$.

In another embodiment of the first aspect of the invention, the compound according to general formula (I) is characterized in that $Ar^1$ represents phenyl or pyridinyl, substituted by zero or one or two or three substituents $R^7$.

In preferred embodiment of the first aspect of the invention, the compound according to general formula (I) is characterized in that $Ar^1$ represents phenyl or pyridinyl, substituted by one or two substituents $R^7$.

Preferably, $R^7$ is independently selected from the group consisting of F; Cl; CN; $C_{1-6}$-alkyl; $CF_3$; $CF_2H$; $CFH_2$;

C(=O)—C$_{1-6}$-alkyl; C(=O)—OH; C(=O)—O—C$_{1-6}$-alkyl; C(=O)—N(H)(OH); C(=O)—NH$_2$; C(=O)—N(H)(C$_{1-6}$-alkyl); C(=O)—N(C$_{1-6}$-alkyl)$_2$; OH; OCF$_3$; OCF$_2$H; OCFH$_2$; OCF$_2$Cl; OCFCl$_2$; O—C$_{1-6}$-alkyl; NH$_2$; N(H)(C$_{1-6}$-alkyl); N(C$_{1-6}$-alkyl)$_2$; N(H)—C(=O)—C$_{1-6}$-alkyl; N(C$_{1-6}$-alkyl)-C(=O)—C$_{1-6}$-alkyl; N(H)—S(=O)$_2$—C$_{1-6}$-alkyl; SCF$_3$; S—C$_{1-6}$-alkyl; S(=O)—C$_{1-6}$-alkyl; S(=O)$_2$—C$_{1-6}$-alkyl; S(=O)$_2$—NH$_2$; S(=O)$_2$—N(H)(C$_{1-6}$-alkyl); S(=O)$_2$—N(C$_{1-6}$-alkyl)$_2$; C$_{3-10}$-cycloalkyl; 3 to 7 membered heterocyclyl; O—C$_{3-10}$-cycloalkyl and 0-(3 to 7 membered heterocyclyl).

In yet another embodiment of the first aspect of the invention, the compound according to general formula (I) is characterized in that Ar$^1$ represents phenyl or pyridinyl, substituted by zero or one or two or three substituents R$^7$, wherein each R$^7$ is independently selected from the group consisting of F; Cl; CN; C$_{1-6}$-alkyl; CF$_3$; CF$_2$H; CFH$_2$; C(=O)—C$_{1-6}$-alkyl; C(=O)—OH; C(=O)—O—C$_{1-6}$-alkyl; C(=O)—N(H)(OH); C(=O)—NH$_2$; C(=O)—N(H)(C$_{1-6}$-alkyl); C(=O)—N(C$_{1-6}$-alkyl)$_2$; OH; OCF$_3$; OCF$_2$H; OCFH$_2$; OCF$_2$Cl; OCFCl$_2$; O—C$_{1-6}$-alkyl; NH$_2$; N(H)(C$_{1-6}$-alkyl); N(C$_{1-6}$-alkyl)$_2$; N(H)—C(=O)—C$_{1-6}$-alkyl; N(C$_{1-6}$-alkyl)-C(=O)—C$_{1-6}$-alkyl; N(H)—S(=O)$_2$—C$_{1-6}$-alkyl; SCF$_3$; S—C$_{1-6}$-alkyl; S(=O)—C$_{1-6}$-alkyl; S(=O)$_2$—C$_{1-6}$-alkyl; S(=O)$_2$—NH$_2$; S(=O)$_2$—N(H)(C$_{1-6}$-alkyl); S(=O)$_2$—N(C$_{1-6}$-alkyl)$_2$; C$_{3-10}$-cycloalkyl; 3 to 7 membered heterocyclyl; O—C$_{3-10}$-cycloalkyl and 0-(3 to 7 membered heterocyclyl).

Preferably, Ar$^1$ represents phenyl or 2-pyridinyl.

In another preferred embodiment of the first aspect of the invention, the compound according to general formula (I) is characterized in that Ar$^1$ represents subformula SF-I

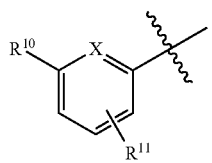

(SF-I)

wherein X is CH or N,
R$^{10}$ is selected from the group consisting of CF$_3$; CF$_2$H; CFH$_2$; OCF$_3$; OCF$_2$H; OCFH$_2$; cyclopropyl; Ocyclopropyl; CH(CH$_3$)$_2$; OCH(CH$_3$)$_2$; C(CH$_3$)$_3$ and OC(CH$_3$)$_3$; and
R$^{11}$ is selected from the group consisting of H; F; Cl; CN; CH$_3$; CH$_2$CH$_3$; CH$_2$CH$_2$CH$_3$; CH(CH$_3$)$_2$; CH(CH$_3$)CH$_2$CH$_3$; CH$_2$CH$_2$CH$_2$CH$_3$; CH$_2$CH(CH$_3$)$_2$; C(CH$_3$)$_3$; CF$_3$; CF$_2$H; CFH$_2$; OCF$_3$; OCH$_3$; OCH$_2$CH$_3$; OCH(CH$_3$)$_2$; S(=O)—CH$_3$ and S(=O)$_2$—CH$_3$.

More preferably, R$^{10}$ is CF$_3$; CF$_2$H; CFH$_2$; OCF$_3$; OCF$_2$H or OCFH$_2$. Even more preferably, R$^{10}$ is CF$_3$ or OCF$_3$.

In yet another embodiment of the first aspect of the invention, the compound according to general formula (I) is characterized in that L is —[C(R$^4$)$_2$]$_x$—(X)$_y$—[C(R$^4$)$_2$]$_z$—, wherein x is 0, 1 or 2, y is 0 or 1 and z is 0, with the proviso that x≥y;
each R$^4$ is independently selected from the group consisting of H and C$_{1-6}$-alkyl, or two R$^4$ form together with the C-atom connecting them a C$_{3-10}$-cycloalkyl or a 3 to 7 membered heterocyclyl or two R$^4$ form together with two adjacent C-atoms connecting them a C$_{3-10}$-cycloalkyl or a 3 to 7 membered heterocyclyl, X is selected from the group consisting of O, S, S(O)$_2$, N(H) or N(C$_{1-6}$-alkyl).

In a preferred embodiment of the first aspect of the invention, the compound according to general formula (I) is characterized in that L is —[C(R$^4$)$_2$]$_x$—(X)$_y$—[C(R$^4$)$_2$]$_z$—, wherein z is 0 and the sum (x+y) is 0 or 2.

Preferably, the compound according to general formula (I) is characterized in that L is —[C(R$^4$)$_2$]$_x$—(X)$_y$—[C(R$^4$)$_2$]$_z$—,
wherein x is 0, 1 or 2, y is 0 or 1 and z is 0, with the proviso that x≥y;
each R$^4$ is independently selected from the group consisting of H and C$_{1-6}$-alkyl, or two R$^4$ form together with the C-atom connecting them a C$_{3-10}$-cycloalkyl, and
X is O.

More preferably, the compound according to general formula (I) is characterized in that L is —[C(R$^4$)$_2$]$_x$—(X)$_y$—[C(R$^4$)$_2$]$_z$—,
wherein x is 0 or 1, y is 0 or 1 and z is 0, with the proviso that x≥y;
each R$^4$ is independently selected from the group consisting of H and C$_{1-6}$-alkyl, or two R$^4$ form together with the C-atom connecting them a C$_{3-10}$-cycloalkyl, and
X is O.

In a preferred embodiment of the first aspect of the invention, the compound according to general formula (I) is characterized in that
L is bond (x=y=z=0); CH$_2$ (x=1; each R$^4$=H; y=z=0); CH$_2$CH$_2$ (x=2; each R$^4$=H; y=z=0); C(CH$_3$)$_2$ (x=2; R$^4$=H and R$^4$=CH$_3$; y=z=0); CH$_2$C(CH$_3$)$_2$ (x=2; R$^4$=H and R$^4$=CH$_3$; y=z=0); C(CH$_3$)$_2$CH$_2$ (x=1; each R$^4$=CH$_3$; y=z=0); CH(CH$_3$) (x=1; R$^4$=H and R$^4$=CH$_3$; y=z=0); CH$_2$O (x=1; each R$^4$=H; y=1; X=O; z=0); C(CH$_3$)$_2$O (x=1; each R$^4$=CH$_3$; y=1; X=O; z=0); CH(CH$_3$)O (x=1; R$^4$=H and R$^4$=CH$_3$; y=1; X=O; z=0);

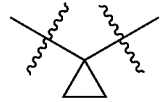

(x=1; two R$^4$ form together with the C-atom connecting them a C$_3$-cycloalkyl; y=z=0); or

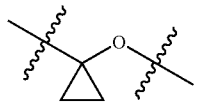 [SMILES: *OC1(*)CC1]

(x=1; two R$^4$ form together with the C-atom connecting them a C$_3$-cycloalkyl; y=1; X=O; z=0).

In case, L contains an oxygen atom, the compound according to the invention characterized in that the oxygen atom is directly bond to Ar$^2$. Therefore, the structural element -L-Ar$^2$ is represented by —Ar$^2$ (L=bond); —CH$_2$—Ar$^2$; —C(CH$_3$)$_2$—Ar$^2$; —CH(CH$_3$)—Ar$^2$; —CH$_2$O—Ar$^2$; —C(CH$_3$)$_2$O—Ar$^2$; —CH(CH$_3$)O—Ar$^2$;

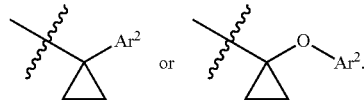

Preferably L is bond, CH₂; C(CH₃)₂; CH₂CH₂; CH₂C(CH₃)₂; C(CH₃)₂CH₂; CH₂O or C(CH₃)₂O, more preferably L is bond or CH₂O.

In another embodiment of the first aspect of the invention, the compound according to general formula (I) is characterized in that Ar² is phenyl or cyclopropyl.

In another embodiment of the first aspect of the invention, the compound according to general formula (I) is characterized in that Ar² represents phenyl, substituted by one or two substituents R⁸,
  wherein each R⁸ is independently selected from the group consisting of F; Cl; CN; C₁₋₆-alkyl; CF₃; CF₂H; CFH₂; OCF₃; OCF₂H; OCFH₂; O—C₁₋₆-alkyl; S—C₁₋₆-alkyl; S(=O)—C₁₋₆-alkyl; S(=O)₂—C₁₋₆-alkyl; C₃₋₁₀-cycloalkyl; 3 to 7 membered heterocyclyl; aryl; heteroaryl; O—C₃₋₁₀-cycloalkyl; O-(3 to 7 membered heterocyclyl); O-aryl; O-heteroaryl; C(=O)—C₃₋₁₀-cycloalkyl; C(=O)-(3 to 7 membered heterocyclyl); C(=O)-aryl; C(=O)-heteroaryl; S(=O)₂—C₃₋₁₀-cycloalkyl; S(=O)₂-(3 to 7 membered heterocyclyl); S(=O)₂-aryl; S(=O)₂-heteroaryl; S(=O)(=NR¹³)—C₃₋₁₀-cycloalkyl; S(=O)(=NR¹³)-(3 to 7 membered heterocyclyl); S(=O)(=NR¹³)-aryl and S(=O)(=NR¹³)-heteroaryl, wherein R¹³ represents H or C₁₋₆-alkyl.

Preferably, R⁸ is selected from the group consisting of F; Cl; CN; CH₃; CH₂CH₃; CH₂CH₂CH₃; CH(CH₃)₂; CH(CH₃)CH₂CH₃; CH₂CH₂CH₂CH₃; CF₃; CF₂H; CFH₂; OCF₃; OCF₂H; OCFH₂; OCH₃; OCH₂CH₃; OCH₂CH₂CH₃; OCH(CH₃)₂; S(=O)CH₃; S(=O)CH₂CH₃; S(=O)₂CH₃; S(=O)₂CH₂CH₃; cyclopropyl; O-cyclopropyl; oxetanyl; 1,1-dioxidothietanyl; (oxetanyl)oxy; (1,1-dioxidothietanyl)oxy; 2-oxopyrrolidin-1-yl; 2-oxopiperidin-1-yl; azetidine-1-carbonyl; pyrrolidine-1-carbonyl; piperidine-1-carbonyl; pyridinyl, pyrimidinyl; (pyridinyl)oxy, (pyrimidinyl)oxy; imidazolyl; triazinyl; pyrazolyl; N-methyl-pyrazolyl; methoxypyridinyl; hydroxypyridinyl; 2-oxopyridinyl; 3-oxo-2,3-dihydro-1H-1,2,4-triazol-1-yl.

In yet another embodiment of the first aspect of the invention, the compound according to general formula (I) is characterized in that Ar² represents subformula SF-II

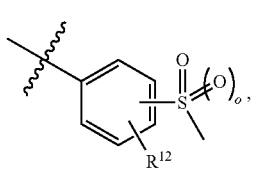

(SF-II)

wherein
o is 0 or 1, preferably o is 1; and
R¹² is selected from the group consisting of H; F; Cl; CN; CH₃; CH₂CH₃; CH₂CH₂CH₃; CH(CH₃)₂; CF₃; CF₂H; CFH₂; OCF₃; OCH₃; OCH₂CH₃; OCH(CH₃)₂; cyclopropyl and Ocyclopropyl.

In another particularly preferred embodiment of the first aspect of the invention, the compound according to general formula (I) is characterized in that
m represents 1, n represents 0, Y is CH₂;
R¹ represents H, CH₃, C₂H₅ or CH₂OCH₃;
R² represents H, CH₃ or C₂H₅;

Ar¹ represents subformula SF-I,

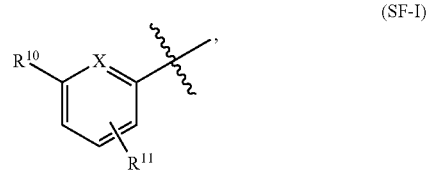

(SF-I)

wherein X is CH or N,
R¹⁰ is selected from the group consisting of CF₃; CF₂H; CFH₂; OCF₃; OCF₂H and OCFH₂; and
R¹¹ is selected from the group consisting of H; F; Cl; CN; CH₃; CH₂CH₃; CH₂CH₂CH₃; CH(CH₃)₂; CH(CH₃)CH₂CH₃; CH₂CH₂CH₂CH₃; CH₂CH(CH₃)₂; C(CH₃)₃; CF₃; CF₂H; CFH₂; OCF₃; OCH₃; OCH₂CH₃; OCH(CH₃)₂; S(=O)—CH₃ and S(=O)₂—CH₃;
L is bond; and
Ar² represents phenyl, substituted by one or two substituents R⁸,
  wherein each R⁸ is independently selected from the group consisting of F; Cl; CN; C₁₋₆-alkyl; CF₃; CF₂H; CFH₂; OCF₃; OCF₂H; OCFH₂; O—C₁₋₆-alkyl; S—C₁₋₆-alkyl; S(=O)—C₁₋₆-alkyl; S(=O)₂—C₁₋₆-alkyl; C₃₋₁₀-cycloalkyl; 3 to 7 membered heterocyclyl; aryl; heteroaryl; O—C₃₋₁₀-cycloalkyl; O-(3 to 7 membered heterocyclyl); O-aryl; O-heteroaryl; C(=O)—C₃₋₁₀-cycloalkyl; C(=O)-(3 to 7 membered heterocyclyl); C(=O)-aryl; C(=O)-heteroaryl; S(=O)₂—C₃₋₁₀-cycloalkyl; S(=O)₂-(3 to 7 membered heterocyclyl); S(=O)₂-aryl; S(=O)₂-heteroaryl; S(=O)(=NR¹³)—C₃₋₁₀-cycloalkyl; S(=O)(=NR¹³)-(3 to 7 membered heterocyclyl); S(=O)(=NR¹³)-aryl and S(=O)(=NR¹³)-heteroaryl, wherein R¹³ represents H or C₁₋₆-alkyl.

In another particularly preferred embodiment of the first aspect of the invention, the compound according to general formula (I) is characterized in that
m represents 1, n represents 0, Y is bond;
R¹ represents H, CH₃, C₂H₅ or CH₂OCH₃;
R² represents H, CH₃ or C₂H₅;
Ar¹ represents subformula SF-I,

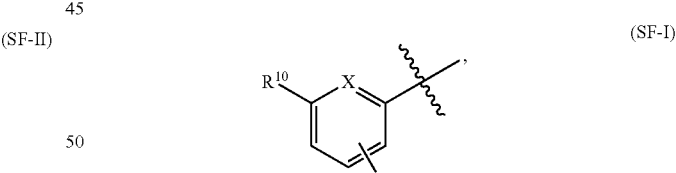

(SF-I)

wherein X is CH or N,
R¹⁰ is selected from the group consisting of CF₃; CF₂H; CFH₂; OCF₃; OCF₂H and OCFH₂; and
R¹¹ is selected from the group consisting of H; F; Cl; CN; CH₃; CH₂CH₃; CH₂CH₂CH₃; CH(CH₃)₂; CH(CH₃)CH₂CH₃; CH₂CH₂CH₂CH₃; CH₂CH(CH₃)₂; C(CH₃)₃; CF₃; CF₂H; CFH₂; OCF₃; OCH₃; OCH₂CH₃; OCH(CH₃)₂; S(=O)—CH₃ and S(=O)₂—CH₃;
L is bond; and
Ar² represents phenyl, substituted by one or two substituents R⁸, wherein each R⁸ is independently selected from the group consisting of F; Cl; CN; C₁₋₆-alkyl; CF₃; CF₂H; CFH₂; OCF₃; OCF₂H; OCFH₂; O—C₁₋₆-alkyl; S—C₁₋₆-alkyl; S(=O)—C₁₋₆-alkyl; S(=O)₂—C₁₋₆-alkyl; C₃₋₁₀- cycloalkyl; 3 to 7 membered heterocyclyl; aryl; heteroaryl; O—C$_{3-10}$-cycloalkyl; O-(3 to 7 membered heterocyclyl); O-aryl; O-heteroaryl; C(=O)—C$_{3-10}$-cycloalkyl; C(=O)-(3 to 7 membered heterocyclyl); C(=O)-aryl; C(=O)-heteroaryl; S(=O)$_2$—C$_{3-10}$-cycloalkyl; S(=O)$_2$-(3 to 7 membered heterocyclyl); S(=O)$_2$-aryl; S(=O)$_2$-heteroaryl; S(=O)(=NR$^{13}$)—C$_{3-10}$-cycloalkyl; S(=O)(=NR$^{13}$)-(3 to 7 membered heterocyclyl); S(=O)(=NR$^{13}$)-aryl and S(=O)(=NR$^{13}$)-heteroaryl, wherein R$^{13}$ represents H or C$_{1-6}$-alkyl.

In yet another particularly preferred embodiment of the first aspect of the invention, the compound according to general formula (I) is characterized in that
m represents 1, n represents 0, Y is bond or CH$_2$;
R$^1$ represents H, CH$_3$, C$_2$H$_5$ or CH$_2$OCH$_3$;
R$^2$ represents H, CH$_3$ or C$_2$H$_5$;
Ar$^1$ represents subformula SF-I,

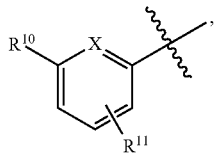

(SF-I)

wherein X is CH or N,
R$^{10}$ is selected from the group consisting of CF$_3$; CF$_2$H; CFH$_2$; OCF$_3$; OCF$_2$H and OCFH$_2$; and
R$^{11}$ is selected from the group consisting of H; F; Cl; CN; CH$_3$; CH$_2$CH$_3$; CH$_2$CH$_2$CH$_3$; CH(CH$_3$)$_2$; CH(CH$_3$)CH$_2$CH$_3$; CH$_2$CH$_2$CH$_2$CH$_3$; CH$_2$CH(CH$_3$)$_2$; C(CH$_3$)$_3$; CF$_3$; CF$_2$H; CFH$_2$; OCF$_3$; OCH$_3$; OCH$_2$CH$_3$; OCH(CH$_3$)$_2$; S(=O)—CH$_3$ and S(=O)$_2$—CH$_3$;
L is bond; and
Ar$^2$ represents subformula SF-II

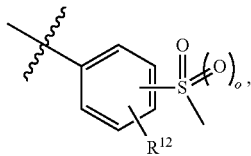

(SF-II)

wherein
o is 0 or 1, preferably o is 1; and
R$^{12}$ is selected from the group consisting of H; F; Cl; CN; CH$_3$; CH$_2$CH$_3$; CH$_2$CH$_2$CH$_3$; CH(CH$_3$)$_2$; CF$_3$; CF$_2$H; CFH$_2$; OCF$_3$; OCH$_3$; OCH$_2$CH$_3$; OCH(CH$_3$)$_2$; cyclopropyl and Ocyclopropyl.

Particularly preferred compounds according to the invention are selected from the group consisting of 1  2-(4-Chlorophenyl)-4-methyl-4-[[3-(trifluoromethyl)phenyl]sulfonyl]-tetrahydro-furan
2  2-[[2-(4-Chlorophenyl)-4-methyl-tetrahydro-pyran-4-yl]sulfonyl]-6-(trifluoromethyl)-pyridine
3  2-(4-Chlorophenyl)-4-[[2-methyl-5-(trifluoromethyl)-phenyl]sulfonyl]-tetrahydro-pyran
4  2-(4-Chlorophenyl)-4-[[2-ethyl-5-(trifluoromethyl)-phenyl]sulfonyl]-tetrahydro-pyran
5  4-Methyl-2-(4-methylsulfonyl-phenyl)-4-[[3-(trifluoromethyl)phenyl]sulfonyl]-tetrahydro-pyran
6  2-(4-Chloro-2-methylsulfonyl-phenyl)-4-methyl-4-[[3-(trifluoromethyl)phenyl]-sulfonyl]-tetrahydro-pyran
7  2-(4-Chlorophenyl)-5-methyl-5-[[3-(trifluoromethyl)phenyl]sulfonyl]-tetrahydro-pyran
8  2-(4-Chlorophenyl)-2-methyl-4-[[3-(trifluoromethyl)phenyl]sulfonyl]-tetrahydro-pyran
9  2-(4-Chlorophenyl)-4-[[2-isopropyl-5-(trifluoromethyl)-phenyl]sulfonyl]-tetrahydro-pyran
10  3-(4-Chlorophenyl)-4-methyl-4-[[3-(trifluoromethyl)phenyl]sulfonyl]-tetrahydro-pyran
11  4-Methyl-2-(2-methyl-5-methylsulfonyl-phenyl)-4-[[3-(trifluoromethyl)phenyl]-sulfonyl]-tetrahydro-pyran
12  4-Methyl-2-[3-methylsulfonyl-5-(trifluoromethyl)-phenyl]-4-[[3-(trifluoromethyl)-phenyl]sulfonyl]-tetrahydro-pyran
13  2-(5-Fluoro-2-methylsulfonyl-phenyl)-4-methyl-4-[[3-(trifluoromethyl)phenyl]-sulfonyl]-tetrahydro-pyran
14  4-Methyl-2-(3-methyl-4-methylsulfonyl-phenyl)-4-[[3-(trifluoromethyl)phenyl]-sulfonyl]-tetrahydro-pyran
15  2-(3-Fluoro-4-methylsulfonyl-phenyl)-4-methyl-4-[[3-(trifluoromethyl)phenyl]-sulfonyl]-tetrahydro-pyran
16  4-Methyl-2-(4-methyl-3-methylsulfonyl-phenyl)-4-[[3-(trifluoromethyl)phenyl]-sulfonyl]-tetrahydro-pyran
17  2-(4-Fluoro-3-methylsulfonyl-phenyl)-4-methyl-4-[[3-(trifluoromethyl)phenyl]-sulfonyl]-tetrahydro-pyran
18  [[2-(4-Chlorophenyl)-4-[[3-(trifluoromethyl)phenyl]sulfonyl]-tetrahydro-pyran-4-yl]-methyl]-dimethyl-amine
19  2-(4-Chlorophenyl)-4-(methoxymethyl)-4-[[3-(trifluoromethyl)phenyl]sulfonyl]-tetrahydro-pyran
20  2-(2-Chloro-4-methylsulfonyl-phenyl)-4-methyl-4-[[3-(trifluoromethyl)phenyl]sulfonyl]-tetrahydro-pyran
21  4-Methyl-2-(3-methylsulfonyl-phenyl)-4-[[3-(trifluoromethyl)phenyl]sulfonyl]-tetrahydro-pyran
22  4-Methyl-2-(2-methylsulfonyl-phenyl)-4-[[3-(trifluoromethyl)phenyl]sulfonyl]-tetrahydro-pyran
23  2-(4-Chloro-2-methyl-phenyl)-4-methyl-4-[[3-(trifluoromethyl)phenyl]sulfonyl]-tetrahydro-pyran
24  2-(4-Chloro-3-methoxy-phenyl)-4-methyl-4-[[3-(trifluoromethyl)phenyl]sulfonyl]-tetrahydro-pyran
25  2-(3-Chloro-4-fluoro-phenyl)-4-methyl-4-[[3-(trifluoromethyl)phenyl]sulfonyl]-tetrahydro-pyran
26  2-(4-Chlorophenyl)-4-ethyl-4-[[3-(trifluoromethyl)phenyl]sulfonyl]-tetrahydro-pyran
27  4-Methyl-2-[2-methylsulfonyl-4-(trifluoromethyl)-phenyl]-4-[[3-(trifluoromethyl)-phenyl]sulfonyl]-tetrahydro-pyran
28  2-(4-Chlorophenyl)-4-(phenylmethoxy-methyl)-4-[[3-(trifluoromethyl)phenyl]sulfonyl]-tetrahydro-pyran
29  4-Methyl-2-[4-methylsulfonyl-3-(trifluoromethyl)-phenyl]-4-[[3-(trifluoromethyl)-phenyl]sulfonyl]-tetrahydro-pyran
30  2-(4-Chloro-3-methylsulfonyl-phenyl)-4-methyl-4-[[3-(trifluoromethyl)phenyl]sulfonyl]-tetrahydro-pyran
31  2-(3-Chloro-4-methylsulfonyl-phenyl)-4-methyl-4-[[3-(trifluoromethyl)phenyl]sulfonyl]-tetrahydro-pyran
32  2-(2-Fluoro-4-methylsulfonyl-phenyl)-4-methyl-4-[[3-(trifluoromethyl)phenyl]sulfonyl]-tetrahydro-pyran
33  2-(3-Chloro-5-methylsulfonyl-phenyl)-4-methyl-4-[[3-(trifluoromethyl)phenyl]sulfonyl]-tetrahydro-pyran
34  6-(4-Chlorophenyl)-2,2,4-trimethyl-4-[[3-(trifluoromethyl)phenyl]sulfonyl]-tetrahydro-pyran
35  2-(4-Chlorophenyl)-4-[[3-fluoro-5-(trifluoromethyl)-phenyl]sulfonyl]-4-methyl-tetrahydro-pyran
36  2-Cyclopropyl-4-ethyl-4-[[3-(trifluoromethyl)phenyl]sulfonyl]-tetrahydro-pyran
37  2-(4-Chlorophenyl)-4-methyl-4-[[3-(trifluoromethyl)phenyl]sulfonyl]-tetrahydro-pyran 38  2-(4-Chlorophenyl)-4-methyl-4-[[3-(trifluoromethyl-oxy)-phenyl]sulfonyl]-tetrahydro-pyran
39  2-(4-Chlorophenyl)-4-[[3-(trifluoromethyl)phenyl]sulfonyl]-tetrahydro-pyran
40  2-[(4-Chloro-phenoxy)-methyl]-4-methyl-4-[[3-(trifluoromethyl)phenyl]sulfonyl]-tetrahydro-pyran
41  2-[(4-Chlorophenyl)-methyl]-4-methyl-4-[[3-(trifluoromethyl)phenyl]sulfonyl]-tetrahydro-pyran
42  2-[3,4-Bis(methylsulfonyl)-phenyl]-4-methyl-4-[[3-(trifluoromethyl)phenyl]sulfonyl]-tetrahydro-pyran
43  1-[4-[4-Methyl-4-[[3-(trifluoromethyl)phenyl]sulfonyl]-tetrahydro-pyran-2-yl]-phenyl]-1H-[1,2,4]triazole
44  2-Fluoro-5-[4-methyl-4-[[3-(trifluoromethyl)phenyl]sulfonyl]-tetrahydro-pyran-2-yl]-benzonitrile
45  2-Fluoro-5-[4-methyl-4-[[3-(trifluoromethyl)phenyl]sulfonyl]-tetrahydro-pyran-2-yl]-benzamide
46  2-(4-Chlorophenyl)-2-methyl-4-[[3-(trifluoromethyl)phenyl]sulfonyl]-tetrahydro-pyran
47  4-[[3-Fluoro-5-(trifluoromethyl)-phenyl]sulfonyl]-4-methyl-2-(4-methylsulfonyl-phenyl)-tetrahydro-pyran
48  2-(3-Fluoro-4-methylsulfonyl-phenyl)-4-methyl-4-[[3-(trifluoromethyl)phenyl]sulfonyl]-tetrahydro-pyran
49  2-[(2-Fluoro-4-methylsulfonyl-phenoxy)-methyl]-4-methyl-4-[[3-(trifluoromethyl)phenyl]sulfonyl]-tetrahydro-pyran
50  2-[(3-Fluoro-4-methylsulfonyl-phenoxy)-methyl]-4-methyl-4-[[3-(trifluoromethyl)phenyl]sulfonyl]-tetrahydro-pyran
51  2-[[2-(3-Fluoro-4-methylsulfonyl-phenyl)-4-methyl-tetrahydro-pyran-4-yl]sulfonyl]-6-(trifluoromethyl)-pyridine
52  2-(2-Chloro-5-methylsulfonyl-phenyl)-4-methyl-4-[[3-(trifluoromethyl)phenyl]sulfonyl]-tetrahydro-pyran
53  4-Methyl-2-[3-methylsulfonyl-4-(trifluoromethyl)-phenyl]-4-[[3-(trifluoromethyl)phenyl]sulfonyl]-tetrahydro-pyran
54  3-Methylsulfonyl-4-[4-methyl-4-[[3-(trifluoromethyl)phenyl]sulfonyl]-tetrahydro-pyran-2-yl]-benzonitrile
55  4-Methyl-2-(2-methyl-4-methylsulfonyl-phenyl)-4-[[3-(trifluoromethyl)phenyl]sulfonyl]-tetrahydro-pyran
56  4-Methyl-2-[4-methylsulfonyl-2-(trifluoromethyl)-phenyl]-4-[[3-(trifluoromethyl)phenyl]sulfonyl]-tetrahydro-pyran
57  3-Methylsulfonyl-5-[4-methyl-4-[[3-(trifluoromethyl)phenyl]sulfonyl]-tetrahydro-pyran-2-yl]-benzonitrile
58  2,2-Difluoro-5-[4-methyl-4-[[3-(trifluoromethyl)phenyl]sulfonyl]-tetrahydro-pyran-2-yl]-1,3-benzodioxole
59  2-Methylsulfonyl-4-[4-methyl-4-[[3-(trifluoromethyl)phenyl]sulfonyl]-tetrahydro-pyran-2-yl]-benzonitrile
60  5-[4-Methyl-4-[[3-(trifluoromethyl)phenyl]sulfonyl]-tetrahydro-pyran-2-yl]-2,3-dihydro-benzofuran
61  2-(3-Fluoro-4-methylsulfonyl-phenyl)-4-methyl-4-[[3-(trifluoromethyloxy)-phenyl]sulfonyl]-tetrahydro-pyran
62  2-Methylsulfonyl-5-[4-methyl-4-[[3-(trifluoromethyl)phenyl]sulfonyl]-tetrahydro-pyran-2-yl]-benzonitrile
63  4-[[3-(Difluoro-methyl)-phenyl]sulfonyl]-2-(3-fluoro-4-methylsulfonyl-phenyl)-4-methyl-tetrahydro-pyran
64  2-(3-Fluoro-4-methylsulfonyl-phenyl)-4-[(3-isopropyl-phenyl)sulfonyl]-4-methyl-tetrahydro-pyran
65  4-Methylsulfonyl-2-[4-methyl-4-[[3-(trifluoromethyl)phenyl]sulfonyl]-tetrahydro-pyran-2-yl]-benzonitrile
66  5-Methylsulfonyl-2-[4-methyl-4-[[3-(trifluoromethyl)phenyl]sulfonyl]-tetrahydro-pyran-2-yl]-benzonitrile
67  2-(2-Cyclopropyl-5-methylsulfonyl-phenyl)-4-methyl-4-[[3-(trifluoromethyl)phenyl]sulfonyl]-tetrahydro-pyran
68  2-Methyl-5-[4-methyl-4-[[3-(trifluoromethyl)phenyl]sulfonyl]-tetrahydro-pyran-2-yl]-benzooxazole
69  2-[2-Fluoro-4-(methylsulfinyl)-phenyl]-4-methyl-4-[[3-(trifluoromethyl)phenyl]sulfonyl]-tetrahydro-pyran
70  2-Ethyl-5-[4-methyl-4-[[3-(trifluoromethyl)phenyl]sulfonyl]-tetrahydro-pyran-2-yl]-benzooxazole
71  2-[[4-[4-Methyl-4-[[3-(trifluoromethyl)phenyl]sulfonyl]-tetrahydro-pyran-2-yl]-phenyl]sulfonyl]-ethanol
72  2-[4-Chloro-2-(methylsulfinyl)-phenyl]-4-methyl-4-[[3-(trifluoromethyl)phenyl]sulfonyl]-tetrahydro-pyran
73  2-[[4-Methyl-2-(4-methylsulfonyl-phenyl)-tetrahydro-pyran-4-yl]sulfonyl]-6-(trifluoromethyl)-pyridine
74  2-(2-Fluoro-5-methylsulfonyl-phenyl)-4-methyl-4-[[3-(trifluoromethyl)phenyl]sulfonyl]-tetrahydro-pyran
75  2-(3-Fluoro-5-methylsulfonyl-phenyl)-4-methyl-4-[[3-(trifluoromethyl)phenyl]sulfonyl]-tetrahydro-pyran
76  2-(2-Fluoro-4-methylsulfonyl-phenyl)-4-[(3-isopropoxy-phenyl)sulfonyl]-4-methyl-tetrahydro-pyran
77  2-(2-Fluoro-4-methylsulfonyl-phenyl)-4-methyl-4-[[3-(trifluoromethyloxy)-phenyl]sulfonyl]-tetrahydro-pyran
78  4-[[3-(Difluoro-methyl)-phenyl]sulfonyl]-2-(2-fluoro-4-methylsulfonyl-phenyl)-4-methyl-tetrahydro-pyran
79  2-(2-Fluoro-4-methylsulfonyl-phenyl)-4-[(3-isopropoxy-phenyl)sulfonyl]-4-methyl-tetrahydro-pyran
80  4-[(3-Cyclopropyl-phenyl)sulfonyl]-2-(2-fluoro-4-methylsulfonyl-phenyl)-4-methyl-tetrahydro-pyran
81  2-(2-Fluoro-4-methylsulfonyl-phenyl)-4-[[3-fluoro-5-(trifluoromethyl)-phenyl]sulfonyl]-4-methyl-tetrahydro-pyran
82  4-[[3-(Difluoro-methoxy)-phenyl]sulfonyl]-2-(2-fluoro-4-methylsulfonyl-phenyl)-4-methyl-tetrahydro-pyran
83  2-[4-(Cyclopropylsulfonyl)-phenyl]-4-methyl-4-[[3-(trifluoromethyl)phenyl]sulfonyl]-tetrahydro-pyran optionally in the form of a single stereoisomer or a mixture of stereoisomers, in the form of the free compound and/or a physiologically acceptable salt or solvate thereof.

Within the scope of the invention, it is understood that the compounds according the aforesaid list may be in the form of a single stereoisomer or any mixture of stereoisomers.

For instance, the given compound 2-(4-chlorophenyl)-4-methyl-4-[[3-(trifluoromethyl)phenyl]sulfonyl]-tetrahydro-pyran (Example 38),

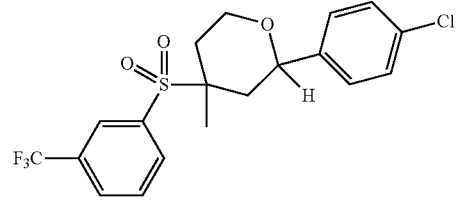 [SMILES: CC1(S(=O)(=O)c2cccc(C(F)(F)F)c2)CCOC(c2ccc(Cl)cc2)C1]

represents
cis-rac-2-(4-chlorophenyl)-4-methyl-4-[[3-(trifluoromethyl)phenyl]sulfonyl]-tetrahydro-pyran:

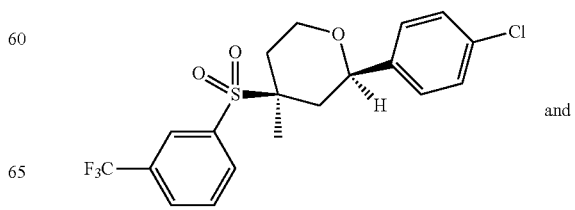

and

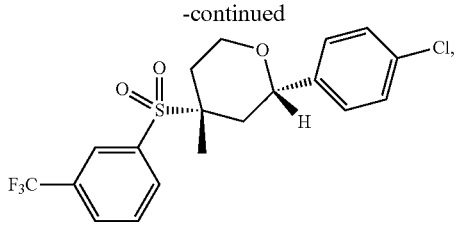

[(2R,4S) and (2S,4R)-2-(4-Chlorophenyl)-4-methyl-4-[[3-(trifluoromethyl)phenyl]sulfonyl]-tetrahydro-pyran], and
trans-rac-2-(4-Chlorophenyl)-4-methyl-4-[[3-(trifluoromethyl)phenyl]sulfonyl]-tetrahydro-pyran:

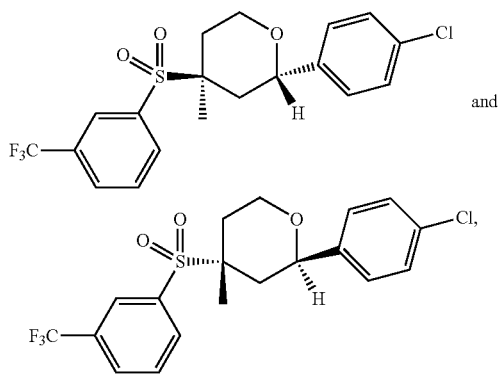

[(2S,4S) and (2R,4R)-2-(4-Chlorophenyl)-4-methyl-4-[[3-(trifluoromethyl)phenyl]sulfonyl]-tetrahydro-pyran], as well as each individual stereoisomer or any other mixture thereof.

Furthermore, preference may be given to compounds according to the invention that cause at least a 50% inhibition, which is present at a concentration of 3 μM, in a fluorescent assay for CaV2.2 channels with HEK293 cells in which human CaV2.2 channels were stably expressed at a concentration of less 3 μM, preferably less than 1000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR 3, Molecular Devices, Sunnyvale, USA), as described hereinafter.

The present invention further relates to a compound according to the present invention for CaV2.2 calcium channel regulation, preferably for use in CaV2.2 calcium channel blockage. The present invention therefore further relates to a compound according to the present invention for the prophylaxis and/or treatment of disorders and/or diseases which are mediated, at least in part, at least in part, by CaV2.2 channels. The term "disorders and/or diseases which are mediated, at least in part, by CaV2.2 channels", is intended to include each of or all of the disease states.

In another aspect of the present invention, the invention therefore also provides pharmaceutical compositions, containing at least one compound according to the invention and optionally one or more suitable, pharmaceutically compatible auxiliaries and/or, if appropriate, one or more further pharmacologically active compounds.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one compound according to the invention, if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective compound according to the invention also in a delayed manner.

The pharmaceutical compositions according to the invention are prepared with the aid of conventional means, devices, methods and process known in the art. The amount to be administered to the patient of the respective compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

CaV2.2 channels are believed to be involved in a variety of diseases or disorders in mammals such as humans. These include pain (e.g.; acute pain, chronic pain, visceral pain, headache pain, inflammatory pain, mixed pain), stroke (the neuronal damage resulting from head trauma), epilepsy, mood disorders, schizophrenia, neurodegenerative disorders.

Another embodiment of the present invention is at least one compound according the present invention for the treatment and/or prophylaxis of one or more disorders selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

Another embodiment of the present invention is at least one compound according to the present invention for the treatment and/or prophylaxis of pain, in particular acute pain and/or chronic pain and/or visceral pain and/or headache pain and/or inflammatory pain and/or mixed pain. Acute pain according to the invention might include nociceptive pain and post-operative or surgical pain. Chronic pain according to the invention might include peripheral neuropathic pain such as post-herpetic neuralgia, traumatic nerve injury, nerve compression or entrapment, small fibre neuropathy, diabetic neuropathy, neuropathic cancer pain, failed back surgery Syndrome, trigeminal neuralgia, phantom limb pain; neuroma pain, complex regional pain syndrome, chronic arthritic pain and related neuralgias, and pain associated with cancer, chemotherapy, HIV and HIV treatment-induced neuropathy; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome. In treating osteoarthritic pain, joint mobility will also improve as the underlying chronic pain is reduced. Thus, at least one compound for treatment of osteoarthritic pain inherently will also improve joint mobility in patients suffering from osteoarthritis. Visceral pain according to the invention might include interstitial cystitis, irritable bowel syndrome, Crohn's disease and chronic pelvic pain syndrome. Inflammatory pain according to the invention might include rheumatoid arthritis and endometriosis. Headachepain according to the invention might include migraine, cluster headache, tension headache syndrome, facial pain and headache caused by other diseases. Mixed pain according to the invention might include lower back pain, neck and shoulder pain, burning mouth syndrome and complex regional pain syndrome.

In another embodiment of the invention, at least one compound according to the present invention is particularly suitable for the treatment and/or prophylaxis of mood disorders. Mood disorders according to the invention might include anxiety disorder, social anxiety disorder, panic disorder, specific phobias, for example, specific animal phobias, social phobias, obsessive-compulsive disorder, agoraphobia, post-traumatic stress syndrome, addiction (including dependence, withdrawal and/or relapse of medication, including opioids, but also drugs such as cocaine, opioids, alcohol and nicotine), generalised anxiety disorders, single episodic or recurrent major depressive disorders and dysthymic disorders, or bipolar disorders, for example, bipolar I disorder, bipolar II disorder and cyclothymic disorder.

In another embodiment of the invention, at least one compound according to the present invention is particularly suitable for the treatment and/or prophylaxis of epilepsy. Epilepsy according to the invention might include partial seizures such as temporal lobe epilepsy, absence seizures generalized seizures, and tonic/clonic seizures.

In yet another embodiment of the invention, at least one compound according to the present invention is particularly suitable for the treatment and/or prophylaxis of neurodegenerative disorders. Neurodegenerative disorders according to the invention might include Parkinson's disease, Alzheimer's disease, multiple sclerosis, neuropathies, Huntington's disease, presbycusis and amyotrophic lateral sclerosis (ALS).

Particularly preferably, at least one compound according to the present invention is suitable for the treatment and/or prophylaxis of one or more disorders and/or diseases selected from the group consisting of pain, preferably of pain selected from the group consisting of acute pain, chronic pain, visceral pain, headache pain, inflammatory pain and mixed pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Another embodiment of the present invention therefore relates to use of at least one compound according to the present invention for the preparation of a pharmaceutical composition for the treatment and/or prophylaxis of one or more disorders or diseases, particularly selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders.

Another aspect of the present invention is a method of treatment and/or prophylaxis of disorders and/or diseases in a mammal, preferably of disorders and/or diseases selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders, which comprises administering an effective amount of at least one compound according to the present invention to the mammal.

All preferred embodiments of the first aspect of the invention are preferred vice versa for the other aspects and embodiments.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour and Smith (J. Pharm. Exp. Ther. 72, 74 79 (1941)) or by the formalin test (e.g. according to D. Dubuisson et al., Pain 1977, 4, 161-174).

EXAMPLES

The compounds according to the invention can be prepared in the manner described below. The following examples further illustrate the invention but are not to be construed as limiting its scope.

All starting materials which are not explicitly described were either commercially available (the details of suppliers such as for example Acros, Avocado, Aldrich, Apollo, Bachem, Fluka, FluoroChem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, repspectively, for example) or can be prepared using the conventional methods known to the person skilled in the art.

The reactions were, if necessary, carried out under an inert atmosphere (mostly $N_2$). The number of equivalents of reagents and the amounts of solvents employed as well as the reaction temperatures and times can vary slightly between different reactions carried out by analogous methods. The work-up and purification methods were adapted according to the characteristic properties of each compound and can vary slightly for analogous methods. The yields of the compounds prepared are not optimized.

All the intermediate products and exemplary compounds were analytically characterized by means of $^1$H-NMR spectroscopy. In addition, mass spectrometry tests (MS, m/z for [M+H]$^+$) were carried out for all the exemplary compounds and selected intermediate products.

The indication "equivalents" ("eq." or "eq" or "equiv.") means molar equivalents, "RT" or "rt" means room temperature T (23±7° C.), "M" are indications of concentration in mol/l, "aq." means aqeous, "sat." means saturated, "sol." means solution, "conc." means concentrated and "anhydr." means anhydrous. The mixing ratios of solvents are usually stated in the volume/volume ratio.

FURTHER ABBREVIATIONS

BINAP=2,2'-bis(diphenylphosphino)-1,1'-binaphthyl; CC=column chromatography; COSY=correlation spectroscopy; d=day(s); DCE=1,2-dichloroethane; DCM=dichloromethane; DEA=diethylamine; DEAD=diethylazodicarboxylat; DIPEA=N,N-diisopropylethylamine; DMF=N,N-dimethylformamide; ee=enantiomeric excess; Et$_2$O=diethyl ether; EtOAc=ethyl acetate; h=hour(s); HATU=1-[bis(dimethylamino)methylene]-1H-1,2,3-triazolo[4,5-b]pyridinium 3-oxid hexafluorophosphate; HMBC=heteronuclear multiple-bond correlation spectroscopy; HMQC=heteronuclear multiple quantum coherence spectroscopy; IPA=iso-propylamine; LAH=lithium aluminiumhydride; LiHMDS=Lithium hexymethyldisilazide; min=minute(s); MeCN=acetonitrile; MeOH=methanol; MS=methanesulfonyl; NMP=N-methyl-2-pyrrolidone; NOE=Nuclear Overhauser Effect; NOESY=Nuclear Overhauser effect spectroscopy; PE=petroleum ether; RM=reaction mixture; RT=room temperature; TEA=triethylamine; TFA=trifluoroacetic acid; THF=tetrahydrofuran.

Instruments:

$^1$H-NMR-spectra (including NOESYs) were recorded at 400 MHz on a Bruker Avance-400 spectrometer or on Agilent 300 & 400 MHz spectrometer.

Analytical Chiral HPLCs were Measured on:

Agilent 1260 Quart. Pump: G1311C, autosampler, ColCom, DAD: Agilent G4212B or

Waters 2695 separation module Detector 2996 & Agilent 1200 series with G 1315B detector Preparative HPLC were Performed on:

Waters 2545 Quaternary gradient module with Autosampler2707 & Waters2545 Quaternary gradient module with Manual mode.

Analytical SFC were performed on Thar SFC analytical.

Preparative SFC were performed THAR-SFC 80.

Instruments Employed for Chiral Separations:

Fraction Collector: Gilson 215 Liquid Handler; HPLC instrument modules: Shimadzu LC8-A preparative pumps, Shimadzu SCL-10Avp system controller, Shimadzu SPD-10Avp UV-VIS detector.

1. Synthesis of Example Compounds 2-(4-Chlorophenyl)-4-methyl-4-[[3-(trifluoromethyl)phenyl]sulfonyl]-tetrahydro-furan (Example 1)

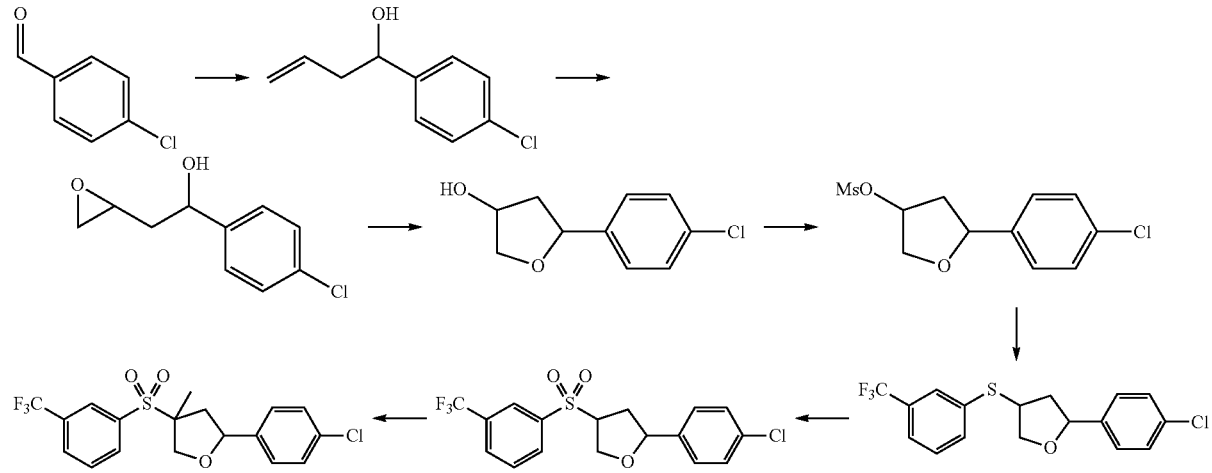

Step 1: 1-(4-Chlorophenyl)but-3-en-1-ol

Zinc dust (18.6 g, 284.7 mmol, 2.0 eq) was added to an ice-cooled stirred solution of 4-chlorobenzaldehyde (20 g, 142.3 mmol, 1.0 eq) and 3-bromoprop-1-ene (18.5 mL, 213.5 mmol, 1.5 eq) in sat. NH$_4$Cl (125 mL) and THF (150 mL). The RM was stirred at RT for 6 h. After completion of the reaction, the RM was filtered on celite bed and the filtrate was diluted with Et$_2$O and H$_2$O. The aq. layer was extracted with Et$_2$O (2×200 mL). Combined organic layers were dried over anhydr. Na$_2$SO$_4$, filtered and concentrated under reduced pressure to get 20 g of desired compound which was directly used to next step without further purification.

1-(4-Chlorophenyl)-2-(oxiran-2-yl)ethanol m-Chloroperbenzoic acid (26.1 g, 151.1 mmol, 2.0 eq) was added to an ice-cold solution of 1-(4-chlorophenyl)but-3-en-1-ol (25.0 g, 137.4 mmol, 1.0 eq) in DCM (50 mL) and the RM was allowed to warm up to RT and then stirred for 16 h. The RM was diluted with EtOAc and $H_2O$. The aq. layer was extracted with EtOAc (2×150 mL). Combined organic layers were washed with sat. $NaHCO_3$ solution and organic layer was dried over anhydr. $Na_2SO_4$, filtered and concentrated under reduced pressure to yield crude product which was then purified by CC to afford desired 1-(4-chlorophenyl)-2-(oxiran-2-yl)ethanol (20 g, 74%) as a pale yellow oil.

5-(4-Chlorophenyl)tetrahydrofuran-3-ol

Concentrated sulfuric acid (5 mL) was added to an ice-cold mixture of 1-(4-chlorophenyl)-2-(oxiran-2-yl)ethanol (22.0 g, 111.1 mmol, 1.0 eq) in 1,4-dioxane (300 mL) and stirred for 6 h at RT. The reaction mass was poured onto crushed ice, neutralized by addition of solid $NaHCO_3$, extracted with DCM (2×150 mL). Combined organic layers were dried over anhydr. $Na_2SO_4$, filtered and concentrated under reduced pressure to yield crude mass which was then purified by CC to afford 5-(4-chlorophenyl)tetrahydrofuran-3-ol (10 g, 46%) as a brown oil.

5-(4-Chlorophenyl)tetrahydrofuran-3-yl methanesulfonate

Methanesulfonyl chloride (2.9 mL, 29.4 mmol, 1.5 eq) was added to an ice-cold solution of 5-(4-chlorophenyl) tetrahydrofuran-3-ol (3.9 g, 19.6 mmol, 1.0 eq) and TEA (8.17 mL, 58.78 mmol, 3.0 eq) in DCM (70 mL) and the RM was stirred at the same temperature for 2 h. The RM was quenched with $H_2O$. The aq. layer was extracted with DCM (2×1000 mL) and the combined organic layers were dried over anhydr. $Na_2SO_4$, filtered and concentrated under reduced pressure to afford crude product which was purified by CC to afford 5-(4-chlorophenyl)tetrahydrofuran-3-yl methanesulfonate (3.8 g, 71%) as a brown liquid.

2-(4-Chlorophenyl)-4-((3-(trifluoromethyl)phenyl) thio)tetrahydrofuran $K_2CO_3$ (3.8 g, 27.8 mmol, 2.0 eq) was added to a solution of 5-(4-chlorophenyl)tetrahydrofuran-3-yl methanesulfonate (3.8 g g, 13.9 mmol, 1.0 eq) and 3-(trifluoromethyl) benzenethiol (3.2 mL, 27.8 mmol, 2 eq) in DMF (70 mL). The RM was stirred at RT for 1 h. Then the RM was quenched with ice and the aq. layer was extracted with EtOAc (2×150 mL). Combined organic layers were dried over anhydr. $Na_2SO_4$, filtered and concentrated under reduced pressure to yield crude mass which was then purified by CC to afford 2-(4-chlorophenyl)-4-((3-(trifluoromethyl)phenyl)thio)-tetrahydrofuran (3.1 g, 62%) as a pale yellow color oil.

2-(4-Chlorophenyl)-4-((3-(trifluoromethyl)phenyl) sulfonyl)tetrahydrofuran

To a stirred ice cold solution of 2-(4-chlorophenyl)-4-((3-(trifluoromethyl)phenyl)thio)tetrahydrofuran (3.8 g, 10.6 mmol, 1.0 eq) in THF:$H_2O$ (3:1) (120 mL) oxone (19.6 g, 31.8 mmol, 3.0 eq) was added and RM was stirred at RT for 4 h. After completion of the reaction it was diluted with $H_2O$ and the product was extracted with EtOAc. The organic layer was washed with $H_2O$, sat. brine and dried over anhydr. sodium sulfate, filtered and evaporated under reduced pressure to get crude product which was further purified by CC to afford 2-(4-chlorophenyl)-4-((3-(trifluoromethyl)phenyl)sulfonyl)tetrahydrofuran (3.8 g, 92%) as a white solid.

2-(4-Chlorophenyl)-4-methyl-4-((3-(trifluoromethyl) phenyl)sulfonyl)tetrahydrofuran To a stirred solution of 2-(4-chlorophenyl)-4-((3-(trifluoromethyl)phenyl)sulfonyl)tetrahydrofuran (2.2 g, 5.6 mmol, 1 eq) in DMF (12 mL), NaH (0.45 g, 11.3 mmol, 2.0 eq) was added portion wise at 0° C. and then stirred at RT for 1 h. The RM was again cooled to 0° C. and methyl iodide (0.53 mL, 8.5 mmol, 1.5 eq) was added. Finally, the RM was stirred at RT for 2 h. After completion of the reaction it was quenched with crushed ice and diluted with EtOAc. The organic layer was separated, washed with chilled $H_2O$ (5×20 mL), brine and finally dried over anhydr. $Na_2SO_4$. Two diastereomers were separated by reverse phase preparative HPLC and the relative configuration (cis or trans) was determined by $^1H$ NMR and NOE experiments.

cis-isomer (SC-101, SC-102): 1H NMR (400 MHz, DMSO-$d_6$, δ ppm): 1.53 (s, 3H), 2.23-2.30 (1H), 2.33-2.51 (1H), 3.67 (d, 1H), 4.63 (d, 1H), 4.95 (dd, 1H), 7.12 (d, 2H), 7.35 (d, 2H), 7.92 (t, 1H), 8.09 (s, 1H), 8.20 (d, 1H), 8.26 (d, 1H).

On irradiating $CH_3$ proton "positive" NOE was observed with OCH proton.

trans-isomer (SC-103, SC-104): 1H NMR (400 MHz, DMSO-$d_6$, δ ppm): 1.41 (s, 3H), 1.78 (dd, 1H), 3.11 (dd, 1H), 3.91 (d, 1H), 4.39 (d, 1H), 4.92 (dd, 1H), 7.39 (s, 4H), 7.95-7.98 (m, 1H), 8.20-23 (m, 2H), 8.30-8.32 (m, 1H).

On irradiating $CH_3$ proton "no" NOE was observed with OCH proton.

Enantiomers from cis and trans diastereomers were separated by chiral HPLC, using chiral pack AD-H column and Ethanol/DEA: (100/0.1) as mobile phase to obtain two cis enantiomers (SC-101 and SC-102) and two trans enantiomers (SC-103 and SC-104).

SC-101: (0.14 g, 6% yield, yellow solid, $1^{st}$ eluted enantiomer; cis-EN1).

SC-102: (0.14 g, 6% yield, yellow solid, $2^{nd}$ eluted enantiomer; cis-EN2).

SC-103: (0.15 g, 7% yellow solid, $1^{st}$ eluted enantiomer; trans-EN1).

SC-104: (0.15 g, 7% yellow solid, $2^{nd}$ eluted enantiomer; trans-EN2).

2-[[2-(4-Chlorophenyl)-4-methyl-tetrahydro-pyran-4-yl]sulfonyl]-6-(trifluoromethyl)-pyridine (Example 2)

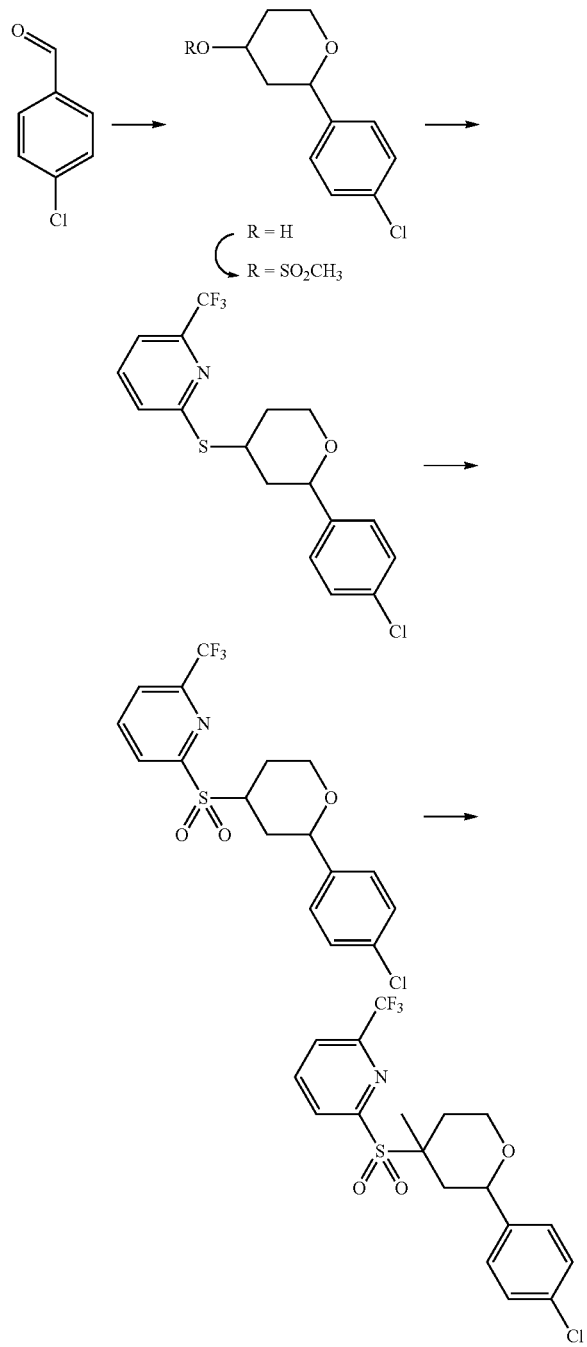

2-(4-Chlorophenyl)tetrahydro-2H-pyran-4-ol

Concentrated sulfuric acid (5.2 mL) was added to an ice-cold mixture of but-3-en-1-ol (6.4 mL, 71.4 mmol, 2.0 eq) and 4-chlorobenzaldehyde (5 g, 35.7 mmol, 1.0 eq) and the mixture was stirred for 14 h at RT. The RM was poured onto crushed ice, neutralized by addition of solid NaHCO$_3$, extracted with DCM (2×150 mL). Combined organic layers were dried over anhydr. Na$_2$SO$_4$, filtered and concentrated under reduced pressure to yield crude mass which was then purified by CC to afford desired compound (3.4 g, 45%) as a colorless oil.

2-(4-Chlorophenyl)tetrahydro-2H-pyran-4-yl methanesulfonate

Methanesulfonyl chloride (0.34 mL, 3.5 mmol, 1.5 eq) was added to an ice-cold solution of 2-(4-chlorophenyl)tetrahydro-2H-pyran-4-ol (0.5 g, 2.4 mmol, 1 eq) and TEA (0.5 mL, 3.5 mmol, 1.5 eq) in DCM (10 mL) and the RM was allowed to warm up to RT and then stirred for 3 h. The RM was diluted with DCM and H$_2$O. The aq. layer was extracted with DCM (2×50 mL). Combined organic layers were dried over anhydr. Na$_2$SO$_4$, filtered and concentrated under reduced pressure to yield crude mass which was then purified by CC to afford 2-(4-chlorophenyl)tetrahydro-2H-pyran-4-yl methanesulfonate (0.4 g, 59%) as a yellow oil.

2-((2-(4-Chlorophenyl)tetrahydro-2H-pyran-4-yl)thio)-6-(trifluoromethyl)pyridine K$_2$CO$_3$ (10.8 g, 78.2 mmol, 2.0 eq) was added to the stirred solution of 2-(4-chlorophenyl)tetrahydro-2H-pyran-4-yl methanesulfonate (11.3 g, 39.1 mmol, 1.0 eq) and 6-(trifluoromethyl)pyridine-2-thiol (7.0 g, 39.1 mmol, 1.0 eq) in DMF (100 mL). The RM was stirred for 4 h at 80° C. Then the RM was cooled to RT and then diluted with EtOAc and H$_2$O. The aq. layer was extracted with EtOAc (2×150 mL). Combined organic layers were dried over anhydr. Na$_2$SO$_4$, filtered and concentrated under reduced pressure to yield crude mass which was then purified by CC to afford 2-((2-(4-chlorophenyl)tetrahydro-2H-pyran-4-yl)thio)-6-(trifluoromethyl)pyridine (4.5 g, 31%) as a pale yellow color oil.

2-((2-(4-Chlorophenyl)tetrahydro-2H-pyran-4-yl)sulfonyl)-6-(trifluoromethyl)pyridine Sodium periodate (3.4 g, 16.1 mmol, 3.0 eq) and RuCl$_3$ (0.02 g, 0.11 mmol, 0.02 eq) were added to the solution of 2-((2-(4-chlorophenyl)tetrahydro-2H-pyran-4-yl)thio)-6-(trifluoromethyl)pyridine (2.0 g, 5.4 mmol, 1.0 eq) in H$_2$O (15 mL) and MeCN (10 mL). The RM was stirred for 2 h at RT. After completion of the reaction the RM was diluted with EtOAc and H$_2$O. The aq. layer was extracted with EtOAc (2×75 mL). Combined organic layers were dried over anhydr. Na$_2$SO$_4$, filtered and concentrated under reduced pressure to yield crude mass which was then purified by CC to afford 2-((2-(4-chlorophenyl)tetrahydro-2H-pyran-4-yl)sulfonyl)-6-(trifluoromethyl)pyridine (1.5 g, 69%) as a white solid.

2-((2-(4-Chlorophenyl)-4-methyltetrahydro-2H-pyran-4-yl)sulfonyl)-6-(trifluoromethyl)pyridine At −78° C. LiHMDS (1M, 8.8 mL, 8.9 mmol, 2.0 eq) was added to a solution of 2-((2-(4-chlorophenyl)tetrahydro-2H-pyran-4-yl)sulfonyl)-6-(trifluoromethyl)pyridine (1.8 g, 4.4 mmol, 1.0 eq) in dry THF (30 mL) and it was stirred at same temperature for 30 min. CH$_3$I (0.56 mL, 8.9 mmol, 2.0 eq) was added and the RM was stirred at −78° C. for 1 h. After completion of the reaction the reaction mass was quenched with sat. NH$_4$Cl solution and extracted with EtOAc (2×75 mL). Combined organic layers were dried over anhydr. Na$_2$SO$_4$, filtered and concentrated under reduced pressure to yield crude mass which was then purified by CC to afford cis (0.5 g, 27%, colorless liquid) and trans isomer (0.64 g, 35%, white solid). The relative configuration (cis or trans) was determined by $^1$H NMR and NOE experiments.

cis-isomer (SC-104, SC-105): $^1$H NMR (400 MHz, DMSO-$d_6$, δ ppm): 1.55-1.60 (4H), 1.77-1.82 (1H), 1.93-1.99 (1H), 2.10-2.20 (1H), 3.68-3.75 (1H), 4.01-4.06 (1H), 4.56-4.58 (1H), 7.32-7.34 (2H), 7.38-7.41 (2H), 8.31-8.37 (2H), 8.45-8.50 (1H).

On irradiating OCH proton "positive" NOE was observed with CH$_3$ protons and vice versa.

trans-isomer (SC-106, SC-107): $^1$H NMR (600 MHz, DMSO-$d_6$, δ ppm): 1.17 (s, 3H), 1.63-1.68 (1H), 1.83-1.89 (1H), 2.39-2.41 (1H), 2.47-2.51 (1H), 3.98-4.01 (1H), 4.17-4.20 (m, 1H), 5.06-5.08 (1H), 7.36-7.37 (2H), 7.41-7.42 (2H), 8.33-8.34 (1H), 8.43-8.45 (1H), 8.49-8.52 (1H).

On irradiating OCH proton "no" NOE was observed with CH$_3$ protons and vice versa. Enantiomers of cis and trans diastereoisomers were separated by chiral HPLC, using chiral pack AD-H column and Ethanol/DEA: (100/0.1) as mobile phase to obtain two desired cis enantiomers (SC-104 and SC-105) and two trans enantiomers (SC-106 and SC-107).

SC-104: (0.157 g, 8.5%, off white solid, 1$^{st}$ eluted enantiomer; cis-EN1).

SC-105: (0.180 g, 9.7%, off white solid, 2$^{nd}$ eluted enantiomer; cis-EN2).

SC-106: (0.131 g, 7.1%, off white solid, 1$^{st}$ eluted enantiomer; trans-EN1).

SC-107: (0.148 g, 8.1%, off white solid, 2$^{nd}$ eluted enantiomer; trans-EN2).

6-(Trifluoromethyl)pyridine-2-thiol

Methyl 3-((6-(trifluoromethyl)pyridin-2-yl)thio) propanoate

Sodium ethoxide (1.9 g, 27.6 mmol, 1.0 eq) was added to an ice cold solution of 2-chloro-6-(trifluoromethyl)pyridine (5.0 g, 27.6 mmol, 1.0 eq) and methyl 3-mercaptopropanoate (3.6 mL, 33.1 mmol, 1.2 eq) in DMF (50 mL) and then RM was stirred at 80° C. for 14 h. After completion of the reaction the RM was diluted with EtOAc and H$_2$O. The aq. layer was extracted with EtOAc (2×100 mL). Combined organic layers were dried over anhydr. Na$_2$SO$_4$, filtered and concentrated under reduced pressure to yield crude mass which was then purified by CC to afford methyl 3-((6-(trifluoromethyl)pyridin-2-yl)thio)propanoate (3.5 g, 48%) as a yellow oil.

6-(Trifluoromethyl)pyridine-2-thiol

Sodium methoxide (5.2 g, 94.3 mmol, 2.5 eq) was added to an ice cold solution of methyl 3-((6-(trifluoromethyl) pyridin-2-yl)thio)propanoate (10 g, 37.9 mmol, 1.0 eq) in MeOH (100 mL) and then RM was stirred at 80° C. for 2 h. After completion of the reaction the RM was concentrated under reduced pressure to give the crude product of 6-(trifluoromethyl)pyridine-2-thiol (7 g) which was directly used to next step without further purification.

2-(4-Chlorophenyl)-4-((2-methyl-5-(trifluoromethyl) phenyl)sulfonyl)tetrahydro-2H-pyran (Example 3)

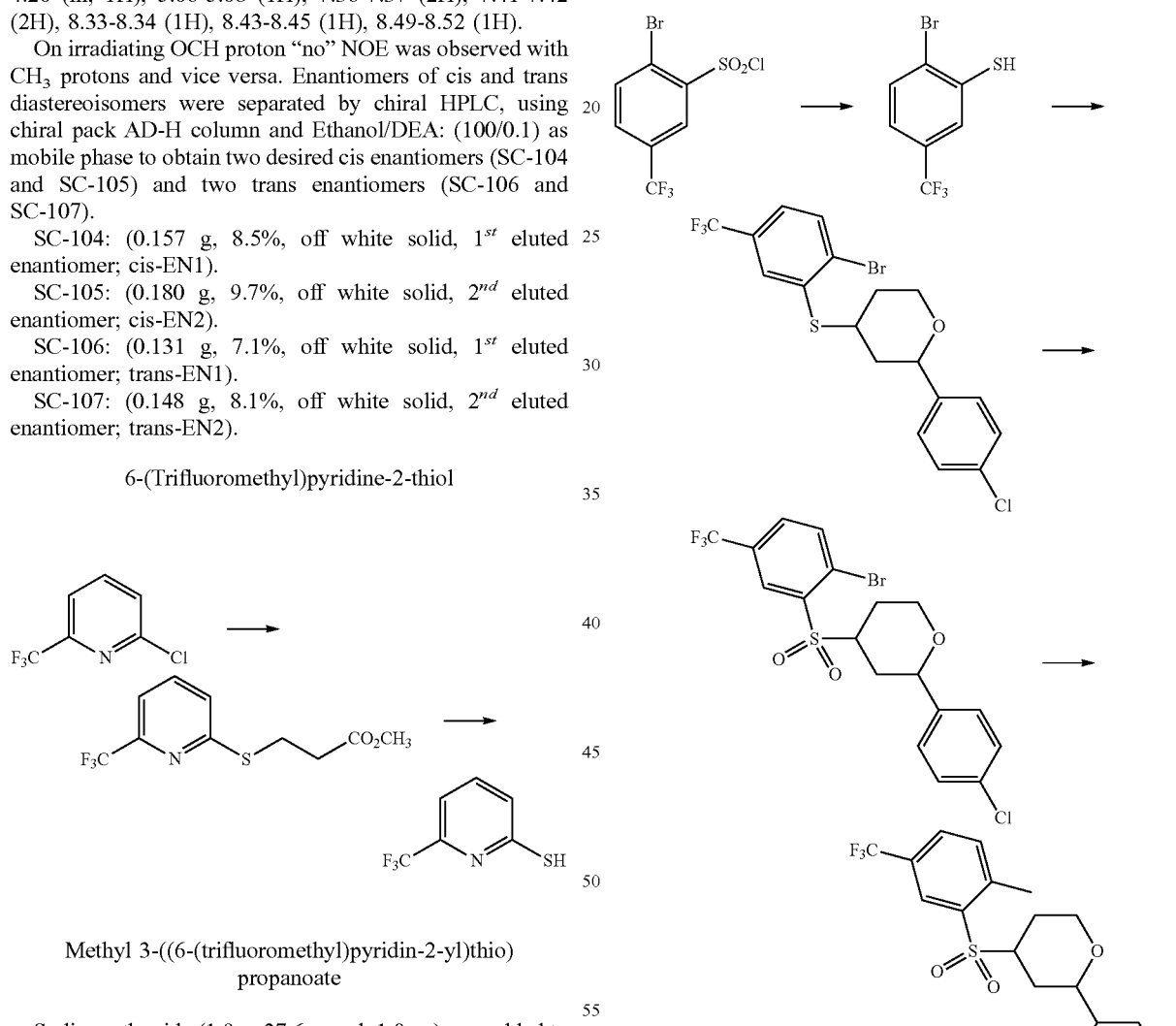

2-Bromo-5-(trifluoromethyl)benzenethiol

To a stirred solution of triphenylphosphine (16.2 g, 61.9 mmol, 4.0 eq) in DCM (40 mL), DMF (0.4 mL) was added at 0° C. followed by addition of 2-bromo-5-(trifluoromethyl)

benzene-1-sulfonyl chloride (5.0 g, 15.5 mmol, 1.0 eq). The RM was allowed to stir for 2 h at RT. The mixture was again cooled to 0° C. and 1N aq. HCl was added and stirred at RT for 1 h. The organic layer was separated and concentrated in vacuo. The residue was triturated with hexane and filtered. The filtrate was discarded and residue was taken in Et$_2$O and 2N aq. NaOH. The aq. layer was separated and acidified with 1N HCl and extracted with Et$_2$O (3×100 mL). The combined organic layers were washed with brine and dried over anhydr. Na$_2$SO$_4$, filtered and concentrated to get 2-bromo-5-(trifluoromethyl)benzenethiol (3.2 g) as a brown oil, which was used as such for the next step without further purification.

4-((2-Bromo-5-(trifluoromethyl)phenyl)thio)-2-(4-chlorophenyl)tetrahydro-2H-pyran K$_2$CO$_3$ (3.4 g, 24.9 mmol, 2.0 eq) was added to the stirred solution of 2-bromo-5-(trifluoromethyl)benzenethiol (3.2 g, 12.5 mmol, 1.0 eq) and 2-(4-chlorophenyl)tetrahydro-2H-pyran-4-yl methanesulfonate (3.6 g, 12.5 mmol, 1.0 eq) in DMF (40 mL). The RM was stirred for 2 h at 80° C. Then the RM was cooled to RT and then diluted with EtOAc and water. The aq. layer was extracted with EtOAc (2×100 mL). Combined organic layers were dried over anhydr. Na$_2$SO$_4$, filtered and concentrated under reduced pressure to yield crude mass which was then purified by CC to afford 4-((2-bromo-5-(trifluoromethyl)phenyl)thio)-2-(4-chlorophenyl) tetrahydro-2H-pyran (1.8 g, 32%) as a pale yellow color oil.

4-((2-Bromo-5-(trifluoromethyl)phenyl)sulfonyl)-2-(4-chlorophenyl)tetrahydro-2H-pyran To a stirred solution of 4-((2-bromo-5-(trifluoromethyl) phenyl)thio)-2-(4-chlorophenyl)tetrahydro-2H-pyran (0.5 g, 1.1 mmol, 1.0 eq) in a mixture of solvent of MeCN (20 mL), H$_2$O (6.6 mL), sodium periodate (0.71 g, 3.3 mmol, 3.0 eq) and RuCl$_3$ (0.005 g, 0.022 mmol, 0.02 eq) were added and stirred for 30 min. After completion, the RM was filtered over celite bed and washed with H$_2$O. Filtrate was extracted with EtOAc and combined organic layers were dried over anhydr. Na$_2$SO$_4$, filtered and evaporated under reduced pressure to get crude product which was then purified by CC to afford pure 4-((2-bromo-5-(trifluoromethyl)phenyl)sulfonyl)-2-(4-chlorophenyl)tetrahydro-2H-pyran (0.4 g, 75%) as a yellow sticky liquid.

2-(4-Chlorophenyl)-4-((2-methyl-5-(trifluoromethyl) phenyl)sulfonyl)tetrahydro-2H-pyran To a stirred solution of 4-((2-bromo-5-(trifluoromethyl) phenyl)sulfonyl)-2-(4-chlorophenyl)tetrahydro-2H-pyran (0.5 g, 1.0 mmol, 1.0 eq) in 1,4-dioxane was added K$_3$PO$_4$ (0.44 g, 2.1 mmol, 2.0 eq) and stirred at RT for 5 min and deoxygenated with Ar.

To this RM was added 2,4,6-trimethyl-1,3,5,2,4,6-trioxatriborinane (0.324 g, 2.57 mmol, 2.5 eq) and Pd(PPh$_3$)$_2$Cl$_2$ (0.07 g, 0.10 mmol, 0.1 eq) and again deoxygenated. The RM was then heated to 130° C. for 40 min and TLC was checked. After completion, the RM was filtered through celite and washed with EtOAc. Organic part was washed with water, brine and dried over anhydr. Na$_2$SO$_4$, filtrated and concentrated to get crude product which was then purified by CC to afford pure 2-(4-chlorophenyl)-4-((2-methyl-5-(trifluoromethyl)phenyl)sulfonyl)tetrahydro-2H-pyran (0.25 g, 58%) as a single diastereomer (yellow oil). The relative configuration (trans) was determined by $^1$H NMR and NOE experiments.

trans-isomer (SC-108, SC-109): 1H NMR (400 MHz, CDCl$_3$, δ ppm): 1.95-1.99 (1H), 2.05-2.12 (2H), 2.27-2.31 (1H), 2.72 (s, 3H), 3.37-3.40 (1H), 3.81-3.86 (1H), 4.11-4.16 (1H), 5.06-5.10 (1H), 7.23-7.25 (2H), 7.30-7.33 (2H), 7.49-7.51 (1H), 7.77-7.79 (1H), 8.29 (s, 1H).

On irradiating SCH proton "no" NOE was observed with OCH proton but "positive" NOE was observed with ortho-substituted protons of 4-chlororphenyl moiety.

Two enantiomers of this single diastereomer were separated by chiral HPLC, using chiral pack AD-H column and Ethanol/DEA: (100/0.1) as mobile phase to obtain two trans enantiomers (SC-108 and SC-109).

SC-108: (0.206 g, 47.9%, off white solid, 1$^{st}$ eluted enantiomer; trans-EN1)

SC-109: (0.101 g, 23.4%, off white solid, 2$^{nd}$ eluted enantiomer; trans-EN2)

2-(4-Chlorophenyl)-4-[[2-ethyl-5-(trifluoromethyl)-phenyl]sulfonyl]-tetrahydro-pyran (Example 4)

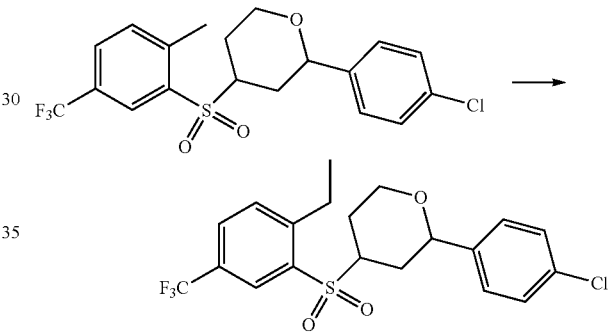

To a stirred solution of trans-2-(4-chlorophenyl)-4-((2-methyl-5-(trifluoromethyl)phenyl)sulfonyl)tetrahydro-2H-pyran (1.5 g, 3.58 mmol, 1.0 eq) in THF (15 mL), KOt-Bu (0.811 g, 7.17 mmol, 2.0 eq) was added portion wise at −78° C. and the mixture was stirred for 5 min. CH$_3$I (1.02 g, 7.17 mmol, 2.0 eq) was added dropwise at the same temperature and stirred at −78° C. for 1 h. Then it was stirred at RT for further 1.5 h. After completion of the reaction, it was quenched with crushed ice and diluted with EtOAc. The inorganics were filtered through celite bed. Organic layers were separated, washed with chilled H$_2$O (5×20 mL), brine and finally dried over anhydr. Na$_2$SO$_4$ and filtrated. Purification was done by reverse phase prep HPLC to obtain 2-(4-chlorophenyl)-4-((2-ethyl-5-(trifluoromethyl)phenyl) sulfonyl)tetrahydro-2H-pyran as a single diastereomer (cis). The relative configuration (cis) was determined by $^1$H NMR, COSY and NOE experiments.

cis-isomer (SC-110, SC-111): 1H NMR (400 MHz, CDCl$_3$, δ ppm): 1.25-1.29 (3H), 1.49-1.58 (1H), 1.69-1.75 (2H), 1.96-2.00 (1H), 3.08-3.14 (2H), 3.51-3.58 (1H), 3.84-3.88 (1H), 4.10-4.13 (1H), 4.43-4.45 (1H), 7.33-7.35 (2H), 7.38-7.40 (2H), 7.82-7.84 (1H), 8.03 (s, 1H), 8.08-8.10 (1H).

On irradiating SCH proton "positive" NOE was observed with OCH proton.

Two enantiomers of this single diastereomer were separated by chiral HPLC, using chiral pack AD-H column and ethanol/DEA: (100/0.1) as mobile phase to obtain two cis enantiomers (SC-110 and SC-111).

SC-110: (0.065 g, 4.2%, off white solid, 1$^{st}$ eluted enantiomer; cis-EN1).

SC-111: (0.039 g, 2.5%, off white solid, 2$^{nd}$ eluted enantiomer; cis-EN2).

2-(4-Chlorophenyl)-5-methyl-5-[[3-(trifluoromethyl)phenyl]sulfonyl]-tetrahydro-pyran (Example 7)

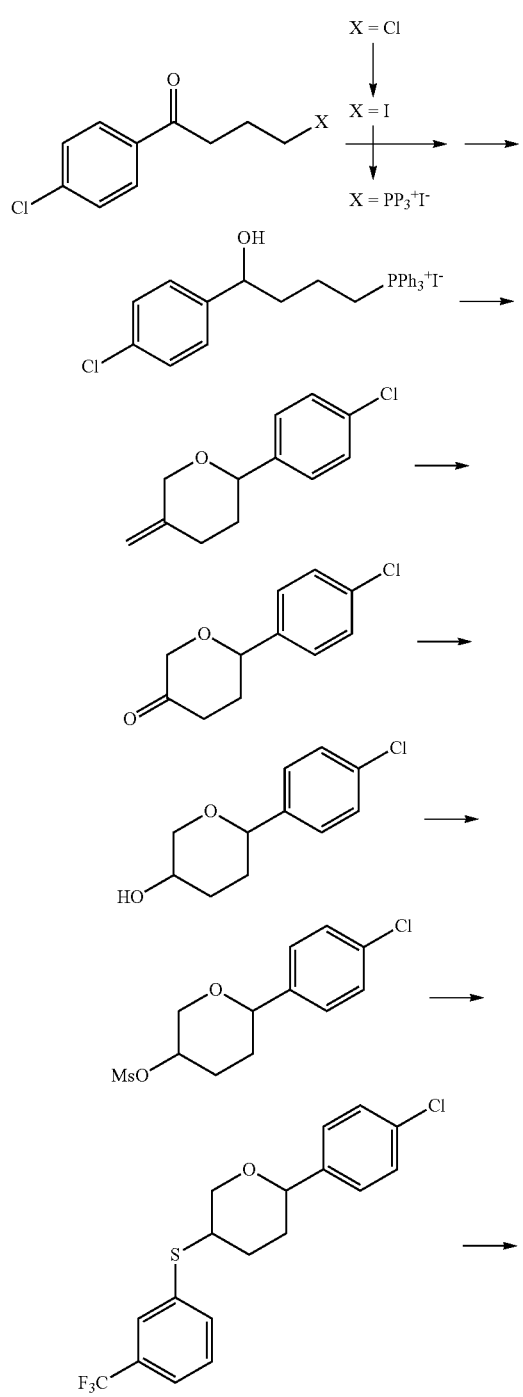

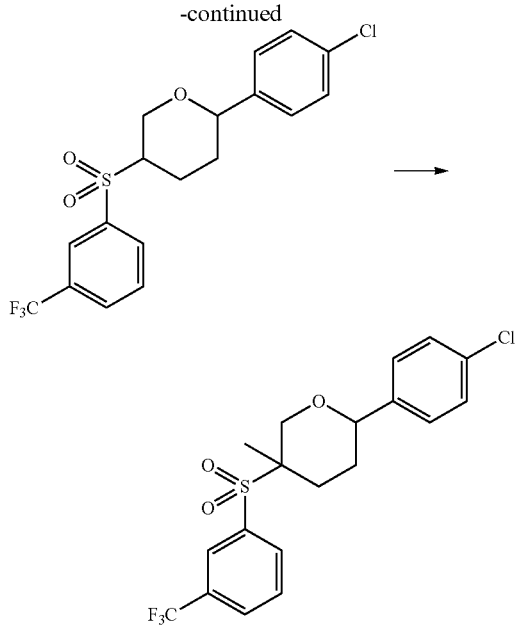

1-(4-Chlorophenyl)-4-iodobutan-1-one

To a stirred solution of 4-chloro-1-(4-chlorophenyl)butan-1-one (1.0 g, 4.6 mmol, 1.0 eq) in acetone (20 mL), NaI (3.5 g, 23.1 mmol, 5.0 eq) was added and the mixture was refluxed for 48 h. The solvent was evaporated and the crude product was diluted with water, extracted with Et$_2$O (2×100 mL). Combined organic layers were separated and washed with brine, dried over anhydr. Na$_2$SO$_4$, filtered and the solvent was evaporated under reduced pressure. Purification of the residue by flash-chromatography afforded the desired product (0.85 g, 63%) as white solid.

(4-(4-Chlorophenyl)-4-oxobutyl)triphenylphosphonium iodide

To a stirred solution of 1-(4-chlorophenyl)-4-iodobutan-1-one (2.0 g, 6.5 mmol, 1.0 eq) in toluene (30 mL) triphenylphophine (1.7 g, 6.5 mmol, 1.0 eq) was added and the mixture was heated up to 120° C. and continued for 16 h. The solution was decanted and washed with toluene, hexane, and dissolved in dry DCM and evaporated under reduced pressure to get crude product (2.1 g) as a yellow solid which was taken as such for the next step.

(4-(4-Chlorophenyl)-4-hydroxybutyl)triphenylphosphonium iodide

To a stirred solution of (4-(4-chlorophenyl)-4-oxobutyl)triphenylphosphonium iodide (7.0 g, 12.3 mmol, 1.0 eq) in MeOH (95 mL), sodium borohydride (0.47 g, 12.3 mmol, 1.0 eq) was added and refluxed for 6 h at 65° C. The RM was quenched with water and concentrated and the crude product was extracted with DCM. The organic layer was dried over anhydr. Na$_2$SO$_4$, filtered and the solvent was evaporated under reduced pressure to give crude alcohol (6.2 g) as an off white solid.

2-(4-Chlorophenyl)-5-methylenetetrahydro-2H-pyran

To a stirred solution of (4-(4-chlorophenyl)-4-hydroxybutyl)triphenylphosphonium iodide (6.0 g, 10.5 mmol, 1.0 eq) in MeCN (260 mL) DBU was added at RT. The mixture was refluxed for 2 h and then paraformaldehyde (3.1 g, 104.9 mmol, 10 eq) was added in one portion. After being refluxed for another 10 h, the RM was poured into water and extracted with DCM (3×200 mL). The combined extract was washed with water, dried over anhydr. Na₂SO₄, filtered and the solvent was evaporated under reduced pressure to give pale yellow oil which was purified by CC using to afford 2-(4-chlorophenyl)-5-methylenetetrahydro-2H-pyran (0.9 g, 38%) as a colorless liquid.

6-(4-Chlorophenyl)dihydro-2H-pyran-3(4H)-one

To a stirred solution of 2-(4-chlorophenyl)-5-methylenetetrahydro-2H-pyran (1.3 g, 6.2 mmol, 1.0 eq) in acetone (35 mL) and H₂O (35 mL) at 0° C., potassium osmatedihydrate (0.08 g, 0.21 mmol, 0.03 eq) was added and the mixture was stirred for 5 min. Then sodium periodate (5.4 g, 25.0 mmol, 4.0 eq) was added in 4 portions at the same temperature and the reaction was continued for 2 h. The RM was evaporated to dryness, diluted with water and extracted with DCM (3×50 mL). The organic portion was washed with H₂O, sat. brine, dried over anhydr. Na₂SO₄, filtered and the solvent was removed under reduced pressure at low temperature to give crude 6-(4-chlorophenyl)dihydro-2H-pyran-3(4H)-one (1.2 g) as a white solid which was taken as such for the next step.

6-(4-Chlorophenyl)tetrahydro-2H-pyran-3-ol

To a stirred solution of 6-(4-chlorophenyl)dihydro-2H-pyran-3(4H)-one (1.2 g, 5.7 mmol, 1.0 eq) in dry MeOH (60 mL), sodiumborohydride (0.43 g, 11.4 mmol, 2.0 eq) was added at 0° C. and the mixture was stirred for 1 h. The RM was quenched with ice water and MeOH was removed under reduced pressure. The crude product was extracted with EtOAc (3×50 mL). The combined organic layers were washed with water, sat. brine and dried over anhydr. Na₂SO₄ and filtered. The crude 6-(4-chlorophenyl)tetrahydro-2H-pyran-3-ol (1.2 g, off white solid) was taken as such for the next step.

6-(4-Chlorophenyl)tetrahydro-2H-pyran-3-yl methanesulfonate

Methanesulfonyl chloride (0.81 mL, 10.3 mmol, 2.0 eq) was added to an ice-cold solution of 6-(4-chlorophenyl) tetrahydro-2H-pyran-3-ol (1.1 g, 5.1 mmol, 1.0 eq) and TEA (1.43 mL, 10.3 mmol, 3.0 eq) in DCM (30 mL). The RM was stirred at the same temperature for 2 h. The RM was then quenched with H₂O. The aq. layer was extracted with DCM (2×100 mL), combined organic layers were dried over anhydr. Na₂SO₄, filtered and concentrated under reduced pressure to yield crude 6-(4-chlorophenyl)tetrahydro-2H-pyran-3-yl methanesulfonate (1.5 g) as a brown liquid which was taken as such for the next step.

2-(4-Chlorophenyl)-5-((3-(trifluoromethyl)phenyl) thio)tetrahydro-2H-pyran

K₂CO₃ (0.2 g, 1.4 mmol, 2.0 eq) was added to the solution of 6-(4-chlorophenyl)tetrahydro-2H-pyran-3-yl methanesulfonate (0.2 g, 0.69 mmol, 1.0 eq) and trifluromethyl benzene thiol (0.20 g, 1.1 mmol, 1.6 eq) in DMF (6 mL). The RM was heated up to 80° C. for 2 h. Then the RM was cooled to RT and then quenched with ice. The aq. layer was extracted with EtOAc (2×30 mL). Combined organic layers were dried over anhydr. Na₂SO₄, filtered and concentrated under reduced pressure to yield crude mass which was then purified by CC to afford 2-(4-chlorophenyl)-5-((3-(trifluoromethyl)phenyl)thio)tetrahydro-2H-pyran (0.12 g, 47%) as a yellow liquid.

2-(4-Chlorophenyl)-5-((3-(trifluoromethyl)phenyl) sulfonyl)tetrahydro-2H-pyran To a stirred solution of 2-(4-chlorophenyl)-5-((3-(trifluoromethyl)phenyl)thio)tetrahydro-2H-pyran (0.8 g, 2.2 mmol, 1.0 eq) in THF:H₂O (45:15) (60 mL) oxone (4.01 g, 6.5 mmol, 3.0 eq) was added and RM was stirred at RT for 4 h. After completion of the reaction, the RM was diluted with water and extracted with EtOAc. The combined organic layers were washed with H₂O, sat. brine and dried over anhydr. Na₂SO₄, filtered and the solvent was evaporated under reduced pressure to get crude product which was further purified by CC to afford 2-(4-chlorophenyl)-5-((3-(trifluoromethyl)phenyl)sulfonyl)tetrahydro-2H-pyran (0.58 g, 66%) as a white solid.

2-(4-Chlorophenyl)-5-methyl-5-[[3-(trifluoromethyl) phenyl]sulfonyl]-tetrahydro-pyran To a stirred solution of 2-(4-chlorophenyl)-5-((3-(trifluoromethyl)phenyl)sulfonyl)tetrahydro-2H-pyran (0.45 g, 1.1 mmol, 1.0 eq) in THF (30 mL), KOt-Bu (0.25 g, 2.2 mmol, 2.0 eq) was added portion wise at −78° C. and the mixture was stirred for 5 min. CH₃I (0.32 g, 2.2 mmol, 2.0 eq) was added dropwise at the same temperature and stirred at −78° C. for 1 h. Then it was stirred at RT for 1.5 h. After completion of the reaction, the RM was quenched with crushed ice and diluted with EtOAc. The inorganics were filtered through celite bed. Organic layer was separated, washed with chilled H₂O (5×20 mL), brine and finally dried over anhydr. Na₂SO₄. Purification was done by reverse phase prep HPLC to obtain 2-(4-chlorophenyl)-5-methyl-5-[[3-(trifluoromethyl)phenyl]sulfonyl]-tetrahydro-pyran (0.14 g, 31%, off white solid) as a single diastereomer.

The relative configuration was determined by ¹H NMR, HMBC, HMQC and NOESY experiments.

¹H NMR (400 MHz, MeOD, δ ppm): 1.22 (s, 3H), 1.64-1.68 (1H), 1.78-2.02 (2H), 2.47-2.52 (1H), 3.60-3.64 (1H), 4.34-4.38 (1H), 4.44-4.48 (1H), 7.10-7.13 (2H), 7.24-7.26 (2H), 7.83-7.86 (1H), 8.05-8.07 (1H), 8.19-8.25 (1H).

2-(4-Chloro-2-methylsulfonyl-phenyl)-4-methyl-4-[[3-(trifluoromethyl)phenyl]sulfonyl]-tetrahydro-pyran (Example 6)

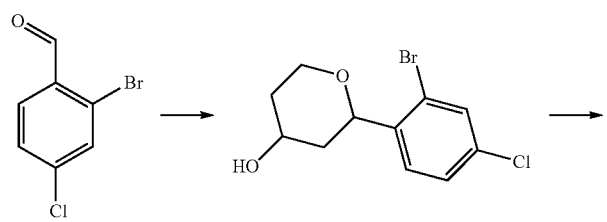

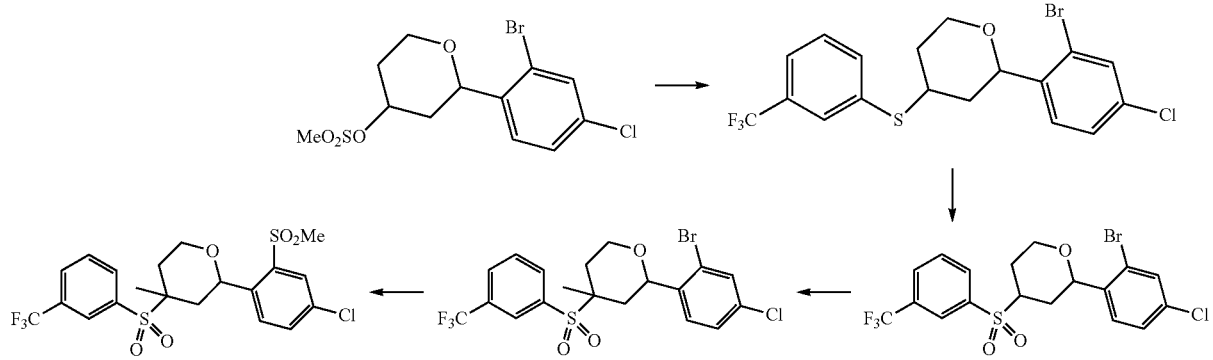

2-(2-bromo-4-chlorophenyl)tetrahydro-2H-pyran-4-ol

Concentrated H₂SO₄ was added drop wise to an ice-cold mixture of 3-buten-1-ol (6.2 mL, 68.5 mmol, 2.0 eq) and 2-bromo-4-chlorobenzaldehyde (7.5 g, 34.25 mmol, 1.0 eq) and the RM was allowed to warm to RT slowly and stirred for 16 h. Then the RM was poured into ice water, basified with sat. NaHCO₃ solution and extracted with DCM (2×100 mL), combined organic layer was dried over anhydr. Na₂SO₄, filtered and concentrated under reduced pressure. The crude product was purified by CC to afford 2-(2-bromo-4-chlorophenyl)tetrahydro-2H-pyran-4-ol (3.6 g, 36%) as deep brown liquid.

2-(2-bromo-4-chlorophenyl)tetrahydro-2H-pyran-4-yl methanesulfonate

Methanesulfonyl chloride (3.8 mL, 48.88 mmol, 1.5 eq) was added to an ice-cold solution of 2-(2-bromo-4-chlorophenyl)tetrahydro-2H-pyran-4-ol (9.5 g, 32.59 mmol, 1.0 eq) and NEt₃ (14.0 mL, 100.63 mmol, 3.1 eq) in DCM (90 mL). The reaction mixture was stirred at 0° C. for 2 h. The RM was quenched with H₂O and extracted with DCM (2×150 mL), combined organic layer was dried over anhydr. Na₂SO₄, filtered and concentrated under reduced pressure to give crude product which was purified by CC to afford 2-(2-bromo-4-chlorophenyl)tetrahydro-2H-pyran-4-yl methanesulfonate (4.1 g, 34%) as sticky liquid.

2-(2-bromo-4-chlorophenyl)-4-((3-(trifluoromethyl)phenyl)thio)tetrahydro-2H-pyran K₂CO₃ (4.59 g, 33.24 mmol, 3.0 eq) was added to the solution of 2-(2-bromo-4-chlorophenyl)tetrahydro-2H-pyran-4-yl methanesulfonate (4.08 g 11.08 mmol, 1.0 eq) and 3-trifluoromethylthiol (2.26 mL, 16.64 mmol, 1.5 eq) in DMF (70 mL). The reaction mixture was stirred at 80° C. for 2 h. Then the RM was cooled to RT and then quenched with ice. The aq. layer was extracted with EtOAc (2×150 mL), combined organic layer was dried over anhydr. Na₂SO₄, filtered and concentrated under reduced pressure to yield crude mass which was then purified by CC to afford 2-(2-bromo-4-chlorophenyl)-4-((3-(trifluoromethyl)phenyl)thio)tetrahydro-2H-pyran (2.68 g, 53%) as pale yellow oil.

2-(2-bromo-4-chlorophenyl)-4-((3-(trifluoromethyl)phenyl)sulfonyl)tetrahydro-2H-pyran To a stirred solution of 2-(2-bromo-4-chlorophenyl)-4-((3-(trifluoromethyl)phenyl)thio)tetrahydro-2H-pyran (2.68 g, 5.94 mmol, 1.0 eq) in THF (90 mL) and H₂O (30 mL) was added oxone (14.59 g, 23.77 mmol, 4.0 eq) and the RM was stirred at RT for 1 h. Then the reaction mixture was diluted with H₂O, extracted with EtOAc (2×100 mL), combined organic layer was washed with H₂O (50 mL) and brine (50 mL), dried over anhydr. Na₂SO₄, filtered and the solvent was evaporated under reduced pressure to get crude compound which was further purified by CC to afford 2-(2-bromo-4-chlorophenyl)-4-((3-(trifluoromethyl)phenyl)sulfonyl)tetrahydro-2H-pyran (2.6 g, 90%) as white solid.

2-(2-bromo-4-chlorophenyl)-4-methyl-4-((3-(trifluoromethyl)phenyl)sulfonyl)tetrahydro-2H-pyran To a stirred solution of 2-(2-bromo-4-chlorophenyl)-4-((3-(trifluoromethyl)phenyl)sulfonyl)tetrahydro-2H-pyran (2.55 g, 5.14 mmol, 1.0 eq) in THF (120 mL) was added t-BuOK (2.32 g, 20.56 mmol, 4.0 eq) followed by 18-crown-6 (5.43 g, 20.56 mmol, 4.0 eq) at −78° C. The RM was stirred at the same temperature for 15 min. Then MeI (1.29 mL, 20.56 mmol, 4.0 eq) was added to the RM at −78° C. and the mixture was allowed to warm gradually to RT and stirred for 2 h. Then the RM was diluted with H₂O and the crude product was extracted with EtOAc (2×50 mL). Combined organic layer was washed with H₂O (50 mL), brine (50 mL), dried over anhydr. Na₂SO₄, filtered and the solvent was evaporated under reduced pressure to get crude product which was further purified by CC to afford 2-(2-bromo-4-chlorophenyl)-4-methyl-4-((3-(trifluoromethyl)phenyl)sulfonyl)tetrahydro-2H-pyran (1.92 g, 73%) as off-white sticky solid.

2-(4-chloro-2-(methylsulfonyl)phenyl)-4-methyl-4-((3-(trifluoromethyl)phenyl)sulfonyl)tetrahydro-2H-pyran To a stirred solution of 2-(2-bromo-4-chlorophenyl)-4-methyl-4-((3-(trifluoromethyl)phenyl)sulfonyl)tetrahydro-2H-pyran (1.6 g, 3.22 mmol, 1.0 eq) in DMSO (40 mL) was added sodiummethanesulfinite (0.428 g, 4.186 mmol, 1.3 eq), and L-proline sodium salt (0.088 g, 0.643 mmol, 0.2 eq). The mixture was degassed for 10 min, CuI (123 mg, 0.643 mmol, 0.2 eq) was added and the RM was heated to 90° C. for 16 h in a sealed tube. Then the RM was diluted with H₂O, extracted with EtOAc (2×50 mL), organic layer was washed with H₂O (25 mL), brine (25 mL), dried over anhydr. Na₂SO₄, filtered and the solvent was evaporated under reduced pressure to get crude product which was further purified by CC to afford 2-(4-chloro-2-(methylsulfonyl)phenyl)-4-methyl-4-((3-(trifluoromethyl)phenyl)sulfonyl)tetrahydro-2H-pyran as mixture of diastereoisomers (0.6 g). The diastereomers were separated by reverse phase HPLC to give cis isomer (0.425 g). The relative configuration (cis) was determined by $^1$H NMR and NOE experiments.

cis-isomer (SC-114, SC-115): 1H NMR (400 MHz, DMSO-$d_6$, δ ppm): 1.46 (s, 3H) 1.47-1.50 (1H), 1.81-1.85 (1H), 1.92-1.94 (1H), 2.15-2.20 (1H), 3.34 (s, 1H), 3.82-3.86 (1H), 4.06-4.09 (1H), 5.20-5.22 (1H), 7.76-7.78 (1H), 7.83-7.85 (1H), 7.88-7.89 (1H), 7.92-7.94 (1H), 8.04 (s, 1H), 8.15-8.16 (1H), 8.20-8.22 (1H).

Two enantiomers of this single diastereomer were separated by normal phase chiral prep HPLC using a YMC-Amylose C column and hexane/ethanol/DEA (80/20/0.1) as mobile phase to obtain two cis enantiomers SC-114 and SC-115.

SC-114: (0.115 g, off white solid, $1^{st}$ eluted enantiomer; cis-EN1)

SC-115: (0.110 g, off white solid, $2^{nd}$ eluted enantiomer; cis-EN2)

2-(4-Chlorophenyl)-2-methyl-4-[[3-(trifluoromethyl)phenyl]sulfonyl]-tetrahydro-pyran (Example 8)

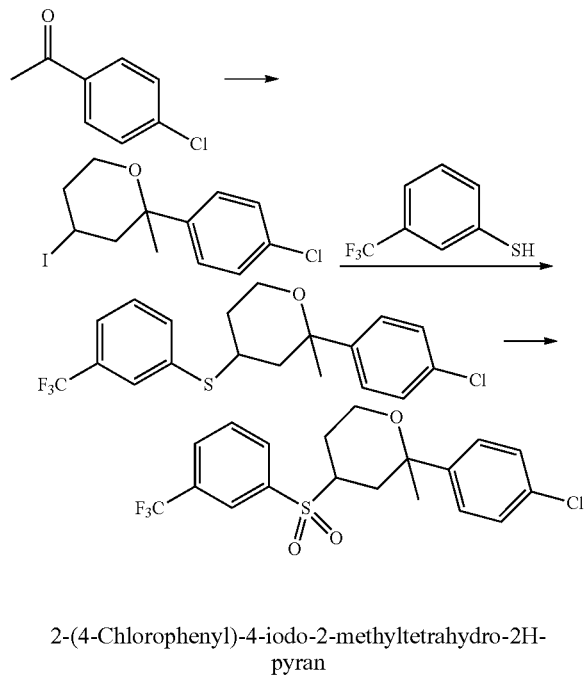

2-(4-Chlorophenyl)-4-iodo-2-methyltetrahydro-2H-pyran

To a stirred solution of 4-chloroacetophenone (10 g, 64.9 mmol) and homoallyl alcohol (4.7 g, 64.9 mmol) in MeCN (40 mL) was added NaI (9.7 g, 64.9 mmol) and the mixture was stirred at RT for 10 min. Then chlorotrimethylsilane (8.2 mL, 64.9 mmol) was added drop wise at RT and the RM was heated up to 70° C. for 16 h. The RM was cooled to RT and quenched with sodium thiosulfate solution. MeCN was evaporated and the concentrated mass was diluted with water (100 mL) and extracted with EtOAc (2×150 mL). Combined organic layer was dried over anhydr. Na$_2$SO$_4$, filtered and concentrated under reduced pressure to yield crude mass which was then purified by CC to afford 2-(4-chlorophenyl)-4-iodo-2-methyltetrahydro-2H-pyran (0.9 g, 4%) as pale yellow colored solid.

2-(4-Chlorophenyl)-2-methyl-4-((3-(trifluoromethyl)phenyl)thio)tetrahydro-2H-pyran To a suspension of sodium hydride (0.11 g, 4.4 mmol) in DMF (12 mL) was added 2-(4-chlorophenyl)-4-iodo-2-methyltetrahydro-2H-pyran (0.5 g, 1.5 mmol, 1.0 eq) and 3-trifluoromethylthiophenol (0.79 g, 4.4 mmol, 3.0 eq) at RT. The RM was stirred at 70° C. for 5 h. Then the RM was cooled to RT and quenched with ice. The RM was extracted with EtOAc (2×50 mL). Combined organic layer was dried over anhydr. Na$_2$SO$_4$, filtered and concentrated under reduced pressure to give crude mass which was then purified by CC to afford 2-(4-chlorophenyl)-2-methyl-4-((3-(trifluoromethyl)phenyl)thio)tetrahydro-2H-pyran (0.04 g, 35%) as a pale yellow color oil.

2-(4-Chlorophenyl)-2-methyl-4-[[3-(trifluoromethyl)phenyl]sulfonyl]-tetrahydro-pyran To a stirred solution of 2-(4-chlorophenyl)-2-methyl-4-((3-(trifluoromethyl)phenyl)thio)tetrahydro-2H-pyran (0.6 g, 15 mmol, 1.0 eq) in a mixture of solvent of MeCN (9 mL) and H$_2$O (3 mL), sodium periodate (1.0 g, 46.0 mmol, 3.0 eq) and RuCl$_3$ (0.006 g, 0.03 mmol, 0.02 eq) were added and the mixture was stirred for 30 min. After completion, the RM was filtered over celite bed and washed with H$_2$O. The filtrate was extracted with EtOAc and combined organic layer was dried over anhydr. Na$_2$SO$_4$, filtered and the solvent was evaporated under reduced pressure to get crude product which was then purified by CC to afford pure 2-(4-chlorophenyl)-2-methyl-4-[[3-(trifluoromethyl)phenyl]sulfonyl]-tetrahydro-pyran (0.18 g, 28%, light brown solid) as a single diastereomer. The relative configuration (trans) was determined by $^1$H NMR, HMBC, HMQC and NOESY experiments.

SC-117: $^1$H NMR (600 MHz, DMSO-$d_6$, δ ppm): 1.32 (s, 3H), 1.57-1.62 (2H), 1.67-1.71 (1H), 2.70-2.72 (1H), 3.19-3.23 (1H), 3.39-3.43 (1H), 3.74-3.77 (1H), 7.20-7.22 (2H), 7.41-7.43 (2H), 7.94-7.96 (1H), 8.16 (s, 1H), 8.20-8.22 (2H).

Two enantiomers of this single diastereomer were separated by chiral prep HPLC using an OJ-H column and hexane/ethanol/DEA (90/10/0.1) as mobile phase to obtain two trans enantiomers SC-140 and SC-141.

SC-140: (0.212 g, off white solid, $1^{st}$ eluted enantiomer; trans-EN1).

SC-141 (0.083 g, off white solid, $2^{nd}$ eluted enantiomer; trans-EN2).

2-(4-Chlorophenyl)-4-[[2-isopropyl-5-(trifluoromethyl)-phenyl]sulfonyl]-tetrahydro-pyran (Example 9)

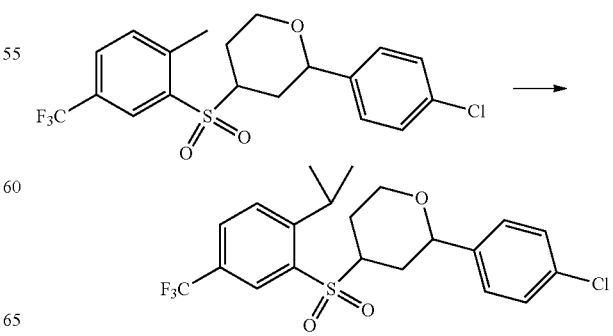

To a stirred solution of trans-2-(4-chlorophenyl)-4-((2-methyl-5-(trifluoromethyl)phenyl)sulfonyl)tetrahydro-2H-pyran (1.5 g, 3.6 mmol, 1.0 eq) in THF (15 mL), KOt-Bu (0.81 g, 7.2 mmol, 2.0 eq) was added portion wise at −78° C. and the mixture was stirred for 5 min. CH$_3$I (1.0 g, 7.2 mmol, 2.0 eq) was added dropwise at the same temperature and stirred at −78° C. for 1 h. Then it was stirred at RT for further 1.5 h. After completion of the reaction it was quenched with crushed ice and diluted with EtOAc. The inorganics were filtered through celite bed. Organic layers were separated, washed with chilled H$_2$O (5×20 mL), brine and finally dried over anhydr. Na$_2$SO$_4$ and filtrated. Purification was done by reverse phase preperative HPLC to obtain 2-(4-chlorophenyl)-4-((2-isopropyl-5-(trifluoromethyl)phenyl)sulfonyl)tetrahydro-2H-pyran as a single diastereomer (cis). The relative configuration (cis) was determined by $^1$H NMR, COSY and NOE experiments.

cis-isomer (SC-118, SC-119): $^1$H NMR (400 MHz, CDCl$_3$, δ ppm): 1.27-1.30 (6H), 1.50-1.60 (1H), 1.69-1.74 (2H), 2.00-2.04 (1H), 3.52-3.59 (1H), 3.76-3.80 (1H), 3.85-3.91 (1H), 4.11-4.14 (1H), 4.45-4.47 (1H), 7.33-7.40 (4H), 7.97-8.00 (1H), 8.04 (s, 1H), 8.09-8.12 (1H).

On irradiating SCH proton "positive" NOE was observed with OCH proton.

Two enantiomers of this single diastereomer were separated by chiral HPLC, using chiral pack AD-H column and ethanol/DEA: (100/0.1) as mobile phase to obtain two cis enantiomers (SC-118 and SC-119).

SC-118: (0.176 g, 11.0%, yellow gummy liquid, 1$^{st}$ eluted enantiomer; cis-EN1).

SC-119: (0.169 g, 10.6%, yellow gummy liquid, 2$^{nd}$ eluted enantiomer; cis-EN2).

3-(4-Chlorophenyl)-4-methyl-4-[[3-(trifluoromethyl)phenyl]sulfonyl]-tetrahydro-pyran (Example 10)

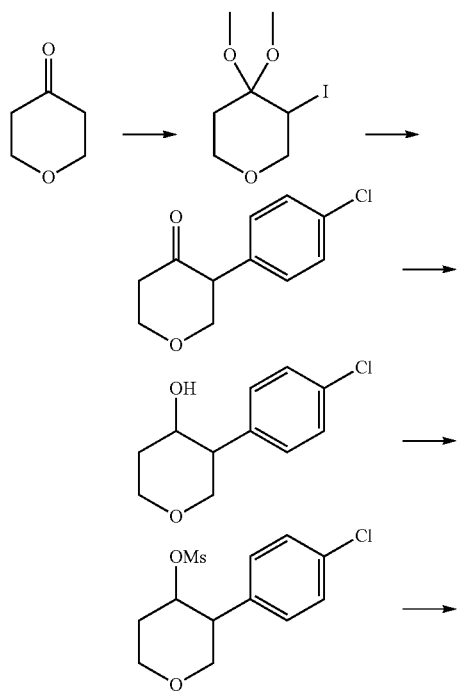

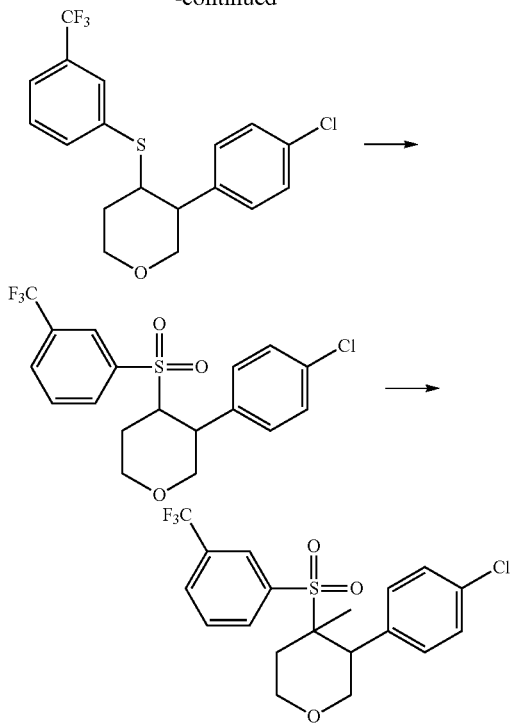

3-Iodo-4,4-dimethoxytetrahydro-2H-pyran

To a mixture of tetrahydro-4H-pyran-4-one (10 g, 0.1 mol, 1.0 eq) and trimethylorthoformate (48.4 g, 0.46 mol, 4.6 eq) at 0° C. was added I$_2$ (25.3 g, 0.1 mol, 1.0 eq) slowly over 10 min. The RM was allowed to stir at 0° C. for 30 min and was then allowed to come to RT and stirred for further 1 h. The RM was then cooled to 0° C. and quenched by the slow addition of sat. aq. sodium thiosulfate solution (20 mL). The resulting mixture was extracted with EtOAc (2×300 mL). The combined organic layers were washed with brine (100 mL), dried over anhydr. Na$_2$SO$_4$, filtered and concentrated in vacuum to get crude compound. The crude residue was purified by flash CC using silica gel to get pure, 3-iodo-4,4-dimethoxytetrahydro-2H-pyran (20 g, 74%) as a light yellow liquid.

3-(4-Chlorophenyl)dihydro-2H-pyran-4(3H)-one

To a stirred mixture of (4-chlorophenyl)boronic acid (11.2 g, 71.0 mmol, 1.5 eq), trans-2-aminocyclohexanol (0.70 g, 4.7 mmol, 0.1 eq) and nickel(II)chloride hexahydrate (0.55 g, 2.3 mmol, 0.05 eq) in THF at 0° C. was added NaHMDS (1M solution in THF) (94 mL, 94 mmol, 2.0 eq) drop wise over 10 min. The RM was splurged with N$_2$ for 15 min. To the RM was added 2-propanol (previously spurged with N$_2$) at 0° C. and the resulting RM was allowed to come to RT at which time 3-iodo-4,4-dimethoxy tetrahydro-2H-pyran (13.0 g, 47 mmol, 1.0 eq) was added drop wise over 5 min. The RM was then heated up to 60° C. and stirred for 16 h. The RM was then cooled to 0° C. and quenched by careful addition of aq. 1N HCl. The resulting RM was extracted with EtOAc (2×400 mL). The combined organic layers were washed with brine (200 mL), dried over anhydr. Na$_2$SO$_4$, filtered and concentrated in vacuum to get crude compound.

The crude residue was purified by flash CC to get pure 3-(4-chlorophenyl)dihydro-2H-pyran-4(3H)-one (4 g, 40%) as a light orange oil.

3-(4-Chlorophenyl)tetrahydro-2H-pyran-4-ol

To a stirred solution of 3-(4-chlorophenyl)dihydro-2H-pyran-4(3H)-one (4.5 g, 21.4 mmol, 1.0 eq) in MeOH (50 mL), NaBH$_4$ (1.2 g, 32.1 mmol, 1.5 eq) was added and the mixture was stirred for 1 h. The RM was distilled under reduced pressure, diluted with H$_2$O and extracted with EtOAc (2×100 mL). The combined organic layers were washed with sat. brine, dried over anhydr. Na$_2$SO$_4$, filtered and concentrated in vacuum to get crude product. The crude residue was purified by flash CC using silica gel to get pure 3-(4-chlorophenyl)tetrahydro-2H-pyran-4-ol (3.5 g, 77%) as a white solid.

3-(4-Chlorophenyl)tetrahydro-2H-pyran-4-yl methanesulfonate

Methanesulfonyl chloride (1.4 mL, 14.1 mmol, 1.5 eq) was added to an ice-cold solution of 3-(4-chlorophenyl)tetrahydro-2H-pyran-4-ol (2.0 g, 9.4 mmol, 1.0 eq) and TEA (4.0 mL, 28.2 mmol, 3 eq) in DCM (25 mL). The RM was stirred at the same temperature for 2 h. The RM was quenched with H$_2$O and the crude product was extracted with DCM (2×100 mL). Combined organic layers were dried over anhydr. Na$_2$SO$_4$, filtered and concentrated under reduced pressure to yield crude product which was purified by CC to afford 3-(4-chlorophenyl)tetrahydro-2H-pyran-4-yl methanesulfonate (2.0 g, 74%) as a brown liquid.

3-(4-Chlorophenyl)-4-((3-(trifluoromethyl)phenyl)thio)tetrahydro-2H-pyran

K$_2$CO$_3$ (2.8 g, 20.6 mmol, 2.0 eq) was added to the solution of 3-(4-chlorophenyl)tetrahydro-2H-pyran-4-yl methanesulfonate (3.0 g 10.3 mmol, 1.0 eq) and 3-(trifluoromethyl)benzenethiol (5.6 mL, 41.3 mmol, 2.0 eq) in DMF (30 mL). The RM was stirred at 60° C. for 16 h. Then the RM was cooled to RT and quenched with ice. The aq. layer was extracted with EtOAc (2×150 mL) and the combined organic layers were dried over anhydr. Na$_2$SO$_4$, filtered and concentrated under reduced pressure to yield crude mass which was then purified by CC to afford 3-(4-chlorophenyl)-4-((3-(trifluoromethyl)phenyl)thio)tetrahydro-2H-pyran (2.5 g, 65%) as a pale yellow color oil).

3-(4-Chlorophenyl)-4-((3-(trifluoromethyl)phenyl)sulfonyl)tetrahydro-2H-pyran To an ice cold solution of 3-(4-chlorophenyl)-4-((3-(trifluoromethyl)phenyl)thio)tetrahydro-2H-pyran (2.0 g, 5.4 mmol, 1.0 eq) in THF:H$_2$O (3:1)(130 mL) oxone (9.9 g, 16.1 mmol, 3.0 eq) was added and RM was stirred at RT for 4 h. After completion of the reaction, the RM was diluted with water and extracted with EtOAc. The combined organic layers were washed with H$_2$O, sat. brine and dried over anhydr. Na$_2$SO$_4$, filtered and evaporated under reduced pressure to get crude product which was further purified by CC to afford 3-(4-chlorophenyl)-4-((3-(trifluoromethyl)phenyl)sulfonyl)tetrahydro-2H-pyran (1.3 g, 60%) as a white solid.

3-(4-Chlorophenyl)-4-methyl-4-((3-(trifluoromethyl)phenyl)sulfonyl)tetrahydro-2H-pyran To a stirred solution of 3-(4-chlorophenyl)-4-((3-(trifluoromethyl)phenyl)sulfonyl)tetrahydro-2H-pyran (0.5 g, 1.2 mmol, 1.0 eq) in THF (20 mL), KOt-Bu (0.28 g, 2.5 mmol, 2.0 eq) and 18-crown-6 was added at −78° C. and the RM was stirred at same temperature for 15 min. At the same temperature CH$_3$I (0.35 g, 2.5 mmol, 2.0 eq) was added and the RM was stirred at same temperature for 1 h. Finally, the RM was stirred at RT for 1 h. After completion of the reaction, it was quenched with crushed ice and diluted with EtOAc. The organic layer was separated, and the combined organic layer was washed with chilled H$_2$O (5×50 mL), brine and finally dried over anhydr. Na$_2$SO$_4$. The different isomers were separated by SFC on a chiral pack OJ-H column. The relative configuration of the diastereomers was determined by $^1$H NMR and NOE experiments.

SC-120: (0.026 g, 5% yield, off white solid; cis)

$^1$H NMR (400 MHz, DMSO-d$_6$, δ ppm): 1.51 (s, 3H), 1.61-1.65 (1H), 2.29-2.32 (1H), 3.08-3.10 (1H), 3.68-3.72 (1H), 3.92-3.98 (2H), 4.06-4.09 (1H), 7.26-7.28 (2H), 7.44-7.47 (2H), 7.65 (s, 1H), 7.78-7.82 (1H), 7.92-7.94 (1H), 8.07-8.09 (1H).

SC-121: (0.067 g, 12.9%, off white solid) 1$^{st}$ eluting enantiomer; trans-EN1.

SC-122: (0.09 g, 17.4%, off white) 2$^{nd}$ eluting enantiomer; trans-EN2.

$^1$H NMR (400 MHz, DMSO-d$_6$, δ ppm): 1.15-1.21 (1H), 1.49 (s, 3H), 2.14-2.21 (1H), 3.52-3.63 (3H), 3.80-3.88 (2H), 7.27-7.34 (4H), 7.83-7.87 (2H), 8.04-8.07 (1H), 8.11-8.13 (1H).

General reaction scheme 1 for the compounds preparation of the compounds of examples 5, 17, 23 to 27 and 39 (SC-204, SC-205, SC-208, SC-209, SC-212, SC-213, SC-218, SC-219, SC-220, SC-221, SC-222, SC-223, SC-224, SC-225, SC-226, SC-227, SC-228, SC-229, SC-230, SC-231, SC-232, SC-233):

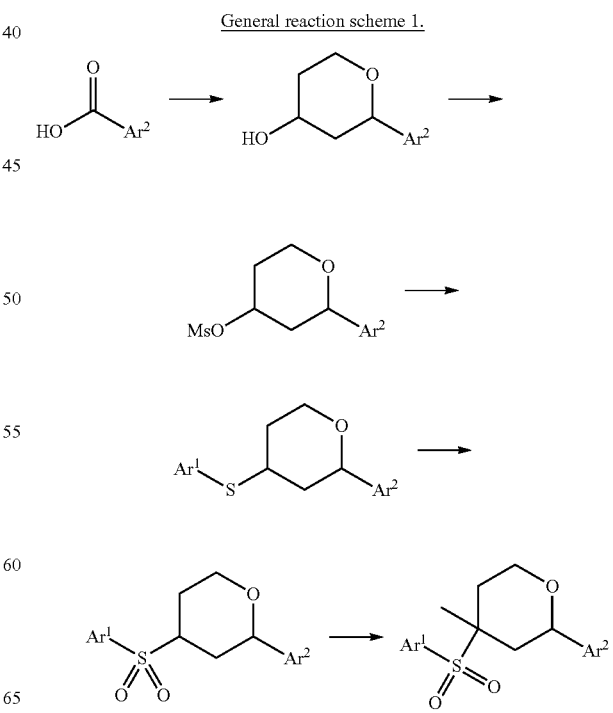

General reaction scheme 1.

4-Methyl-2-(4-methylsulfonyl-phenyl)-4-[[3-(trifluoromethyl)phenyl]sulfonyl]-tetrahydro-pyran (Example 5)

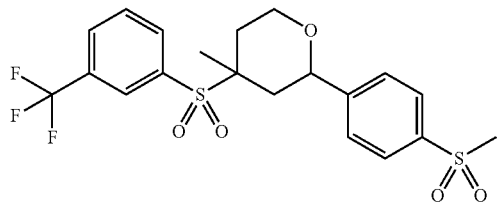 [SMILES: CC1(S(=O)(=O)c2cccc(C(F)(F)F)c2)CCOC(c2ccc(S(C)(=O)=O)cc2)C1]

Step 1: 2-(4-Methylsulfonyl-phenyl)-tetrahydro-pyran-4-ol

4-Methylsulfonyl-benzaldehyde (2 g, 10.86 mmol) was dissolved in DCE (40 mL) and cooled in an ice bath. TFA (16 mL) followed by 3-butenol (1.13 mL, 13.03 mmol) were added and the mixture stirred at RT for 67 h. The mixture was diluted with $H_2O$ (100 mL), basified with 6 M NaOH (aq) and extracted with DCM (100 mL). The organic layer was separated and washed with brine, dried ($Na_2SO_4$) and concentrated under reduced pressure to get crude. The crude product was dissolved in MeOH (20 mL) and LiOH (1.19 g, 28.40 mmol) was added. The reaction was stirred at RT for 5 h. MeOH was concentrated under reduced pressure and the residue was diluted with DCM (100 mL) and washed with water (50 mL), brine (50 mL), dried ($Na_2SO_4$) and concentrated in vacuo to get crude. The crude compound was triturated with n-hexane (10 mL) and $Et_2O$ (10 mL) to give 2-(4-Methylsulfonyl-phenyl)-tetrahydro-pyran-4-ol (1.8 g; 64%) as pale yellow solid.

Step 2: Methanesulfonic acid [2-(4-methylsulfonyl-phenyl)-tetrahydro-pyran-4-yl]ester Methanesulfonyl chloride (0.72 mL, 9.34 mmol) was added to a solution of 2-(4-Methylsulfonyl-phenyl)-tetrahydro-pyran-4-ol (1.6 g, 6.25 mmol) and DIPEA (2.72 mL, 15.55 mmol) in DCM (15 mL) at 0° C.; allowed to warm to RT and stirred for 16 h. The mixture was diluted with DCM (100 mL) and washed sequentially with 1 N HCl (50 mL), sat. $NaHCO_3$ solution (50 mL), water (50 mL), brine (50 mL), dried ($Na_2SO_4$) and concentrated under reduced pressure to get crude Methanesulfonic acid [2-(4-methyl-sulfonyl-phenyl)-tetrahydro-pyran-4-yl]ester (2 g) as a solid.

Step 3: 2-(4-Methylsulfonyl-phenyl)-4-[[3-(trifluoromethyl)phenyl]sulfanyl]-tetrahydro-pyran 3-Trifluoromethyl thiophenol (2.2 mL, 16.12 mmol) was added to a suspension of Methanesulfonic acid [2-(4-methylsulfonyl-phenyl)-tetrahydro-pyran-4-yl]ester (1.8 g, 5.38 mmol) and $K_2CO_3$ (1.48 g, 10.70 mmol) in DMF (20 mL) and the RM was heated at 50° C. for 4 h and then stirred at RT for 16 h. After completion of reaction, the mixture was diluted with $H_2O$ (100 mL) and extracted with EtOAc (250 mL). The organic extract was washed with water (100 mL), brine (100 mL), dried ($Na_2SO_4$) and concentrated under reduced pressure to get crude compound. The crude compound was purified by CC (silica gel, 0-12% EtOAc in PE) to obtain 2-(4-Methylsulfonyl-phenyl)-4-[[3-(trifluoromethyl)phenyl]sulfanyl]-tetrahydro-pyran (1.8 g, 73%) as a light brown solid.

Step 4: 2-(4-Methylsulfonyl-phenyl)-4-[[3-(trifluoromethyl)phenyl]sulfonyl]-tetrahydro-pyran 2-(4-Methylsulfonyl-phenyl)-4-[[3-(trifluoromethyl)phenyl]sulfanyl]-tetrahydro-pyran (1.8 g, 4.32 mmol) was dissolved in MeOH (65 mL) and a solution of OXONE (5.3 g, 8.65 mmol) in $H_2O$ (43 mL) was added. After stirring at RT for 1 h, additional OXONE (2.66 g, 4.33 mmol) in $H_2O$ (12 mL) was added to it and stirring then continued at RT for 16 h. MeOH was concentrated in vacuo; the residue was diluted with $H_2O$ (80 mL) and extracted with EtOAc (2×100 mL). The combined organic extract was washed with brine (100 mL), dried ($Na_2SO_4$) and concentrated to get crude. The crude compound was purified by CC (silica gel, 0-60% EtOAc in PE) to obtain 2-(4-Methylsulfonyl-phenyl)-4-[[3-(trifluoromethyl)phenyl]sulfonyl]-tetrahydropyran (1.8 g, 90%) as a solid.

Step 5: 4-Methyl-2-(4-methylsulfonyl-phenyl)-4-[[3-(trifluoromethyl)phenyl]sulfonyl]-tetrahydro-pyran A solution of 2-(4-methylsulfonyl-phenyl)-4-[[3-(trifluoromethyl)phenyl]sulfonyl]-tetrahydro-pyran (500 mg, 1.11 mmol) in THF (10 mL) was cooled to −78° C. and KOt-Bu (1 M solution in THF; 1.67 mL, 1.60 mmol) was added drop-wise. $CH_3I$ (0.13 mL, 2.18 mmol) was added and the resulting mixture was warmed to RT and stirred for 16 h. The reaction mass was diluted with EtOAc (100 mL) and washed with $H_2O$ (30 mL) and brine (30 mL), dried ($Na_2SO_4$) and concentrated under reduced pressure to get crude compound. The crude compound was purified by CC (silica gel, 0-15% EtOAc in PE) followed by prep. HPLC to obtain cis-rac 4-methyl-2-(4-methylsulfonyl-phenyl)-4-[[3-(trifluoromethyl)phenyl]sulfonyl]-tetrahydro-pyran (100 mg, 20%) as a white solid.

$^1$H-NMR (600 MHz, [$d_6$]-DMSO): δ =8.20-8.22 (1H), 8.15-8.17 (1H), 8.04 (1H), 7.88-7.97 (3H), 7.60-7.61 (2H), 4.68-4.70 (2H), 4.07-4.11 (1H), 3.71-3.78 (1H), 3.21 (3H), 2.11-2.17 (1H), 1.83-1.87 (1H), 1.77-1.80 (1H), 1.46-1.54 (4H) ppm.

NOE: C-2 proton & methyl=cis

2-(4-Fluoro-3-methylsulfonyl-phenyl)-4-methyl-4-[[3-(trifluoromethyl)phenyl]sulfonyl]-tetrahydro-pyran (Example 17)

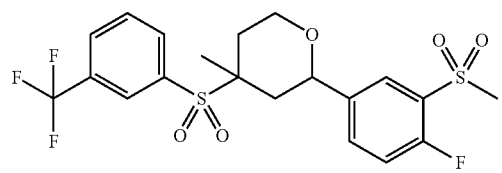 [SMILES: CC1(S(=O)(=O)c2cccc(C(F)(F)F)c2)CCOC(c2ccc(F)c(S(C)(=O)=O)c2)C1]

Step 1: 2-(3-Bromo-4-fluoro-phenyl)-tetrahydro-pyran-4-ol

To a solution of 3-bromo-4-fluorobenzaldehdye (10 g, 49.50 mmol) in DCE (200 mL) was added 3-buten-1-ol (5.34 g, 74.25 mmol) and TFA (80 mL) and the RM was stirred for 2 d at RT. The RM was quenched with ice-water (200 mL) and basified using 6N NaOH solution to pH=8, the aq layer was extracted with DCM (2×200 mL). The combined organic layer was washed with H$_2$O (100 mL), brine (100 mL), dried (Na$_2$SO$_4$) and concentrated under reduced pressure to get crude (10 g). The crude compound (10 g, 37.17 mmol) was dissolved in MeOH (100 mL), LiOH was added (7.8 g, 42 mmol) and stirred for 5 h at RT. The RM was concentrated under reduced pressure and the residue was diluted with DCM (300 mL). The organic layer was washed with H$_2$O (100 mL), brine (100 mL), dried (Na$_2$SO$_4$) and concentrated in vacuo to get crude. The crude was purified by CC (silica gel, 0-30% EtOAc in PE) to obtain 2-(3-Bromo-4-fluoro-phenyl)-tetrahydro-pyran-4-ol (8 g, 58%).

Step 2: Methanesulfonic acid [2-(3-bromo-4-fluoro-phenyl)-tetrahydro-pyran-4-yl]ester Methanesulfonylchloride (4.62 mL, 60 mmol) was added to a solution of 2-(3-bromo-4-fluoro-phenyl)-tetrahydro-pyran-4-ol (11 g, 40 mmol) and DIPEA (17.4 mL, 100 mmol) in DCM (100 mL) at 0° C. and stirred for 16 h at RT. After completion of reaction, the mixture was poured in ice water (200 mL) and extracted with DCM (2×300 mL). The combined organic layer was washed with sat. NaHCO$_3$ solution (100 mL), water (100 mL), brine (100 mL), dried (Na$_2$SO$_4$) and the solvent was distilled off under reduced pressure to obtain methanesulfonic acid [2-(3-bromo-4-fluoro-phenyl)-tetrahydro-pyran-4-yl]ester (14 g, crude).

Step 3: 2-(3-Bromo-4-fluoro-phenyl)-4-[[3-(trifluoromethyl)phenyl]sulfanyl]-tetrahydro-pyran To a solution of methanesulfonic acid [2-(3-bromo-4-fluoro-phenyl)-tetrahydro-pyran-4-yl]ester (14 g, 39.66 mmol) in DMF (140 mL) was added K$_2$CO$_3$ (16.41 g, 118.98 mmol) and 3-trifluoromethylthiophenol (10.87 g, 79.32 mmol) and the RM was heated to 50° C. for 5 h, then stirred at RT for 16 h. After completion of reaction, the mixture was diluted with H$_2$O (400 mL) and extracted with EtOAc (2×500 mL). The organic layer was washed with brine (200 mL), dried (Na$_2$SO$_4$) and concentrated in vacuo to get crude. The crude compound was purified by CC (silica-gel; 0-5% EtOAc in PE) to obtain 2-(3-bromo-4-fluoro-phenyl)-4-[[3-(trifluoromethyl)phenyl]sulfanyl]-tetrahydro-pyran (15 g, 90%).

Step 4: 2-(3-Bromo-4-fluoro-phenyl)-4-[[3-(trifluoromethyl)phenyl]sulfonyl]-tetrahydro-pyran OXONE (63.51 g, 103.44 mmol) in H$_2$O (375 mL, 25 vol) was added to a solution of 2-(3-Bromo-4-fluoro-phenyl)-4-[[3-(trifluoromethyl)phenyl]sulfanyl]-tetrahydro-pyran (15 g, 34.48 mmol) in MeOH (450 mL, 30 vol) at RT and stirred for 16 h. After completion of reaction, distilled off MeOH under reduced pressure, the residue was diluted with H$_2$O (300 mL) and extracted with DCM (2×400 mL). The organic layer was washed with brine (100 mL), dried (Na$_2$SO$_4$) and concentrated to get semi pure compound. The semi pure compound was purified by CC (silica-gel; 0-30% EtOAc in PE) to obtain 2-(3-bromo-4-fluoro-phenyl)-4-[[3-(trifluoromethyl)phenyl]sulfonyl]-tetrahydro-pyran (15 g, 93%).

Step 5: 2-(3-Bromo-4-fluoro-phenyl)-4-methyl-4-[[3-(trifluoromethyl)phenyl]sulfonyl]-tetrahydro-pyran A solution of 2-(3-Bromo-4-fluoro-phenyl)-4-[[3-(trifluoromethyl)phenyl]sulfonyl]-tetrahydro-pyran (10 g, 21.41 mmol) in THF (100 mL, 10 vol) was cooled to −78° C. and KOt-Bu (1M solution in THF) (43 mL, 42.82 mmol) was added drop-wise. After stirring for 30 min CH$_3$I was added (3.31 mL, 53.53 mmol) and the resulting mixture was allowed to warm to RT and further stirred for 16 h. The RM was quenched with H$_2$O (200 mL) and extracted with EtOAc (2×100 mL). The combined organic extract was washed with brine (50 mL), dried (Na$_2$SO$_4$) and concentrated under reduced pressure to get crude compound. The crude compound was purified by CC (silica gel; 0-30% EtOAc in PE) to obtain 2-(3-bromo-4-fluoro-phenyl)-4-methyl-4-[[3-(trifluoromethyl)phenyl]sulfonyl]-tetrahydro-pyran (8 g, 80%).

Step 6: 2-(4-Fluoro-3-methylsulfanyl-phenyl)-4-methyl-4-[[3-(trifluoromethyl)phenyl]sulfonyl]-tetrahydro-pyran A solution of 2-(3-bromo-4-fluoro-phenyl)-4-methyl-4-[[3-(trifluoromethyl)phenyl]sulfonyl]-tetrahydro-pyran (4 g, 8.31 mmol) and DIPEA (2.97 mL, 16.63 mmol) in toluene (40 mL) was degassed for 10 min, added Xantphos (0.33 g, 0.58 mmol) followed by Pd$_2$(dba)$_3$ (0.53 g, 0.58 mmol) and degassed again for 10 min. Sodium thiomethoxide (0.87 g, 12.42 mmol) was then added and further degassed for 5 min. The RM was heated at 110° C. for 16 h under Ar. The RM was filtered through celite and the filtrate concentrated to yield the crude product. The crude product was purified by CC (silica gel; 0-25% EtOAc in pet-ether) to obtain 2-(4-fluoro-3-methylsulfanyl-phenyl)-4-methyl-4-[[3-(trifluoromethyl)phenyl]sulfonyl]-tetrahydro-pyran (3.2 g, 86%).

Step 7: 2-(4-Fluoro-3-methylsulfonyl-phenyl)-4-methyl-4-[[3-(trifluoromethyl)phenyl]sulfonyl]-tetrahydro-pyran OXONE (10.27 g, 16.74 mmol) in H$_2$O (62 mL, 25 vol) was added to a solution of 2-(4-Fluoro-3-methylsulfanyl-phenyl)-4-methyl-4-[[3-(trifluoromethyl)phenyl]sulfonyl]-tetrahydro-pyran (2.5 g, 5.58 mmol) in MeOH (75 mL, 30 vol) at RT and stirred for 16 h. After completion of reaction, distilled off MeOH under reduced pressure and the residue was diluted with H$_2$O (80 mL) and extracted with DCM (2×100 mL). The organic layer was washed with brine (100 mL), dried (Na$_2$SO$_4$) and concentrated to get the crude compound. The crude compound was purified by CC (silica-gel; 0-40% EtOAc in PE) to obtain 2-(4-fluoro-3-methylsulfonyl-phenyl)-4-methyl-4-[[3-(trifluoromethyl)phenyl]sulfonyl]-tetrahydro-pyran (1.5 g, 56%).

$^1$H-NMR (600 MHz, [d$_6$]-DMSO): δ =8.21-8.22 (1H), 8.16-8.17 (1H), 8.05 (1H), 7.93-7.96 (1H), 7.84-7.85 (1H), 7.74-7.77 (1H), 7.49-7.52 (1H), 4.69-4.70 (1H), 4.07-4.11 (1H), 3.69-3.74 (1H), 3.33 (3H), 2.13-2.19 (1H), 1.85-1.88 (1H), 1.79-1.81 (1H), 1.50 (3H), 1.46-1.48 (1H).

NOE: C-2 proton & methyl=cis

Chiral resolution of 2-(4-Fluoro-3-methylsulfonyl-phenyl)-4-methyl-4-[[3-(trifluoromethyl)phenyl]sulfonyl]-tetrahydro-pyran Cis-rac 2-(4-Fluoro-3-methylsulfonyl-phenyl)-4-methyl-4-[[3-(trifluoromethyl)phenyl]sulfonyl]-tetrahydro-pyran was subjected to preparative chiral-SFC (Chiralpak-IC column, co-solvent EtOH) to give cis-EN1 SC-212 and cis-EN2 SC-213.

Cis-EN1 SC-212—analytical HPLC: Chiralpak IA (250× 4.6 mm 5μ), 1 ml/min, RT, 0.1% TFA in hexane/EtOH 50/50, Ret. Time 5.49; ee>95%

Cis-EN2 SC-213—analytical HPLC: Chiralpak IA (250× 4.6 mm 5μ), 1 ml/min, RT, 0.1% TFA in hexane/EtOH 50/50, Ret. Time 6.48; ee>95%

2-(4-Chloro-2-methyl-phenyl)-4-methyl-4-[[3-(trifluoromethyl)phenyl]sulfonyl]-tetrahydro-pyran (Example 23)

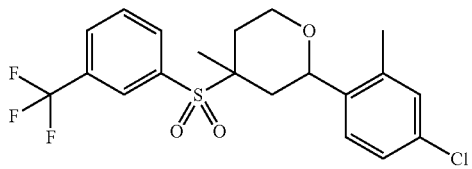 [SMILES: Cc1cc(Cl)ccc1C1CC(C)(S(=O)(=O)c2cccc(C(F)(F)F)c2)CCO1]

Step 1: 2-(4-chloro-2-methylphenyl)tetrahydro-2H-pyran-4-ol 4-chloro-2-methyl-benzaldehyde (10 g, 64.93 mmol) was dissolved in DCE (200 mL), cooled in an ice bath and TFA (80 mL) followed by 3-butenol (6.76 mL, 77.79 mmol) was added and stirred at RT for 62 h. The mixture was concentrated in vacuo and the residue diluted with water (500 mL), basified with 6M NaOH (aq) and extracted with DCM (800 mL). The organic layer was separated and washed with brine, dried ($Na_2SO_4$) and concentrated under reduced pressure to get the crude product. The crude product was dissolved in MeOH (125 mL) and LiOH (13.63 g, 324.52 mmol) was added. The reaction was stirred at RT for 5 h. MeOH was concentrated under reduced pressure and the residue was diluted with DCM (200 mL) and washed with water (100 mL), brine (100 mL), dried ($Na_2SO_4$) and concentrated in vacuo to get crude. Purification by CC (silica gel, 0-15% EtOAc in PE) gave 2-(4-chloro-2-methylphenyl)tetrahydro-2H-pyran-4-ol (7.8 g; 54%) as a thick liquid.

Step 2: 2-(4-chloro-2-methylphenyl)tetrahydro-2H-pyran-4-ylmethanesulfonate Methanesulfonyl chloride (3.59 mL, 46.43 mmol) was added to a solution of 2-(4-chloro-2-methylphenyl)tetrahydro-2H-pyran-4-ol (7 g, 30.97 mmol) and DIPEA (13.39 mL, 77.36 mmol) in DCM (70 mL) at 0° C. The RM was allowed to warm to RT and stirred for 16 h. The mixture was diluted with DCM (500 mL) and washed sequentially with 1N HCl (100 mL), sat. $NaHCO_3$ solution (100 mL), $H_2O$ (100 mL), brine (100 mL), dried ($Na_2SO_4$) and concentrated under reduced pressure to get crude 2-(4-chloro-2-methyl-phenyl)tetrahydro-2H-pyran-4-ylmethanesulfonate (9.7 g) as a thick liquid.

Step 3: 2-(4-chloro-2-methyl phenyl)-4-(3-(trifluoromethyl)phenylthio)tetrahydro-2H-pyran 3-Trifluoromethyl thiophenol (13 mL, 95.67 mmol) was added to a suspension of 2-(4-chloro-2-methylphenyl)tetrahydro-2H-pyran-4-ylmethanesulfonate (9.7 g, 31.90 mmol) and $K_2CO_3$ (8.81 g, 63.74 mmol) in DMF (140 mL) and the RM was heated to 50° C. for 5 h and continued at RT for 16 h. After completion of reaction, the RM was diluted with water (250 mL) and extracted with EtOAc (500 mL). The organic extract was washed with $H_2O$ (200 mL), brine (100 mL), dried ($Na_2SO_4$) and concentrated under reduced pressure to get crude compound. The crude compound was purified by CC (silica gel, 0-1.5% EtOAc in PE) to obtain 2-(4-chloro-2-methylphenyl)-4-(3-(trifluoromethyl)phenylthio)tetrahydro-2H-pyran (7 g, 56%) as a thick liquid.

Step 4: 2-(4-chloro-2-methyl phenyl)-4-(3-(trifluoromethyl)phenylsulfonyl)tetrahydro-2H-pyran 2-(4-chloro-2-methylphenyl)-4-(3-(trifluoromethyl)phenylthio)tetrahydro-2H-pyran (7 g, 18.13 mmol) was dissolved in MeOH (200 mL) and a solution of OXONE (22.26 g, 36.26 mmol) in Water (120 mL) was added and stirred at RT for 1 h and additional OXONE (9.9 g, 16.12 mmol) in Water (60 mL) was added to it and stirred continued at RT for 16 h. MeOH was concentrated in vacuo; the residue was diluted with water (100 mL) and extracted with EtOAc (500 mL). The organic extract was washed with brine (150 mL), dried ($Na_2SO_4$) and concentrated to get crude. The crude compound was purified by CC (silica gel, 0-18% EtOAc in PE) to obtain 2-(4-chloro-2-methylphenyl)-4-(3-(trifluoromethyl)phenylsulfonyl)tetrahydro-2H-pyran (5 g, 66%) as a solid.

Step 5: 2-(4-Chloro-2-methyl-phenyl)-4-methyl-4-[[3-(trifluoromethyl)phenyl]sulfonyl]-tetrahydro-pyran A solution of 2-(4-chloro-2-methylphenyl)-4-(3-(trifluoromethyl)phenylsulfonyl)tetrahydro-2H-pyran (2 g, 4.78 mmol) in THF (40 mL) was cooled to −78° C. and KOt-Bu (1M solution in THF; 9.56 mL) was added drop-wise, then added $CH_3I$ (0.74 mL, 11.90 mmol) and the resulting mixture was warmed to RT and stirred for 48 h. The RM was diluted with EtOAc (200 mL) and washed with $H_2O$ (50 mL), brine (50 mL), dried over ($Na_2SO_4$) and concentrated under reduced pressure to get crude compound. The crude compound was purified by CC (silica gel, 0-15% EtOAc in PE) to obtain 2-(4-Chloro-2-methyl-phenyl)-4-methyl-4-[[3-(trifluoromethyl)phenyl]sulfonyl]-tetrahydro-pyran (1 g, 48%) as a white solid.

$^1$H-NMR (600 MHz, [$d_6$]-DMSO): δ =8.20-8.22 (1H), 8.16-8.18 (1H), 8.05 (1H), 7.93-7.96 (1H), 7.34-7.35 (1H), 7.24-7.25 (2H), 4.69-4.71 (1H), 4.03-4.06 (1H), 3.72-3.75 (1H), 2.24 (3H), 2.12-2.17 (1H), 1.84-1.88 (1H), 1.64-1.67 (1H), 1.52 (3H), 1.46-1.48 (1H) ppm.

NOE: C-2 proton & methyl=cis

Chiral resolution of 2-(4-Chloro-2-methyl-phenyl)-4-methyl-4-[[3-(trifluoromethyl)phenyl]sulfonyl]-tetrahydro-pyran Cis-rac 2-(4-Chloro-2-methyl-phenyl)-4-methyl-4-[[3-(trifluoromethyl)phenyl]sulfonyl]-tetrahydro-pyran (900 mg) was subjected to preparative chiral-LC (Chiralpak-IE column, Hexane:EtOH, 70:30)) to give 385 mg of cis-EN1 SC-224 and 390 mg of cis-EN2 SC-225.

cis-EN1 SC-224—analytical HPLC: Chiralpak IE (250× 4.6 mm 5µ), 1 ml/min, RT, hexane/EtOH 60/40, Ret. Time 4.880; ee>95% cis-EN2 SC-225—analytical HPLC: Chiralpak IE (250× 4.6 mm 5µ), 1 ml/min, RT, hexane/EtOH 60/40, Ret. Time 5.820; ee>95%

2-(4-Chloro-3-methoxy-phenyl)-4-methyl-4-[[3-(trifluoromethyl)phenyl]sulfonyl]-tetrahydro-pyran (Example 24)

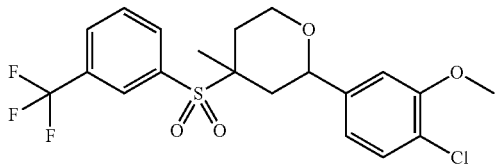 [SMILES: COc1cc(C2CC(C)(S(=O)(=O)c3cccc(C(F)(F)F)c3)CCO2)ccc1Cl]

Step 1:
2-(4-chloromethoxyphenyl)tetrahydro-2H-pyran-4-ol

TFA (48 mL) was added to a stirred solution of 4-chloro-3-methoxy benzaldehyde (6 g, 35.16 mmol) in DCE (120 mL) at 0° C. and 3-buten-1-ol (2.53 g, 35.16 mmol) was added dropwise to the RM at the same temperature and stirred it for 3 d at RT. The RM was diluted with $H_2O$ (100 mL) and the aq. layer was basify with 6 N NaOH (pH-10), the aq layer was extracted with DCM (2×100 mL). The combined organic layer was successively washed with $H_2O$ (100 mL), brine (100 mL), then dried ($Na_2SO_4$), filtered and evaporated to give crude. LiOH (7.38 g, 35.16 mmol) was added to a stirred solution of the crude compound in MeOH (120 mL) at RT. The RM was stirred for 16 h at RT. The RM was evaporated to give the residue, the residue was diluted with $H_2O$ (150 mL) and extracted with EtOAc (3×1 00 mL), the combined organic layer was washed with brine (100 ml).), then dried ($Na_2SO_4$), filtered and evaporated the solvent under vacuo to give crude. Which was purified by CC (silica gel, 25-30% EtOAc in PE) to give 2-(4-chloromethoxyphenyl)tetrahydro-2H-pyran-4-ol (6 g, 70%) as a liquid.

Step 2: 2-(4-chloro-3-metoxyphenyl)tetrahydro-2H-pyran-4-yl methanesulfonate

DIPEA (10.82 ml, 61.97 mmol) was added to a stirred solution of 2-(4-chloromethoxyphenyl)tetrahydro-2H-pyran-4-ol (6 g, 24.79 mmol) in DCM (60 mL) at 0° C., then methane sulfonylchloride (2.89 mL, 37.19 mmol) was added at the same temperature, and stirred for 16 h at RT, the RM was poured in ice $H_2O$ (150 mL), and separate the organic layer. The aq layer was extracted with DCM (2×100 mL). The organic layer was successively washed with sat $NaHCO_3$ solution (50 mL), water (50 mL) and brine (50 mL), The organic layer was dried ($Na_2SO_4$), filtered and evaporated under vaccuo to give 2-(4-chloro-3-methoxyphenyl)tetrahydro-2H-pyran-4-yl methanesulfonate (12 g) as a black color thick compound. This crude was used for next step without further purification.

Step 3: 2-(4-chloro-3-methoxyphenyl)-4-(3-(trifluoromethyl)phenylthio)tetrahydro-2H-pyran $K_2CO_3$ (7.76 g, 56.24 mmol) was added to a stirred solution of 2-(4-chloro-3-metoxyphenyl)tetrahydro-2H-pyran-4-yl methanesulfonate (8 g, 25.12 mmol) in DMF (90 mL), then 3-trifloromethylthiophenol (10 mL, 75.37 mmol) was added and the RM was heated to 50° C. for 6 h, the RM was allowed to cool to RT, then the RM was diluted with water and extracted with EtOAc (3×100 mL). The organic layer was washed with brine (100 mL), then dried ($Na_2SO_4$), filtered and evaporated the solvent under vacuo to give crude, which was purified by CC (silicagel, 10% EtOAc in PE) to give 2-(4-chloro-3-methoxyphenyl)-4-(3-(trifluoromethyl)phenylthio)tetrahydro-2H-pyran (8 g, 78%), as a brown color liquid.

Step 4: 2-(4-chlor-3-methoxyophenyl)-4-(3-(trifluoromethyl)phenylsulfonyl)tetrahydro-2H-pyran Oxone (21.37 g, 34.82 mmol) in $H_2O$ (14 7 mL) was added to a stirred solution of 2-(4-chloro-3-methoxyphenyl)-4-(3-(trifluoromethyl)phenylthio)tetrahydro-2H-pyran (7.0 g, 17.12 mmol) in MeOH (210 mL) at RT. After stirring for 30 min, again Oxone (10.68 g, 17.41 mmol) in $H_2O$ (28 mL) were added and then the RM was stirred for 16 h at RT. The RM was concentrated to give the residue, the residue was diluted with EtOAc (100 mL) and washed with water (200 mL), the aq. layer was extracted with EtOAc (3×100 mL). The combined organic layer was washed with brine (100 mL), then dried ($Na_2SO_4$), filtered and evaporated the solvent under vaccuo to give crude, which as purified by CC (silica-gel, 20-23% EtOAc in PE) to give 2-(4-chlor-3-methoxyophenyl)-4-(3-(trifluoromethyl)phenylsulfonyl)tetrahydro-2H-pyran (7 g, 81%) as a white solid.

Step 5: 2-(4-Chloro-3-methoxy-phenyl)-4-methyl-4-[[3-(trifluoromethyl)phenyl]sulfonyl]-tetrahydropyran KOt-Bu (9.21 mL, 9.21 mmol, 1 M in THF) was added to a stirred solution of 2-(4-chlor-3-methoxyphenyl)-4-(3-(trifluoromethyl)phenylsulfonyl)tetrahydro-2H-pyran (2.0 g, 4.60 mmol) in THF (40 mL) at −78° C., then stirred for 5 min. $CH_3I$ (0.71 mL, 11.50 mmol) was added and stirred for 1 h at −78° C., the RM was slowly warmed to RT and stirred for 18 h, the RM was poured into ice-water (50 mL) and extracted with EtOAc (3×100 mL). The combined organic layer was washed with brine, then dried ($Na_2SO_4$), filtered and evaporated the solvent under vacuo to give crude, which was purified by CC (silica gel, 20-25% EtOAc in PE) to give 2-(4-chloro-3-methoxy-phenyl)-4-methyl-4-[[3-(trifluoromethyl)phenyl]sulfonyl]-tetrahydro-pyran (1.0 g, 48.5%) as a white solid.

$^1$H-NMR (600 MHz, [$d_6$]-DMSO): δ =8.21-8.22 (1H), 8.15-8.17 (1H), 8.04 (1H), 7.93-7.96 (1H), 7.36-7.37 (1H), 7.07 (1H), 6.90-6.91 (1H), 4.54-4.56 (1H), 4.04-4.08 (1H), 3.84 (3H), 3.67-3.72 (1H), 2.10-2.16 (1H), 1.86-1.89 (1H), 1.73-1.75 (1H), 1.50 (3H), 1.46-1.48 (1H) ppm.

NOE: C-2 proton & methyl=cis

Chiral resolution of 2-(4-Chloro-3-methoxy-phenyl)-4-methyl-4-[[3-trifluoromethyl)phenyl]sulfonyl]-tetrahydro-pyran Cis-rac 2-(4-Chloro-3-methoxy-phenyl)-4-methyl-4-[[3-(trifluoromethyl)phenyl]sulfonyl]-tetrahydro-pyran (1 g)

was subjected to preparative chiral-LC (Chiralpak-IA column, Hexane:Ethanol: (90:10)) to give 176 mg of cis-EN1 SC-226 and 167 mg of cis-EN2 SC-227.

cis-EN1 SC-226—analytical HPLC: Chiralpak IA (250× 4.6 mm 5μ), 1 ml/min, RT, 0.1% TFA in hexane/iPrOH 80/20, Ret. Time 6.527; ee>95%/specific rotation $[\alpha]_D^{25.1}$ −11.0° (c 0.67; DCM).

cis-EN2 SC-227—analytical HPLC: Chiralpak IA (250× 4.6 mm 5μ), 1 ml/min, RT, 0.1% TFA in hexane/iPrOH 80/20, Ret. Time 10.277; ee>95%/specific rotation $[\alpha]_D^{25.1}$ +10.9° (c 0.81; DCM).

2-(3-Chloro-4-fluoro-phenyl)-4-methyl-4-[[3-(trifluoromethyl)phenyl]sulfonyl]-tetrahydro-pyran (Example 25)

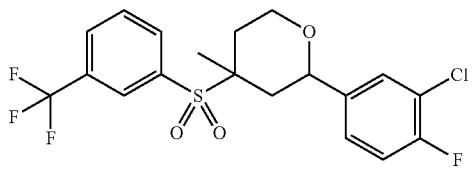 [SMILES: CC1(S(=O)(=O)c2cccc(C(F)(F)F)c2)CCOC(c2ccc(F)c(Cl)c2)C1]

Step 1: 2-(3-chloro-4-fluorophenyl)tetrahydro-2H-pyran-4-ol 3-buten-1-ol (3.95 mL, 45.48 mmol) was added to a solution of 3-chloro-4-fluoro benzaldehyde (6 g, 38.21 mmol) in DCE (120 mL), followed by TFA (48 mL) and the RM was stirred for 72 h at RT. After completion of reaction, the solvent was removed under reduced pressure. The residue was diluted with H₂O (100 mL) and basified using 6 N NaOH solution, the aq layer was extracted with DCM (500 mL). The organic layer was washed with H₂O (100 mL), brine (100 mL) and concentrated under reduced pressure to get the crude compound. The crude compound was dissolved in MeOH (70 mL), added LiOH (4.5 g, 107 mmol) and stirred for 5 h at RT. The RM was concentrated under reduced pressure and the residue was diluted with DCM (300 mL); and was subsequently washed with H₂O (100 mL) and brine (100 mL), dried (Na₂SO₄) and concentrated in vacuo to get crude. Purification by CC (silica gel, 0-18% EtOAc in PE) gave 2-(3-chloro-4-fluorophenyl)tetrahydro-2H-pyran-4-ol (5.5 g; 64%) as thick liquid.

Step 2: 2-(3-chloro-4-fluorophenyl)tetrahydro-2H-pyran-4-yl methanesulfonate

Methanesulfonylchloride (3 mL, 39 mmol) was added to a solution of 2-(3-chloro-4-fluorophenyl)-tetrahydro-2H-pyran-4-ol (6 g, 26 mmol) and DIPEA (11.3 mL, 65 mmol) in DCM (60 mL) at 0° C. and stirred for 16 h at RT. After completion of reaction, the RM was poured in ice water (100 mL) and extracted with DCM (2×200 mL). The combined organic layer was washed with sat NaHCO₃ solution (100 mL), H₂O (100 mL) and brine (100 mL) solution, dried (Na₂SO₄). Distilled off solvent under reduced pressure to get 2-(3-chloro-4-fluorophenyl)tetrahydro-2H-pyran-4-yl methanesulfonate (7.1 g) as a thick liquid. The crude compound was used in the next step without any further purification.

Step 3: 2-(3-chloro-4-fluorophenyl)-4-(3-(trifluoromethyl)phenylthio)tetrahydro-2H-pyran K₂CO₃ (10.97 g, 79.49 mmol) and 3-trifluoromethylthiophenol (12.14 mL, 68.18 mmol) were added to a solution of 2-(3-chloro-4-fluorophenyl)tetrahydro-2H-pyran-4-yl methanesulfonate (7 g, 22.72 mmol) in DMF (70 mL) was and the RM was heated to 50° C. for 4 h, then stirred at RT for 16 h. After completion of reaction, the mixture was diluted with H₂O (100 mL) and extracted with EtOAc (2×200 mL). The organic layer was washed with brine (100 mL), dried (Na₂SO₄) and concentrated in vacuo to get crude. The crude compound was purified by CC (silica-gel, eluent as 0-2% EtOAc in PE to yield 2-(3-chloro-4-fluorophenyl)-4-(3-(trifluoromethyl)phenylthio)tetrahydro-2H-pyran (4.8 g, 54%), as a liquid.

Step 4: 2-(3-chloro-4-fluorophenyl)-4-(3-(trifluoromethyl)phenylsulfonyl)tetrahydro-2H-pyran OXONE (14.8 g, 24.10 mmol) in H₂O (35 mL) was added to a solution of 2-(3-chloro-4-fluorophenyl)-4-(3-(trifluoromethyl)phenylthio)tetrahydro-2H-pyran (4.7 g, 12.05 mmol) in MeOH (40 mL) at RT and stirred for 30 min, again added OXONE (7.4 g, 12.05 mmol) in H₂O (25 mL) and stirred for 16 h at RT. After completion of reaction distilled off MeOH under reduced pressure and the residue was diluted with H₂O (100 mL) and extracted with EtOAc (2×200 mL). The organic layer was washed with brine (100 mL), dried (Na₂SO₄) and concentrated to get crude compound which was purified by silica-gel CC; using 30% EtOAc in PE to get 2-(3-chloro-4-fluorophenyl)-4-(3-(trifluoromethyl)phenylsulfonyl)tetrahydro-2H-pyran (3 g, 59%) as a white solid.

Step 5: 2-(3-Chloro-4-fluoro-phenyl)-4-methyl-4-[[3-(trifluoromethyl)phenyl]sulfonyl]-tetrahydro-pyran A solution of 2-(3-chloro-4-fluorophenyl)-4-(3-(trifluoromethyl)phenylsulfonyl)tetrahydro-2H-pyran (1.5 g, 3.55 mmol) in THF (30 mL) was cooled to −78° C. and KOt-Bu (1 M solution in THF; 7 mL, 7.0 mmol) was added dropwise, then added CH₃I (0.55 mL, 8.87 mmol) and the resulting mixture was warmed to RT and stirred for 16 h. The RM was diluted with EtOAc (200 mL) and washed with H₂O (50 mL), brine (50 mL), dried (Na₂SO₄) and concentrated under reduced pressure to get crude compound. The crude compound was purified by CC (silica gel, 0-25% EtOAc in PE) to obtain 2-(3-chloro-4-fluoro-phenyl)-4-methyl-4-[[3-(trifluoromethyl)phenyl]sulfonyl]-tetrahydro-pyran (0.9 g, 58%) as a white solid.

¹H-NMR (600 MHz, [d₆]-dmso): δ =8.20-8.22 (1H), 8.16-8.17 (1H), 8.05 (1H), 7.93-7.96 (1H), 7.53-7.54 (1H), 7.34-7.40 (2H), 4.56-4.58 (1H), 4.04-4.07 (1H), 3.68-3.71 (1H), 2.10-2.16 (1H), 1.83-1.87 (1H), 1.74-1.76 (1H), 1.46-1.49 (4H) ppm.

NOE: C-2 proton & methyl=cis

Chiral resolution of 2-(3-Chloro-4-fluoro-phenyl)-4-methyl-4-[[3-(trifluoromethyl)phenyl]sulfonyl]-tetrahydro-pyran Cis-rac 2-(3-Chloro-4-fluoro-phenyl)-4-methyl-4-[[3-(trifluoromethyl)phenyl]sulfonyl]-tetrahydro-pyran (900 mg) was subjected to preparative chiral-LC (Chiralpak-IC column, Hexane:iPrOH: (90:10)) to give 121 mg of cis-EN1 SC-228 and 70 mg of cis-EN2 SC-229.

cis-EN1 SC-228—analytical HPLC: Chiralpak IC (250× 4.6 mm 5μ), 1 ml/min, RT, hexane/iPrOH 90/10, Ret. Time 9.91; ee>95% cis-EN2 SC-229—analytical HPLC: Chiralpak IC (250× 4.6 mm 5μ), 1 ml/min, RT, hexane/iPrOH 90/10, Ret. Time 11.28; ee>95%

2-(4-Chlorophenyl)-4-ethyl-4-[[3-(trifluoromethyl)phenyl]sulfonyl]-tetrahydro-pyran (Example 26)

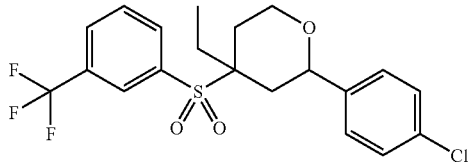 [SMILES: CCC1(S(=O)(=O)c2cccc(C(F)(F)F)c2)CCOC(c2ccc(Cl)cc2)C1]

2-(4-Chlorophenyl)-4-ethyl-4-[[3-(trifluoromethyl)phenyl]sulfonyl]-tetrahydro-pyran A solution of cis-2-(4-chlorophenyl)-4-(3-(trifluoromethyl)phenylsulfonyl)tetrahydro-2H-pyran (2.0 g, 4.95 mmol) in THF (40 mL) was cooled to −78° C. and KOt-Bu (1M solution in THF; 10 mL, 10 mmol) was added dropwise, then added $C_2H_5I$ (1 mL, 12.37 mmol) and the resulting mixture was allowed to RT and stirred for 16 h. The RM was diluted with EtOAc (200 mL) and washed with $H_2O$ (50 mL), brine (50 mL), dried over ($Na_2SO_4$) and concentrated under reduced pressure to get crude compound. The crude compound was purified by CC (silica gel, 0-25% EtOAc in PE) to obtain 2-(4-chlorophenyl)-4-ethyl-4-[[3-(trifluoromethyl)phenyl]sulfonyl]-tetrahydro-pyran (0.8 g, 37%) as a white solid.

$^1$H-NMR (600 MHz, [$d_6$]-DMSO): δ =8.21-8.22 (1H), 8.14-8.16 (1H), 8.02 (1H), 7.93-7.96 (1H), 7.39-7.40 (2H), 7.32-7.33 (2H), 4.54-4.56 (1H), 4.01-4.03 (1H), 3.66-3.69 (1H), 1.99-2.05 (3H), 1.85-1.87 (1H), 1.75-1.79 (1H), 1.65-1.67 (1H), 1.01-1.04 (3H) ppm.

NOE: ethyl & C2-Proton=cis

Chiral resolution of 2-(4-Chlorophenyl)-4-ethyl-4-[[3-(trifluoromethyl)phenyl]sulfonyl]-tetrahydro-pyran Cis-rac 2-(4-Chlorophenyl)-4-ethyl-4-[[3-(trifluoromethyl)phenyl]sulfonyl]-tetrahydro-pyran (800 mg) was subjected to preparative chiral-LC (Chiralpak-IE column, Hexane:iPrOH: (90:10)) to give 129 mg of cis-EN1 SC-230 and 125 mg of cis-EN2 SC-231.

cis-EN1 SC-230—analytical HPLC: Chiralpak IE (250× 4.6 mm 5μ), 1 ml/min, RT, 0.1% iPrNH$_2$ in hexane/iPrOH 90/10, Ret. Time 11.556; ee>95% cis-EN2 SC-231—analytical HPLC: Chiralpak IE (250× 4.6 mm 5μ), 1 ml/min, RT, hexane/iPrOH 90/10, Ret. Time 12.46; ee>95%

4-Methyl-2-[2-methylsulfonyl-4-(trifluoromethyl)phenyl]-4-[[3-(trifluoromethyl)phenyl]sulfonyl]-tetrahydro-pyran (Example 27)

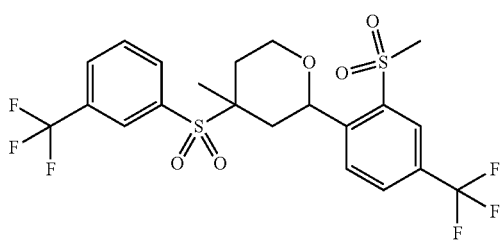 [SMILES: CC1(S(=O)(=O)c2cccc(C(F)(F)F)c2)CCOC(c2ccc(C(F)(F)F)cc2S(C)(=O)=O)C1]

Step 1: 2-(2-bromo-4-(trifluoromethyl)phenyl)tetrahydro-2H-pyran-4-ol 2-bromo-4-(trifluoromethyl)benzaldehyde (2 g, 7.90 mmol) was dissolved in DCE (40 mL) and cooled in an ice bath. TFA (16 mL) followed by 3-butenol (0.82 mL, 9.48 mmol) were added and the mixture stirred at RT for 48 h. The mixture was diluted with $H_2O$ (100 mL), basified with 6 M NaOH (aq) and extracted with DCM (100 mL). Organic layer was separated and washed with brine, dried ($Na_2SO_4$) and concentrated under reduced pressure to get crude. The crude product was dissolved in MeOH (35 mL) and LiOH (1.6 g, 42.16 mmol) was added. The reaction was stirred at RT for 16 h. MeOH was concentrated under reduced pressure and the residue was diluted with DCM (100 mL) and washed with $H_2O$ (50 mL), brine (50 mL), dried ($Na_2SO_4$) and concentrated in vacuo to get crude. The crude compound was purified by CC (silica gel, 0-20% EtOAc in PE) to obtain 2-(2-bromo-4-(trifluoromethyl)phenyl)tetrahydro-2H-pyran-4-ol (2.0 g, 80%) as pale yellow solid.

Step 2: 2(2-bromo-4-(trifluoromethyl)phenyl)tetrahydro-2H-pyran-4-ylmethanesulfonate Methanesulfonyl chloride (0.9 mL, 11.53 mmol) was added to a solution of 2-(2-bromo-4-(trifluoromethyl)phenyl)tetrahydro-2H-pyran-4-ol (2.5 g, 7.69 mmol) and DIPEA (3.3 mL, 19.23 mmol) in DCM (25 mL) at 0° C.; allowed to warm to RT and stirred for 16 h. The mixture was diluted with DCM (100 mL) and washed sequentially with 1 N HCl (50 mL), sat. NaHCO$_3$ solution (50 mL), $H_2O$ (50 mL), brine (50 mL), dried ($Na_2SO_4$) and concentrated under reduced pressure to get crude 2(2-bromo-4-(trifluoromethyl)-phenyl)tetrahydro-2H-pyran-4-ylmethanesulfonate (3 g) as a solid.

Step 3: 2-(2-bromo-4-(trifluoromethyl)phenyl)-4-(3-(trifluoromethyl)phenylthio)tetrahydro-2H-pyran 3-Trifluoromethyl thiophenol (3.0 mL, 22.33 mmol) was added to a suspension of 2(2-bromo-4-(trifluoromethyl)phenyl)tetrahydro-2H-pyran-4-ylmethanesulfonate (3.0 g, 7.44 mmol) and K$_2$CO$_3$ (2.0 g, 14.88 mmol) in DMF (30 mL) and the RM was heated at 60° C. for 6 h and then stirred at RT for 16 h. After completion of reaction, the RM was diluted with $H_2O$ (100 mL) and extracted with EtOAc (250 mL). The organic extract was washed with $H_2O$ (100 mL), brine (100 mL), dried (Na$_2$SO$_4$) and concentrated under reduced pressure to get crude compound. The crude compound was purified by CC (silica gel, 0-10% EtOAc in PE) to obtain 2-(2-bromo-4-(trifluoromethyl)phenyl)-4-(3-(trifluoromethyl)phenylthio)tetrahydro-2H-pyran (2.4 g, 66%) as a yellow oily liquid.

Step 4: 2-(2-bromo-4-(trifluoromethyl)lphenyl)-4-(3-(trifluoromethyl)phenylsulfonyl)tetrahydro-2H-pyran 2-(2-bromo-4-(trifluoromethyl)phenyl)-4-(3-(trifluoromethyl)phenylthio)tetrahydro-2H-pyran (2.4 g, 4.94 mmol) was dissolved in MeOH (72 mL) and a solution of OXONE (15.2 g, 24.74 mmol) in $H_2O$ (60 mL) was added. The total reaction mass was stirred at RT for 16 h. MeOH was concentrated in vacuo; the residue was diluted with $H_2O$ (80 mL) and extracted with EtOAc (2×100 mL). The combined organic extract was washed with brine (100 mL), dried (Na$_2$SO$_4$) and concentrated to get crude. The crude compound was purified by CC (silica gel, 0-20% EtOAc in PE) to obtain 2-(2-bromo-4-(trifluoromethyl)phenyl)-4-(3-(trifluoromethyl)phenylsulfonyl)tetrahydro-2H-pyran (1.6 g, 66%) as a solid.

Step 5: 2-(2-bromo-4-(trifluoromethylphenyl)-4-methyl-4-(3-(trifluoromethyl)phenylsulfonyl)tetrahydro-2H-pyran A solution of 2-(2-bromo-4-(trifluoromethyl)lphenyl)-4-(3-(trifluoromethyl)phenylsulfonyl)tetrahydro-2H-pyran (1.6 g, 3.09 mmol) in THF (10 mL) was cooled to −78° C. and KOt-Bu (1 M solution in THF; 6.18 mL, 6.18 mmol) was added dropwise. CH₃I (0.5 mL, 7.73 mmol) was added and the resulting mixture was warmed to RT and stirred for 16 h. The reaction mass was diluted with EtOAc (100 mL) and washed with H₂O (30 mL) and brine (30 mL), dried (Na₂SO₄) and concentrated under reduced pressure to get crude compound. The crude compound was washed with n-pentane to obtain 2-(2-bromo-4-(trifluoromethylphenyl)-4-methyl-4-(3-(trifluoromethyl)phenylsulfonyl)tetrahydro-2H-pyran (1.5 g, 82%) as a white solid.

Step 6: 2-(2-methylthio)-4-(trifluoromethylphenyl)-4-(3-(trifluoromethyl)phenylsulfonyl)tetrahydro-2H-pyran Sodium thiomethoxide (0.203 g, 2.90 mmol) was added to a clear solution of 2-(2-bromo-4-(trifluoromethylphenyl)-4-methyl-4-(3-(trifluoromethyl)phenylsulfonyl)tetrahydro-2H-pyran (0.5 g, 0.96 mmol) in DMF (10 mL) at 0° C. The total reaction mass was stirred at RT for 4 h. The reaction mass was dumped into ice water, solid was precipitated; the solid was filtered and washed with chilled H₂O. The compound was kept for drying for 3 h to obtain 2-(2-methylthio)-4-(trifluoromethylphenyl)-4-(3-(trifluoromethyl)phenylsulfonyl)-tetrahydro-2H-pyran (0.4 g, 83%) as a white solid.

Step 7: 4-Methyl-2-[2-methylsulfonyl-4-(trifluoromethyl)-phenyl]-4-[[3-(trifluoromethyl)phenyl]sulfonyl]-tetrahydro-pyran 2-(2-methylthio)-4-(trifluoromethyl phenyl)-4-(3-(trifluoromethyl)phenylsulfonyl)tetrahydro-2H-pyran (0.4 g, 0.80 mmol) was dissolved in MeOH (12 mL) and a solution of OXONE (2.46 g, 4.016 mmol) in H₂O (10 mL) was added. The total reaction mass was stirred at RT for 16 h. MeOH was concentrated in vacuo; the residue was diluted with H₂O (80 mL) and extracted with EtOAc (2×100 mL). The combined organic extract was washed with brine (100 mL), dried (Na₂SO₄) and concentrated to get crude. The crude compound was purified by CC (silica gel, 0-30% EtOAc in PE) to obtain cis-rac 4-methyl-2-[2-methylsulfonyl-4-(trifluoromethyl)-phenyl]-4-[[3-(trifluoromethyl)phenyl]sulfonyl]-tetrahydro-pyran (0.22 g, 51%) as a solid.

¹H-NMR (600 MHz, [d₆]-DMSO): δ =8.20-8.22 (1H), 8.13-8.18 (3H), 8.05 (1H), 7.98-8.01 (1H), 7.91-7.95 (1H), 5.27-5.31 (1H), 4.08-4.13 (1H), 3.86-3.91 (1H), 3.39 (3H), 2.17-2.23 (1H), 1.97-2.01 (1H), 1.83-1.88 (1H), 1.50-1.53 (1H), 1.48 (3H) ppm.

NOE: C-2 proton & methyl=cis 2-(4-Chlorophenyl)-4-[[3-(trifluoromethyl)phenyl] sulfonyl]-tetrahydro-pyran (Example 39)

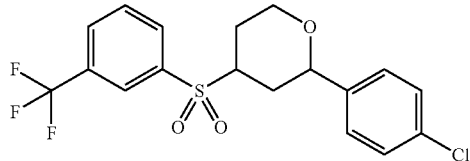 [SMILES: O=S(=O)(c1cccc(C(F)(F)F)c1)C1CCOC(c2ccc(Cl)cc2)C1]

Step 1: 2-(4-chlorophenyl)tetrahydro-2H-pyran-4-ol

To a solution of 4-chlorobenzaldehyde (10 g, 71.13 mmol) in DCE (200 mL) was added 3-buten-1-ol (8.19 g, 113.82 mmol), TFA (80 mL) and the RM was stirred for 2 d at RT. After completion of the reaction, the solvent is removed under reduced pressure. The residue was diluted with H₂O (100 mL) and basified using 6 N NaOH solution, the aq layer was extracted with DCM (2×200 mL). The organic layer was washed with H₂O (100 mL), brine (100 mL) and concentrated under reduced pressure to get the crude compound. The crude compound was dissolved in MeOH (100 mL), added LiOH (8.5 g, 356.65 mmol) and stirred for 5 h at RT. MeOH was concentrated under reduced pressure, then diluted with EtOAc (300 mL) and subsequently washed with H₂O (100 mL), brine (100 mL), dried (Na₂SO₄) and concentrated in vacuo to get the crude product, which was purified by CC (silica gel, 0-30% EtOAc in PE) gave 2-(4-chlorophenyl)tetrahydro-2H-pyran-4-ol (10 g; 72%) as pale-yellow solid.

Step 2: 2-(4-chlorophenyl)tetrahydro-2H-pyran-4-yl methanesulfonate

Methane sulfonylchloride (5.45 mL, 70.74 mmol) was added to a solution of 2-(4-chlorophenyl)tetrahydro-2H-pyran-4-ol (10 g, 47.16 mmol) and DIPEA (15.2 g, 117.9 mmol) in DCM (100 mL) at 0° C. and stirred for 16 h at RT. After completion of reaction, the RM was poured in ice water (150 mL) and extracted with DCM (2×200 mL). The combined organic layer was washed with sat NaHCO₃ solution (50 mL), water (50 mL) and brine (50 mL) solution, dried (Na₂SO₄). Distilled off solvent under reduced pressure to get 2-(4-chlorophenyl)tetrahydro-2H-pyran-4-yl methanesulfonate (12 g) as a thick liquid. The crude compound was used in the next step without any further purification.

Step 3: 2-(4-chlorophenyl)-4-(3-(trifluoromethyl) phenylthio)tetrahydro-2H-pyran To a solution of 2-(4-chlorophenyl)tetrahydro-2H-pyran-4-yl methanesulfonate (12 g, 41.38 mmol) in DMF (100 mL) was added K₂CO₃ (11.42 g, 82.75 mmol) and 3-trifluoromethylthiophenol (17 mL, 124.14 mmol) and the RM was heated to 50° C. for 4 h, then stirred at RT for 16 h. After completion of reaction, the RM was diluted with H₂O (300 mL) and extracted with EtOAc (2×300 mL). The organic layer was washed with brine (100 mL), dried (Na₂SO₄) and concentrated in vacuo to get crude. The crude compound was purified by CC (silica-gel, 0-5% EtOAc in PE) to yield 2-(4-chlorophenyl)-4-(3-(trifluoromethyl)phenylthio)tetrahydro-2H-pyran (7.5 g, 48.73%), as a brown color liquid.

Step 4: 2-(4-chlorophenyl)-4-(3-(trifluoromethyl)phenylsulfonyl)tetrahydro-2H-pyran oxone (19.8 g, 32.24 mmol) in H₂O (135 mL) was added to a solution of 2-(4-chlorophenyl)-4-(3-(trifluoromethyl)phenylthio)tetrahydro-2H-pyran (6 g, 16.12 mmol) in MeOH (210 mL) at RT and stirred for 30 min, again added oxone (9.9 g, 16.12 mmol) in H₂O (40 mL) and stirred for 16 h at RT. After completion of reaction distilled off MeOH under reduced pressure and the residue was diluted with H₂O (100 mL) and extracted with EtOAc (2×200 mL). The organic layer was washed with brine (100 mL), dried (Na₂SO₄) and concentrated to get semi pure compound. The semi pure compound was purified by CC (silica-gel, 30% EtOAc in PE) to get cis-2-(4-chlorophenyl)-4-(3-(trifluoromethyl)phenylsulfonyl)tetrahydro-2H-pyran (4 g, 61%) as a white solid (SC-401).

trans-2-(4-chlorophenyl)-4-(3-(trifluoromethyl)phenylsulfonyl)tetrahydro-2H-pyran (SC-402)

2-(4-chlorophenyl)-4-(3-(trifluoromethyl)phenylsulfonyl)tetrahydro-2H-pyran (100 mg, 0.2470 mmol) was dissolved in THF (2 mL, 24.6 mmol) and the solution placed under N₂ and cooled to −78° C. KOt-Bu (1.0 mol/L in THF) (1.5 equiv., 0.3706 mmol) was added and the reaction stirred at −78° C. for 45 min, quenched with excess ammonium hydroxide and allowed to warm to RT. The RM was diluted with EtOAc (20 ml) then washed with water (20 ml) and brine (20 ml). Organics were dried over MgSO₄ and solvent was evaporated under reduced pressure. Purification by flash chromatography (10 g silica column, PE/0% to 25% acetone gradient) followed by evaporation of solvent from the appropriate fractions afforded the desired trans-product (55 mg, 0.1359 mmol, 55%) as a white solid.

The following compounds were prepared in analogy to 2-(4-fluoro-3-methylsulfonyl-phenyl)-4-methyl-4-[[3-(trifluoromethyl)phenyl]sulfonyl]-tetrahydro-pyran (Example 17): Examples 11 to 16; Examples 18 to 22; Examples 29 to 33.

4-Methyl-2-(2-methyl-5-methylsulfonyl-phenyl)-4-[[3-(trifluoromethyl)phenyl]sulfonyl]-tetrahydro-pyran (Example 11)

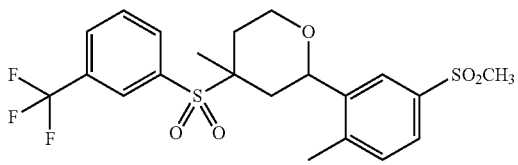 [SMILES: Cc1ccc(S(C)(=O)=O)cc1C1CC(C)(S(=O)(=O)c2cccc(C(F)(F)F)c2)CCO1]

¹H-NMR (600 MHz, [d₆]-DMSO): δ =8.20-8.22 (1H), 8.15-8.17 (1H), 8.06 (1H), 7.93-7.96 (1H) 7.86 (1H), 7.73-7.76 (1H), 7.43-7.45 (1H), 4.82-4.84 (1H), 4.06-4.12 (1H), 3.75-3.79 (1H), 3.18 (3H), 2.33 (3H), 2.17-2.23 (1H), 1.87-1.92 (1H), 1.71-1.74 (1H), 1.53 (3H), 1.46-1.48 (1H).
NOE: C-2 proton & methyl=cis

Chiral resolution of 4-Methyl-2-(2-methyl-5-methylsulfonyl-phenyl)-4-[[3-(trifluoromethyl)phenyl]sulfonyl]-tetrahydro-pyran

[Cis-rac] 4-Methyl-2-(2-methyl-5-methylsulfonyl-phenyl)-4-[[3-(trifluoromethyl)phenyl]sulfonyl]-tetrahydro-pyran was subjected to preparative chiral-SFC (Chiralpak-AD-H column, 0.5% DEA in MeOH, 20%)) to give [cis-EN1] SC-200 and [cis-EN2] SC-201.

[cis-EN1] SC-200—analytical SFC: Chiralcel OJ-H (250×4.6 mm 5μ), 3 g/min, RT, 0.5% IPA in MeOH, 10%, Ret. Time 5.14; ee>95%

[cis-EN2] SC-201—analytical SFC: Chiralcel OJ-H (250×4.6 mm 5μ), 3 g/min, RT, 0.5% IPA in MeOH, 10%, Ret. Time 6.45; ee>95%

4-Methyl-2-[3-methylsulfonyl-5-(trifluoromethyl)-phenyl]-4-[[3-(trifluoromethyl)phenyl]sulfonyl]-tetrahydro-pyran (Example 12)

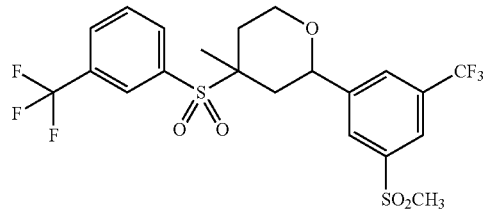 [SMILES: CC1(S(=O)(=O)c2cccc(C(F)(F)F)c2)CCOC(c2cc(C(F)(F)F)cc(S(C)(=O)=O)c2)C1]

¹H-NMR (600 MHz, [d₆]-DMSO): δ =8.21-8.22 (2H), 8.17-8.18 (2H), 8.05-8.07 (2H), 7.93-7.96 (1H), 4.80-4.83 (1H), 4.12-4.15 (1H), 3.72-3.77 (1H), 3.34 (3H), 2.15-2.21 (1H), 1.94-1.97 (1H), 1.87-1.91 (1H), 1.47-1.52 (4H).
NOE: C-2 proton & methyl=cis

Chiral resolution of 4-Methyl-2-[3-methylsulfonyl-5-(trifluoromethyl)-phenyl]-4-[[3-(trifluoromethyl)phenyl]sulfonyl]-tetrahydro-pyran

[Cis-rac] 4-Methyl-2-[3-methylsulfonyl-5-(trifluoromethyl)-phenyl]-4-[[3-(trifluoromethyl)phenyl]sulfonyl]-tetrahydro-pyran was subjected to preparative chiral-SFC (Chiralcel-OJ-H column, 0.5% IPA in MeOH, 15%)) to give [cis-EN1] SC-202 and [cis-EN2] SC-203.

[cis-EN1] SC-202—analytical HPLC: Chiralcel OJ-H (250×4.6 mm 5μ), 1 mL/min, RT, 0.5% IPA in hexanes: EtOH, 65:35, Ret. Time 9.56; ee>95%

[cis-EN2] SC-203—analytical HPLC: Chiralcel OJ-H (250×4.6 mm 5μ), 1 mL/min, RT, 0.5% IPA in hexanes: EtOH, 65:35, 10%, Ret. Time 11.3; ee>95%

2-(5-Fluoro-2-methylsulfonyl-phenyl)-4-methyl-4-[[3-(trifluoromethyl)phenyl]sulfonyl]-tetrahydro-pyran (Example 13)

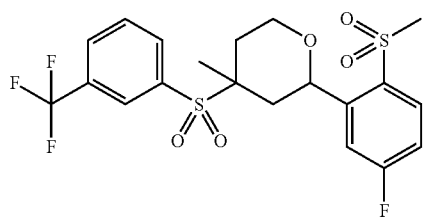 [SMILES: CC1(S(=O)(=O)c2cccc(C(F)(F)F)c2)CCOC(c2cc(F)ccc2S(C)(=O)=O)C1]

¹H-NMR (600 MHz, [d₆]-DMSO): δ =8.20-8.22 (1H), 8.16-8.18 (1H), 8.05 (1H), 7.97-8.00 (1H), 7.92-7.95 (1H), 7.49-7.51 (1H), 7.43-7.46 (1H), 5.20-5.22 (1H), 4.07-4.10

(1H), 3.83-3.87 (1H), 3.27 (3H), 2.16-2.22 (1H), 1.96-1.97 (1H), 1.83-1.87 (1H), 1.46-1.50 (4H).

NOE: C-2 proton & methyl=cis

Chiral resolution of 2-(5-Fluoro-2-methylsulfonyl-phenyl)-4-methyl-4-[[3-(trifluoromethyl)phenyl]sulfonyl]-tetrahydro-pyran Cis-rac 2-(5-Fluoro-2-methylsulfonyl-phenyl)-4-methyl-4-[[3-(trifluoromethyl)phenyl]sulfonyl]-tetrahydro-pyran was subjected to preparative chiral-SFC (Chiralpak-IE column, co-solvent MeOH) to give cis-EN1 SC-204 and cis-EN2 SC-205.

cis-EN1 SC-204—analytical SFC: Chiralpak IE (250×4.6 mm 5μ), 3 g/min, RT, 0.5% diethylamine in MeOH (30%), Ret. Time 2.07; ee>95% cis-EN2 SC-205—analytical SFC: Chiralpak IE (250×4.6 mm 5μ), 3 g/min, RT, 0.5% diethylamine in MeOH (30%), Ret. Time 2.37; ee>95%

4-Methyl-2-(3-methyl-4-methylsulfonyl-phenyl)-4-[[3-(trifluoromethyl)phenyl]sulfonyl]-tetrahydro-pyran (example 14)

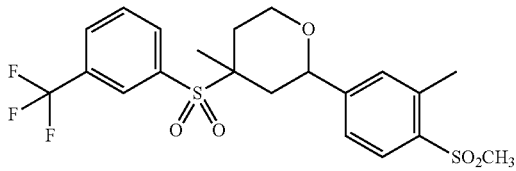

$^1$H-NMR (600 MHz, [d$_6$]-DMSO): δ =8.21-8.22 (1H), 8.15-8.16 (1H), 8.04 (1H), 7.93-7.96 (1H), 7.86-7.87 (1H), 7.40-7.41 (2H), 4.62-4.65 (1H), 4.06-4.08 (1H), 3.69-3.73 (1H), 3.20 (3H), 2.63 (3H), 2.11-2.16 (1H), 1.84-1.88 (1H), 1.76-1.78 (1H), 1.51 (3H), 1.44-1.49 (1H).

NOE: C-2 proton & methyl=cis

Chiral resolution of 4-Methyl-2-(3-methyl-4-methylsulfonyl-phenyl)-4-[[3-(trifluoromethyl)phenyl]sulfonyl]-tetrahydro-pyran

[Cis-rac] 4-Methyl-2-(3-methyl-4-methylsulfonyl-phenyl)-4-[[3-(trifluoromethyl)phenyl]sulfonyl]-tetrahydro-pyran was subjected to preparative chiral-SFC (Chiralcel-OJ-H column, 0.5% DEA in MeOH, 20%)) to give [cis-EN1] SC-206 and [cis-EN2] SC-207.

[cis-EN1] SC-206—analytical SFC: Chiralcel OJ-H (250×4.6 mm 5μ), 3 g/min, RT, 0.5% DEA in MeOH, 40%, Ret. Time 1.91; ee>95%

[cis-EN2] SC-207—analytical SFC: Chiralcel OJ-H (250×4.6 mm 5μ), 3 g/min, RT, 0.5% DEA in MeOH, 40%, Ret. Time 2.16; ee>95%

2-(3-Fluoro-4-methylsulfonyl-phenyl)-4-methyl-4-[[3-(trifluoromethyl)phenyl]sulfonyl]-tetrahydro-pyran (Example 15)

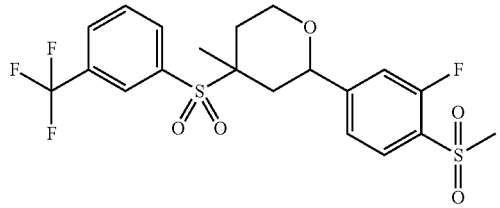 [SMILES: CC1(S(=O)(=O)c2cccc(C(F)(F)F)c2)CCOC(c2ccc(S(C)(=O)=O)c(F)c2)C1]

$^1$H-NMR (600 MHz, [d$_6$]-DMSO): δ =8.21-8.22 (1H), 8.15-8.17 (1H), 8.05 (1H), 7.93-7.96 (1H), 7.83-7.86 (1H), 7.47-7.49 (1H), 7.44-7.45 (1H), 4.69-4.71 (1H), 4.08-4.11 (1H), 3.71-3.75 (1H), 3.32 (3H), 2.11-2.16 (1H), 1.83-1.84 (2H), 1.48-1.51 (4H).

NOE: C-2 proton & methyl=cis

Chiral resolution of 2-(3-Fluoro-4-methylsulfonyl-phenyl)-4-methyl-4-[[3-(trifluoromethyl)phenyl]sulfonyl]-tetrahydro-pyran cis-rac 2-(3-Fluoro-4-methylsulfonyl-phenyl)-4-methyl-4-[[3-(trifluoromethyl)phenyl]sulfonyl]-tetrahydro-pyran was subjected to preparative chiral-SFC (Chiralpak-OJ-H column, co-solvent 0.5% diethylamine in MeOH) to give cis-EN1 SC-208 and cis-EN2 SC-209.

cis-EN1 SC-208—analytical HPLC: Chiralpak IA (250×4.6 mm 5μ), 1 ml/min, RT, 0.1% TFA in hexane/EtOH 60/40, Ret. Time 7.25; ee>95%/specific rotation [α]$_D^{27.6}$ +16.3° (c 0.75; DCM);

cis-EN2 SC-209—analytical HPLC: Chiralpak IA (250×4.6 mm 5μ), 1 ml/min, RT, 0.1% TFA in hexane/EtOH 60/40, Ret. Time 11.28; ee>95%/specific rotation [α]$_D^{28.3}$ −19.6° (c 0.83; DCM).

4-Methyl-2-(4-methyl-3-methylsulfonyl-phenyl)-4-[[3-(trifluoromethyl)phenyl]sulfonyl]-tetrahydro-pyran (xxample 16)

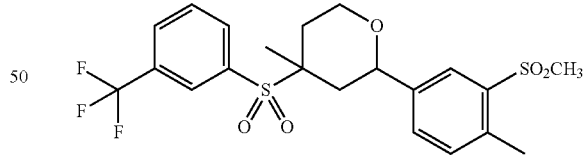

$^1$H-NMR (600 MHz, [d$_6$]-DMSO): δ =8.20-8.22 (1H), 8.15-8.16 (1H), 8.04 (1H), 7.93-7.95 (1H), 7.88 (1H), 7.55-7.57 (1H), 7.43-7.44 (1H), 4.64-4.66 (1H), 4.06-4.09 (1H), 3.68-3.73 (1H), 3.20 (3H), 2.62 (3H), 2.12-2.17 (1H), 1.85-1.90 (1H), 1.75-1.77 (1H), 1.45-1.50 (4H).

NOE: C-2 proton & methyl=cis

Chiral resolution of 4-Methyl-2-(4-methyl-3-methylsulfonyl-phenyl)-4-[[3-(trifluoromethyl)phenyl]sulfonyl]-tetrahydro-pyran

[Cis-rac] 4-Methyl-2-(4-methyl-3-methylsulfonyl-phenyl)-4-[[3-(trifluoromethyl)phenyl]sulfonyl]-tetrahydropyran was subjected to preparative chiral-SFC (Chiralpak-IA column, 0.5% DEA in MeOH, 35%)) to give [cis-EN1] SC-210 and [cis-EN2] SC-211.

[cis-EN1] SC-210—analytical SFC: Chiralpak IC (250× 4.6 mm 5μ), 4 g/min, RT, 0.5% DEA in MeOH, 40%, Ret. Time 2.41; ee>95%

[cis-EN2] SC-211—analytical SFC: Chiralpak IC (250× 4.6 mm 5μ), 4 g/min, RT, 0.5% DEA in MeOH, 40%, Ret. Time 2.98; ee>95%

[[2-(4-Chlorophenyl)-4-[[3-(trifluoromethyl)phenyl]sulfonyl]-tetrahydro-pyran-4-yl]-methyl]-dimethyl-amine (Example 18)

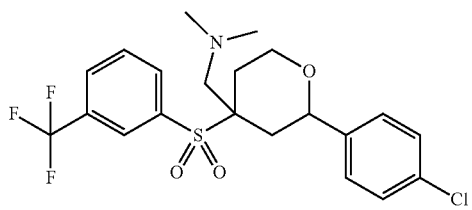 [SMILES: CN(C)CC1(S(=O)(=O)c2cccc(C(F)(F)F)c2)CCOC(c2ccc(Cl)cc2)C1]

A solution of 2-(4-chlorophenyl)-4-[[3-(trifluoromethyl)phenyl]sulfonyl]-tetrahydro-pyran (5 g, 12.37 mmol) in dry THF (100 mL) was cooled to −78° C. and added n-butyl lithium (2.5M) (9.90 mL, 24.75 mmol), stirred for 2 h and added N, N-dimethylmethylene iminium iodide (5.72 g, 30.92 mmol) and the whole mixture was allowed to attain RT and stirred for 16 h. The reaction mass was quenched with aq. NH$_4$Cl solution and extracted with EtOAc (2×400 mL). Combined organic layer was washed with brine solution (100 mL), dried (Na$_2$SO$_4$) and concentrated under reduced pressure to get crude. The crude upon purification by CC (silica gel 0-13% EtOAc in PE) gave [[2-(4-Chlorophenyl)-4-[[3-(trifluoromethyl)phenyl]sulfonyl]-tetrahydro-pyran-4-yl]-methyl]-dimethyl-amine (1.3 g, 23%) as an off-white solid.

$^1$H-NMR (600 MHz, [d$_6$]-DMSO): δ =8.13 (3H); 7.85 (1H), 7.41-7.39 (2H), 7.32 (2H), 4.65-4.62 (1H), 4.06-4.02 (1H), 3.73 (1H), 3.13-3.06 (2H), 2.18 (6H), 2.08-2.07 (2H), 1.89-1.85 (2H), 1.65-1.62 (1H).

NOE: C-2 proton & CH$_2$ (of CH$_2$NMe$_2$ group)=cis

Chiral resolution of [[2-(4-Chlorophenyl)-4-[[3-(trifluoromethyl)phenyl]sulfonyl]-tetrahydro-pyran-4-yl]-methyl]-dimethyl-amine cis-rac [[2-(4-Chlorophenyl)-4-[[3-(trifluoromethyl)phenyl]sulfonyl]-tetrahydro-pyran-4-yl]-methyl]-dimethyl-amine was subjected to preparative chiral-SFC (Chiralcel-OJ-H column, co-solvent 0.5% diethylamine in MeOH) to give cis-EN1 SC-214 and cis-EN2 SC-215.

cis-EN1 SC-214—analytical SFC: Chiralcel-OJ-H (250× 4.6 mm 5μ), 3 g/min, RT, 0.5% diethylamine in MeOH (30%), Ret. Time 1.82; ee>95% cis-EN2 SC-215—analytical SFC: Chiralcel-OJ-H (250× 4.6 mm 5μ), 3 g/min, RT, 0.5% diethylamine in MeOH (30%), Ret. Time 2.00; ee>95%

2-(4-Chlorophenyl)-4-(methoxymethyl)-4-[[3-(trifluoromethyl)phenyl]sulfonyl]-tetrahydro-pyran (Example 19)

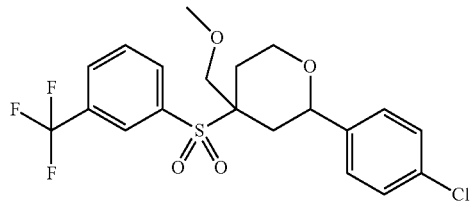 [SMILES: COCC1(S(=O)(=O)c2cccc(C(F)(F)F)c2)CCOC(c2ccc(Cl)cc2)C1]

A solution of 2-(4-chlorophenyl)-4-[[3-(trifluoromethyl)phenyl]sulfonyl]-tetrahydro-pyran (5 g, 12.37 mmol) in dry THF (100 mL) was cooled to −78° C. and added n-butyl lithium (2.5 M) (9.90 mL, 24.75 mmol), stirred for 2 h and added chloromethyl methyl ether (2.33 mL, 30.92 mmol) and the whole mixture was allowed to attain RT and stirred for 16 h. The reaction mass was quenched with aq. NH$_4$Cl solution and extracted with EtOAc (2×300 mL). Combined organic layer was washed with brine solution (100 mL), dried (Na$_2$SO$_4$) and concentrated under reduced pressure to get crude. The crude upon purification by CC (silica gel 100-200 mesh, 0-13% EtOAc in PE) gave 2-(4-Chlorophenyl)-4-(methoxymethyl)-4-[[3-(trifluoromethyl)phenyl]sulfonyl]-tetrahydro-pyran (1.1 g, 20%) as an off-white solid.

$^1$H-NMR (600 MHz, [d$_6$]-DMSO): δ =8.15-8.09 (2H), 8.04 (1H), 7.85 (1H), 7.41 (2H), 7.34 (2H), 4.57 (1H), 4.07-4.03 (1H), 3.99-3.92 (2H), 3.69 (1H), 3.08 (3H), 2.16-2.14 (1H), 1.91 (1H), 1.78 (1H), 1.61 (1H).

NOE: C-2 proton & CH$_2$ (MOM-Group)=cis

Chiral resolution of 2-(4-Chlorophenyl)-4-(methoxymethyl)-4-[[3-(trifluoromethyl)phenyl]sulfonyl]-tetrahydro-pyran cis-rac 2-(4-Chlorophenyl)-4-(methoxymethyl)-4-[[3-(trifluoromethyl)phenyl]sulfonyl]-tetrahydro-pyran (1.0 g) was subjected to preparative chiral-SFC (Chiralcel-OJ-H column, co-solvent 0.5% diethylamine in MeOH) to give cis-EN1 SC-216 (165 mg) and cis-EN2 SC-217 (168 mg).

cis-EN1 SC-216—analytical SFC: Chiralcel OJ-H (250× 4.6 mm 5μ), 3 g/min, RT, 0.5% diethylamine in MeOH (30%), Ret. Time 1.92; ee>95% cis-EN2 SC-217—analytical SFC: Chiralcel OJ-H (250× 4.6 mm 5μ), 3 g/min, RT, 0.5% diethylamine in MeOH (30%), Ret. Time 2.16; ee>95%

2-(2-Chloro-4-methylsulfonyl-phenyl)-4-methyl-4-[[3-(trifluoromethyl)phenyl]sulfonyl]-tetrahydro-pyran (Example 20)

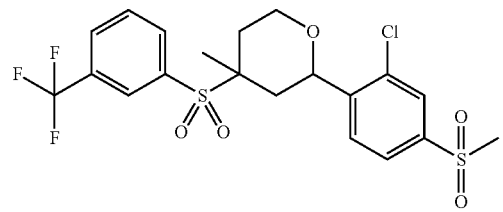 [SMILES: CC1(S(=O)(=O)c2cccc(C(F)(F)F)c2)CCOC(c2ccc(S(C)(=O)=O)cc2Cl)C1]

¹H-NMR (600 MHz, [d₆]-DMSO): δ =8.21-8.22 (1H), 8.17-8.18 (1H), 8.06 (1H), 7.98 (1H), 7.93-7.95 (2H), 7.77-7.78 (1H), 4.91-4.93 (1H), 4.10-4.14 (1H), 3.81-3.84 (1H), 3.29 (3H), 2.14-2.20 (1H), 1.88-1.90 (1H), 1.76-1.80 (1H), 1.50-1.53 (4H).

NOE: C-2 proton & methyl=cis

Chiral resolution of 2-(2-Chloro-4-methylsulfonyl-phenyl)-4-methyl-4-[[3-(trifluoromethyl)phenyl]sulfonyl]-tetrahydro-pyran cis-rac 2-(2-Chloro-4-methylsulfonyl-phenyl)-4-methyl-4-[[3-(trifluoromethyl)phenyl]sulfonyl]-tetrahydro-pyran was subjected to preparative chiral-SFC (Chiralpak-AD-H column, co-solvent 0.5% diethylamine in MeOH) to give cis-EN1 SC-218 and cis-EN2 SC-219.

cis-EN1 SC-218—analytical SFC: Chiralpak AD-H (250×4.6 mm 5µ), 3 g/min, RT, 0.5% diethylamine in MeOH (30%), Ret. Time 4.00; ee>95% cis-EN2 SC-219—analytical SFC: Chiralpak AD-H (250×4.6 mm 5µ), 3 g/min, RT, 0.5% diethylamine in MeOH (30%), Ret. Time 4.50; ee>95%

4-Methyl-2-(3-methylsulfonyl-phenyl)-4-[[3-(trifluoromethyl)phenyl]sulfonyl]-tetrahydro-pyran (Example 21)

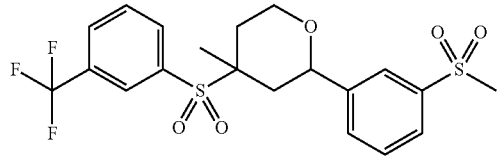 [SMILES: CC1(S(=O)(=O)c2cccc(C(F)(F)F)c2)CCOC(c2cccc(S(C)(=O)=O)c2)C1]

¹H-NMR (600 MHz, [d₆]-DMSO): δ =8.21-8.22 (1H), 8.16-8.18 (1H), 7.93-7.96 (1H), 7.90 (1H), 7.85-7.86 (1H), 7.69-7.70 (1H), 7.62-7.65 (1H), 4.70-4.72 (1H), 4.08-4.11 (1H), 3.71-3.75 (1H), 3.21 (3H), 2.14-2.19 (1H), 1.88-1.92 (1H), 1.81-1.83 (1H), 1.52 (3H), 1.48-1.50 (1H).

NOE: C-2 proton & methyl=cis

Chiral resolution of 4-Methyl-2-(3-methylsulfonyl-phenyl)-4-[[3-(trifluoromethyl)phenyl]sulfonyl]-tetrahydro-pyran Cis-rac 4-Methyl-2-(3-methylsulfonyl-phenyl)-4-[[3-(trifluoromethyl)phenyl]sulfonyl]-tetrahydro-pyran was subjected to preparative chiral-SFC (Chiralpak-IC column, co-solvent EtOH) to give cis-EN1 SC-220 and cis-EN2 SC-221.

cis-EN1 SC-220—analytical HPLC: Chiralcel IA (250× 4.6 mm 5µ), 1 ml/min, RT, 0.1% TFA in hexane/EtOH 50/50, Ret. Time 5.06; ee>95% cis-EN2 SC-221—analytical HPLC: Chiralcel IA (250× 4.6 mm 5µ), 1 ml/min, RT, 0.1% TFA in hexane/EtOH 50/50, Ret. Time 6.05; ee>95%

4-Methyl-2-(2-methylsulfonyl-phenyl)-4-[[3-(trifluoromethyl)phenyl]sulfonyl]-tetrahydro-pyran (Example 22)

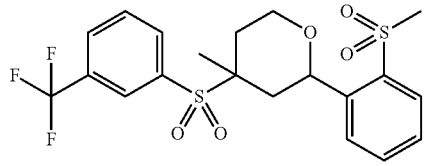 [SMILES: CC1(S(=O)(=O)c2cccc(C(F)(F)F)c2)CCOC(c2ccccc2S(C)(=O)=O)C1]

¹H-NMR (600 MHz, [d₆]-DMSO): δ =8.20-8.22 (1H), 8.16-8.17 (1H), 8.04 (1H), 7.91-7.95 (2H), 7.75-7.76 (2H), 7.58-7.61 (1H), 5.24-5.26 (1H), 4.07-4.10 (1H), 3.82-3.86 (1H), 3.27 (3H), 2.17-2.22 (1H), 1.94-1.96 (1H), 1.85-1.89 (1H), 1.48-1.51 (4H).

NOE: C-2 proton & methyl=cis

Chiral resolution of 4-Methyl-2-(2-methylsulfonyl-phenyl)-4-[[3-(trifluoromethyl)phenyl]sulfonyl]-tetrahydro-pyran Cis-rac 4-Methyl-2-(2-methylsulfonyl-phenyl)-4-[[3-(trifluoromethyl)phenyl]sulfonyl]-tetrahydro-pyran was subjected to preparative chiral-SFC (Chiralpak-IE column, co-solvent 0.5% formic acid in MeOH) to give cis-EN1 SC-223 and cis-EN2 SC-222.

cis-EN1 SC-223—analytical HPLC: Chiralcel OX-H (250×4.6 mm 5µ), 1 ml/min, RT, 0.1% TFA in hexane/EtOH 60/40, Ret. Time 6.48; ee>95% cis-EN2 SC-222—analytical HPLC: Chiralcel OX-H (250×4.6 mm 5µ), 1 ml/min, RT, 0.1% TFA in hexane/EtOH 60/40, Ret. Time 8.00; ee>95%

4-Methyl-2-[4-methylsulfonyl-3-(trifluoromethyl)-phenyl]-4-[[3-(trifluoromethyl)phenyl]sulfonyl]-tetrahydro-pyran (example 29)

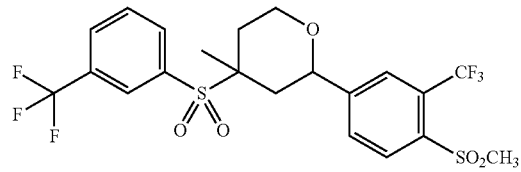 [SMILES: CC1(S(=O)(=O)c2cccc(C(F)(F)F)c2)CCOC(c2ccc(S(C)(=O)=O)c(C(F)(F)F)c2)C1]

¹H-NMR (600 MHz, [d₆]-DMSO): δ =8.21-8.23 (1H), 8.16-8.17 (1H), 8.05 (1H), 7.97 (1H), 7.93-7.95 (2H), 4.78-4.81 (1H), 4.11-4.14 (1H), 3.72-3.76 (1H), 2.12-2.16 (1H), 1.89-1.91 (1H), 1.82-1.86 (1H), 1.48-1.52 (4H).

NOE: C-2 proton & methyl=cis

Chiral resolution of 4-Methyl-2-[4-methylsulfonyl-3-(trifluoromethyl)-phenyl]-4-[[3-(trifluoromethyl)phenyl]sulfonyl]-tetrahydro-pyran

[Cis-rac] 4-Methyl-2-[4-methylsulfonyl-3-(trifluoromethyl)-phenyl]-4-[[3-(trifluoromethyl)phenyl]sulfonyl]-tetrahydro-pyran was subjected to preparative chiral-SFC (Chiralcel-OJ-H column, 0.5% DEA in MeOH, 10%)) to give [cis-EN1] SC-235 and [cis-EN2] SC-236.

[cis-EN1] SC-235—analytical SFC: Chiralcel OJ-H (250×4.6 mm 5μ), 3 g/min, RT, 0.5% DEA in MeOH, 20%, Ret. Time 2.19; ee>95%

[cis-EN2] SC-236—analytical SFC: Chiralcel OJ-H (250×4.6 mm 5μ), 3 g/min, RT, 0.5% DEA in MeOH, 20%, Ret. Time 2.47; ee>95%

2-(4-Chloro-3-methylsulfonyl-phenyl)-4-methyl-4-[[3-(trifluoromethyl)phenyl]sulfonyl]-tetrahydro-pyran (example 30)

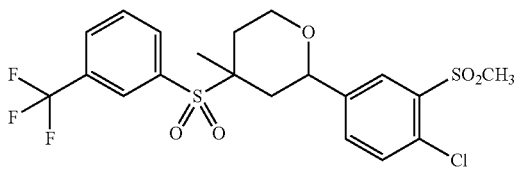 [SMILES: CC1(S(=O)(=O)c2cccc(C(F)(F)F)c2)CCOC(c2ccc(Cl)c(S(C)(=O)=O)c2)C1]

$^1$H-NMR (600 MHz, [d$_6$]-DMSO): δ =8.21-8.22 (1H), 8.16-8.17 (1H), 8.05 (1H), 8.03 (1H), 7.93-7.95 (1H), 7.69-7.73 (2H), 4.71-4.73 (1H), 4.08-4.11 (1H), 3.70-3.74 (1H), 3.37 (3H), 2.13-2.18 (1H), 1.80-1.89 (2H), 1.51 (3H), 1.46-1.49 (1H).

NOE: C-2 proton & methyl=cis

Chiral resolution of 2-(4-Chloro-3-methylsulfonyl-phenyl)-4-methyl-4-[[3-(trifluoromethyl)phenyl]sulfonyl]-tetrahydro-pyran

[Cis-rac] 2-(4-Chloro-3-methylsulfonyl-phenyl)-4-methyl-4-[[3-(trifluoromethyl)phenyl]sulfonyl]-tetrahydro-pyran was subjected to preparative chiral-SFC (Chiralpak-IC column, MeOH, 30%)) to give [cis-EN1] SC-237 and [cis-EN2] SC-238.

[cis-EN1] SC-237—analytical SFC: Chiralpak IC (250× 4.6 mm 5μ), 3 g/min, RT, MeOH, 35%, Ret. Time 3.62; ee>95%

[cis-EN2] SC-238—analytical SFC: Chiralpak IC (250× 4.6 mm 5μ), 3 g/min, RT, MeOH, 35%, Ret. Time 4.17; ee>95%

2-(3-Chloro-4-methylsulfonyl-phenyl)-4-methyl-4-[[3-(trifluoromethyl)phenyl]sulfonyl]-tetrahydro-pyran (example 31)

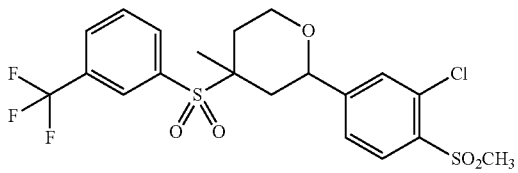 [SMILES: CC1(S(=O)(=O)c2cccc(C(F)(F)F)c2)CCOC(c2ccc(S(C)(=O)=O)c(Cl)c2)C1]

$^1$H-NMR (600 MHz, [d$_6$]-DMSO): δ =8.21-8.22 (1H), 8.15-8.16 (1H), 8.05 (1H), 8.02-8.03 (1H), 7.93-7.96 (1H), 7.69 (1H), 7.58-7.60 (1H), 4.68-4.71 (1H), 4.08-4.11 (1H), 3.70-3.74 (1H), 3.36 (3H), 2.11-2.16 (1H), 1.81-1.86 (2H), 1.48-1.51 (4H).

NOE: C-2 proton & methyl=cis

Chiral resolution of 2-(3-Chloro-4-methylsulfonyl-phenyl)-4-methyl-4-[[3-(trifluoromethyl)phenyl]sulfonyl]-tetrahydro-pyran

[Cis-rac] 2-(3-Chloro-4-methylsulfonyl-phenyl)-4-methyl-4-[[3-(trifluoromethyl)phenyl]sulfonyl]-tetrahydro-pyran was subjected to preparative chiral-SFC (Chiralcel-OJ-H column, MeOH, 20%)) to give [cis-EN1] SC-239 and [cis-EN2] SC-240.

[cis-EN1] SC-239—analytical SFC: Chiralcel-OJ-H (250×4.6 mm 5μ), 3 g/min, RT, MeOH, 35%, Ret. Time 2.33; ee>95%

[cis-EN2] SC-240—analytical SFC: Chiralcel OJ-H (250×4.6 mm 5μ), 3 g/min, RT, MeOH, 35%, Ret. Time 2.93; ee>95%

2-(2-Fluoro-4-methylsulfonyl-phenyl)-4-methyl-4-[[3-(trifluoromethyl)phenyl]sulfonyl]-tetrahydro-pyran (example 32)

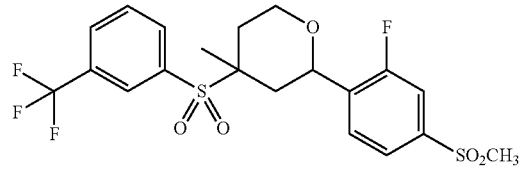 [SMILES: CC1(S(=O)(=O)c2cccc(C(F)(F)F)c2)CCOC(c2ccc(S(C)(=O)=O)cc2F)C1]

$^1$H-NMR (600 MHz, [d$_6$]-DMSO): δ =8.21-8.22 (1H), 8.17-8.18 (1H), 8.06 (1H), 7.93-7.96 (1H), 7.77-7.81 (2H), 7.73-7.75 (1H), 4.91-4.93 (1H), 4.08-4.11 (1H), 3.77-3.81 (1H), 3.28 (3H), 2.14-2.19 (1H), 1.94-1.98 (1H), 1.74-1.76 (1H), 1.50-1.52 (4H).

NOE: C-2 proton & methyl=cis

Chiral resolution of 2-(2-Fluoro-4-methylsulfonyl-phenyl)-4-methyl-4-[[3-(trifluoromethyl)phenyl]sulfonyl]-tetrahydro-pyran

[Cis-rac] 2-(2-Fluoro-4-methylsulfonyl-phenyl)-4-methyl-4-[[3-(trifluoromethyl)phenyl]sulfonyl]-tetrahydro-pyran was subjected to preparative chiral-SFC (Chiralpak-IE column, EtOH, 30%)) to give [cis-EN1] SC-241 and [cis-EN2] SC-242.

[cis-EN1] SC-241—analytical SFC: Chiralpak-IE (250× 4.6 mm 5μ), 3 g/min, RT, EtOH, 25%, Ret. Time 5.3; ee>95%/specific rotation $[α]_D^{25.4}$ −23.4° (c 0.92; DCM).

[cis-EN2] SC-242—analytical SFC: Chiralpak-IE (250× 4.6 mm 5μ), 3 g/min, RT, EtOH, 25%, Ret. Time 5.91; ee>95%/specific rotation $[α]_D^{25.4}$ +23.1° (c 0.95; DCM).

2-(3-Chloro-5-methylsulfonyl-phenyl)-4-methyl-4-[[3-(trifluoromethyl)phenyl]sulfonyl]-tetrahydro-pyran (example 33)

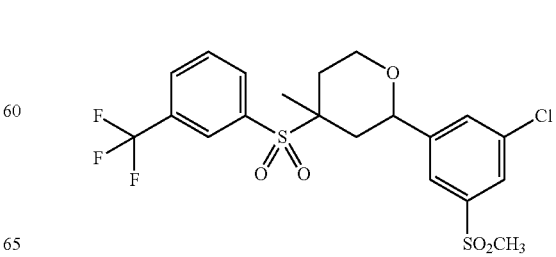

¹H-NMR (600 MHz, [d₆]-DMSO): δ =8.21-8.22 (1H), 8.17.8.18 (1H), 8.05 (1H), 7.93-7.96 (1H), 7.90 (1H), 7.87 (1H), 7.78 (1H), 4.70-4.72 (1H), 4.09-4.12 (1H), 3.70-3.74 (1H), 3.29 (3H), 2.13-2.18 (1H), 1.84-1.90 (2H), 1.42-1.51 (4H).

NOE: C-2 proton & methyl=cis

Chiral resolution of 2-(3-Chloro-5-methylsulfonyl-phenyl)-4-methyl-4-[[3-(trifluoromethyl)phenyl]sulfonyl]-tetrahydro-pyran

[Cis-rac] 2-(3-Chloro-5-methylsulfonyl-phenyl)-4-methyl-4-[[3-(trifluoromethyl)phenyl]sulfonyl]-tetrahydro-pyran was subjected to preparative chiral-SFC (Chiralpak-AS-H column, MeOH, 30%)) to give [cis-EN1] SC-243 and [cis-EN2] SC-244.

[cis-EN1] SC-243—analytical SFC: Chiralpak-AS-H (250×4.6 mm 5μ), 3 g/min, RT, MeOH, 20%, Ret. Time 3.51; ee>95%

[cis-EN2] SC-244—analytical SFC: Chiralpal-AS-H (250×4.6 mm 5μ), 3 g/min, RT, MeOH, 20%, Ret. Time 4.42; ee>95%.

The following compound was prepared in analogy to 2-(4-chlorophenyl)-4-(methoxymethyl)-4-[[3-(trifluoromethyl)phenyl]sulfonyl]-tetrahydro-pyran (Example 19):

2-(4-Chlorophenyl)-4-(phenylmethoxy-methyl)-4-[[3-(trifluoromethyl)phenyl]sulfonyl]-tetrahydro-pyran (example 28)

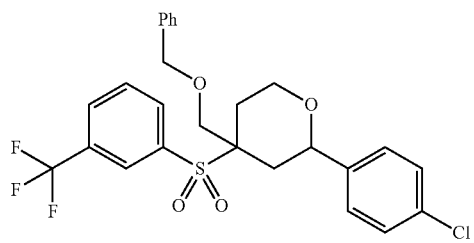 [SMILES: O=S(=O)(c1cccc(C(F)(F)F)c1)C1(COCc2ccccc2)CCOC(c2ccc(Cl)cc2)C1]

¹H-NMR (600 MHz, [d₆]-DMSO): δ =8.10-8.11 (1H), 8.02-8.04 (2H), 7.77-7.79 (1H), 7.41-7.42 (2H), 7.31-7.32 (2H), 7.23-7.27 (3H), 6.96-6.98 (2H), 4.52-4.54 (1H), 4.33-4.38 (2H), 4.04-4.12 (3H), 3.65-3.69 (1H), 2.18-2.23 (1H), 1.89-1.97 (2H), 1.72-1.74 (1H).

NOE: C-2 proton & —CH₂—O=cis (SC-234).

6-(4-Chlorophenyl)-2,2,4-trimethyl-4-[[3-(trifluoromethyl)phenyl]sulfonyl]-tetrahydro-pyran (Example 34)

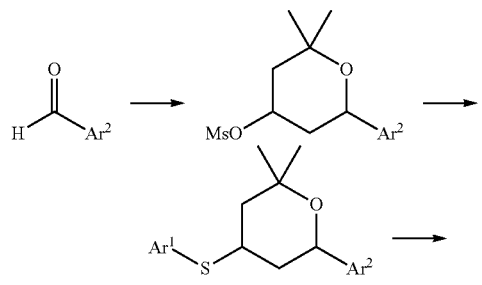

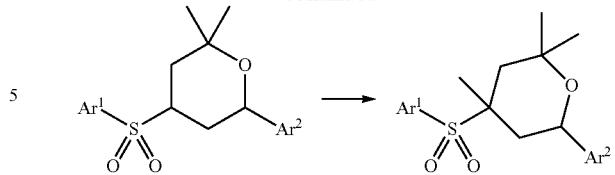

Step 1: 6-(4-Chlorophenyl)-2,2-dimethyltetrahydro-2H-pyran-4-yl methanesulfonate A solution of 4-chlorobenzaldehyde (10 g, 71.1 mmol) and 2-methylpent-4-en-2-ol (7.84 g, 78 mmol) in CH₂Cl₂ (150 mL) was cooled in a NaCl/ice-bath to −16° C. under N₂. A solution of methanesulfonic acid (46.2 mL, 711 mmol) in DCM (50 mL) was added dropwise over 30 min, keeping the temperature below −10° C. The mixture was stirred for 15 min. The RM was cautiously basified with a solution of aq. 1.4M Na₂CO₃ (500 mL) and the product was extracted with i-Pr₂O (2×300 mL). The combined organic layers were washed with sat. aq. NaHCO₃ (2×100 mL) and brine (2×100 mL) before drying on Na₂SO₄ and concentration in vacuo. The product was purified using flash chromatography (silica, gradient heptane/acetone, 97:3→7:3) to give the desired product (5.4 g, 23%) as a light yellow oil.

Step 2: 6-(4-Chlorophenyl)-2,2-dimethyl-4-((3-(trifluoromethyl)phenyl)thio)tetrahydro-2H-pyran A solution of 6-(4-chlorophenyl)-2,2-dimethyltetrahydro-2H-pyran-4-yl methanesulfonate (4 g, 12.55 mmol) in dry DMF (80 mL) was degassed by bubbling Ar for 1 h. Cs₂CO₃ (18.4 g, 56.5 mmol) was added and after 5 min, 3-(trifluoromethyl)benzenethiol (11.7 mL, 88 mmol) was added. The mixture was stirred at 80° C. under Ar for 20 h. The RM was cooled down to RT and carefully acidified with aq. 1M KHSO₄ (60 mL). The product was extracted with EtOAc/i-Pr₂O (1/1, v/v, 2×60 mL) and the combined organic layers were washed with aq. 1M KHSO₄ (2×40 mL) and brine (2×40 mL) before drying on Na₂SO₄ and concentration in vacuo. The product was filtered over silica (heptane/EtOAc, 100:0→1:1) and subsequently purified using flash chromatography (silica, gradient heptane/acetone, 99:1→95:5) to give the desired product (3.21 g, 63%) as a colorless oil.

Step 3: 6-(4-Chlorophenyl)-2,2-dimethyl-4-((3-(trifluoromethyl)phenyl)sulfonyl)tetrahydro-2H-pyran Oxone (9.85 g, min. 27.7 mmol) was dissolved in H₂O (70 mL) upon slight heating and this solution was added in one portion to a solution of 6-(4-chlorophenyl)-2,2-dimethyl-4-((3-(trifluoromethyl)phenyl)thio)tetrahydro-2H-pyran (3.21 g, 8.01 mmol) in MeOH (100 mL). An exothermic reaction took place, after which an ice bath was applied. The mixture was stirred at 0° C. for 10 min, then at RT for 20 h. MeOH was distilled off in vacuo and the residue was partitioned between H₂O (100 mL) and EtOAc (100 mL). The aq. layer was extracted with EtOAc (100 mL) and the combined organic layers were washed with H₂O (2×50 mL), sat. aq. NaHCO₃ (2×50 mL) and brine (2×50 mL) before drying on Na₂SO₄ and concentration in vacuo. The product was purified using flash chromatography (silica, gradient heptane/acetone, 99:1→8:2) to give 3.29 g (95%) of the desired product.

Step 4: 6-(4-Chlorophenyl)-2,2,4-trimethyl-4-[[3-(trifluoromethyl)phenyl]sulfonyl]-tetrahydro-pyran This reaction was carried out under Ar. A solution of 6-(4-chlorophenyl)-2,2-dimethyl-4-((3-(trifluoromethyl)phenyl)sulfonyl)tetrahydro-2H-pyran (0.965 g, 2.229 mmol) in dry THF (12 mL) was cooled to −78° C., 1M KOt-Bu in THF (6.69 mL, 6.69 mmol) was added dropwise over 5 min, keeping the temperature below −75° C. The mixture was stirred at −78° C. for 20 min, then MeI (555 µL, 8.92 mmol) was added and the stirring was continued from −78° C. to RT for 20 h. More MeI (0.139 mL, 2.229 mmol) was added and the stirring was continued at RT for 4 h. The RM was poured out in sat. aq. NaHCO$_3$ (50 mL) and extracted with EtOAc (100 mL). The organic layer was washed with sat. aq. NaHCO$_3$ (2×25 mL), aq. 1M Na$_2$S$_2$O$_3$ (2×25 mL) and brine (2×25 mL) before drying on Na$_2$SO$_4$ and concentration in vacuo. The product was purified using flash chromatography (silica, gradient heptane/EtOAc, 95:5→60:40) to give 334 mg (33%) of cis-rac 6-(4-chlorophenyl)-2,2,4-trimethyl-4-[[3-(trifluoromethyl)phenyl]sulfonyl]-tetrahydro-pyran as a colorless oil/foam. The cis-rac 6-(4-chlorophenyl)-2,2,4-trimethyl-4-[[3-(trifluoromethyl)phenyl]sulfonyl]-tetrahydro-pyran fractions were combined with cis-rac 6-(4-chlorophenyl)-2,2,4-trimethyl-4-[[3-(trifluoromethyl)phenyl]sulfonyl]-tetrahydro-pyran of two additional reactions (both started with 100 mg of 6-(4-chlorophenyl)-2,2-dimethyl-4-((3-(trifluoromethyl)phenyl)sulfonyl)tetrahydro-2H-pyran). The product was purified using flash chromatography (silica, gradient heptane/EtOAc, 1:0→1:1) and combined with the earlier obtained batch to give cis-rac 6-(4-chlorophenyl)-2,2,4-trimethyl-4-[[3-(trifluoromethyl)phenyl]sulfonyl]-tetrahydro-pyran (403 mg, 33%) as a colorless oil/foam. This crude product was purified further using flash chromatography (silica, gradient heptane/EtOAc, 95:5→60:40) to give trans-rac 6-(4-chlorophenyl)-2,2,4-trimethyl-4-[[3-(trifluoromethyl)phenyl]sulfonyl]-tetrahydro-pyran SC-302 (146 mg, 12%) as a colorless oil.

$^1$H NMR (400 MHz, CDCl$_3$) of cis-rac 6-(4-chlorophenyl)-2,2,4-trimethyl-4-[[3-(trifluoromethyl)phenyl]sulfonyl]-tetrahydro-pyran: δ 8.12 (s, 1H), 8.02 (d, J=7.9 Hz, 1H), 7.94 (d, J=7.8 Hz, 1H), 7.73 (t, J=7.8 Hz, 1H), 7.35-7.27 (m, 4H), 4.62 (dd, J=11.5, 1.9 Hz, 1H), 2.26 (d, J=13.3 Hz, 1H), 2.08 (t, J=12.2 Hz, 1H), 1.68 (dt, J=12.9, 1.9 Hz, 1H), 1.63 (s, 3H), 1.57-1.51 (m, 1.9H) [overlap with H$_2$O signal], 1.38 (s, 3H), 1.35 (s, 3H).

$^1$H-NMR (400 MHz, CDCl$_3$) of trans-rac 6-(4-chlorophenyl)-2,2,4-trimethyl-4-[[3-(trifluoromethyl)phenyl]sulfonyl]-tetrahydro-pyran SC-302: δ 8.15 (s, 1H), 8.08 (d, J=7.9 Hz, 1H), 7.95 (d, J=7.9 Hz, 1H), 7.75 (t, J=7.8 Hz, 1H), 7.36-7.28 (m, 4H), 4.99 (dd, J=11.0, 4.1 Hz, 1H), 2.58 (dd, J=14.8, 4.1 Hz, 1H), 2.48 (d, J=14.5 Hz, 1H), 1.65-1.51 (m, 5.5H) [overlap with H$_2$O signal], 1.46 (s, 3H), 1.43 (s, 3H), 1.37 (s, 3H).

The relative stereochemistry was assigned by comparing the central ring signals in the $^1$H-NMRs with the spectra of cis-rac and trans-rac (2-(4-chlorophenyl)-4-methyl-4-[[3-(trifluoromethyl)phenyl]sulfonyl]-tetrahydro-pyran.

Chiral resolution of cis-rac 6-(4-chlorophenyl)-2,2,4-trimethyl-4-[[3-(trifluoromethyl)phenyl]sulfonyl]-tetrahydro-pyran cis-rac 6-(4-chlorophenyl)-2,2,4-trimethyl-4-[[3-(trifluoromethyl)phenyl]sulfonyl]-tetrahydro-pyran (403 mg, 0.902 mmol) was subjected to preparative chiral-LC (AD-H-column, heptane/i-PrOH, 97.5:2.5). The solvents were removed under reduced pressure to give 170 mg (42%) of cis-EN1 SC-300 and 173 mg (43%) of cis-EN2 SC-301.

cis-EN1 SC-300—analytical chiral HPLC: chiracel AD-H (250×4.6 mm 5µ), 1 ml/min, 35° C., heptane/iPrOH 98/2, Ret. Time 14.283; ee>95% cis-EN2 SC-301—analytical chiral HPLC: chiracel AD-H (250×4.6 mm 5µ), 1 ml/min, 35° C., heptane/iPrOH 98/2, Ret. Time 17.708; ee>95%

2-(4-Chlorophenyl)-4-[[3-fluoro-5-(trifluoromethyl)-phenyl]sulfonyl]-4-methyl-tetrahydro-pyran (Example 35)

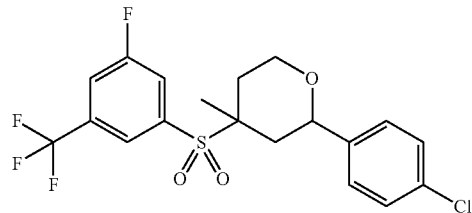 [SMILES: CC1(S(=O)(=O)c2cc(F)cc(C(F)(F)F)c2)CCOC(c2ccc(Cl)cc2)C1]

The synthesis was carried out in analogy to 2-(4-chlorophenyl)-4-methyl-4-[[3-(trifluoromethyloxy)-phenyl]sulfonyl]-tetrahydro-pyran (see above).

The crude product obtained in the last step was coated on silica (4 g) and purified using flash chromategraphy (silica, gradient heptane/EtOAc, 1:0→3:1) to give 510 mg (56%) of cis-rac 2-(4-chlorophenyl)-4-[[3-fluoro-5-(trifluoromethyl)-phenyl]sulfonyl]-4-methyl-tetrahydro-pyran and 90 mg (10%) of trans-rac 2-(4-chlorophenyl)-4-[[3-fluoro-5-(trifluoromethyl)-phenyl]sulfonyl]-4-methyl-tetrahydro-pyran SC-305.

$^1$H NMR (400 MHz, CDCl$_3$) of cis-rac 2-(4-chlorophenyl)-4-[[3-fluoro-5-(trifluoromethyl)-phenyl]sulfonyl]-4-methyl-tetrahydro-pyran: δ 7.93 (s, 1H), 7.76 (d, J=7.1 Hz, 1H), 7.66 (d, J=7.7 Hz, 1H), 7.36-7.30 (m, 2H), 7.29-7.21 (m, 6H) [overlap with CHCl$_3$ signal], 4.42 (dd, J=11.4, 2.0 Hz, 1H), 4.22-4.14 (m, 1H), 3.71 (td, J=12.4, 2.2 Hz, 1H), 2.35 (td, J=12.7, 5.3 Hz, 1H), 2.13 (t, J=12.3 Hz, 1H), 1.75 (dt, J=13.0, 2.2 Hz, 1H), 1.58 (s, 3H), 1.56-1.51 (m, 1H).

$^1$H-NMR (400 MHz, CDCl$_3$) of trans-rac 2-(4-chlorophenyl)-4-[[3-fluoro-5-(trifluoromethyl)-phenyl]sulfonyl]-4-methyl-tetrahydro-pyran SC-305: δ 7.97 (s, 1H), 7.81 (d, J=7.2 Hz, 1H), 7.68 (d, J=7.8 Hz, 1H), 7.37-7.28 (m, 4H), 5.16 (dd, J=11.7, 2.3 Hz, 1H), 4.39 (td, J=12.4, 2.5 Hz, 1H), 4.07 (dd, J=12.0, 4.4 Hz, 1H), 2.43 (d, J=15.4 Hz, 1H), 2.29-2.21 (m, 1H), 1.85 (ddd, J=15.5, 12.7, 5.7 Hz, 1H), 1.62 (dd, J=15.4, 11.7 Hz, 1H), 1.24 (s, 3H).

The relative stereochemistry was assigned by comparing the central ring signals in the $^1$H-NMRs with the spectra of cis-rac and trans-rac (2-(4-chlorophenyl)-4-methyl-4-[[3-(trifluoromethyl)phenyl]sulfonyl]-tetrahydropyran.

Chiral resolution of cis-rac 2-(4-chlorophenyl)-4-[[3-fluoro-5-(trifluoromethyl)-phenyl]sulfonyl]-4-methyl-tetrahydro-pyran cis-rac 2-(4-chlorophenyl)-4-[[3-fluoro-5-(trifluoromethyl)-phenyl]sulfonyl]-4-methyl-tetrahydro-pyran (510 mg, 1.167 mmol) was subjected to preparative chiral LC (IC-column, heptane/i-PrOH 95:5). This gave 199 mg (39%) of cis-EN1 SC-303 as a white solid and 185 mg (36%) of cis-EN2 SC-304 also as a white solid.

cis-EN1 SC-303—analytical chiral HPLC: chiralpak IC (250×4.6 mm 5μ), 1 ml/min, 35° C., heptane/iPrOH 95/5, Ret. Time 8.992; ee>90% cis-EN2 SC-304—analytical chiral HPLC: chiralpak IC (250×4.6 mm 5μ), 1 ml/min, 35° C., heptane/iPrOH 95/5, Ret. Time 11.884; ee>95%

2-Cyclopropyl-4-ethyl-4-[[3-(trifluoromethyl)phenyl]sulfonyl]-tetrahydro-pyran (Example 36)

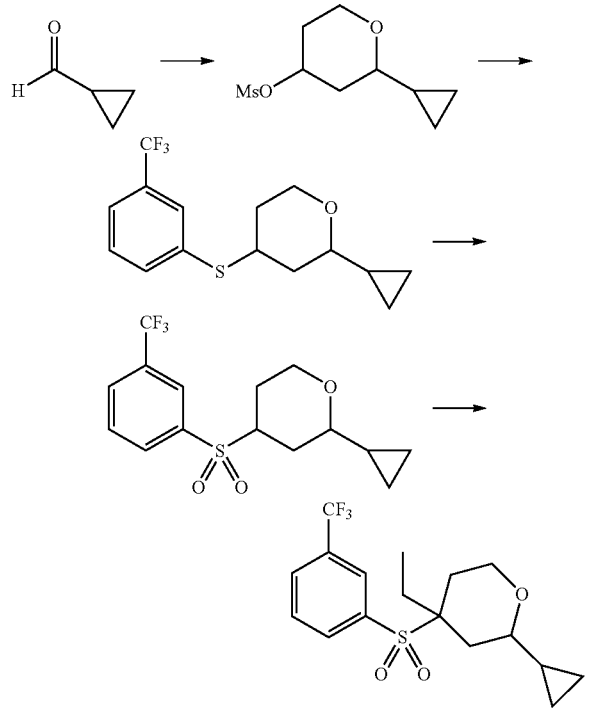

Step 1: 2-Cyclopropyltetrahydro-2H-pyran-4-yl methanesulfonate

A solution of cyclopropanecarbaldehyde (2.132 mL, 28.5 mmol) in DCM (25 mL) was prepared, followed by applying an ice/water bath and dropwise addition of methanesulfonic acid (18.5 mL, 285 mmol). Subsequently, 3-buten-1-ol (2.95 mL, 34.2 mmol) was added dropwise. The RM was stirred at 0° C. for 1.5 h. A solution of K₃PO₄ (45.4 g, 214 mmol) in H₂O (400 mL) was prepared and immersed in an ice/water bath. The RM was transferred into a separation funnel and added dropwise to the stirred and chilled aq. K₃PO₄ solution. The temperature was kept below 5° C. Subsequently, DCM (125 mL) was added, followed by some sat. aq. Na₂CO₃ to set the pH at 7-8. Addition of DCM (100 mL) and H₂O (100 mL) was followed by separation of the phases. The aq. layer was extracted with DCM (50 mL). The combination of organic layers was washed with sat. aq. NaHCO₃ (50 mL), dried (2× brine and Na₂SO₄) and concentrated to yield 5.74 g (91%) of the desired product as a slightly brown oil.

Step 2: 2-Cyclopropyl-4-((3-(trifluoromethyl)phenyl)thio)tetrahydro-2H-pyran A solution of 2-cyclopropyltetrahydro-2H-pyran-4-yl methanesulfonate (2.00 g, 9.08 mmol) in dry MeCN (100 mL) was degassed by N₂ bubbling for 1 h. K₂CO₃ (2.510 g, 18.16 mmol) was added, followed by 3-(trifluoromethyl)benzenethiol (2.414 mL, 18.16 mmol). The RM was stirred at 50° C. overnight. Addition of EtOAc (100 mL) and silica (2.5 g) was followed by filtration over a cotton plug. The residue was washed with EtOAc (2×25 mL), the combination of filtrates was concentrated. The residue was absorbed on silica and used for flash chromatography (silica, gradient heptane/EtOAc, 1:0→8:2) to result in 1.40 g (51%) of the desired product as a slightly yellow oil.

Step 3: 2-Cyclopropyl-4-((3-(trifluoromethyl)phenyl)sulfonyl)tetrahydro-2H-pyran 2-Cyclopropyl-4-((3-(trifluoromethyl)phenyl)thio)tetrahydro-2H-pyran (1.38 g, 4.56 mmol) was dissolved in MeOH (45 mL). An ice/water bath was applied. Oxone (7.01 g, min. 19.7 mmol) was almost completely dissolved in H₂O (25 mL), the turbid solution was added portionwise. During the addition, a raise of temperature was observed, the temperature was kept below 15° C. The RM was stirred vigorously at RT for 4 h. The major part of the MeOH was removed from the RM by rotary evaporation. The resulting suspension was mixed with H₂O (150 mL) and EtOAc (150 mL) to result in a clear two phase system. The layers were separated and the aq. layer was extracted with EtOAc (50 mL). The combined organic layers were washed with sat. aq. NaHCO₃ (50 mL), dried (brine and Na₂SO₄) and concentrated. The resulting oil was dissolved in CH₂Cl₂ (10 mL), this solution was added to heptane (50 mL). The turbid solution was concentrated to around 20 mL, the solution was separated from the oily precipitate and discarded. The oily precipitate was concentrated to yield 1.42 g (93%) of the desired product as a clear syrup.

Step 4: 2-Cyclopropyl-4-ethyl-4-((3-(trifluoromethyl)phenyl)sulfonyl)tetrahydro-2H-pyran A solution of 2-cyclopropyl-4-((3-(trifluoromethyl)phenyl)sulfonyl)tetrahydro-2H-pyran (1.39 g, 4.16 mmol) in dry THF (20 mL) was prepared, the temperature was lowered to −78° C., 1 M KOt-Bu in THF (4.57 mL, 4.57 mmol) was added dropwise and the RM was stirred for 10 min. Addition of C₂H₅I (0.665 mL, 8.31 mmol) was followed by stirring at −78° C. for 1 h. The flask was left in the cooling bath. Consequently, the temperature was kept at −78° C. for a few hours, followed by slow raise of temperature to RT and stirring overnight at RT. The RM was combined with aq. 0.5 M HCl (100 mL), some ice and EtOAc (100 mL) to result in a two phase system. The layers were separated, the aq. layer was extracted with EtOAc (25 mL). The combination of organic layers was washed with aq. 1 M Na₂S₂O₃ (2×30 mL), sat. aq. NaHCO₃ (50 mL) and dried (brine and Na₂SO₄), followed by concentration. The residue was used for flash chromatography (silica, gradient heptane/EtOAc, 99:1→7:3) to provide different fractions. One fraction contained mainly cis-rac 2-cyclopropyl-4-ethyl-4-[[3-(trifluoromethyl)phenyl]sulfonyl]-tetrahydro-pyran and was processed further in this procedure. Another fraction contained mainly the starting material 2-cyclopropyl-4-((3-(trifluoromethyl)phenyl)sulfonyl)tetrahydro-2H-pyran (0.72 g) and was used for a second synthesis (see below).

A solution of 2-cyclopropyl-4-((3-(trifluoromethyl)phenyl)sulfonyl)tetrahydro-2H-pyran (0.72 g, 2.153 mmol) in dry THF (10 mL) was prepared, the temperature was lowered to −40° C. with a dry ice/MeCN cooling bath, 1 M KOt-Bu in THF (6.46 mL, 6.46 mmol) was added dropwise and the RM was stirred for 10 min. Dropwise addition of C₂H₅I (0.861 mL, 10.77 mmol) was followed by stirring at −40° C. for 30 min. The flask was left in the cooling bath. Consequently, the temperature was kept at −40° C. for a few hours, followed by slow raise of temperature to RT and stirring overnight at RT. The RM was combined with aq. 0.5 M HCl (100 mL) and EtOAc (100 mL) to result in a two phase system. The layers were separated, the aq. layer was extracted with EtOAc (25 mL). The combination of organic layers was washed with aq. 1 M Na₂S₂O₃ (30 mL), sat. aq. NaHCO₃ (50 mL) and dried (brine and Na₂SO₄), followed by concentration. The residue was dissolved in CH₂Cl₂ (2 mL), combined with the fraction from the first reaction (containing mainly cis-rac 2-cyclopropyl-4-ethyl-4-[[3-(trifluoromethyl)phenyl]sulfonyl]-tetrahydro-pyran) and purified by flash chromatography (silica, gradient heptane/EtOAc, 95:5→8:2) to provide different fractions. The first eluting fraction contained predominantly trans-rac 2-cyclopropyl-4-ethyl-4-[[3-(trifluoromethyl)phenyl]sulfonyl]-tetrahydro-pyran SC-308 (trans:cis, 7:3). This residue was co-evaporated with MeCN (10 mL) and dissolved in MeCN (2 mL). After H₂O (2 mL) was added the resulting mixture was freeze dried to result in 109 mg (9%) of trans-rac 2-cyclopropyl-4-ethyl-4-[[3-(trifluoromethyl)phenyl]sulfonyl]-tetrahydro-pyran SC-308 (trans:cis, 7:3). Then, later eluting fractions were combined and concentrated to result in predominantly cis-rac 2-cyclopropyl-4-ethyl-4-[[3-(trifluoromethyl)phenyl]sulfonyl]-tetrahydro-pyran. The residue was dissolved in i-PrOH (3 mL) upon warming, followed by portionwise addition of heptane (14 mL) to start crystallisation. The crystals were filtered off, washed with heptane and dried on a filter to yield 220 mg (14%) of pure cis-rac 2-cyclopropyl-4-ethyl-4-[[3-(trifluoromethyl)phenyl]sulfonyl]-tetrahydro-pyran.

¹H NMR (400 MHz, CDCl₃) of cis-rac 2-cyclopropyl-4-ethyl-4-[[3-(trifluoromethyl)phenyl]sulfonyl]-tetrahydropyran: δ 8.13 (s, 1H), 8.08 (d, J=7.8 Hz, 1H), 7.95 (d, J=7.8 Hz, 1H), 7.76 (t, J=7.8 Hz, 1H), 3.96 (dd, J=11.9, 5.1 Hz, 1H), 3.47 (td, J=12.2, 1.8 Hz, 1H), 2.69-2.55 (m, 1H), 2.05 (td, J=12.8, 5.3 Hz, 1H), 2.00-1.80 (m, 4H), 1.67-1.55 (m, 1H), 1.08 (t, J=7.5 Hz, 3H), 0.94-0.80 (m, 1H), 0.66-0.47 (m, 2H), 0.41-0.25 (m, 1H), 0.22-0.09 (m, 1H).

¹H-NMR (400 MHz, CDCl₃) of trans-rac 2-cyclopropyl-4-ethyl-4-[[3-(trifluoromethyl)phenyl]sulfonyl]-tetrahydropyran SC-308 (trans:cis, 7:3): δ 8.13 (s, 0.3H), 8.08 (s, 1H), 8.04 (d, J=7.9 Hz, 0.7H), 7.95 (d, J=7.7 Hz, 1H), 7.77 (t, J=7.8 Hz, 1H), 4.24 (td, J=12.0, 2.3 Hz, 0.7H), 4.09-3.84 (m, 1H), 3.53-3.44 (m, 0.3H), 3.43-3.30 (m, 0.7H), 2.71-2.58 (m, 0.3H), 2.28-1.80 (m, 4H), 1.78-1.39 (m, 3H), 1.08 (t, J=7.5 Hz, 1H), 0.97 (t, J=7.4 Hz, 2H), 0.93-0.74 (m, 1H), 0.68-0.50 (m, 2H), 0.50-0.42 (m, 0.7H), 0.41-0.33 (m, 0.3H), 0.32-0.22 (m, 0.7H), 0.21-0.09 (m, 0.3H).

The relative stereochemistry was assigned by 2D-NMR. For trans-rac 2-cyclopropyl-4-ethyl-4-[[3-(trifluoromethyl)phenyl]sulfonyl]-tetrahydro-pyran SC-308 (trans:cis, 7:3) a NOE was observed for the aromatic protons with H4$_{ax}$ and H2$_{ax}$, while for cis-rac 2-cyclopropyl-4-ethyl-4-[[3-(trifluoromethyl)phenyl]sulfonyl]-tetrahydro-pyran this interaction was not present.

Chiral resolution of cis-rac 2-cyclopropyl-4-ethyl-4-[[3-(trifluoromethyl)phenyl]sulfonyl]-tetrahydropyran cis-rac 2-cyclopropyl-4-ethyl-4-[[3-(trifluoromethyl)phenyl]sulfonyl]-tetrahydro-pyran (403 mg, 0.902 mmol) was subjected to preparative chiral-LC (IC-column, heptane/EtOH, 95:5). Both enantiomers were dissolved in EtOAc (20 mL), followed by concentration. Both residues were dissolved in DCM (5 mL), added to heptane (30 mL) followed by concentration. The residues were suspended in heptane (2 mL). Filtration and drying on a filter provided 82 mg (37%) of cis-EN1 SC-307 and 84 mg (38%) of cis-EN2 SC-306.

cis-EN1 SC-307—analytical chiral HPLC: chiralpak IC (250×4.6 mm 5µ), 1 ml/min, 35° C., heptane/EtOH 80/20, Ret. Time 8.052; ee>95% cis-EN2 SC-306—analytical chiral HPLC: chiralpak IC (250×4.6 mm 5µ), 1 ml/min, 35° C., heptane/EtOH 80/20, Ret. Time 10.001; ee>95%

(2-(4-Chlorophenyl)-4-methyl-4-[[3-(trifluoromethyl)phenyl]sulfonyl]-tetrahydro-pyran (Example 37)

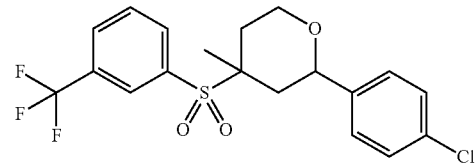 [SMILES: CC1(S(=O)(=O)c2cccc(C(F)(F)F)c2)CCOC(c2ccc(Cl)cc2)C1]

Step 1 & 2:
2-(4-Chlorophenyl)tetrahydro-2H-pyran-4-ol

To a solution of 4-chlorobenzaldehyde (10 g, 71.1 mmol) in a mixture of TFA (79 mL, 1032 mmol) and DCM (150 mL) was added but-3-en-1-ol (6.12 mL, 71.1 mmol) at RT. The mixture was stirred at RT for 26 h. The RM was concentrated in vacuo, cooled in an ice bath and basified with aq. 6M NaOH. The product was extracted with EtOAc (2×100 mL). The combined organic layers were washed with sat. aq. NaHCO₃ (2×50 mL), aq. 1M KHSO₄ (2×50 mL) and brine (2×50 mL) before drying on Na₂SO₄ and concentration in vacuo to give a mixture of 2-(4-chlorophenyl)tetrahydro-2H-pyran-4-yl 2,2,2-trifluoroacetate and 2-(4-chlorophenyl)tetrahydro-2H-pyran-4-ol as a dark yellow oil. The product was dissolved in MeOH (50 mL) and LiOH.H₂O (1.85 g, 44 mmol) was added. The mixture was stirred at RT for 30 min. The RM was concentrated in vacuo and the residue was diluted with EtOAc (100 mL) before acidification with aq. 1M KHSO₄. The product was extracted with EtOAc (1×100 mL) and the combined organic layers were washed with aq. 1M KHSO₄ (2×50 mL) and brine (2×50 mL) before drying on Na₂SO₄ and concentration in vacuo to give a yellow oil. The product was purified using CC (silica, heptane/acetone, 99:1→1:1) to give 2-(4-chlorophenyl)tetrahydro-2H-pyran-4-ol (4.02 g, 26%) as a white solid. Also, impure fractions were obtained which were combined, concentrated in vacuo and purified using flash chromatography (silica, gradient heptane/acetone, 99:1→1:1) to give another batch of 2-(4-chlorophenyl)tetrahydro-2H-pyran-4-ol (3.70 g, 24%) as a white solid. Total yield: 7.73 g (51%).

Step 3: 2-(4-Chlorophenyl)tetrahydro-2H-pyran-4-yl methanesulfonate

A solution of 2-(4-chlorophenyl)tetrahydro-2H-pyran-4-ol (7.52 g, 35.4 mmol) in DCM (50 mL) was cooled in an ice bath under N₂. DIPEA (17 mL, 97 mmol) was added, followed by slow addition of MsCl (4.2 mL, 54.3 mmol) via a syringe. The mixture was stirred at RT for 24 h. The RM was concentrated in vacuo and the residue was partitioned between a mixture of aq. 1M $KHSO_4$ (100 mL), brine (50 mL), $H_2O$ (50 mL) and EtOAc/i-$Pr_2O$ (1/1, v/v, 200 mL). The aq. layer was extracted with EtOAc/i-$Pr_2O$ (1/1, v/v, 100 mL) and the combined organic layers were washed with aq. 1M $KHSO_4$ (2×50 mL), sat. aq. $NaHCO_3$ (2×50 mL) and brine (2×50 mL) before drying on $Na_2SO_4$ and concentration in vacuo to give a dark orange oil. The product was purified using flash chromatography (silica, gradient heptane/acetone, 99:1→1:1) to give 9.25 g (90%) of the desired product.

Step 4: 2-(4-Chlorophenyl)-4-((3-(trifluoromethyl)phenyl)thio)tetrahydro-2H-pyran A solution of 2-(4-chlorophenyl)tetrahydro-2H-pyran-4-yl methanesulfonate (9 g, 31.0 mmol) in dry DMF (200 mL) was degassed by alternating vacuum and Ar 5 times over 10 min. $K_2CO_3$ (8.56 g, 61.9 mmol) was added and the mixture was degassed two more times. Via a syringe, 3-(trifluoromethyl)-benzenethiol (27.6 g, 155 mmol) was added over 2 min and the mixture was degassed two more times. The mixture was stirred at 50° C. under Ar for 20 h. The RM was partitioned between $H_2O$ (250 mL) and i-$Pr_2O$ (250 mL). The layers were separated and the aq. layer was extracted with i-$Pr_2O$ (250 mL). The combined organic layers were washed with $H_2O$ (2×100 mL), sat. aq. $NaHCO_3$ (3×100 mL), aq. 1M $KHSO_4$ (3×100 mL) and brine (2×100 mL) before drying on $Na_2SO_4$ and concentration in vacuo to give a yellow oil. The product was purified using flash chromatography (silica, gradient, heptane/acetone, 100:0→3:1) to give the desired product (10.74 g, 93%) as a light yellow oil.

Step 5: 2-(4-Chlorophenyl)-4-((3-(trifluoromethyl)phenyl)sulfonyl)tetrahydro-2H-pyran To a cooled solution of 2-(4-chlorophenyl)-4-((3-(trifluoromethyl)phenyl)thio)tetrahydro-2H-pyran (5 g, 13.41 mmol) in MeOH (160 mL) was added a solution of oxone (16.49 g, min. 46.4 mmol) in $H_2O$ (110 mL) at such rate the temperature did not exceed 20° C. The white suspension was stirred at 0° C. for 1 h, then at RT for 20 h. MeOH was distilled off in vacuo and the residue was extracted with EtOAc (2×150 mL). The organic layer was washed with sat. aq. $NaHCO_3$ (3×50 mL) and brine (2×50 mL) before drying on $Na_2SO_4$ and concentration in vacuo to give a white solid. The product was coated onto silica (14 g) and subsequently purified using flash chromatography (silica, gradient heptane/acetone, 1:0 to 3:1) to give 4.14 g (76%) of the desired product as a white solid.

Step 6: (2-(4-Chlorophenyl)-4-methyl-4-[[3-(trifluoromethyl)phenyl]sulfonyl]-tetrahydro-pyran To a cooled (−78° C., acetone/dry ice) solution of 2-(4-chlorophenyl)-4-((3-(trifluoromethyl)phenyl)sulfonyl)tetrahydro-2H-pyran (1.7 g, 4.20 mmol) in dry THF (25 mL) under $N_2$, KOt-Bu (0.707 g, 6.30 mmol) was added followed by MeI (0.525 mL, 8.40 mmol). The RM was stirred at −78° C. for 1 h. Subsequently, the RM was allowed to warm to RT over the course of 18 h. The RM was combined with a RM prepared in the same manner starting from 1.7 g of 2-(4-chlorophenyl)-4-((3-(trifluoromethyl)phenyl)-sulfonyl)tetrahydro-2H-pyran. The combined mixtures were quenched with half sat. aq. $NH_4Cl$ (2 mL), diluted with EtOAc (100 mL) and subsequently approximately half of the solvents were removed under reduced pressure in order to remove most of the THF. The mixture was diluted with EtOAc (100 mL) and washed with sat. aq. $NaHCO_3$ (1×100 mL), half sat. aq. NaCl (100 mL) and brine (100 mL). The organics were dried over $Na_2SO_4$ and concentrated under reduced pressure to obtain an orange oil which was immediately diluted with $CH_2Cl_2$ (5 mL) to prevent solidification. The product was purified using flash chromatography (silica, gradient heptane/acetone, 1:0→3:1) to give 2.77 g (77%) of trans-rac (2-(4-chlorophenyl)-4-methyl-4-[[3-(trifluoromethyl)phenyl]sulfonyl]-tetrahydro-pyran and impure cis-rac product which was purified further using flash chromatography (silica, gradient heptane/acetone, 1:0→3:1) to give 160 mg (5%) of cis-rac (2-(4-chlorophenyl)-4-methyl-4-[[3-(trifluoromethyl)-phenyl]sulfonyl]-tetrahydro-pyran.

$^1$H-NMR (400 MHz, $CDCl_3$) of cis-rac (2-(4-chlorophenyl)-4-methyl-4-[[3-(trifluoromethyl)phenyl]sulfonyl]-tetrahydro-pyran: δ 8.13 (s, 1H), 8.04 (d, J=7.9 Hz, 1H), 7.94 (d, J=7.8 Hz, 1H), 7.73 (t, J=7.8 Hz, 1H), 7.34-7.28 (m, 2H), 7.28-7.19 (m, 2H), 4.41 (dd, J=11.5, 2.0 Hz, 1H), 4.21-4.11 (m, 1H), 3.70 (td, J=12.4, 2.2 Hz, 1H), 2.35 (td, J=12.8, 5.4 Hz, 1H), 2.14 (t, J=12.3 Hz, 1H), 1.74 (dt, J=13.0, 2.2 Hz, 1H), 1.62-1.50 (s, 4H).

$^1$H-NMR (400 MHz, $CDCl_3$) of trans-rac (2-(4-chlorophenyl)-4-methyl-4-[[3-(trifluoromethyl)phenyl]sulfonyl]-tetrahydro-pyran: δ 8.17 (s, 1H), 8.10 (d, J=7.9 Hz, 1H), 7.97 (d, J=7.8 Hz, 1H), 7.77 (t, J=7.8 Hz, 1H), 7.36-7.29 (m, 4H), 5.20 (dd, J=11.7, 2.4 Hz, 1H), 4.41 (td, J=12.4, 2.5 Hz, 1H), 4.12-3.98 (m, 1H), 2.42 (dt, J=15.3, 2.0 Hz, 1H), 2.32-2.21 (m, 1H), 1.83 (ddd, J=15.4, 12.7, 5.7 Hz, 1H), 1.67-1.53 (m, 1H), 1.22 (s, 3H).

The relative stereochemistry was assigned by 2D-NMR. For trans-rac (2-(4-chlorophenyl)-4-methyl-4-[[3-(trifluoromethyl)phenyl]sulfonyl]-tetrahydro-pyran a NOE was observed for the sulfone aromate with $H2_{ax}$ and $H4_{ax}$. For cis-rac (2-(4-chlorophenyl)-4-methyl-4-[[3-(trifluoromethyl)phenyl]sulfonyl]-tetrahydro-pyran a NOE was observed for the sulfone aromate with $H1_{ax}$ en $H5_{ax}$ and also a NOE was observed for the Me-group with $H4_{ax}$.

Chiral resolution of cis-rac (2-(4-chlorophenyl)-4-methyl-4-[[3-(trifluoromethyl)phenyl]sulfonyl]-tetrahydro-pyran cis-rac (2-(4-chlorophenyl)-4-methyl-4-[[3-(trifluoromethyl)phenyl]sulfonyl]-tetrahydro-pyran (160 mg, 0.382 mmol) was subjected to preparative chiral-LC (IC-column, heptane/i-PrOH, 95:5) to give 49 mg (31%) of cis-EN1 SC-309 and 47 mg (29%) of cis-EN2 SC-310.

cis-EN1 SC-309—analytical HPLC: chiralpak IC (250× 4.6 mm 5μ), 1 ml/min, 35° C., heptane/iPrOH 95/5, Ret. Time 14.214; ee>95%/specific rotation $[α]_D^{25.1}$ −18.5° (c 0.99; DCM);

cis-EN2 SC-310—analytical HPLC: chiralpak IC (250× 4.6 mm 5μ), 1 ml/min, 35° C., heptane/iPrOH 95/5, Ret. Time 17.158; ee>95%/specific rotation $[α]_D^{25.3}$ +19.3° (c 0.96; DCM).

Chiral resolution of trans-rac (2-(4-chlorophenyl)-4-methyl-4-[[3-(trifluoromethyl)phenyl]sulfonyl]-tetrahydro-pyran

[Trans racemic](2-(4-chlorophenyl)-4-methyl-4-[[3-(trifluoromethyl)phenyl]sulfonyl]-tetrahydro-pyran (650 mg, 1.552 mmol) was subjected to preparative chiral-LC (IC-column, heptane/i-PrOH, 95:5) to give 282 mg (43%) of trans-EN1 SC-311 and 251 mg (39%) of trans-EN2 SC-312.

trans-EN1 SC-311—analytical chiral HPLC: chiralpak IC (250×4.6 mm 5µ), 1 ml/min, 35° C., heptane/iPrOH 95/5, Ret. Time 8.292; ee>95% trans-EN2 SC-312—analytical chiral HPLC: chiralpak IC (250×4.6 mm 5µ), 1 ml/min, 35° C., heptane/iPrOH 95/5, Ret. Time 14.196; ee>95%

2-(4-Chlorophenyl)-4-methyl-4-[[3-(trifluoromethyl-oxy)-phenyl]sulfonyl]-tetrahydro-pyran (Example 38)

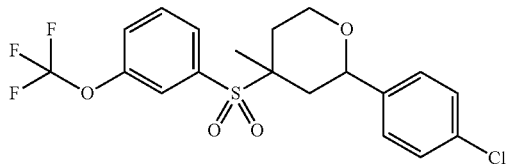 [SMILES: CC1(S(=O)(=O)c2cccc(OC(F)(F)F)c2)CCOC(c2ccc(Cl)cc2)C1]

Step 1 & 2:
2-(4-Chlorophenyl)tetrahydro-2H-pyran-4-ol

This reaction was carried out in a 500 mL flask equipped with a CaCl$_2$ drying tube. To a solution of 4-chlorobenzaldehyde (10 g, 71.1 mmol) in CH$_2$Cl$_2$ (150 mL), TFA (79 mL, 1032 mmol) was added. Subsequently, but-3-en-1-ol (6.12 mL, 71.1 mmol) was added. The RM was stirred at RT for 114 h. The RM was concentrated under reduced pressure. Aq. 6M NaOH (50 mL) was added in small portions and the mixture was stirred for 1 h. The RM was extracted with EtOAc (2×100 mL) and the combined organic layer washed with sat. aq. NaHCO$_3$ (2×50 mL), aq. 1 M KHSO$_4$ (2×50 mL) and dried over Na$_2$SO$_4$. The solvent was removed under reduced pressure. The product was purified using CC (silica, heptane/acetone, 99:1→1:1) to give 9.91 g (66%) of the desired product as an off-white solid.

Step 3: 2-(4-Chlorophenyl)tetrahydro-2H-pyran-4-yl methanesulfonate

A solution of 2-(4-chlorophenyl)tetrahydro-2H-pyran-4-ol (9.9 g, 46.6 mmol) in CH$_2$Cl$_2$ (50 mL) and DIPEA (20.33 mL, 116 mmol) was cooled to 0° C. Subsequently, methanesulfonyl chloride (5.44 mL, 69.8 mmol) was added dropwise to the solution which was subsequently stirred for 48 h at RT. The RM was concentrated under reduced pressure and the dark brown residue was partitioned between a mixture of aq. 1M KHSO$_4$ (100 mL), brine (50 mL) and H$_2$O (50 mL) and EtOAc/i-Pr$_2$O (1/1, v/v, 200 mL). The aq. layer was extracted with EtOAc/i-Pr$_2$O (1/1, v/v, 100 mL) and the combined organic layers were washed with aq. 1M KHSO$_4$ (2×100 mL), sat. aq. NaHCO$_3$ (2×100 mL) and brine (2×50 mL) before drying on Na$_2$SO$_4$ and concentration in vacuo. The product was purified using flash chromatography (silica, gradient heptane/acetone, 99:1→3:1) to give 12 g (90%) of the desired product as a tan solid.

Step 4: 2-(4-Chlorophenyl)-4-((3-(trifluoromethoxy) phenyl)thio)tetrahydro-2H-pyran To an argon flushed suspension of 2-(4-chlorophenyl) tetrahydro-2H-pyran-4-yl methanesulfonate (3571 mg, 12.28 mmol) and K$_2$CO$_3$ (3395 mg, 24.56 mmol) in dry MeCN (35 mL), 3-(trifluoromethoxy)benzenethiol (4885 mg, 25.2 mmol) was added and the RM was stirred at 50° C. for 5 h and subsequently for 18 h at RT. Subsequently, the RM was combined with a RM prepared in the same manner from 150 mg (0.52 mmol) of 2-(4-chlorophenyl)tetrahydro-2H-pyran-4-yl methanesulfonate, diluted with EtOAc (100 mL) and filtered over silica and sand. The residue was coated on silica and purified using flash chromatography (silica, gradient heptane/i-Pr$_2$O, 1:0→4:1) to give 4.7 g (94%) of the desired product as a colorless oil.

Step 5: 2-(4-Chlorophenyl)-4-((3-(trifluoromethoxy) phenyl)sulfonyl)tetrahydro-2H-pyran To a cooled (0° C.) solution of 2-(4-chlorophenyl)-4-((3-(trifluoromethoxy)phenyl)thio)tetrahydro-2H-pyran (4.7 g, 12.09 mmol) in MeOH (160 mL) was added a solution of oxone (14.86 g, min. 41.8 mmol) in H$_2$O (110 mL) at such rate the temperature did not exceed 20° C. The white suspension was stirred at 0° C. for 1 h and subsequently at RT for 20 h. The majority of the MeOH was removed under reduced pressure and the residue partitioned between half sat. aq. NaHCO$_3$ (100 mL) and EtOAc (100 mL). Subsequently, the aq. layer was washed with EtOAc (50 mL). The organics were combined and washed with brine (100 mL), dried over Na$_2$SO$_4$ and concentrated under reduced pressure to afford the product as a colorless oil which solidified upon standing. The product was dissolved in EtOAc (100 mL) and co-evaporated with heptane (100 mL). The white solids were co-evaporated with pentane (2×30 mL) to give 4.95 g (97%) of the desired product as a white solid.

Step 6: 2-(4-Chlorophenyl)-4-methyl-4-[[3-(trifluoromethyloxy)-phenyl]sulfonyl]-tetrahydro-pyran To a cooled (−78° C.) solution of 2-(4-chlorophenyl)-4-((3-(trifluoromethoxy)phenyl)sulfonyl)tetrahydro-2H-pyran (4.95 g, 11.76 mmol) in dry THF (60 mL) under N$_2$ atmosphere, 1M KOt-Bu in THF (17.64 mmol, 17.64 mL) was added and the mixture was stirred for 10 min. Subsequently, MeI (1.471 mL, 23.52 mmol) was added. The RM was stirred at −78° C. for 1 h and subsequently for 18 h at RT. The RM was quenched with sat. aq. NH$_4$Cl (4 mL), and the THF was removed under reduced pressure. The residue was partitioned between half sat. NaCl (100 mL) and EtOAc (200 mL). Subsequently, the organic layer was washed with half sat. NaCl (100 mL) and brine (100 mL). The organics were dried over Na$_2$SO$_4$ and the solvent was removed under reduced pressure. The residue was diluted with DCM (10 mL) and purified using flash chromatography (silica, gradient heptane/acetone, 1:0→4:1) to give 2.45 g (48%) of cis-rac 2-(4-chlorophenyl)-4-methyl-4-[[3-(trifluoromethyloxy)-phenyl]sulfonyl]-tetrahydro-pyran. The remaining impure residue was subjected to an additional flash CC (silica, gradient heptane/EtOAc 1:0→8:2). The product was lyophilized using MeCN/H$_2$O (3/1, v/v, 2 mL) to give 478 mg (9.3%) of trans-rac 2-(4-chlorophenyl)-4-methyl-4-[[3-(trifluoromethyloxy)-phenyl]sulfonyl]-tetrahydro-pyran SC-315 as a white solid.

$^1$H NMR (400 MHz, CDCl$_3$) of cis-rac 2-(4-chlorophenyl)-4-methyl-4-[[3-(trifluoromethyloxy)-phenyl]sulfonyl]-tetrahydro-pyran: δ 7.79 (d, J=7.8 Hz, 1H), 7.72 (s, 1H), 7.63 (t, J=8.0 Hz, 1H), 7.58-7.50 (m, 1H), 7.35-7.29 (m, 2H), 7.24 (d, J=8.5 Hz, 2H), 4.40 (dd, J=11.5, 2.0 Hz, 1H), 4.21-4.11 (m, 1H), 3.70 (td, J=12.4, 2.1 Hz, 1H), 2.34 (td, J=12.8, 5.4 Hz, 1H), 2.13 (t, J=12.3 Hz, 1H), 1.73 (dt, J=13.0, 2.2 Hz, 1H), 1.60-1.48 (m, 5H) [overlap with H$_2$O signal].

¹H-NMR (400 MHz, CDCl₃) of trans-rac 2-(4-chlorophenyl)-4-methyl-4-[[3-(trifluoromethyloxy)-phenyl]sulfonyl]-tetrahydro-pyran SC-315: δ 7.85 (d, J=7.8 Hz, 1H), 7.76 (s, 1H), 7.67 (t, J=8.0 Hz, 1H), 7.56 (d, J=8.3 Hz, 1H), 7.36-7.23 (m, 8H) [overlap with CHCl₃ signal], 5.19 (dd, J=11.7, 2.3 Hz, 1H), 4.40 (td, J=12.4, 2.4 Hz, 1H), 4.04 (dd, J=11.9, 4.6 Hz, 1H), 2.44 (d, J=15.4 Hz, 1H), 2.31-2.22 (m, 1H), 1.82 (ddd, J=15.4, 12.7, 5.6 Hz, 1H), 1.56 (s, 5H) [overlap with H₂O signal], 1.22 (s, 3H).

The relative stereochemistry was assigned by comparing the central ring signals in the ¹H-NMRs with the spectra of cis-rac and trans-rac (2-(4-chlorophenyl)-4-methyl-4-[[3-(trifluoromethyl)phenyl]sulfonyl]-tetrahydro-pyran.

Chiral resolution of cis-rac 2-(4-chlorophenyl)-4-methyl-4-[[3-(trifluoromethyloxy)-phenyl]sulfonyl]-tetrahydro-pyran cis-rac 2-(4-chlorophenyl)-4-methyl-4-[[3-(trifluoromethyloxy)-phenyl]sulfonyl]-tetrahydro-pyran (600 mg, 1.380 mmol) was subjected to preparative chiral-LC (AD-H-column, heptane/i-PrOH 95:5). The solvents were removed under reduced pressure and the products lyophilised to give 254 mg (42%) of cis-EN1 SC-313 and 250 mg (42%) of cis-EN1 SC-314.

cis-EN1 SC-313—analytical chiral HPLC: Chiralcel AD-H (250×4.6 mm 5μ), 1 ml/min, 35° C., heptane/iPrOH 95/5, Ret. Time 16.643; ee>95% cis-EN2 SC-314—analytical chiral HPLC: Chiralcel AD-H (250×4.6 mm 5μ), 1 ml/min, 35° C., heptane/iPrOH 95/5, Ret. Time 19.680; ee>95%

2-((4-chlorophenoxy)methyl)-4-methyl-4-((3-(trifluoromethyl)phenyl)sulfonyl)tetrahydro-2H-pyran (Example 40)

To a stirred solution of (4-methyl-4-((3-(trifluoromethyl)phenyl)sulfonyl)tetrahydro-2H-pyran-2-yl)methanol (0.90 g, 2.6 mmol, 1 eq) and 4-chlorophenol (0.34 g, 2.6 mmol 1 eq) in THF (20 mL), triphenyl phosphine (1.02 g, 3.9 mmol, 1.5 eq) was added followed by addition of DEAD (0.616 g, 3.8 mmol, 1.5 eq) at 0° C. The reaction mixture was stirred for 12 h at RT. The reaction was monitored by TLC and the mixture was diluted with ethyl acetate (50 mL), washed with water (2×30 mL), brine (50 mL), dried over anhydr. sodium sulfate, filtered and evaporated under reduced pressure to get crude product which was purified by column chromatography to afford pure compound mixture of diastereomers (0.380 g, 34.5%) as white solid. Diastereomers separation was done by reverse phase prep HPLC. Major isomer was characterized as cis diastereomer by ¹H-NMR and NOE experiments.

cis-isomer (SC-128, SC-129): 1H NMR (400 MHz, DMSO-d₆, δ ppm): 1.39-1.41 (4H), 1.58-1.62 (1H), 1.84-1.90 (1H), 1.98-2.02 (1H), 3.52-3.58 (1H), 3.80-3.84 (1H), 3.88-3.98 (3H), 6.93-6.96 (2H), 2.28-7.32 (1H), 7.94-7.99 (1H), 8.03 (s, 1H), 8.15-8.18 (1H), 8.22-8.25 (1H).

Two enantiomers of this single diastereomer were separated by chiral prep HPLC using an AD-H column and MeOH/DEA (100/0.1) as mobile phase to obtain two cis enantiomers SC-127 and SC-128.

SC-127: (0.100 g, off white solid, 1ˢᵗ eluted enantiomer).

SC-128 (0.093 g, off white solid, 2ⁿᵈ eluted enantiomer).

General Reaction Scheme 2 for the Compounds Preparation of the Compounds of Examples 41

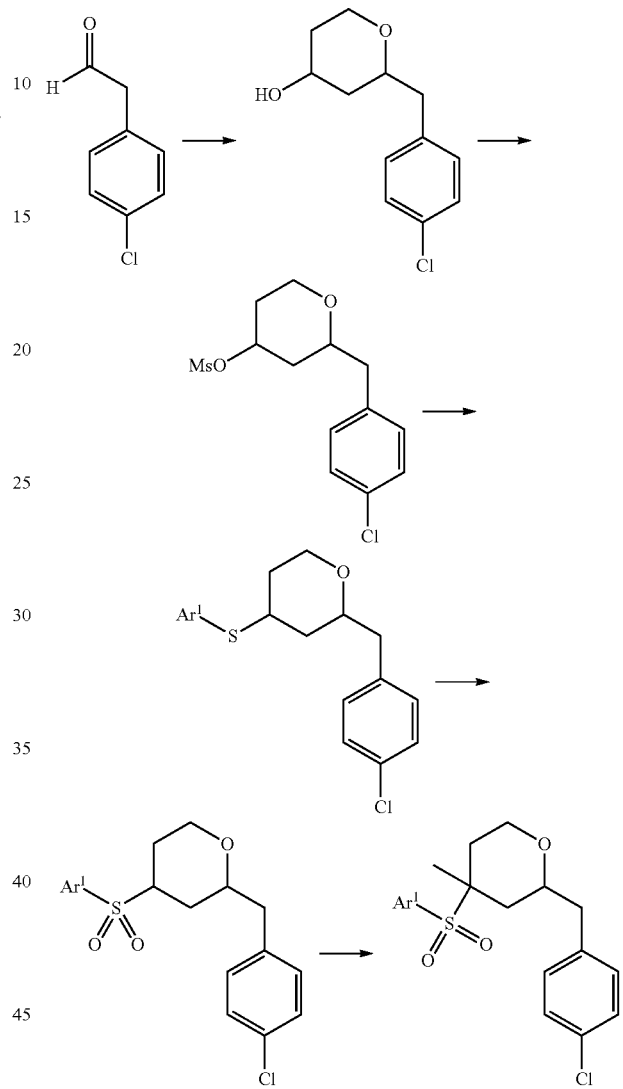

General reaction scheme 2

2-[(4-Chlorophenyl)-methyl]-4-methyl-4-[[3-(trifluoromethyl)phenyl]sulfonyl]-tetrahydro-pyran (Example 41)

Starting from 2-(4-chlorophenyl)acetaldehyde 2-[(4-chlorophenyl)-methyl]-4-methyl-4-[[3-(trifluoromethyl)phenyl]sulfonyl]-tetrahydro-pyran was prepared in analogy to Example 23 following general reaction scheme 2.

Diastereomeric mixture of 2-[(4-chlorophenyl)-methyl]-4-methyl-4-[[3-(trifluoromethyl)phenyl]sulfonyl]-tetrahydro-pyran was separated by reverse phase HPLC and structure of major diastereomer was determined to be cis by NMR experiments.

cis-isomer (SC-130, SC-131): 1H NMR (400 MHz, DMSO-d₆, δ ppm): 1.32 (s, 3H), 1.34-1.37 (1H), 1.41-1.45

(1H), 1.67-1.74 (1H), 1.92-2.00 (1H), 2.70-2.72 (2H), 3.40-3.46 (1H), 3.60-3.65 (1H), 3.81-3.86 (1H), 7.21-7.23 (2H), 7.28-7.30 (2H), 7.92-7.97 (1H), 8.00 (s, 1H), 8.13-8.16 (1H), 8.20-8.22 (1H).

Two enantiomers of this single diastereomer were separated by chiral prep HPLC using CHIRALPAK-IC column and Hexane/EtOH/DEA (90/10/0.1) as mobile phase to obtain two cis enantiomers SC-130 and SC-131.

SC-130: (0.21 g, off white solid, 1$^{st}$ eluted enantiomer).
SC-131 (0.21 g, off white solid, 2$^{nd}$ eluted enantiomer).

2-[3,4-Bis(methylsulfonyl)-phenyl]-4-methyl-4-[[3-(trifluoromethyl)phenyl]sulfonyl]-tetrahydro-pyran (Example 42)

Step 1: 2-(4-bromo-3-fluorophenyl)-4-methyl-4-((3-(trifluoromethyl)phenyl)sulfonyl)tetrahydro-2H-pyran Starting from 4-bromo-3-fluorobenzaldehyde 2-(4-bromo-3-fluorophenyl)-4-methyl-4-((3-(trifluoromethyl) phenyl)sulfonyl)tetrahydro-2H-pyran was prepared in analogy to Example 23 following general reaction scheme 1.

Step 2: 2-[3,4-Bis(methylsulfonyl)-phenyl]-4-methyl-4-[[3-(trifluoromethyl)phenyl]sulfonyl]-tetrahydro-pyran To a stirred solution of 2-(4-bromo-3-fluorophenyl)-4-methyl-4-((3-(trifluoromethyl)phenyl)sulfonyl)tetrahydro-2H-pyran (6.0 g, 0.0124 mol, 1 eq) in DMSO (60 mL) was added sodiummethanesulfinate (1.52 g, 0.0149 mol, 1.2 eq) and L-proline sodium salt (0.34 g, 0.0024 mol, 0.2 eq). The reaction mixture was degassed for 10 min and then CuI (0.23 g, 0.00124 mol, 0.1 eq) was added and the reaction mixture was heated up to 90° C. for 16 h in a sealed tube. Then the reaction mass was diluted with H$_2$O, extracted with EtOAc (2×150 mL), organic layer was washed with H$_2$O (200 mL) and brine (150 mL), dried over anhydr. Na$_2$SO$_4$ and the solvent was evaporated under reduced pressure to get crude product which was further purified by CC to afford two set of compounds (one is mono sulfomethyl (SC-144) and other is disulfomethyl (SC132, SC-133) and both were cis as confirmed by NMR experiments.

cis-isomer (SC-132, SC-133): 1H NMR (400 MHz, DMSO-d$_6$, δ ppm): 1.47-1.52 (4H), 1.87-1.89 (2H), 2.13-2.20 (1H), 3.46-3.48 (6H), 3.71-3.77 (1H), 4.10-4.15 (1H), 4.82-4.86 (1H), 7.92-8.00 (2H), 9.06 (s, 1H), 8.15-8.17 (1H), 8.21-8.23 (3H).

Two enantiomers of this single diastereomer were separated by chiral SFC using a OJ-H column to obtain two cis enantiomers SC-132 and SC-133.

SC-132: (1.30 g, off white solid, 1$^{st}$ eluted enantiomer).
SC-133: (1.35 g, off white solid, 2$^{nd}$ eluted enantiomer).

1-[4-[4-Methyl-4-[[3-(trifluoromethyl)phenyl]sulfonyl]-tetrahydro-pyran-2-yl]-phenyl]-1H-[1,2,4]triazole (Example 43)

Step 1: 2-(4-bromophenyl)-4-methyl-4-((3-(trifluoromethyl)phenyl)sulfonyl)tetrahydro-2H-pyran Starting from 4-bromobenzaldehyde 2-(4-bromophenyl)-4-methyl-4-((3-(trifluoromethyl)phenyl)sulfonyl)tetrahydro-2H-pyran was prepared in analogy to Example 23 following general reaction scheme 1.

Step 2: 1-(4-(4-methyl-4-((3-(trifluoromethyl)phenyl)sulfonyl)tetrahydro-2H-pyran-2-yl)phenyl)-1H-1,2,4-triazole To a stirred solution of 2-(4-bromophenyl)-4-methyl-4-((3-(trifluoromethyl)phenyl)sulfonyl)tetrahydro-2H-pyran (0.1 g, 2.16 mmol, 1 eq) in toluene (10 mL) was added 1H-[1,2,4]triazole (0.074 g, 1.079 mmol, 5 eq), K$_3$PO$_4$ (0.091 g, 0.432 mmol, 2 eq) and N,N-dimethylcyclohexadiamine (0.04 mL, 0.216 mmol, 1 eq). The reaction mixture was degassed for 10 min and then CuI (50 mg, 0.259 mmol, 1.2 eq) was added and the mixture was again degassed for 10 min. The reaction mixture was heated up to 150° C. for 72 h in a sealed tube. After completion of reaction (monitored by TLC), the reaction mass was diluted with H$_2$O (20 mL), extracted with EtOAc (2×35 mL), organic layer was washed with brine (20 mL), dried over anhydr. Na$_2$SO$_4$, filtered and evaporated under reduced pressure to get crude product which was further purified by column chromatography to afford 1-(4-(4-methyl-4-((3-(trifluoromethyl)phenyl)sulfonyl)tetrahydro-2H-pyran-2-yl)phenyl)-1H-1,2,4-triazole as a mixture of diastereiomers that were separated by reverse phase prep HPLC to afford cis diasterisomer as the major isomer (confirmed by NMR).

cis-isomer (SC-134, SC-135): 1H NMR (400 MHz, DMSO-d$_6$, δ ppm): 1.47-1.51 (4H), 1.73-1.76 (1H), 1.86-1.93 (1H), 2.12-2.17 (1H), 3.69-3.75 (1H), 4.06-4.10 (1H), 4.61-4.64 (1H), 7.49-7.52 (2H), 7.82-7.85 (2H), 8.05 (s, 1H), 8.15-8.17 (1H), 8.20-8.23 (2H).

Two enantiomers of this single diastereomer were separated by chiral SFC using an IC column to obtain two cis enantiomers SC-134 and SC-135.

SC-134: (0.051 g, off white solid, 1$^{st}$ eluted enantiomer).
SC-135: (0.060 g, off white solid, 2$^{nd}$ eluted enantiomer).

2-Fluoro-5-[4-methyl-4-[[3-(trifluoromethyl)phenyl]sulfonyl]-tetrahydro-pyran-2-yl]-benzonitrile (Example 44)

Step 1: 2-(3-bromo-4-fluorophenyl)-4-methyl-4-((3-(trifluoromethyl)phenyl)sulfonyl)tetrahydro-2H-pyran Starting from 3-bromo-4-fluorobenzaldehyde 2-(3-bromo-4-fluorophenyl)-4-methyl-4-((3-(trifluoromethyl) phenyl)sulfonyl)tetrahydro-2H-pyran was prepared in analogy to Example 23 following general reaction scheme 1.

Step 2: 2-Fluoro-5-[4-methyl-4-[[3-(trifluoromethyl) phenyl]sulfonyl]-tetrahydro-pyran-2-yl]-benzonitrile To a stirred solution of 2-(3-bromo-4-fluorophenyl)-4-methyl-4-((3-(trifluoromethyl)-phenyl)sulfonyl)tetrahydro-2H-pyran (1.8 g, 3.74 mmol, 1 eq) in NMP (15 mL) was added CuCN (0.402 g, 4.49 mmol, 1.2 eq) and the mixture was continued to stir for 30 h. After completion of reaction (monitored by TLC), reaction mass was quenched with H$_2$O, extracted with ethyl acetate (2×50 mL), organic layer was washed with H$_2$O (20 mL), brine (20 mL), dried over anhydr. Na$_2$SO$_4$ and the solvent was evaporated under reduced pressure to get crude product which was further purified by column chromatography to afford 2-fluoro-5-(4-methyl-4-((3-(trifluoromethyl)phenyl)sulfonyl)tetrahydro-2H-pyran-2-yl)benzonitrile (0.90 g, 56%) as off white solid.

The diastereomeric mixture was separated by reverse phase HPLC and major diastereomer was considered to be cis.

cis-isomer (SC-136, SC-137): 1H NMR (400 MHz, DMSO-d$_6$, δ ppm): 1.46-1.49 (4H), 1.76-1.88 (2H), 2.10-2.14 (1H), 3.67-3.73 (1H), 4.04-4.09 (1H), 4.60-4.63 (1H), 7.49-7.53 (1H), 7.74-7.78 (1H), 7.92-7.96 (1H), 8.05 (s, 1H), 8.15-8.17 (1H), 8.20-8.23 (1H).

Two enantiomers of this single diastereomer were separated by chiral prep HPLC using OD-H column and Hexane/EtOH/DEA (90/10/0.1) as mobile phase to obtain two cis enantiomers SC-136 and SC-137.

SC-136: (0.102 g, off white solid, 1$^{st}$ eluted enantiomer).
SC-137: (0.069 g, off white solid, 2$^{nd}$ eluted enantiomer).

2-Fluoro-5-[4-methyl-4-[[3-(trifluoromethyl)phenyl] sulfonyl]-tetrahydro-pyran-2-yl]-benzamide (Example 45)

To a stirred solution of cis-2-fluoro-5-(4-methyl-4-((3-(trifluoromethyl)phenyl)sulfonyl)tetrahydro-2H-pyran-2-yl) benzonitrile (SC-136, SC-137) (0.9 g, 2.105 mmol, 1 eq) in DMSO (15 mL) was added K$_2$CO$_3$ (0.116 g, 0.842 mmol, 0.4 eq) and the reaction mixture was cooled to 0° C. Then H$_2$O$_2$ (40%) (0.107 g, 3.158 mmol, 1.5 eq) was added drop wise and reaction mixture was stirred for 2 h at RT. After completion of reaction (monitored by TLC), reaction mass was quenched with H$_2$O, extracted with EtOAc (2×50 mL), organic layer was washed with H$_2$O (20 mL), brine (20 ml), dried over anhydr. Na$_2$SO$_4$ and evaporated under reduced pressure to get crude product which was further purified by CC to afford cis-2-fluoro-5-[4-methyl-4-[[3-(trifluoromethyl)phenyl]sulfonyl]-tetrahydro-pyran-2-yl]-benzamide (0.450 g, 48%) as white solid.

cis-isomer (SC-138, SC-139): 1H NMR (400 MHz, DMSO-d$_6$, δ ppm): 1.45-1.50 (4H), 1.70-1.73 (1H), 1.84-1.90 (1H), 2.10-2.18 (1H), 3.66-3.72 (1H), 4.03-4.08 (1H), 4.57-4.60 (1H), 7.21-7.26 (1H), 7.44-7.48 (1H), 7.61-7.69 (3H), 7.92-7.96 (1H), 8.04 (s, 1H), 8.14-8.17 (1H), 8.20-8.22 (1H).

Two enantiomers of this single diastereomer were separated by chiral prep HPLC using CHIRALPAK IA column and EtOH/DEA (100/0.1) as mobile phase to obtain two cis enantiomers SC-138 and SC-139.

SC-138: (0.174 g, off white solid, 1$^{st}$ eluted enantiomer).
SC-139: (0.177 g, off white solid, 2$^{nd}$ eluted enantiomer).

2-(4-Chlorophenyl)-2-methyl-4-[[3-(trifluoromethyl) phenyl]sulfonyl]-tetrahydro-pyran (Example 46)

Enantiomer separation of trans diastereomer (SC-117) by chiral Prep HPLC gave 1$^{st}$ eluting enantiomer as SC-140 (0.2117 g) and 2$^{nd}$ eluting enantiomer as SC-141 (0.083 g). Both the compounds are off-white solids.

4-[[3-Fluoro-5-(trifluoromethyl)-phenyl]sulfonyl]-4-methyl-2-(4-methylsulfonyl-phenyl)-tetrahydro-pyran (Example 47)

Step 1: 2-(4-bromophenyl)-4-((3-fluoro-5-(trifluoromethyl)phenyl)sulfonyl)-4-methyltetrahydro-2H-pyran Starting from 4-bromobenzaldehyde, 2-(4-bromophenyl)-4-((3-fluoro-5-(trifluoromethyl)phenyl)sulfonyl)-4-methyl-tetrahydro-2H-pyran was prepared in analogy to Example 23 following general reaction scheme 1.

Step 2: 4-((3-fluoro-5-(trifluoromethyl)phenyl)sulfonyl)-4-methyl-2-(4-(methylthio)phenyl)tetrahydro-2H-pyran A suspension of 2-(4-bromophenyl)-4-((3-fluoro-5-(trifluoromethyl)phenyl)sulfonyl)-4-methyltetrahydro-2H-pyran (0.9 g. 18.69 mmol, 1 eq), dimethyl disulfide (0.105 g, 11.21 mmol, 0.6 eq) and zinc dust (0.122 g, 1.869 mmol, 1 eq) in DMF (10 mL) was deoxygenated well by Ar gas for 10 min. Palladium acetate (0.0125 gm, 0.03987 mmol, 0.03 eq) and BINAP (0.037 gm, 0.0431 mmol, 0.0607 eq) were then added to the reaction mixture and again deoxygenated by argon for 10 min. The reaction mixture then stirred for 16 h at 110° C. The reaction mixture cooled to RT and then filtered through celite bed. The filtrate was diluted with EtOAc (50 mL) and washed by water (5×10 mL) and brine (10 mL). The organic layer dried over anhydr. Na$_2$SO$_4$, concentrated under reduced pressure to get crude product which was purified by CC to afford 4-((3-fluoro-5-(trifluoromethyl)phenyl)sulfonyl)-4-methyl-2-(4-(methylthio)phenyl)tetrahydro-2H-pyran (0.67 g, 75%) as off white solid.

Step 3: 4-[[3-fluoro-5-(trifluoromethyl)-phenyl]sulfonyl]-4-methyl-2-(4-methylsulfonyl-phenyl)-tetrahydro-pyran To a stirred solution of 4-((3-fluoro-5-(trifluoromethyl) phenyl)sulfonyl)-4-methyl-2-(4-(methylthio)phenyl)tetrahydro-2H-pyran (1.0 g, 2.22 mmol, 1 eq) in THF:H$_2$O (3:1) oxone (5.47 g, 8.9 mmol, 4 eq) was added and reaction mixture was stirred at RT for 2 h. After completion of the reaction the mixture was diluted with water and extracted with EtOAc. The combined organic layer was washed with water, sat. brine and dried over anhydr. Na$_2$SO$_4$ and the solvent was evaporated under reduced pressure to get crude product which was further purified by CC to afford 4-[[3-fluoro-5-(trifluoromethyl)-phenyl]sulfonyl]-4-methyl-2-(4-methylsulfonyl-phenyl)-tetrahydro-pyran (0.7 g, 70%) as a white solid and as a single diasteroisomer which was confirmed to be cis by NOE experiments.

cis-isomer (SC-142, SC-143): 1H NMR (400 MHz, DMSO-d$_6$, δ ppm): 1.49-1.54 (4H), 1.80-1.92 (2H), 2.13-2.21 (1H), 3.21 (s, 3H), 3.70-3.76 (1H), 4.07-4.11 (1H), 4.68-4.71 (1H), 7.60-7.62 (2H), 7.89-7.92 (2H), 8.08-8.10 (1H), 8.25-8.27 (1H).

Two enantiomers of this single diastereomer were separated by chiral prep HPLC using CHIRALPAK IA column and EtOH/DCM/DEA (90/10/0.1) as mobile phase to obtain two cis enantiomers SC-142 and SC-143.

SC-142: (0.081 g, off white solid, 1$^{st}$ eluted enantiomer).
SC-143: (0.06 g, off white solid, 2$^{nd}$ eluted enantiomer).

2-(3-Fluoro-4-methylsulfonyl-phenyl)-4-methyl-4-[[3-(trifluoromethyl)phenyl]sulfonyl]-tetrahydropyran (Example 48)

To a stirred solution of 2-(4-bromo-3-fluorophenyl)-4-methyl-4-((3-(trifluoromethyl)phenyl)sulfonyl)tetrahydro-2H-pyran (6.0 g, 0.0124 mol, 1 eq) in DMSO (60 mL) was added sodiummethanesulfinate (1.52 g, 0.0149 mol, 1.2 eq) and L-proline sodium salt (0.34 g, 0.0024 mol, 0.2 eq). The reaction mixture was degassed for 10 min and then CuI (0.23 g, 0.00124 mol, 0.1 eq) was added and the reaction mixture was heated up to 90° C. for 16 h in a sealed tube. Then the reaction mass was diluted with H$_2$O, extracted with EtOAc (2×150 mL), organic layer was washed with H$_2$O (200 mL) and brine (150 mL), dried over anhydr. Na$_2$SO$_4$ and the solvent was evaporated under reduced pressure to get crude product which was further purified by CC to afford 2 set of compounds (one is mono sulfomethyl (SC-144) and other is disulfomethyl (SC132, SC-133) and both were cis as confirmed by NMR experiments.

cis-isomer (SC-144): 1H NMR (400 MHz, DMSO-d$_6$, δ ppm): 1.51-1.56 (4H), 1.77-1.81 (1H), 2.03-2.10 (1H), 2.30-2.39 (1H), 3.21 (s, 3H), 3.66-3.72 (1H), 4.16-4.21 (1H), 4.48-4.51 (1H), 7.21-7.27 (2H), 7.72-7.76 (1H), 7.90-7.96 (2H), 8.02-8.04 (1H), 8.11 (s, 1H).

2-[(2-Fluoro-4-methylsulfonyl-phenoxy)-methyl]-4-methyl-4-[[3-(trifluoromethyl)phenyl]sulfonyl]-tetrahydro-pyran (Example 49)

To a stirred solution of (4-methyl-4-((3-(trifluoromethyl)phenyl)sulfonyl)tetrahydro-2H-pyran-2-yl)methyl methanesulfonate (0.3 g, 0.88 mmol, 1 eq) in THF (10 mL) was added 2-fluoro-4-methanesulfonyl-phenol (0.168 g, 0.88 mmol, 1 eq), PPh$_3$ (0.345 g, 1.32 mmol, 1.5 eq) and the mixture was heated to reflux. Then DEAD (0.208 mL, 1.32 mmol, 1.5 eq) was added and heating was continued for 16 h. Then the reaction mass was cooled to RT and the mixture was diluted with H$_2$O and extracted with EtOAc (2×20 mL), washed with brine (15 mL), dried over Na$_2$SO$_4$ and concentrated. The crude product was purified by reverse phase prep. HPLC to get pure 2-[(2-fluoro-4-methylsulfonyl-phenoxy)-methyl]-4-methyl-4-[[3-(trifluoromethyl)phenyl]sulfonyl]-tetrahydro-pyran as a single diastereoisomer (cis).

cis-isomer (SC-148, SC-149): 1H NMR (400 MHz, DMSO-d$_6$, δ ppm): 1.40-1.44 (4H), 1.60-1.64 (1H), 1.86-1.93 (1H), 1.97-2.03 (1H), 3.21 (s, 3H), 3.55-3.61 (1H), 3.89-3.94 (2H), 4.14-4.23 (2H), 7.39-7.44 (1H), 7.68-7.71 (1H), 7.75-7.79 (1H), 7.95-7.99 (1H), 8.04 (s, 1H), 8.16-8.18 (1H), 8.23-8.25 (1H).

Two enantiomers of cis isomer were separated by chiral HPLC, using chiral pack-IA column and Ethanol/DEA: (100/0.1) as mobile phase to obtain two desired cis enantiomers (SC-148, SC-149).

SC-148: (0.075 g, 1$^{st}$ eluted enantiomer).
SC-149: (0.08 g, 2$^{nd}$ eluted enantiomer).

3-Methylsulfonyl-5-[4-methyl-4-[[3-(trifluoromethyl)phenyl]sulfonyl]-tetrahydro-pyran-2-yl]-pyridine (Example 50)

Step 1: (2-fluoro-4-nitrophenyl)(methyl)sulfane

To a stirred solution of 1,2-difluoro-4-nitro-benzene (5 g, 31 mmol, 1 eq) was added sodium methane thiolate (2 g, 29 mmol, 0.95 eq) and the mixture was stirred for 16 h at RT. Then the reaction mass poured into H$_2$O and extracted with EtOAc (2×40 mL), washed with brine (20 mL), dried over Na$_2$SO$_4$ and concentrated. The crude product was purified by flash column chromatography to afford (2-fluoro-4-nitrophenyl)(methyl)sulfane (1.2 g, 20%) as an off white solid.

Step 2: 3-fluoro-4-(methylthio)aniline

To a stirred solution of (2-fluoro-4-nitrophenyl)(methyl)sulfane (0.8 g, 4.27 mmol, 1 eq) in AcOH/H$_2$O (3:1) (18 mL) was added Fe (0.04 g, 0.716 mmol, 0.17 eq) and the mixture was stirred for 2 h at the RT. Then the reaction mass was concentrated and basified with sat. NaHCO$_3$ solution and extracted with EtOAc (2×30 mL), washed with brine (10 mL), dried over Na$_2$SO$_4$ and concentrated. The crude product was purified by flash column chromatography to afford 3-fluoro-4-(methylthio)aniline (0.36 g, 54%) as yellow gum.

Step 3: 3-fluoro-4-(methylthio)phenol

To a stirred solution of 3-fluoro-4-(methylthio)aniline (0.25 g, 1.59 mmol, 1 eq) in THF/H$_2$O (1:1) (2 mL) was added conc. H$_2$SO$_4$ (1 mL) slowly at 0° C. followed by NaNO$_2$ (0.219 g, 3.18 mmol, 2 eq) dissolved in H$_2$O and stirred for 2 h. Then this mixture was added to a mixture of Cu(NO$_3$)$_2$ and Cu$_2$O in H$_2$O slowly and stirred for 15 min. Then the mixture was extracted with EtOAc (2×20 mL), washed with brine (10 mL), dried over Na$_2$SO$_4$ and concentrated. The crude product was purified by flash column chromatography to afford 3-fluoro-4-(methylthio)phenol (0.07 g, 25%) as yellow gum.

Step 4: 3-fluoro-4-(methylsulfonyl)phenol

To a stirred solution of 3-fluoro-4-methylsulfanyl-phenol (0.07 g, 0.443 mmol, 1 eq) in THF/H$_2$O (2:1) (4.3 mL) was added oxone (0.279 g, 0.908 mmol, 2.05 eq) and the mixture was stirred for 1 h at the RT. Then the mixture was poured into sat. NaHCO$_3$ solution and extracted with EtOAc (2×15 mL), washed with brine (10 mL), dried over Na$_2$SO$_4$ and concentrated. The crude product was purified by flash column chromatography to afford 3-fluoro-4-(methylsulfonyl)phenol (0.05 g) as yellow gum.

Step 5: 2-((3-fluoro-4-(methylsulfonyl)phenoxy)methyl)-4-methyl-4-((3-(trifluoromethyl)phenyl)sulfonyl)tetrahydro-2H-pyran To a solution of (4-methyl-4-((3-(trifluoromethyl)phenyl)sulfonyl)tetrahydro-2H-pyran-2-yl)methyl methanesulfonate (1.1 g, 2.6 mmol, 1 eq) in DMF (15 mL) was added 3-fluoro-4-methylsulfonyl-phenol (0.552 g, 2.9 mmol, 1.1 eq), Cs$_2$CO$_3$ (2.1 g, 6.9 mmol, 2.5 eq) and the mixture was heated up to 80° C. for 48 h. Then the reaction mass was cooled to RT and diluted with H$_2$O (15 mL), extracted with EtOAc (2×30 mL), washed with H$_2$O (15 mL), brine (15 mL), dried over Na$_2$SO$_4$ and concentrated. The crude product was purified by reverse phase prep. HPLC to give pure 2-((3-fluoro-4-(methylsulfonyl)phenoxy)methyl)-4-methyl-4-((3-(trifluoromethyl)phenyl)sulfonyl)tetrahydro-2H-pyran (0.35 g) as a single diastereoisomer (cis).

cis-isomer (SC-150, SC-151): 1H NMR (400 MHz, DMSO-d$_6$, δ ppm): 1.38-1.42 (4H), 1.60-1.63 (1H), 1.84-1.90 (1H), 1.99-2.02 (1H), 3.23 (s, 3H), 3.51-3.59 (1H), 3.87-3.93 (2H), 4.07-4.16 (2H), 6.97-7.00 (1H), 7.12-7.16 (1H), 7.71-7.75 (1H), 7.95-7.99 (1H), 8.04 (s, 3H), 8.16-8.18 (1H), 8.22-8.25 (1H).

Two enantiomers of cis racemic were separated by chiral HPLC, using chiral pack-IA column and EtOH/DEA: (100/0.1) as mobile phase to obtain two desired cis enantiomers (SC-150 and SC-51).

SC-150: (0.09 g, 1$^{st}$ eluted enantiomer).
SC-151: (0.095 g, 2$^{nd}$ eluted enantiomer).

The following example compounds (Examples 51 to 57, 59, 61 to 64, 66, 67 and 73 to 75) were prepared in analogy to 2-(4-fluoro-3-methylsulfonyl-phenyl)-4-methyl-4-[[3-(trifluoromethyl)phenyl]sulfonyl]-tetrahydro-pyran (Example 17):

2-[[2-(3-Fluoro-4-methylsulfonyl-phenyl)-4-methyl-tetrahydro-pyran-4-yl]sulfonyl]-6-(trifluoromethyl)-pyridine (Example 51)

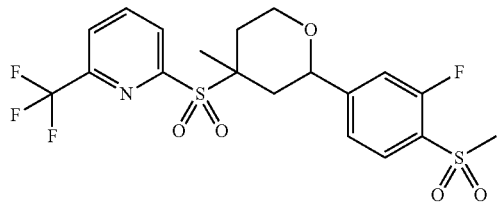 [SMILES: CC1(S(=O)(=O)c2cccc(C(F)(F)F)n2)CCOC(c2ccc(S(C)(=O)=O)c(F)c2)C1]

¹H-NMR (600 MHz, [d₆]-DMSO): δ =8.46-8.49 (1H), 8.36-8.37 (1H), 8.32-8.33 (1H), 7.84-7.86 (1H), 7.42-7.46 (2H), 4.71-4.73 (1H), 4.08-4.11 (1H), 3.72-3.78 (1H), 3.32 (3H), 2.12-2.17 (1H), 1.92-1.97 (2H), 1.58-1.62 (4H).
NOE: C-2 proton & methyl=cis

Chiral resolution of 2-[[2-(3-Fluoro-4-methylsulfonyl-phenyl)-4-methyl-tetrahydro-pyran-4-yl]sulfonyl]-6-(trifluoromethyl)-pyridine

[Cis-rac] 2-[[2-(3-Fluoro-4-methylsulfonyl-phenyl)-4-methyl-tetrahydro-pyran-4-yl]sulfonyl]-6-(trifluoromethyl)-pyridine was subjected to preparative chiral-SFC (Chiralpak-OJ-H column, 0.5% DEA in MeOH, 15%)) to give [cis-EN1] SC-245 and [cis-EN2] SC-246.

[cis-EN1] SC-245—analytical SFC: Chiralpak-AD-H (250×4.6 mm 5μ), 3 g/min, RT, 0.5% DEA in MeOH, 30%, Ret. Time 3.19; ee>95%

[cis-EN2] SC-246—analytical SFC: Chiralpak-AD-H (250×4.6 mm 5μ), 3 g/min, RT, 0.5% DEA in MeOH, 30%, Ret. Time 3.72; ee>95%

2-(2-Chloro-5-methylsulfonyl-phenyl)-4-methyl-4-[[3-(trifluoromethyl)phenyl]sulfonyl]-tetrahydro-pyran (Example 52)

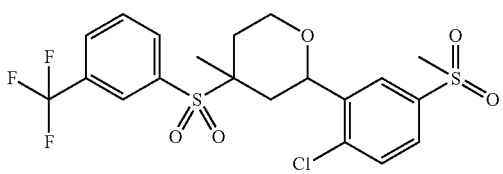 [SMILES: CC1(S(=O)(=O)c2cccc(C(F)(F)F)c2)CCOC(c2cc(S(C)(=O)=O)ccc2Cl)C1]

¹H-NMR (600 MHz, [d₆]-DMSO): δ =8.20-8.22 (1H), 8.16-8.18 (1H), 8.05 (1H), 7.98-7.99 (1H), 7.93-7.96 (1H), 7.88-7.90 (1H), 7.73-7.75 (1H), 4.89-4.91 (1H), 4.13-4.16 (1H), 3.79-3.83 (1H), 3.23 (3H), 2.18-2.23 (1H), 1.82-1.91 (2H), 1.48-1.52 (4H).
NOE: C-2 proton & methyl=cis

Chiral resolution of 2-(2-Chloro-5-methylsulfonyl-phenyl)-4-methyl-4-[[3-(trifluoromethyl)phenyl]sulfonyl]-tetrahydro-pyran

[Cis-rac] 2-(2-Chloro-5-methylsulfonyl-phenyl)-4-methyl-4-[[3-(trifluoromethyl)phenyl]sulfonyl]-tetrahydro-pyran was subjected to preparative chiral-SFC (Lux Cellulose-2 column, MeOH, 25%)) to give [cis-EN1] SC-247 and [cis-EN2] SC-248.

[cis-EN1] SC-247—analytical SFC: Lux Cellulose-2 (250×4.6 mm 5μ), 3 g/min, RT, MeOH, 30%, Ret. Time 3.51; ee>95%

[cis-EN2] SC-248—analytical SFC: Chiralpal-AS-H (250×4.6 mm 5μ), 3 g/min, RT, MeOH, 30%, Ret. Time 4.28; ee>95%

4-Methyl-2-[3-methylsulfonyl-4-(trifluoromethyl)-phenyl]-4-[[3-(trifluoromethyl)phenyl]sulfonyl]-tetrahydro-pyran (Example 53)

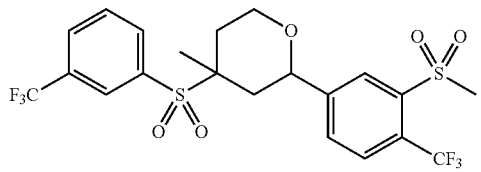 [SMILES: CC1(S(=O)(=O)c2cccc(C(F)(F)F)c2)CCOC(c2ccc(C(F)(F)F)c(S(C)(=O)=O)c2)C1]

¹H-NMR (600 MHz, [d₆]-DMSO): δ =8.20-8.22 (2H), 8.16-8.18 (1H), 8.05 (1H), 8.02-8.04 (1H), 7.89-7.96 (2H), 4.80-4.86 (1H), 4.10-4.15 (1H), 3.71-3.76 (1H), 2.14-2.20 (1H), 1.87-1.90 (2H), 1.47-1.53 (4H).
NOE: C-2 proton & methyl=cis

Chiral resolution of 4-Methyl-2-[3-methylsulfonyl-4-(trifluoromethyl)-phenyl]-4-[[3-(trifluoromethyl)phenyl]sulfonyl]-tetrahydro-pyran

[Cis-rac] 4-Methyl-2-[3-methylsulfonyl-4-(trifluoromethyl)-phenyl]-4-[[3-(trifluoromethyl)phenyl]sulfonyl]-tetrahydro-pyran was subjected to preparative chiral-SFC (Chiralpak AS-H column, iPrOH, 25%)) to give [cis-EN1] SC-249 and [cis-EN2] SC-250.

[cis-EN1] SC-249—analytical SFC: Chiralpak AS-H (250×4.6 mm 5μ), 3 g/min, RT, MeOH, 10%, Ret. Time 3.58; ee>95%

[cis-EN2] SC-250—analytical SFC: Chiralpal-AS-H (250×4.6 mm 5μ), 3 g/min, RT, MeOH, 10%, Ret. Time 4.38; ee>95%

3-Methylsulfonyl-4-[4-methyl-4-[[3-(trifluoromethyl)phenyl]sulfonyl]-tetrahydro-pyran-2-yl]-benzonitrile (Example 54)

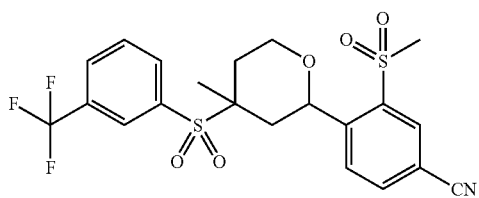 [SMILES: CC1(S(=O)(=O)c2cccc(C(F)(F)F)c2)CCOC(c2ccc(C#N)cc2S(C)(=O)=O)C1]

¹H-NMR (600 MHz, [d₆]-DMSO): δ =8.30-8.31 (1H), 8.21-8.23 (2H), 8.15-8.17 (1H), 8.04 (1H), 7.93-7.96 (2H), 5.28-5.31 (1H), 4.09-4.12 (1H), 3.84-3.88 (1H), 3.3-3.5 (3H), 2.17-2.22 (1H), 1.97-2.00 (1H), 1.79-1.86 (1H), 1.50-1.52 (1H), 1.47 (3H).
NOE: C-2 proton & methyl=cis

Chiral resolution of 3-Methylsulfonyl-4-[4-methyl-4-[[3-(trifluoromethyl)phenyl]sulfonyl]-tetrahydro-pyran-2-yl]-benzonitrile

[Cis-rac] 3-Methylsulfonyl-4-[4-methyl-4-[[3-(trifluoromethyl)phenyl]sulfonyl]-tetrahydro-pyran-2-yl]-benzonitrile was subjected to preparative chiral-SFC (Chiralpak AS-H column, MeOH, 35%)) to give [cis-EN1] SC-251 and [cis-EN2] SC-252.

[cis-EN1] SC-251—analytical SFC: Chiralpak AS-H (250×4.6 mm 5µ), 3 g/min, RT, MeOH, 20%, Ret. Time 2.12; ee>95%

[cis-EN2] SC-252—analytical SFC: Chiralpak-AS-H (250×4.6 mm 5µ), 3 g/min, RT, MeOH, 20%, Ret. Time 3.48; ee>95%

4-Methyl-2-(2-methyl-4-methylsulfonyl-phenyl)-4-[[3-(trifluoromethyl)phenyl]sulfonyl]-tetrahydro-pyran (Example 55)

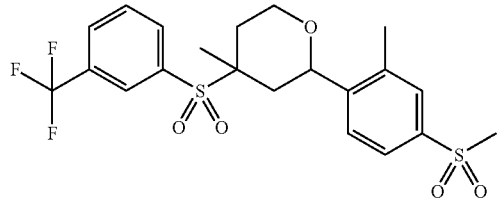 [SMILES: Cc1cc(S(C)(=O)=O)ccc1C1CC(C)(S(=O)(=O)c2cccc(C(F)(F)F)c2)CCO1]

$^1$H-NMR (600 MHz, [d$_6$]-DMSO): δ =8.21-8.22 (1H), 8.16-8.18 (1H), 8.06 (1H), 7.93-7.96 (1H), 7.76-7.77 (1H), 7.73 (1H), 7.61-7.62 (1H), 4.81-4.83 (1H), 4.07-4.10 (1H), 3.75-3.79 (1H), 3.19 (3H), 2.34 (3H), 2.14-2.20 (1H), 1.84-1.88 (1H), 1.70-1.73 (1H), 1.54 (3H), 1.48-1.51 (1H).

NOE: C-2 proton & methyl=cis

Chiral resolution of 4-Methyl-2-(2-methyl-4-methylsulfonyl-phenyl)-4-[[3-(trifluoromethyl)phenyl]sulfonyl]-tetrahydro-pyran

[Cis-rac] 4-Methyl-2-(2-methyl-4-methylsulfonyl-phenyl)-4-[[3-(trifluoromethyl)phenyl]sulfonyl]-tetrahydro-pyran was subjected to preparative chiral-SFC (Chiralcel OX-H column, MeOH, 40%)) to give [cis-EN1] SC-253 and [cis-EN2] SC-254.

[cis-EN1] SC-253—analytical SFC: Chiralcel OX-H (250×4.6 mm 5µ), 4 g/min, RT, MeOH, 40%, Ret. Time 2.19; ee>95%

[cis-EN2] SC-254—analytical SFC: Chiralcel OX-H (250×4.6 mm 5µ), 4 g/min, RT, MeOH, 40%, Ret. Time 4.28; ee>95%

4-Methyl-2-[4-methylsulfonyl-2-(trifluoromethyl)-phenyl]-4-[[3-(trifluoromethyl)phenyl]sulfonyl]-tetrahydro-pyran (Example 56)

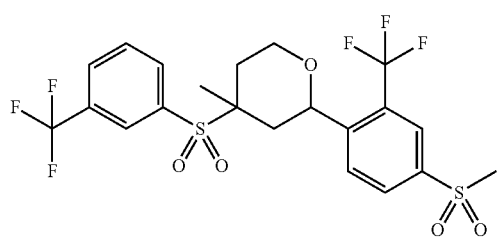 [SMILES: CC1(S(=O)(=O)c2cccc(C(F)(F)F)c2)CCOC(c2ccc(S(C)(=O)=O)cc2C(F)(F)F)C1]

$^1$H-NMR (600 MHz, [d$_6$]-DMSO): δ =8.28-8.30 (1H), 8.22-8.23 (1H), 8.16-8.18 (2H), 8.04-9.06 (2H), 7.93-7.96 (1H), 4.87-4.88 (1H), 4.11-4.14 (1H), 3.79-3.84 (1H), 3.33 (3H), 2.20-2.25 (1H), 1.95-1.99 (1H), 1.70-1.73 (1H), 1.50-1.53 (1H), 1.47 (3H).

NOE: C-2 proton & methyl=cis

Chiral resolution of 4-Methyl-2-[4-methylsulfonyl-2-(trifluoromethyl)-phenyl]-4-[[3-(trifluoromethyl)phenyl]sulfonyl]-tetrahydro-pyran

[Cis-rac] 4-Methyl-2-[4-methylsulfonyl-2-(trifluoromethyl)-phenyl]-4-[[3-(trifluoromethyl)phenyl]sulfonyl]-tetrahydro-pyran was subjected to preparative chiral-SFC (Chiralpak AD-H column, MeOH, 12%)) to give [cis-EN1] SC-255 and [cis-EN2] SC-256.

[cis-EN1] SC-255—analytical SFC: Chiralpak AD-H (250×4.6 mm 5µ), 3 g/min, RT, MeOH, 15%, Ret. Time 1.98; ee>95%

[cis-EN2] SC-256—analytical SFC: Chiralpak AD-H (250×4.6 mm 5µ), 3 g/min, RT, MeOH, 15%, Ret. Time 2.65; ee>95%

3-Methylsulfonyl-5-[4-methyl-4-[[3-(trifluoromethyl)phenyl]sulfonyl]-tetrahydro-pyran-2-yl]-benzonitrile (Example 57)

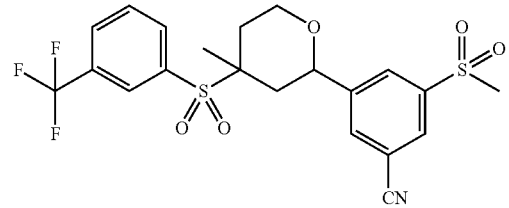 [SMILES: CC1(S(=O)(=O)c2cccc(C(F)(F)F)c2)CCOC(c2cc(C#N)cc(S(C)(=O)=O)c2)C1]

$^1$H-NMR (600 MHz, [d$_6$]-DMSO): δ =8.34-8.35 (1H), 8.17-8.22 (4H), 8.06 (1H), 7.94-7.96 (1H), 4.76-4.78 (1H), 4.12-4.15 (1H), 3.72-3.77 (1H), 3.32 (3H), 2.15-2.20 (1H), 1.88-1.94 (2H), 1.49-1.52 (4H).

NOE: C-2 proton & methyl=cis

Chiral resolution of 3-Methylsulfonyl-5-[4-methyl-4-[[3-(trifluoromethyl)phenyl]sulfonyl]-tetrahydro-pyran-2-yl]-benzonitrile

[Cis-rac] 3-Methylsulfonyl-5-[4-methyl-4-[[3-(trifluoromethyl)phenyl]sulfonyl]-tetrahydro-pyran-2-yl]-benzonitrile was subjected to preparative chiral-SFC (Chiralcel OJ-H column, MeOH, 40%)) to give [cis-EN1] SC-257 and [cis-EN2] SC-258.

[cis-EN1] SC-257—analytical SFC: Chiralcel OJ-H (250×4.6 mm 5µ), 3 g/min, RT, MeOH, 25%, Ret. Time 2.69; ee>95%

[cis-EN2] SC-258—analytical SFC: Chiralcel OJ-H (250×4.6 mm 5µ), 3 g/min, RT, MeOH, 25%, Ret. Time 3.41; ee>95%

2-Methylsulfonyl-4-[4-methyl-4-[[3-(trifluoromethyl)phenyl]sulfonyl]-tetrahydro-pyran-2-yl]-benzonitrile (Example 59)

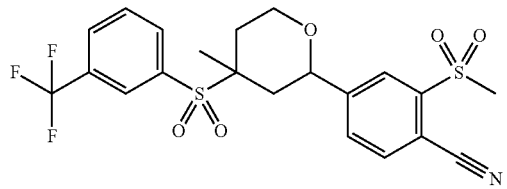 [SMILES: CC1(S(=O)(=O)c2cccc(C(F)(F)F)c2)CCOC(c2ccc(C#N)c(S(C)(=O)=O)c2)C1]

$^1$H-NMR (600 MHz, [d$_6$]-DMSO): δ =8.21-8.23 (1H), 8.16-8.19 (2H), 8.11-8.12 (1H), 8.05 (1H), 7.94-7.96 (1H), 7.89-7.90 (1H), 4.80-4.82 (1H), 4.11-4.15 (1H), 3.72-3.77 (1H), 2.14-2.20 (1H), 1.84-1.91 (1H), 1.48-1.56 (4H).
NOE: C-2 proton & methyl=cis

Chiral resolution of 2-Methylsulfonyl-4-[4-methyl-4-[[3-(trifluoromethyl)phenyl]sulfonyl]-tetrahydro-pyran-2-yl]-benzonitrile

[Cis-rac] 2-Methylsulfonyl-4-[4-methyl-4-[[3-(trifluoromethyl)phenyl]sulfonyl]-tetrahydro-pyran-2-yl]-benzonitrile was subjected to preparative chiral-SFC (Chiralpal-AD-H column, MeOH, 25%)) to give [cis-EN1] SC-261 and [cis-EN2] SC-262.

[cis-EN1] SC-261—analytical SFC: Chiralpal-AD-H (250×4.6 mm 5µ), 3 g/min, RT, MeOH, 25%, Ret. Time 3.54; ee>95%

[cis-EN2] SC-262—analytical SFC: Chiralpal-AD-H (250×4.6 mm 5µ), 3 g/min, RT, MeOH, 25%, Ret. Time 4.27; ee>95%

2-(3-Fluoro-4-methylsulfonyl-phenyl)-4-methyl-4-[[3-(trifluoromethyloxy)-phenyl]sulfonyl]-tetrahydro-pyran (Example 61)

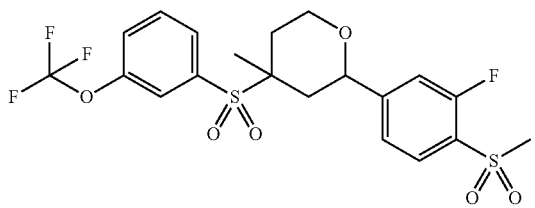 [SMILES: CC1(S(=O)(=O)c2cccc(OC(F)(F)F)c2)CCOC(c2ccc(S(C)(=O)=O)c(F)c2)C1]

$^1$H-NMR (600 MHz, [d$_6$]-DMSO): δ =7.88-7.90 (1H), 7.83-7.88 (3H), 7.76 (1H), 7.43-7.48 (2H), 4.68-4.71 (1H), 4.08-4.11 (1H), 3.71-3.76 (1H), 3.32 (3H), 2.10-2.15 (1H), 1.77-1.85 (2H), 1.49-1.51 (4H).
NOE: C-2 proton & methyl=cis

Chiral resolution of 2-(3-Fluoro-4-methylsulfonyl-phenyl)-4-methyl-4-[[3-(trifluoromethyloxy)-phenyl]sulfonyl]-tetrahydro-pyran

[Cis-rac] 2-(3-Fluoro-4-methylsulfonyl-phenyl)-4-methyl-4-[[3-(trifluoromethyloxy)-phenyl]sulfonyl]-tetrahydro-pyran was subjected to preparative chiral-SFC (Chiralpak OJ-H column, 0.5% DEA in MeOH, 15%)) to give [cis-EN1] SC-265 and [cis-EN2] SC-266.

[cis-EN1] SC-265—analytical SFC: Chiralcel OJ-H (250×4.6 mm 5µ), 3 g/min, RT, MeOH, 30%, Ret. Time 1.97; ee>95%

[cis-EN2] SC-266—analytical SFC: Chiralcel OJ-H (250×4.6 mm 5µ), 3 g/min, RT, MeOH, 30%, Ret. Time 2.45; ee 93%

2-Methylsulfonyl-5-[4-methyl-4-[[3-(trifluoromethyl)phenyl]sulfonyl]-tetrahydro-pyran-2-yl]-benzonitrile (Example 62)

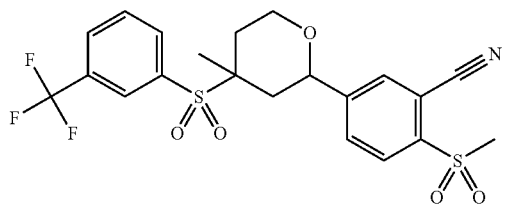 [SMILES: CC1(S(=O)(=O)c2cccc(C(F)(F)F)c2)CCOC(c2ccc(S(C)(=O)=O)c(C#N)c2)C1]

$^1$H-NMR (600 MHz, [d$_6$]-DMSO): δ =8.21-8.23 (1H), 8.16-8.18 (1H), 8.12-8.14 (2H), 8.06 (1H), 7.93-7.97 (1H), 4.75-4.77 (1H), 4.11-4.14 (1H), 3.72-3.77 (1H), 2.14-2.18 (1H), 1.83-1.92 (2H), 1.49-1.52 (4H).
NOE: C-2 proton & methyl=cis

Chiral resolution of 2-Methylsulfonyl-5-[4-methyl-4-[[3-(trifluoromethyl)phenyl]sulfonyl]-tetrahydro-pyran-2-yl]-benzonitrile

[Cis-rac] 2-Methylsulfonyl-5-[4-methyl-4-[[3-(trifluoromethyl)phenyl]sulfonyl]-tetrahydro-pyran-2-yl]-benzonitrile was subjected to preparative chiral-SFC (Chiralpak AD-H column, MeOH, 30%)) to give [cis-EN1] SC-267 and [cis-EN2] SC-268.

[cis-EN1] SC-267—analytical SFC: Chiralpak AD-H (250×4.6 mm 5µ), 3 g/min, RT, MeOH, 30%, Ret. Time 3.98; ee>95%

[cis-EN2] SC-268—analytical SFC: Chiralpak AD-H (250×4.6 mm 5µ), 3 g/min, RT, MeOH, 30%, Ret. Time 5.33; ee>95%

4-[[3-(Difluoro-methyl)-phenyl]sulfonyl]-2-(3-fluoro-4-methylsulfonyl-phenyl)-4-methyl-tetrahydro-pyran (Example 63)

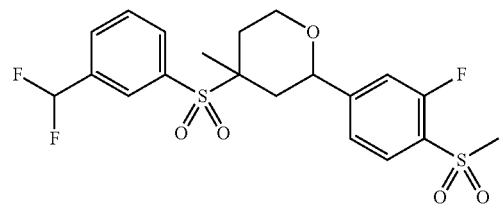 [SMILES: CC1(S(=O)(=O)c2cccc(C(F)F)c2)CCOC(c2ccc(S(C)(=O)=O)c(F)c2)C1]

$^1$H-NMR (600 MHz, [d$_6$]-DMSO): δ =7.99-8.03 (3H), 7.84-7.86 (2H), 7.43-7.48 (2H), 7.10-7.29 (1H), 4.67-4.70 (1H), 4.08-4.11 (1H), 3.70-3.75 (1H), 3.31 (3H), 2.10-2.15 (1H), 1.80-1.85 (1H), 1.47-1.50 (4H).
NOE: C-2 proton & methyl=cis Chiral resolution of 4-[[3-(Difluoro-methyl)-phenyl]sulfonyl]-2-(3-fluoro-4-methylsulfonyl-phenyl)-4-methyl-tetrahydro-pyran

[Cis-rac] 4-[[3-(Difluoro-methyl)-phenyl]sulfonyl]-2-(3-fluoro-4-methylsulfonyl-phenyl)-4-methyl-tetrahydro-pyran was subjected to preparative chiral-SFC (Chiralcel OJ-H column, MeOH, 30%)) to give [cis-EN1] SC-269 and [cis-EN2] SC-270.

[cis-EN1] SC-269—analytical SFC: Chiralcel OJ-H (250×4.6 mm 5µ), 3 g/min, RT, 0.5% DEA in MeOH, 25%, Ret. Time 3.88; ee>95%

[cis-EN2] SC-270—analytical SFC: Chiralcel OJ-H (250×4.6 mm 5µ), 3 g/min, RT, 0.5% DEA in MeOH, 25%, Ret. Time 4.71; ee>95%

2-(3-Fluoro-4-methylsulfonyl-phenyl)-4-[(3-isopropyl-phenyl)sulfonyl]-4-methyl-tetrahydro-pyran (Example 64)

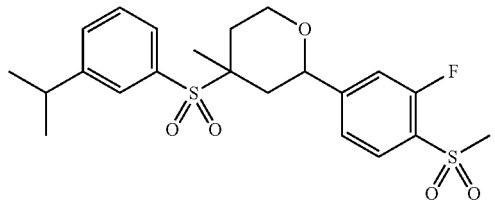 [SMILES: CC(C)c1cccc(S(=O)(=O)C2(C)CCOC(c3ccc(S(C)(=O)=O)c(F)c3)C2)c1]

$^1$H-NMR (600 MHz, [d$_6$]-DMSO): δ =7.83-7.86 (1H), 7.68-7.69 (1H), 7.59-7.64 (3H), 7.42-7.46 (2H), 4.67-4.69 (1H), 4.06-4.09 (1H), 3.68-3.72 (1H), 3.31 (3H), 3.00-3.06 (1H), 2.07-2.12 (1H), 1.76-1.82 (2H), 1.43-1.47 (4H), 1.21-1.24 (6H).

NOE: C-2 proton & methyl=cis

Chiral resolution of 2-(3-Fluoro-4-methylsulfonyl-phenyl)-4-[(3-isopropyl-phenyl)sulfonyl]-4-methyl-tetrahydro-pyran

[Cis-rac] 2-(3-Fluoro-4-methylsulfonyl-phenyl)-4-[(3-isopropyl-phenyl)sulfonyl]-4-methyl-tetrahydro-pyran was subjected to preparative chiral-SFC (Chiralcel OJ-H column, MeOH, 30%)) to give [cis-EN1] SC-271 and [cis-EN2] SC-272.

[cis-EN1] SC-271—analytical SFC: Chiralcel OJ-H (250×4.6 mm 5µ), 3 g/min, RT, 0.5% DEA in MeOH, 30%, Ret. Time 2.46; ee>95%

[cis-EN2] SC-272—analytical SFC: Chiralcel OJ-H (250×4.6 mm 5µ), 3 g/min, RT, 0.5% DEA in MeOH, 30%, Ret. Time 2.94; ee>95%

5-Methylsulfonyl-2-[4-methyl-4-[[3-(trifluoromethyl)phenyl]sulfonyl]-tetrahydro-pyran-2-yl]-benzonitrile (Example 66)

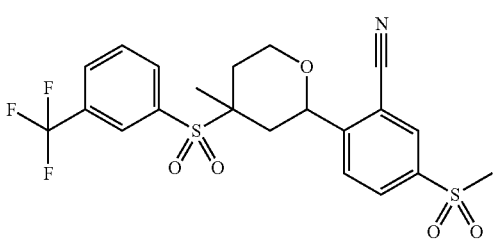 [SMILES: CC1(S(=O)(=O)c2cccc(C(F)(F)F)c2)CCOC(c2ccc(S(C)(=O)=O)cc2C#N)C1]

$^1$H-NMR (600 MHz, [d$_6$]-DMSO): δ =8.39-8.40 (1H), 8.18-8.25 (3H), 8.08 (1H), 7.94-7.96 (1H), 7.88-7.89 (1H), 4.93-4.96 (1H), 4.12-4.15 (1H), 3.89-3.84 (1H), 3.31 (3H), 2.14-2.20 (1H), 1.95-1.99 (1H), 1.88-1.91 (1H), 1.52-1.55 (4H).

NOE: C-2 proton & methyl=cis

Chiral resolution of 5-Methylsulfonyl-2-[4-methyl-4-[[3-(trifluoromethyl)phenyl]sulfonyl]-tetrahydro-pyran-2-yl]-benzonitrile

[Cis-rac] 5-Methylsulfonyl-2-[4-methyl-4-[[3-(trifluoromethyl)phenyl]sulfonyl]-tetrahydro-pyran-2-yl]-benzonitrile was subjected to preparative chiral-SFC (Chiralpak AD-H column, MeOH, 25%)) to give [cis-EN1] SC-275 and [cis-EN2] SC-276.

[cis-EN1] SC-275—analytical SFC: Chiralpak-AD-H (250×4.6 mm 5µ), 3 g/min, RT, 0.5% DEA in MeOH, 25%, Ret. Time 3.29; ee>95%

[cis-EN2] SC-276—analytical SFC: Chiralpak-AD-H (250×4.6 mm 5µ), 3 g/min, RT, 0.5% DEA in MeOH, 25%, Ret. Time 4.03; ee>95%

2-(2-Cyclopropyl-5-methylsulfonyl-phenyl)-4-methyl-4-[[3-(trifluoromethyl)phenyl]sulfonyl]-tetrahydro-pyran (Example 67)

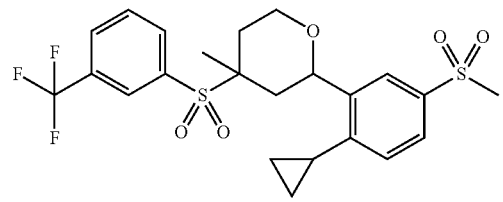 [SMILES: CC1(S(=O)(=O)c2cccc(C(F)(F)F)c2)CCOC(c2cc(S(C)(=O)=O)ccc2C2CC2)C1]

$^1$H-NMR (600 MHz, [d$_6$]-DMSO): δ =8.22-8.23 (1H), 8.17-8.18 (1H), 8.06 (1H), 7.94-7.97 (1H), 7.87-7.89 (1H), 7.74-7.75 (1H), 5.09-5.11 (1H), 4.15-4.18 (1H), 3.80-3.84 (1H), 3.18 (3H), 2.22-2.27 (1H), 1.97-1.99 (1H), 1.85-1.93 (2H), 1.52-1.54 (4H), 0.89-0.96 (2H), 0.81-0.86 (1H), 0.50-0.54 (1H).

NOE: C-2 proton & methyl=cis

Chiral resolution of 2-(2-Cyclopropyl-5-methylsulfonyl-phenyl)-4-methyl-4-[[3-(trifluoromethyl)phenyl]sulfonyl]-tetrahydro-pyran

[Cis-rac] 2-(2-Cyclopropyl-5-methylsulfonyl-phenyl)-4-methyl-4-[[3-(trifluoromethyl)phenyl]sulfonyl]-tetrahydro-pyran was subjected to preparative chiral-SFC (Chiralpak AD-H column, MeOH, 30%)) to give [cis-EN1] SC-277 and [cis-EN2] SC-278.

[cis-EN1] SC-277—analytical SFC: Chiralpak-AD-H (250×4.6 mm 5µ), 3 g/min, RT, 0.5% DEA in MeOH, 30%, Ret. Time 1.98; ee>95%

[cis-EN2] SC-278—analytical SFC: Chiralpak-AD-H (250×4.6 mm 5µ), 3 g/min, RT, 0.5% DEA in MeOH, 30%, Ret. Time 2.73; ee>95%

2-[[4-Methyl-2-(4-methylsulfonyl-phenyl)-tetrahydro-pyran-4-yl]sulfonyl]-6-(trifluoromethyl)-pyridine (Example 73)

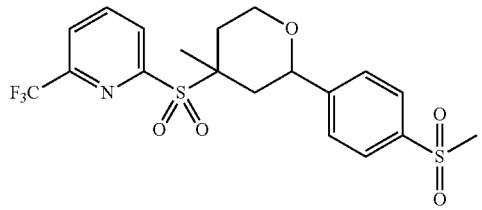 [SMILES: CC1(S(=O)(=O)c2cccc(C(F)(F)F)n2)CCOC(c2ccc(S(C)(=O)=O)cc2)C1]

$^1$H-NMR (600 MHz, [d$_6$]-DMSO): δ =8.47-8.49 (1H), 8.37-8.38 (1H), 8.32-8.33 (1H), 7.90-7.92 (2H), 7.59-7.61 (2H), 4.71-4.73 (1H), 4.08-4.11 (1H), 3.74-3.79 (1H), 3.21 (3H), 2.15-2.20 (1H), 1.96-2.00 (1H), 1.88-1.91 (1H), 1.60-1.63 (4H).
NOE: C-2 proton & methyl=cis

Chiral resolution of 2-[[4-Methyl-2-(4-methylsulfonyl-phenyl)-tetrahydro-pyran-4-yl]sulfonyl]-6-(trifluoromethyl)-pyridine

[Cis-rac] 2-[[4-Methyl-2-(4-methylsulfonyl-phenyl)-tetrahydro-pyran-4-yl]sulfonyl]-6-(trifluoromethyl)-pyridine was subjected to preparative chiral-SFC (Chiralpak OJ-H column, 0.5% DEA in MeOH, 15%)) to give [cis-EN1] SC-292 and [cis-EN2] SC-293.

[cis-EN1] SC-292—analytical SFC: Chiralcel-OJ-H (250×4.6 mm 5µ), 3 g/min, RT, 0.5% DEA in MeOH, 25%, Ret. Time 2.74; ee>95%

[cis-EN2] SC-293—analytical SFC: Chiralcel-OJ-H (250×4.6 mm 5µ), 3 g/min, RT, 0.5% DEA in MeOH, 25%, Ret. Time 3.56; ee>95%

2-(2-Fluoro-5-methylsulfonyl-phenyl)-4-methyl-4-[[3-(trifluoromethyl)phenyl]sulfonyl]-tetrahydro-pyran (Example 74)

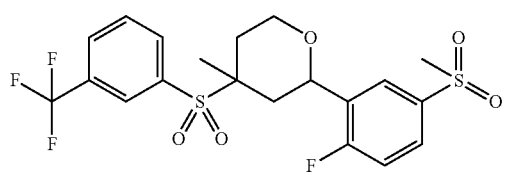 [SMILES: CC1(S(=O)(=O)c2cccc(C(F)(F)F)c2)CCOC(c2cc(S(C)(=O)=O)ccc2F)C1]

$^1$H-NMR (600 MHz, [d$_6$]-DMSO): δ =8.22-8.23 (1H), 8.17-8.19 (1H), 8.07 (1H), 7.98-8.00 (1H), 7.94-7.97 (2H), 7.48-7.52 (1H), 4.10-4.13 (1H), 3.75-3.80 (1H), 3.24 (3H), 2.17-2.22 (1H), 2.00-2.04 (1H), 1.74-1.77 (1H), 1.49-1.51 (4H).
NOE: C-2 proton & methyl=cis

Chiral resolution of 2-(2-Fluoro-5-methylsulfonyl-phenyl)-4-methyl-4-[[3-(trifluoromethyl)phenyl]sulfonyl]-tetrahydro-pyran

[Cis-rac] 2-(2-Fluoro-5-methylsulfonyl-phenyl)-4-methyl-4-[[3-(trifluoromethyl)phenyl]sulfonyl]-tetrahydro-pyran was subjected to preparative chiral-SFC (Chiralpak AD-H column, MeOH, 25%)) to give [cis-EN1] SC-294 and [cis-EN2] SC-295.

[cis-EN1] SC-294—analytical SFC: Chiralpak-AD-H (250×4.6 mm 5µ), 3 g/min, RT, MeOH, 20%, Ret. Time 2.32; ee>95%

[cis-EN2] SC-295—analytical SFC: Chiralpak-AD-H (250×4.6 mm 5µ), 3 g/min, RT, MeOH, 20%, Ret. Time 2.91; ee>95%

2-(3-Fluoro-5-methylsulfonyl-phenyl)-4-methyl-4-[[3-(trifluoromethyl)phenyl]sulfonyl]-tetrahydro-pyran (Example 75)

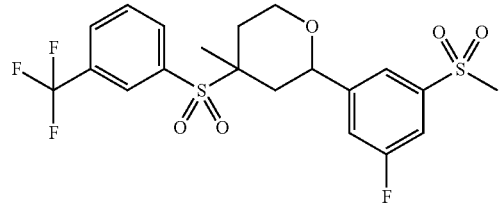 [SMILES: CC1(S(=O)(=O)c2cccc(C(F)(F)F)c2)CCOC(c2cc(F)cc(S(C)(=O)=O)c2)C1]

$^1$H-NMR (600 MHz, [d$_6$]-DMSO): δ =8.20-8.22 (1H), 8.17-8.18 (1H), 8.06 (1H), 7.94-7.96 (1H), 7.78 (H), 7.70-7.72 (1H) 7.56-7.58 (1H), 4.71-4.73 (1H), 4.09-4.13 (1H), 3.71-3.75 (1H), 3.27 (3H), 2.14-2.19 (1H), 1.87-1.89 (1H), 1.48-1.51 (4H).
NOE: C-2 proton & methyl=cis

Chiral resolution of 2-(3-Fluoro-5-methylsulfonyl-phenyl)-4-methyl-4-[[3-(trifluoromethyl)phenyl]sulfonyl]-tetrahydro-pyran

[Cis-rac] 2-(3-Fluoro-5-methylsulfonyl-phenyl)-4-methyl-4-[[3-(trifluoromethyl)phenyl]sulfonyl]-tetrahydro-pyran was subjected to preparative chiral-SFC (Chiralpak AS-H column, MeOH, 25%)) to give [cis-EN1] SC-296 and [cis-EN2] SC-297.

[cis-EN1] SC-297—analytical SFC: Chiralpak-AS-H (250×4.6 mm 5µ), 3 g/min, RT, MeOH, 20%, Ret. Time 2.42; ee>95%

[cis-EN2] SC-296—analytical SFC: Chiralpak-AS-H (250×4.6 mm 5µ), 3 g/min, RT, MeOH, 20%, Ret. Time 3.02; ee>95%

The following example compounds (Example 58, 60 and 68) were prepared in analogy to 2-(4-Chlorophenyl)-4-[[3-(trifluoromethyl)phenyl]sulfonyl]-tetrahydro-pyran (Example 38):

2,2-Difluoro-5-[4-methyl-4-[[3-(trifluoromethyl)phenyl]sulfonyl]-tetrahydro-pyran-2-yl]-1,3-benzodioxole (Example 58)

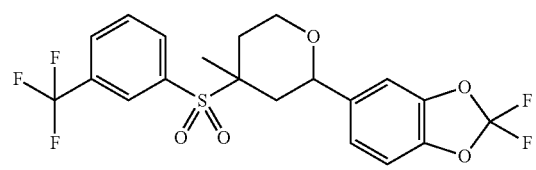 [SMILES: CC1(S(=O)(=O)c2cccc(C(F)(F)F)c2)CCOC(c2ccc3c(c2)OC(F)(F)O3)C1]

$^1$H-NMR (600 MHz, [d$_6$]-DMSO): δ =8.20-8.21 (1H), 8.15-8.17 (1H), 8.04 (1H), 7.93-7.96 (1H), 7.34-7.36 (2H), 7.17-7.19 (2H), 4.57-4.59 (1H), 4.04-4.08 (1H), 3.68-3.72 (1H), 2.11-2.16 (1H), 1.86-1.90 (1H), 1.71-1.73 (1H), 1.46-1.49 (4H).
NOE: C-2 proton & methyl=cis

Chiral resolution of 4-Methylsulfonyl-2-[4-methyl-4-methyl-4-[[3-(trifluoromethyl)phenyl]sulfonyl]-tetrahydro-pyran-2-yl]-benzonitrile

[Cis-rac] 4-Methylsulfonyl-2-[4-methyl-4-[[3-(trifluoromethyl)phenyl]sulfonyl]-tetrahydro-pyran-2-yl]-benzonitrile was subjected to preparative chiral-SFC (Chiralpak-OJ-H column, iPrOH, 10%)) to give [cis-EN1] SC-259 and [cis-EN2] SC-260.

[cis-EN1] SC-259—analytical SFC: Chiralcel OJ-H (250×4.6 mm 5μ), 3 g/min, RT, iPrOH, 10%, Ret. Time 2.59; ee>95%

[cis-EN2] SC-260—analytical SFC: Chiralcel OJ-H (250×4.6 mm 5μ), 3 g/min, RT, iPrOH, 10%, Ret. Time 3.08; ee>95%

5-[4-Methyl-4-[[3-(trifluoromethyl)phenyl]sulfonyl]-tetrahydro-pyran-2-yl]-2,3-dihydro-benzofuran (Example 60)

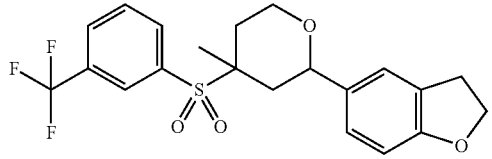 [SMILES: CC1(S(=O)(=O)c2cccc(C(F)(F)F)c2)CCOC(c2ccc3c(c2)CCO3)C1]

$^1$H-NMR (600 MHz, [d$_6$]-DMSO): δ =8.20-8.22 (1H), 8.15-8.17 (1H), 8.04 (1H), 7.94-7.96 (1H), 7.18 (1H), 7.00-7.02 (1H), 6.69-6.70 (1H), 4.50-4.52 (2H), 4.43-4.46 (1H), 4.00-4.03 (1H), 3.64-3.69 (1H), 3.11-3.18 (2H), 2.09-2.14 (1H), 1.90-1.95 (1H), 1.59-1.62 (1H), 1.44-1.48 (4H).

NOE: C-2 proton & methyl=cis

Chiral resolution of 5-[4-Methyl-4-[[3-(trifluoromethyl)phenyl]sulfonyl]-tetrahydro-pyran-2-yl]-2,3-dihydro-benzofuran

[Cis-rac] 5-[4-Methyl-4-[[3-(trifluoromethyl)phenyl]sulfonyl]-tetrahydro-pyran-2-yl]-2,3-dihydro-benzofuran was subjected to preparative chiral-SFC (Chiralpak IC column, MeOH, 15%)) to give [cis-EN1] SC-263 and [cis-EN2] SC-264.

[cis-EN1] SC-263—analytical SFC: Chiralpak IC (250×4.6 mm 5μ), 3 g/min, RT, MeOH, 20%, Ret. Time 3.38; ee>95%

[cis-EN2] SC-264—analytical SFC: Chiralpak IC (250×4.6 mm 5μ), 3 g/min, RT, MeOH, 20%, Ret. Time 4.13; ee>95%

2-Methyl-5-[4-methyl-4-[[3-(trifluoromethyl)phenyl]sulfonyl]-tetrahydro-pyran-2-yl]-benzooxazole (Example 68)

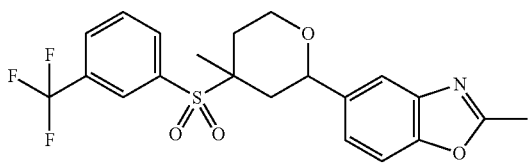 [SMILES: Cc1nc2cc(C3CC(C)(S(=O)(=O)c4cccc(C(F)(F)F)c4)CCO3)ccc2o1]

$^1$H-NMR (600 MHz, [d$_6$]-DMSO): δ =8.21-8.22 (1H), 8.16-8.17 (1H), 8.05 (1H), 7.93-7.96 (1H), 7.58-7.61 (2H), 7.31-7.32 (1H), 4.65-4.68 (1H), 4.07-4.10 (1H), 3.71-3.75 (1H), 2.60 (3H), 2.14-2.19 (1H), 1.92-1.96 (1H), 1.72-1.75 (1H), 1.49-1.53 (4H).

NOE: C-2 proton & methyl=cis

Chiral resolution of 2-Methyl-5-[4-methyl-4-[[3-(trifluoromethyl)phenyl]sulfonyl]-tetrahydro-pyran-2-yl]-benzooxazole

[Cis-rac] 2-Methyl-5-[4-methyl-4-[[3-(trifluoromethyl)phenyl]sulfonyl]-tetrahydro-pyran-2-yl]-benzooxazole was subjected to preparative chiral-SFC (Chiralpak AS-H column, MeOH, 33%)) to give [cis-EN1] SC-279 and [cis-EN2] SC-280.

[cis-EN1] SC-279—analytical SFC: Chiralpak-AD-H (250×4.6 mm 5μ), 3 g/min, RT, EtOH, 20%, Ret. Time 7.00; ee>95%

[cis-EN2] SC-280—analytical SFC: Chiralpak-AD-H (250×4.6 mm 5μ), 3 g/min, RT, EtOH, 20%, Ret. Time 8.69; ee>95%

4-Methylsulfonyl-2-[4-methyl-4-[[3-(trifluoromethyl)phenyl]sulfonyl]-tetrahydro-pyran-2-yl]-benzonitrile (Example 65)

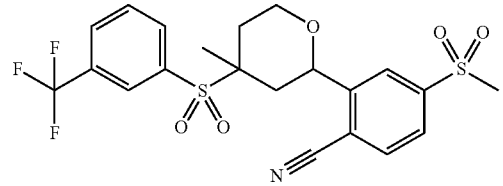 [SMILES: CC1(S(=O)(=O)c2cccc(C(F)(F)F)c2)CCOC(c2cc(S(C)(=O)=O)ccc2C#N)C1]

Step 1: 2-(2,5-dibromophenyl)tetrahydro-2H-pyran-4-ol 2,5-di bromobenzaldehyde (30 g, 114.5 mmol) was dissolved in DCE (600 mL) and cooled in an ice bath. TFA (240 mL) followed by 3-buten-1-ol (12.36 g, 171.7 mmol) were added and the mixture stirred at RT for 37 h. The mixture was diluted with ice water (500 mL), basified with 6 M NaOH (aq) and extracted with DCM (200 mL×5). Organic layer was separated and washed with brine (500 mL), dried (Na$_2$SO$_4$) and concentrated under reduced pressure to get crude. The crude product was dissolved in MeOH (200 mL) and LiOH.H$_2$O (16.7 g, 274 mmol) was added. The reaction was stirred at RT for 16 h. MeOH was concentrated under reduced pressure and the residue was diluted with DCM (500 mL) and washed with water (300 mL), brine (200 mL), dried (Na$_2$SO$_4$) and concentrated in vacuo to get crude. The crude compound was purified by column chromatography (silica gel, 0-20% EtOAc in PE) to obtain 2-(2,5-di-bromophenyl)tetrahydro-2H-pyran-4-ol (25 g, 65%) as an oil.

Step 2: 2-(2,5-dibromophenyl)tetrahydro-2H-pyran-4-yl methanesulfonate

Methanesulphonyl chloride (10.3 g, 90.63 mmol) was added to a solution of 2-(2,5-dibromophenyl)tetrahydro-2H-pyran-4-ol (25.0 g, 75.52 mol) and DIPEA (27 mL, 151 mmol) in DCM (250 mL) at 0° C.; allowed to warm to RT and stirred for 7 h. The mixture was diluted with DCM (100 mL) and washed sequentially with sat. NaHCO$_3$ solution (200 mL), water (200 mL), brine (150 mL), dried (Na$_2$SO$_4$) and concentrated under reduced pressure to get crude 2-(2,5-dibromophenyl)tetrahydro-2H-pyran-4-yl methanesulfonate (32 g crude) as a thick brown oil. This was taken to the next step without further purification.

Step 3: 2-(2,5-dibromophenyl)-4-((3-(trifluoromethyl)phenyl)thio)tetrahydro-2H-pyran 3-Trifluoromethyl thiophenol (13.9 g, 78.23 mmol) was added to a suspension of 2-(2,5-dibromophenyl)tetrahydro-2H-pyran-4-yl methanesulfonate (16 g crude, 39.1 mmol) and K$_2$CO$_3$ (10.8 g, 78.23 mmol) in DMF (160 mL), heated at 55° C. for 9 h and then stirred at RT for 16 h. After completion of reaction, the mixture was diluted with water (25 0 mL) and extracted with EtOAc (250 mL×3). The organic extract was washed with water (300 mL), brine (200 mL), dried (Na$_2$SO$_4$) and concentrated under reduced pressure to get crude compound. The crude compound was purified by CC (silica gel, 0-10% EtOAc in PE) to obtain 2-(2,5-dibromophenyl)-4-((3-(trifluoromethyl)phenyl)thio)tetrahydro-2H-pyran (13.5 g, 70%) as pale yellow thick liquid.

Step 4: 2-(2,5-dibromophenyl)-4-((3-(trifluoromethyl)phenyl)sulfonyl)tetrahydro-2H-pyran 2-(2,5-dibromophenyl)-4-((3-(trifluoromethyl)phenyl)thio)tetrahydro-2H-pyran (13 g, 26.42 mmol) was dissolved in MeOH (390 mL) and a solution of OXONE (49 g, 79.26 mmol) in Water (325 mL) was added. The total reaction mass was stirred at RT for 16 h. MeOH was concentrated in vacuo; the residue was diluted with water (300 mL) and extracted with EtOAc (3×200 mL). The combined organic extract was washed with brine (200 mL), dried (Na$_2$SO$_4$) and concentrated to get crude. The crude compound was purified by CC (silica gel, 0-20% EtOAc in PE) to obtain 2-(2,5-dibromophenyl)-4-((3-(trifluoromethyl)phenyl)sulfonyl)tetrahydro-2H-pyran (11 g, 79%) as a solid.

Step 5: 2-(2,5-dibromophenyl)-4-methyl-4-((3-(trifluoromethyl)phenyl)sulfonyl)tetrahydro-2H-pyran A solution of 2-(2,5-dibromophenyl)-4-((3-(trifluoromethyl)phenyl)sulfonyl)tetrahydro-2H-pyran (11 g, 20.99 mmol) in THF (110 mL) was cooled to −78° C. and KOt-Bu (1 M solution in THF; 42 mL, 42 mmol) was added drop-wise and stirred for 30 min at −78° C. CH$_3$I (2.5 mL, 42 mmol) was added and the resulting mixture was warmed to RT and stirred for 16 h. The reaction mass was diluted with EtOAc (200 mL) and washed with water (100 mL) and brine (100 mL), dried (Na$_2$SO$_4$) and concentrated under reduced pressure to get crude compound. The crude compound was purified by CC (silica gel, 0-10% EtOAc in PE) to obtain 2-(2,5-dibromophenyl)-4-methyl-4-((3-(trifluoromethyl)phenyl)sulfonyl)tetrahydro-2H-pyran (5 g, 44.6%) as off white solid.

Step 6: 4-bromo-2-(4-methyl-4-((3-(trifluoromethyl)phenyl)sulfonyl)tetrahydro-2H-pyran-2-yl)benzonitrile CuCN (1 g, 11.111 mol) was added to a solution of 2-(2,5-dibromophenyl)-4-methyl-4-((3-(trifluoromethyl)phenyl)sulfonyl)tetrahydro-2H-pyran (5 g, 9.25 mmol) in DMF (50 mL) and stirred for 17 h at 120° C. The RM was cooled to RT and filtered, cake was washed with EtOAc (100 mL) and washed with water (100 mL) and brine (100 mL), dried (Na$_2$SO$_4$) and concentrated under reduced pressure to get crude compound. The crude compound was purified by column chromatography (silica gel, 0-15% EtOAc in PE) to obtain 4-bromo-2-(4-methyl-4-((3-(trifluoromethyl)phenyl)sulfonyl)tetrahydro-2H-pyran-2-yl)benzonitrile (1.6 g, 35%) as a pale yellow solid.

Step 7: 2-(4-methyl-4-((3-(trifluoromethyl)phenyl)sulfonyl)tetrahydro-2H-pyran-2-yl)-4-(methylthio)benzonitrile A solution of 4-bromo-2-(4-methyl-4-((3-(trifluoromethyl)phenyl)sulfonyl)tetrahydro-2H-pyran-2-yl)benzonitrile (2 g, 4.10 mmol) and DIPEA (2.3 mL, 12.32 mmol) in toluene (20 mL) was degassed for 10 min, added Xantphos (165 mg, 0.02 mmol) followed by Pd$_2$(dba)$_3$ (0.263 g, 0.02 mmol) and degassed again for 10 min. Sodium thiomethoxide (344 mg, 4.92 mmol) was then added and further degassed for 5 min. The resulting mixture was heated at 120° C. for 16 h under argon. Reaction mass was filtered through celite and the filtrate concentrated to yield crude product. The crude product was purified by CC (silica gel 0-20% EtOAc in pet-ether) to obtain 2-(4-methyl-4-((3-(trifluoromethyl)phenyl)sulfonyl)tetrahydro-2H-pyran-2-yl)-4-(methylthio)benzonitrile (1.2 g, 64%) as pale yellow solid.

Step 8: 2-(4-methyl-4-((3-(trifluoromethyl)phenyl)sulfonyl)tetrahydro-2H-pyran-2-yl)-4-(methylsulfonyl)benzonitrile 2-(4-methyl-4-((3-(trifluoromethyl)phenyl)sulfonyl)tetrahydro-2H-pyran-2-yl)-4-(methylthio)benzonitrile (2 g, 4.39 mmol) dissolved in MeOH (60 mL) and a solution of OXONE (8 g, 13.18 mmol) in Water (50 mL) was added. The total reaction mass was stirred at RT for 16 h. Methanol was concentrated in vacuo; the residue was diluted with water (200 mL) and extracted with DCM (3×50 mL). The combined organic extract was washed with brine (200 mL), dried (Na$_2$SO$_4$) and concentrated to get crude. The crude compound was purified by column chromatography (silica gel, 0-35% EtOAc in PE) to obtain 2-(4-methyl-4-((3-(trifluoromethyl)phenyl)sulfonyl)tetrahydro-2H-pyran-2-yl)-4-(methylsulfonyl)benzonitrile (1.2 g, 57%) as off white solid.

$^1$H-NMR (600 MHz, [d$_6$]-DMSO): δ =8.19-8.23 (2H), 8.13-8.15 (1H), 8.05-8.08 (3H), 7.94-7.97 (1H), 4.94-4.97 (1H), 4.13-4.17 (1H), 3.80-3.84 (1H), 3.32 (3H), 2.18-2.23 (1H), 2.03-2.08 (1H), 1.89-1.91 (1H), 1.52-1.54 (4H).

NOE: C-2 proton & methyl=cis

Chiral resolution of 4-Methylsulfonyl-2-[4-methyl-4-methyl-4-[[3-(trifluoromethyl)phenyl]sulfonyl]-tetrahydro-pyran-2-yl]-benzonitrile

[Cis-rac] 4-Methylsulfonyl-2-[4-methyl-4-[[3-(trifluoromethyl)phenyl]sulfonyl]-tetrahydro-pyran-2-yl]-benzonitrile was subjected to preparative chiral-SFC (Chiralpak AS-H column, MeOH, 33%)) to give [cis-EN1] SC-273 and [cis-EN2] SC-274.

[cis-EN1] SC-273—analytical SFC: Chiralpak-AS-H (250×4.6 mm 5μ), 3 g/min, RT, 0.5% DEA in MeOH, 15%, Ret. Time 3.00; ee>95%

[cis-EN2] SC-274—analytical SFC: Chiralpak-AS-H (250×4.6 mm 5μ), 3 g/min, RT, 0.5% DEA in MeOH, 15%, Ret. Time 3.62; ee>95%

2-[2-Fluoro-4-(methylsulfinyl)-phenyl]-4-methyl-4-[[3-(trifluoromethyl)phenyl]sulfonyl]-tetrahydro-pyran (Example 69)

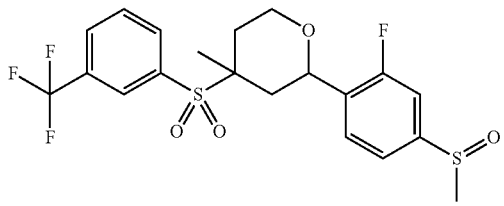 [SMILES: CS(=O)c1ccc(C2CC(C)(S(=O)(=O)c3cccc(C(F)(F)F)c3)CCO2)c(F)c1]

Sodium metaperiodate (0.95 g, 4.46 mmol) was added to a stirred solution of 2-(2-fluoro-4-(methylthio)phenyl)-4-methyl-4-((3-(trifluoromethyl)phenyl)sulfonyl)tetrahydro-2H-pyran (1 g, 2.23 mmol) in MeOH (100 mL), Water (20 mL) and stirred for 24 h at RT. The reaction mixture was concentrated under reduced pressure to remove MeOH. The aq. layer was diluted with water (100 mL), extracted with DCM (3×50 mL). The combined organic layer was washed with brine (50 mL), dried (Na2SO4), filtered and evaporated the solvent under vacuo to give crude, which was purified by CC (silica gel 60-120 mesh, 5% MeOH in DCM) to give 2-[[4-[4-Methyl-4-[[3-(trifluoromethyl)phenyl]sulfonyl]-tetrahydro-pyran-2-yl]-phenyl]sulfonyl]-ethanol (0.9 g, 90%) as an off white solid.

NOE: C-2 proton & methyl=cis

Chiral resolution of 2-[2-Fluoro-4-(methylsulfinyl)-phenyl]-4-methyl-4-[[3-(trifluoromethyl)phenyl]sulfonyl]-tetrahydro-pyran 2-[2-Fluoro-4-(methylsulfinyl)-phenyl]-4-methyl-4-[[3-(trifluoromethyl)phenyl]sulfonyl]-tetrahydro-pyran was subjected to preparative chiral-SFC (Chiralpak AD-H column, MeOH, 30%)) to give [EN1] SC-281, [EN2] SC-282 and a mixture of [EN3] SC-283 and [EN4] SC-284.

[EN1] SC-281—analytical SFC: Chiralpak-AD-H (250× 4.6 mm 5μ), 3 g/min, RT, EtOH, 20%, Ret. Time 3.81; ee>95%, [α]$^{25}_{589}$ (c=1.0, CHCl$_3$)=−109.8°; $^1$H-NMR (600 MHz, [d$_6$]-DMSO): δ =8.20-8.22 (1H), 8.17-8.19 (1H), 8.06 (1H), 7.94-7.96 (1H), 7.65-7.67 (1H), 7.51-7.56 (2H), 4.85-4.87 (1H), 4.07-4.10 (1H), 3.74-3.79 (1H), 2.78 (3H), 2.14-2.19 (1H), 1.97-2.01 (1H), 1.71-1.74 (1H), 1.48-1.51 (4H).

[EN2] SC-282—analytical SFC Chiralpak-AD-H (250× 4.6 mm 5μ), 3 g/min, RT, EtOH, 20%, Ret. Time 4.67; ee>95%, [α]$^{25}_{589}$ (c=1.0, CHCl$_3$)=+91.0°; $^1$H-NMR (600 MHz, [d$_6$]-DMSO): δ =8.21-8.22 (1H), 8.18-8.19 (1H), 8.06 (1H), 7.94-7.96 (1H), 7.65-7.67 (1H), 7.52-7.56 (2H), 4.85-4.87 (1H), 4.07-4.10 (1H), 3.74-3.79 (1H), 2.78 (3H), 2.14-2.19 (1H), 1.97-2.01 (1H), 1.71-1.74 (1H), 1.48-1.51 (4H).

The mixture of [EN3] SC-283 and [EN4] SC-284 was subjected to preparative chiral-SFC (Chiralpak AD-H column, iPrOH, 35%)) to give [EN3] SC-283 and [EN4] SC-284.

[EN3] SC-283—analytical SFC: Chiralpak-AD-H (250× 4.6 mm 5μ), 3 g/min, RT, EtOH, 20%, Ret. Time 5.59; ee>95%, [α]$^{25}_{589}$ (c=1.0, CHCl$_3$)=−33.2°; $^1$H-NMR (600 MHz, [d$_6$]-DMSO): δ =8.17-8.21 (2H), 8.06 (1H), 7.94-7.96 (1H), 7.64-7.67 (1H), 7.51-7.56 (1H), 4.85-4.87 (1H), 4.06-4.10 (1H), 3.74-3.78 (1H), 2.78 (3H), 2.13-2.19 (1H), 1.97-2.02 (1H), 1.71-1.74 (1H), 1.48-1.51 (4H).

[EN4] SC-284—analytical SFC Chiralpak-AD-H (250× 4.6 mm 5μ), 3 g/min, RT, EtOH, 20%, Ret. Time 6.28; ee>95%, [α]$^{25}_{589}$ (c=1.0, CHCl$_3$)=+33.6°; $^1$H-NMR (600 MHz, [d$_6$]-DMSO): δ =8.17-8.21 (2H), 8.06 (1H), 7.94-7.96 (1H), 7.64-7.67 (1H), 7.51-7.56 (1H), 4.85-4.87 (1H), 4.06-4.10 (1H), 3.74-3.78 (1H), 2.78 (3H), 2.13-2.19 (1H), 1.97-2.02 (1H), 1.71-1.74 (1H), 1.48-1.51 (4H).

2-Ethyl-5-[4-methyl-4-[[3-(trifluoromethyl)phenyl]sulfonyl]-tetrahydro-pyran-2-yl]-benzooxazole (Example 70)

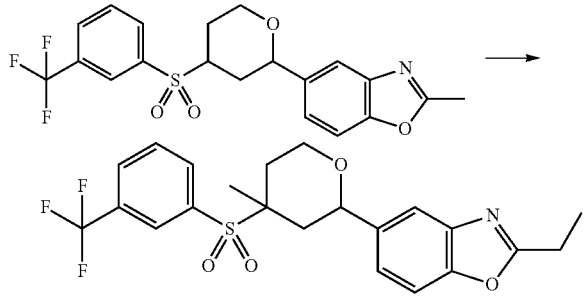

KOt-Bu (23.5 mL, 23.54 mmol, 1 M in THF) was added to a stirred solution of 2-methyl-5-(4-((3-(trifluoromethyl)phenyl)sulfonyl)tetrahydro-2H-pyran-2-yl)benzo[d]oxazole (Example 68; 5.0 g, 11.76 mmol) in THF (100 mL) at −78° C., then stirred for 30 min. MeI (1.45 mL, 23.54 mmol) was added, slowly warmed to RT and stirred for 18 h. The RM was diluted with water (100 mL) extracted with EtOAc (3×100 mL). The combined organic layer was washed with brine, dried (Na$_2$SO$_4$), filtered and evaporated the solvent under vacuo to give crude, which was purified by CC (0-10% EtOAc in PE as eluent) to give 2-methyl-5-[4-methyl-4-[[3-(trifluoromethyl)phenyl]sulfonyl]-tetrahydro-pyran-2-yl]-benzooxazole (1.3 g, 25%) and 2-ethyl-5-[4-methyl-4-[[3-(trifluoromethyl)phenyl]sulfonyl]-tetrahydro-pyran-2-yl]-benzooxazole (SC-285, 30 mg, 0.5%) as a white solid.

$^1$H-NMR (600 MHz, [d$_6$]-DMSO): δ =8.20-8.21 (1H), 8.15-8.16 (1H), 8.04 (1H), 7.93-7.95 (1H), 7.59-7.61 (2H), 7.30-7.32 (1H), 4.65-4.67 (1H), 4.06-4.09 (1H), 3.70-3.75 (1H), 2.92-2.96 (2H), 2.13-2.19 (1H), 1.92-1.96 (1H), 1.70-1.73 (1H), 1.48-1.52 (4H), 1.32-1.35 (3H).

2-[[4-[4-Methyl-4-[[3-(trifluoromethyl)phenyl]sulfonyl]-tetrahydro-pyran-2-yl]-phenyl]sulfonyl]-ethanol (Example 71)

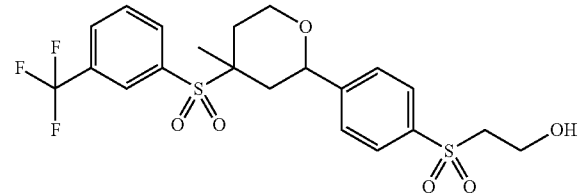 [SMILES: CC1(S(=O)(=O)c2cccc(C(F)(F)F)c2)CCOC(c2ccc(S(=O)(=O)CCO)cc2)C1]

Step 1: 2-(4-bromophenyl)tetrahydro-2H-pyran-4-ol 4-bromobenzaldehyde (20 g, 108.69 mmol) was dissolved in DCE (400 mL) and cooled in an ice bath. TFA (160 mL) followed by 3-butenol (9.4 mL, 108.69 mmol) were added and the mixture stirred at RT for 48 h. The mixture was diluted with water (500 mL), basified with 6 M NaOH (aq) and extracted with DCM (200 mL×4). Organic layer was separated and washed with brine (300 mL), dried ($Na_2SO_4$) and concentrated under reduced pressure to get crude. The crude product was dissolved in MeOH (300 mL) and LiOH (21.7 g, 519.03 mmol) was added. The reaction was stirred at RT for 16 h. MeOH was concentrated under reduced pressure and the residue was diluted with DCM (400 mL) and washed with water (200 mL), brine (200 mL), dried ($Na_2SO_4$) and concentrated in vacuo to get crude. The crude compound was purified by CC (silica gel 60-120 mesh, 0-20% EtOAc in PE) to obtain 2-(4-bromophenyl)tetrahydro-2H-pyran-4-ol (18.0 g, 70%) as off white semi solid.

Step 2: 2(4-bromophenyl)tetrahydro-2H-pyran-4-ylmethanesulfonate

Methanesulphonyl chloride (3.5 mL, 46.69 mmol) was added to a solution of 2-(4-bromophenyl)tetrahydro-2H-pyran-4-ol (8.0 g, 31.12 mmol) and DIPEA (13.5 mL, 77.82 mmol) in DCM (180 mL) at 0° C.; allowed to warm to RT and stirred for 16 h. The mixture was diluted with DCM (200 mL) and washed sequentially with, sat. $NaHCO_3$ solution (150 mL), water (150 mL), brine (150 mL), dried ($Na_2SO_4$) and concentrated under reduced pressure to get crude 2-(4-bromophenyl)tetrahydro-2H-pyran-4-yl-methanesulfonate (10 g crude) as a liquid oil.

Step 3: 2-(4-bromophenyl)-4-(3-(trifluoromethyl)phenylthio)tetrahydro-2H-pyran 3-Trifluoromethyl thiophenol (8.1 mL, 59.70 mmol) was added to a suspension of 2(4-bromophenyl)tetrahydro-2H-pyran-4-ylmethanesulfonate (10.0 g crude, 29.85 mmol) and $K_2CO_3$ (8.2 g, 59.70 mmol) in DMF (100 mL) and the reaction mixture was heated at 60° C. for 6 h and then stirred at RT for 16 h. After completion of reaction, the mixture was diluted with water (200 mL) and extracted with EtOAc (150 mL×3). The organic extract was washed with water (200 mL), brine (150 mL), dried ($Na_2SO_4$) and concentrated under reduced pressure to get crude compound. The crude compound was purified by CC (silica gel 100-200 mesh, 0-10% EtOAc in PE) to obtain 2-(4-bromophenyl)-4-(3-(trifluoromethyl)phenylthio)tetrahydro-2H-pyran (5.6 g, 45.6%) as a yellow oily liquid

Step 4: 2-(4-bromophenyl)-4-(3-(trifluoromethyl)phenylsulfonyl)tetrahydro-2H-pyran 2-(4-bromophenyl)-4-(3-(trifluoromethyl)phenylthio)tetrahydro-2H-pyran (5.5 g, 13.18 mmol) was dissolved in MeOH (140 mL) and a solution of OXONE (24.2 g, 39.56 mmol) in water (125 mL) was added. The total reaction mass was stirred at RT for 16 h. Methanol was concentrated in vacuo; the residue was diluted with water (200 mL) and extracted with EtOAc (3×100 mL). The combined organic extract was washed with brine (100 mL), dried (Na2SO4) and concentrated to get crude. The crude compound was purified by CC (silica gel 60-120 mesh, 0-20% EtOAc in PE) to obtain 2-(4-bromophenyl)-4-(3-(trifluoromethyl)phenylsulfonyl)tetrahydro-2H-pyran (4.0 g, 67.2%) as a solid.

Step 5: 2-(4-bromphenyl)-4-methyl-4-(3-(trifluoromethyl)phenylsulfonyl)tetrahydro-2H-pyran A solution of 2-(4-bromophenyl)-4-(3-(trifluoromethyl)phenylsulfonyl)tetrahydro-2H-pyran (4.0 g, 8.92 mmol) in THF (80 mL) was cooled to −78° C. and KOt-Bu (1M solution in THF; 17.8 mL, 17.8 5 mmol) was added dropwise. $CH_3I$ (3.1 mL, 22.32 mmol) was added and the resulting mixture was warmed to RT and stirred for 16 h. The reaction mass was diluted with EtOAc (200 mL) and washed with water (100 mL) and brine (100 mL), dried ($Na_2SO_4$) and concentrated under reduced pressure to get crude compound. The crude compound was purified by CC (silica gel 100-200 mesh, 0-10% EtOAc in PE) to obtain 2-(4-bromophenyl)-4-methyl-4-(3-(trifluoromethyl)phenylsulfonyl)tetrahydro-2H-pyran (2.6 g, 63%) as a solid.

Step 6: 4-methy-4-1(3-(trifluoromethyl)phenylsulfonyl)tetrahydro-2H-pyran-2-yl)phenylthio)ethanol A solution of 2-(4-bromphenyl)-4-methyl-4-(3-(trifluoromethyl)phenylsulfonyl)tetrahydro-2H-pyran (1.5 g, 3.24 mmol) and DIPEA (1.1 mL, 6.49 mmol) in toluene (20 mL) was degassed for 10 min, added Xantphos (94 mg, 0.16 mmol) followed by $Pd_2(dba)_3$ (149 mg, 0.16 mmol) and degassed again for 10 min. 2-mercaptoethanol (508 mg, 6.49 mmol) was then added and further degassed for 5 min. The resulting mixture was heated at 120° C. for 16 h under argon. Reaction mass was filtered through celite and the filtrate concentrated to yield crude product. The crude product was purified by CC (silica gel 100-200 mesh 0-15% EtOAc in PE) to obtain 4-methy-4-1(3-(trifluoromethyl)phenylsulfonyl)tetrahydro-2H-pyran-2-yl)phenylthio)ethanol (800 mg, 57.5%) as solid.

Step 7: 2-(4-bromphenyl)-4-methyl-4-(3-(trifluoromethyl)phenylsulfonyl)tetrahydro-2H-pyran-2-yl)phenylsulfonyl)ethanol 4-methy-4-1(3-(trifluoromethyl)phenylsulfonyl)tetrahydro-2H-pyran-2-yl)phenylthio)ethanol (800 mg, 1.73 mmol) was dissolved in MeOH (18.5 mL) and a solution of OXONE (3.2 g, 5.21 mmol) in Water (16 mL) was added and stirred at RT for 16 h. MeOH was concentrated in vacuo; the residue was diluted with water (100 mL) and extracted with DCM (3×100 mL). The organic extract was washed with brine (100 mL), dried (Na2SO4) and concentrated to get crude. The crude compound was purified by CC (silica gel 100-200 mesh, 0-20% EtOAc in Pet ether) to obtain 2-(4-bromphenyl)-4-methyl-4-(3-(trifluoromethyl)phenylsulfonyl)tetrahydro-2H-pyran-2-yl)phenylsulfonyl)ethanol (700 mg, 58%) as a white solid.

$^1$H-NMR (600 MHz, [d$_6$]-DMSO): δ =8.21-8.22 (1H), 8.16-8.17 (1H), 8.05 (1H), 7.94-7.96 (1H), 7.87-7.88 (2H), 7.59-7.61 (2H), 488-4.91 (1H), 4.68-4.71 (1H), 4.08-4.11 (1H), 3.67-3.75 (3H), 2.13-2.18 (1H), 1.85-1.89 (1H), 1.78-1.81 (1H), 1.48-1.52 (4H).

NOE: C-2 proton & methyl=cis

Chiral resolution of 2-(4-bromphenyl)-4-methyl-4-(3-(trifluoromethyl)phenylsulfonyl)tetrahydro-2H-pyran-2-yl)phenylsulfonyl)ethanol

[Cis-rac] 2-(4-bromphenyl)-4-methyl-4-(3-(trifluoromethyl)phenylsulfonyl)tetrahydro-2H-pyran-2-yl)phenylsulfonyl)ethanol was subjected to preparative chiral-SFC (Chiralcel-OJ-H column, MeOH, 25%) to give [cis-EN1] SC-286 and [cis-EN2] SC-287.

[cis-EN1] SC-286—analytical SFC: Chiralcel-OJ-H (250×4.6 mm 5μ), 3 g/min, RT, 0.5% DEA in MeOH, 25%, Ret. Time 2.21; ee>95%

[cis-EN2] SC-287—analytical SFC: Chiralcel-OJ-H (250×4.6 mm 5μ), 3 g/min, RT, 0.5% DEA in MeOH, 25%, Ret. Time 3.02; ee>95%

2-[4-Chloro-2-(methylsulfinyl)-phenyl]-4-methyl-4-[[3-(trifluoromethyl)phenyl]sulfonyl]-tetrahydropyran (Example 72)

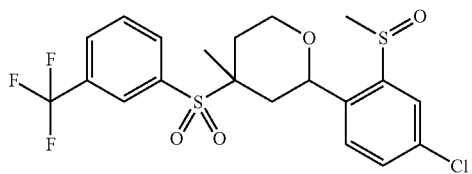 [SMILES: CS(=O)c1cc(Cl)ccc1C1CC(C)(S(=O)(=O)c2cccc(C(F)(F)F)c2)CCO1]

Chiral resolution of 2-(4-chloro-2-(methylthio)phenyl)-4-methyl-4-((3-(trifluoromethyl)phenyl)sulfonyl)tetrahydro-2H-pyran

[Cis-rac] 2-(4-chloro-2-(methylthio)phenyl)-4-methyl-4-((3-(trifluoromethyl)phenyl)sulfonyl)tetrahydro-2H-pyran was subjected to preparative chiral-SFC (Chiralpak-AD-H column, 0.5% DEA in MeOH, 20%)) to give [cis-EN1]-2-(4-chloro-2-(methylthio)phenyl)-4-methyl-4-((3-(trifluoromethyl)phenyl)sulfonyl)tetrahydro-2H-pyran and [cis-EN2]-2-(4-chloro-2-(methylthio)phenyl)-4-methyl-4-((3-(trifluoromethyl)phenyl)sulfonyl)tetrahydro-2H-pyran.

[cis-EN1]-2-(4-chloro-2-(methylthio)phenyl)-4-methyl-4-((3-(trifluoromethyl)phenyl)sulfonyl)tetrahydro-2H-pyran—analytical SFC: LUX-Amylose-2 (250×4.6 mm 5μ), 3 g/min, RT, 0.5% DEA in MeOH, 30%, Ret. Time 2.09; ee>95%;

NOE: C-2 proton & methyl=cis

[cis-EN1]-2-(4-chloro-2-(methylthio)phenyl)-4-methyl-4-((3-(trifluoromethyl)phenyl)sulfonyl)tetrahydro-2H-pyran—analytical SFC: LUX-Amylose-2 (250×4.6 mm 5μ), 3 g/min, RT, 0.5% DEA in MeOH, 30%, Ret. Time 2.47; ee>95%;

NOE: C-2 proton & methyl=cis

Sodium metaperiodate (0.73 g, 3.44 mmol) was added to a stirred solution of [cis-EN1]-2-(4-chloro-2-(methylthio)phenyl)-4-methyl-4-((3-(trifluoromethyl)phenyl)sulfonyl)tetrahydro-2H-pyran (0.8 g, 1.72 mmol) in MeOH (80 mL), Water (16 mL) and stirred for 24 h at RT. The reaction mixture was concentrated under reduced pressure to remove MeOH. The Aq. layer was diluted with water (100 mL), extracted with DCM (3×50 mL). The combined organic layer was washed with brine (50 mL), dried (Na$_2$SO$_4$), filtered and evaporated the solvent under vacuo to give crude, which was purified by CC (silica gel, 5% MeOH in DCM) to give [Epi-Mix1]2-[4-chloro-2-(methylsulfinyl)-phenyl]-4-methyl-4-[[3-(trifluoromethyl)phenyl]-sulfonyl]-tetrahydro-pyran (0.6 g, 72%) as an off white solid.

Chiral resolution of [Epi-Mix1] 2-[4-Chloro-2-(methylsulfinyl)-phenyl]-4-methyl-4-[[3-(trifluoromethyl)phenyl]sulfonyl]-tetrahydro-pyran

[Epi-Mix1]2-[4-Chloro-2-(methylsulfinyl)-phenyl]-4-methyl-4-[[3-(trifluoromethyl)phenyl]sulfonyl]-tetrahydropyran was subjected to preparative chiral-SFC (Chiralpak-AS-H column, MeOH, 25%)) to give [EN1] SC-288 and [EN2] SC-289.

[EN1] SC-288—analytical SFC: Chiralpak AD-H (250× 4.6 mm 5μ), 3 g/min, RT, iPrOH, 20%, Ret. Time 4.22; ee>95; [α]$^{25}_{589}$ (c=1.0, CHCl$_3$)=−68.2°; $^1$H-NMR (600 MHz, [d$_6$]-DMSO): δ=8.21-8.24 (2H), 8.11 (1H), 7.95-7.98 (1H), 7.88 (1H), 7.61-7.63 (1H), 7.52-7.54 (1H), 4.69-4.71 (1H), 3.99-4.02 (1H), 3.72-3.77 (1H), 2.74 (3H), 2.07-2.13 (2H), 1.91-1.94 (1H), 1.48-1.51 (4H).

[EN2] SC-289—analytical SFC: Chiralpak AD-H (250× 4.6 mm 5μ), 3 g/min, RT, iPrOH, 20%, Ret. Time 5.75; ee>95%; [α]$^{25}_{589}$ (c=1.0, CHCl$_3$)=+54.0°; $^1$H-NMR (600 MHz, [d$_6$]-DMSO): δ =8.17-8.22 (2H), 8.06 (1H), 7.93-7.96 (2H), 7.57-7.59 (1H), 7.46-7.47 (1H), 4.81-4.83 (1H), 4.05-4.08 (1H), 3.66-3.70 (1H), 2.70 (3H), 2.16-2.26 (2H), 1.59-1.62 (1H), 1.49-1.51 (4H).

Sodium metaperiodate (0.73 g, 3.44 mmol) was added to a stirred solution of [cis-EN2]-2-(4-chloro-2-(methylthio)phenyl)-4-methyl-4-((3-(trifluoromethyl)phenyl)sulfonyl) tetrahydro-2H-pyran (0.8 g, 1.72 mmol) in methanol (80 mL), Water (16 mL) and stirred for 24 h at RT. The reaction mixture was concentrated under reduced pressure to remove MeOH. The Aq. layer was diluted with water (100 mL), extracted with DCM (3×50 mL). The combined organic layer was washed with brine (50 mL), dried (Na$_2$SO$_4$), filtered and evaporated the solvent under vacuo to give crude, which was purified by CC (silica gel, 5% MeOH in DCM) to give [Epi-Mix2]2-[4-Cchloro-2-(methylsulfinyl)-phenyl]-4-methyl-4-[[3-(trifluoromethyl)-phenyl]sulfonyl]-tetrahydro-pyran (0.6 g, 72%) as an off white solid.

Chiral resolution of [Epi-Mix2] 2-[4-Chloro-2-(methylsulfinyl)-phenyl]-4-methyl-4-[[3-(trifluoromethyl)phenyl]sulfonyl]-tetrahydro-pyran

[Epi-Mix2]2-[4-Chloro-2-(methylsulfinyl)-phenyl]-4-methyl-4-[[3-(trifluoromethyl)phenyl]sulfonyl]-tetrahydropyran was subjected to preparative chiral-SFC (Chiralpak-AS-H column, MeOH, 25%)) to give [EN3] SC-290 and [EN4] SC-291.

[EN3] SC-290—analytical SFC: Chiralpak AD-H (250× 4.6 mm 5μ), 3 g/min, RT, iPrOH, 20%, Ret. Time 5.46; ee>95; [α]$^{25}_{589}$ (c=1.0, CHCl$_3$)=−75.6°; $^1$H-NMR (600 MHz, [d$_6$]-DMSO): δ=8.21-8.22 (1H), 8.17-8.18 (1H), 8.06 (1H), 7.93-7.95 (2H), 7.57-7.59 (1H), 7.46-7.47 (1H), 4.81-4.83 (1H), 4.04-4.08 (1H), 3.66-3.70 (1H), 2.70 (3H), 2.16-2.25 (2H), 1.59-1.62 (1H), 1.48-1.51 (4H).

[EN4] SC-291—analytical SFC: Chiralpak AD-H (250× 4.6 mm 5μ), 3 g/min, RT, iPrOH, 20%, Ret. Time 3.87; ee>95%; [α]$^{25}_{589}$ (c=1.0, CHCl$_3$)=+66.0°; $^1$H-NMR (600 MHz, [d$_6$]-DMSO): δ =8.21-8.24 (2H), 8.11 (1H), 7.95-7.98 (1H), 7.88 (1H), 7.61-7.63 (1H), 7.52-7.54 (1H), 4.69-4.71 (1H), 3.99-4.02 (1H), 3.72-3.77 (1H), 2.74 (3H), 2.06-2.13 (2H), 1.91-1.94 (1H), 1.49-1.51 (4H).

Synthesis of Examples 76 to 82

Cis/Trans Assignment of Examples 76 to 82

The cis racemic [cis-rac] and trans racemic [trans-rac] compounds were separated after the methylation step using CC or prep-HPLC. The assignment of cis racemic [cis-rac] versus trans racemic [trans-rac] was carried out by NOE studies. In some cases only the cis racemic [cis-rac] compound was assigned by NOE studies at this stage (after the methylation step). In these cases the trans racemic [trans-rac] compound was confirmed by NOE studies on the final trans racemic [trans-rac]target molecule. Formation of the cis racemic [cis-rac] isomer is generally favoured over formation of the trans racemic [trans-rac] isomer (generally yield<10%).

2-(2-Fluoro-4-methylsulfonyl-phenyl)-4-[(3-iso-propoxy-phenyl)sulfonyl]-4-methyl-tetrahydro-pyran (Example 76)

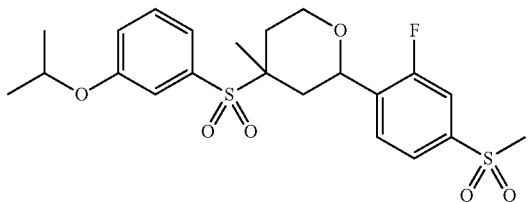 [SMILES: CC(C)Oc1cccc(S(=O)(=O)C2(C)CCOC(c3ccc(S(C)(=O)=O)cc3F)C2)c1]

Step 1:
2-(4-Bromo-2-fluorophenyl)tetrahydro-2H-pyran-4-ol

Stage 1:
To a solution of 4-bromo-2-fluorobenzaldehyde (60 g, 295.56 mmol, 1 eq) in DCE (500 ml) was added 3-buten-1-ol (30 ml, 354.67 mmol, 1.2 eq) and TFA (440 ml) at 0° C. and the RM was stirred at RT for 66 h. The reaction was quenched with ice-water (500 ml) and basified using 6N NaOH solution to pH=8. The aq. layer was extracted with DCM (3×500 ml). The combined organic layers were washed with brine (400 ml), dried (Na$_2$SO$_4$) concentrated in vacuo.

Stage 2:
To a solution of the product from stage 1(108 g, 291.89 mmol, 1 eq) dissolved in MeOH (500 ml) was added lithium hydroxide (31 g, 758.91 mmol, 2.6 eq) and the mixture was stirred for 18 h at RT. MeOH was concentrated under reduced pressure and the residue was diluted with DCM (500 ml). The organic layer was washed with water (500 ml) and brine (500 ml), dried (Na$_2$SO$_4$) and concentrated in vacuo. The crude was purified by CC (silica gel, 0-20% EtOAc in PE) to afford the desired product (50 g, 61%).

Step 2:
2-(4-Bromo-2-fluorophenyl)tetrahydro-2H-pyran-4-yl methanesulfonate

Methanesulfonyl chloride (4.2 ml, 114.5 mmol, 1.5 eq) was added to a solution of 2-(4-bromo-2-fluorophenyl) tetrahydro-2H-pyran-4-ol (10 g, 36.49 mmol, 1 eq) and DIPEA (15.86 ml, 90.69 mmol, 2.5 eq) in DCM (100 ml) at 0° C. and the mixture was stirred for 3 h at RT. After completion of the reaction, the mixture was diluted with DCM (300 ml), washed with water (200 ml) and brine solution (100 ml), dried (Na$_2$SO$_4$) and concentrated under reduced pressure to afford the desired product (10 g).

Step 3: (2-(4-Bromo-2-fluorophenyl)-4-((3-iso-propoxyphenyl)thio)tetrahydro-2H-pyran To a solution of 2-(4-Bromo-2-fluorophenyl)tetrahydro-2H-pyran-4-yl methanesulfonate (6.3 g, 17.83 mmol, 1.0 eq) in DMF (75 ml) was added K$_2$CO$_3$ (6.15 g, 44.6 mmol, 2.5 eq) and 3-trifluoromethylthiophenol (3.0 g, 17.83 mmol, 1.0 eq), and the RM was heated to 50° C. for 20 h. After completion of the reaction, the mixture was diluted with EtOAc (200 ml), washed with water (3×100 ml) and brine (100 ml), dried (Na$_2$SO$_4$) and concentrated in vacuo. The crude product was purified by CC (silica-gel, 0-5% EtOAc in PE) to afford the desired product (2.2 g, 30%).

Step 4: 2-(4-Bromo-2-fluorophenyl)-4-((3-iso-propoxyphenyl)sulfonyl)tetrahydro-2H-pyran Oxone (9.6 g, 15.6 mmol, 3.0 eq) in water (20 ml) was added to a solution of 2-(4-bromo-2-fluorophenyl)-4-((3-isopropoxyphenyl)thio)tetrahydro-2H-pyran (2.2 g, 5.20 mmol, 1.0 eq) in MeOH (60 ml) at RT and the mixture was stirred for 18 h. After completion of the reaction, MeOH was removed under reduced pressure. The residue was diluted with water (80 ml) and extracted with EtOAc (3×75 ml). The organic layer was washed with brine (100 ml), dried (Na$_2$SO$_4$) and concentrated. The crude product was purified by CC (silica-gel, 10-20% EtOAc in PE) to afford the desired product (1.4 g, 59%).

Step 5: 2-(4-Bromo-2-fluorophenyl)-4-((3-iso-propoxyphenyl)sulfonyl)-4-methyltetrahydro-2H-pyran A solution of 2-(4-bromo-2-fluorophenyl)-4-((3-isopropoxyphenyl)sulfonyl)tetrahydro-2H-pyran (1.4 g, 3.07 mmol, 1.0 eq) in THF (30 ml) was cooled to −78° C. and t-BuOK (1M solution in THF) (6.2 ml, 6.14 mmol, 2.0 eq) was added dropwise. The mixture was stirred for 30 min and CH$_3$I (0.3 ml, 4.61 mmol, 1.5 eq) was added. The resulting mixture was allowed to warm to RT and stirred for 18 h. The RM was quenched with water (80 ml) and extracted with EtOAc (3×70 ml). The combined organic extract was washed with water (100 ml) and brine (100 ml), dried (Na$_2$SO$_4$) and concentrated under reduced pressure. The residue upon purification by CC (EtOAc-PE; 1:9 to 2:8) afforded the desired [cis-rac] product (700 mg, 49%).

The fractions from the column consisting of a mixture of cis & trans isomers were purification further by prep-HPLC to afford the desired [trans-rac] product (45 mg).

Step 6: 2-(2-Fluoro-4-(methylthio)phenyl)-4-((3-isopropoxyphenyl)sulfonyl)-4-methyltetrahydro-2H-pyran A solution of [cis-rac] 2-(4-bromo-2-fluorophenyl)-4-((3-isopropoxyphenyl)sulfonyl)-4-methyltetrahydro-2H-pyran (700 mg, 1.50 mmol, 1.0 eq), DIPEA (0.52 ml, 3.0 mmol, 2.0 eq) and sodium thiomethoxide (156 mg, 2.25 mmol, 1.5 eq) in toluene (40 ml) was degassed for 10 min. Xantphos (61 mg, 0.105 mmol, 0.07 eq) was added, followed by Pd$_2$(dba)$_3$ (97 mg, 0.105 mmol, 0.07 eq), and the mixture was degassed again for 10 min. The resulting RM was heated to 110° C. for 18 h under argon. The RM was diluted with water (40 ml) and extracted with EtOAc (2×30 ml). The combined organic extracts were washed with water (50 ml) and brine (50 ml), dried (Na$_2$SO$_4$) and concentrated under reduced pressure. The crude product was purified by flash chromatography (silica gel, 0-20% EtOAc in PE) to afford the desired [cis-rac] product (420 mg, 64%).

Step 7: 2-(2-Fluoro-4-methylsulfonyl-phenyl)-4-[(3-isopropoxy-phenyl)sulfonyl]-4-methyl-tetrahydro-pyran Oxone (1.8 g, 2.88 mmol, 3.0 eq) in water (7.0 ml) was added to a solution of [cis-rac] 2-(2-fluoro-4-(methylthio)

phenyl)-4-((3-isopropoxyphenyl)sulfonyl)-4-methyltetrahydro-2H-pyran (420 mg, 0.96 mmol, 1.0 eq) in MeOH (20 ml) at RT and the mixture was stirred for 18 h. After completion of the reaction MeOH was distilled off under reduced pressure. The residue was diluted with EtOAc (75 ml), washed with water (2×50 ml) and brine (75 ml), dried (Na₂SO₄) and concentrated. The crude product was purified flash chromatography (silica-gel, 20-30% EtOAc in PE) to afford [cis-rac] 2-(2-fluoro-4-methylsulfonyl-phenyl)-4-[(3-isopropoxy-phenyl)sulfonyl]-4-methyl-tetrahydro-pyran (300 mg, 66%) [TLC system: EtOAc-PE; 2:3; Rf: 0.40].

Chiral resolution of [cis-rac] 2-(2-fluoro-4-methyl-sulfonyl-phenyl)-4-[(3-isopropoxy-phenyl)sulfonyl]-4-methyl-tetrahydro-pyran

[Cis-rac] 2-(2-fluoro-4-methylsulfonyl-phenyl)-4-[(3-isopropoxy-phenyl)sulfonyl]-4-methyl-tetrahydro-pyran was subjected to chiral prep-SFC purification to give 95 mg of [cis-EN1] SC-500 and 100 mg of [cis-EN2] SC-501. Preparative SFC Conditions: Column/dimensions: Chiralpak AD-H (250×30) mm; CO2: 60%; Co solvent: 40% MeOH; Total Flow: 100 g/min; Back Pressure: 100 bar; UV: 223 nm.

[cis-EN1] SC-500—analytical SFC: Chiralpak AD-H (250×4.6 mm 5µ), 26° C., 3 g/min, 100 bar, 40% of 0.5% DEA in MeOH, Ret. Time 3.11 min

[cis-EN2] SC-501—analytical SFC: Chiralpak AD-H (250×4.6 mm 5µ), 26° C., 3 g/min, 100 bar, 40% of 0.5% DEA in MeOH, Ret. Time 3.55 min

[Trans-rac] 2-(2-fluoro-4-methylsulfonyl-phenyl)-4-[(3-isopropoxy-phenyl)sulfonyl]-4-methyl-tetrahydro-pyran The corresponding [trans rac] isomer was prepared in analogy to step 6 and 7 starting from [trans rac] 2-(4-bromo-2-fluorophenyl)-4-((3-isopropoxyphenyl)sulfonyl)-4-methyltetrahydro-2H-pyran (45 mg, see step 5) to yield [trans-rac] 2-(2-fluoro-4-methylsulfonyl-phenyl)-4-[(3-isopropoxy-phenyl)sulfonyl]-4-methyl-tetrahydro-pyran SC-511 (28 mg, 62%; over 2 steps) [TLC system: EtOAc-PE; 2:3; Rf: 0.40].

2-(2-Fluoro-4-methylsulfonyl-phenyl)-4-methyl-4-[[3-(trifluoromethyloxy)-phenyl]sulfonyl]-tetrahydro-pyran (Example 77)

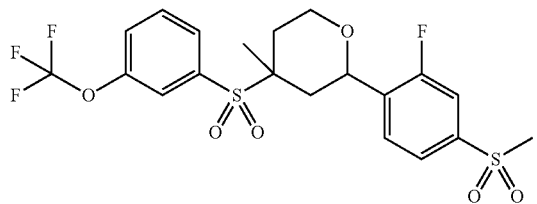 [SMILES: CC1(S(=O)(=O)c2cccc(OC(F)(F)F)c2)CCOC(c2ccc(S(C)(=O)=O)cc2F)C1]

The synthesis was carried out in analogy to Example 76 to give [cis rac] 2-(2-fluoro-4-methylsulfonyl-phenyl)-4-methyl-4-[[3-(trifluoromethyloxy)-phenyl]sulfonyl]-tetrahydro-pyran [TLC system: EtOAc-PE; 4:6; Rf: 0.38] and [trans rac] 2-(2-fluoro-4-methylsulfonyl-phenyl)-4-methyl-4-[[3-(trifluoromethyloxy)-phenyl]sulfonyl]-tetrahydro-pyran SC-504 [TLC system: EtOAc-PE; 4:6; Rf: 0.49].

Chiral resolution of [cis-rac] 2-(2-fluoro-4-methyl-sulfonyl-phenyl)-4-methyl-4-[[3-(trifluoromethyl-oxy)-phenyl]sulfonyl]-tetrahydro-pyran

[Cis-rac] 2-(2-fluoro-4-methylsulfonyl-phenyl)-4-methyl-4-[[3-(trifluoromethyloxy)-phenyl]sulfonyl]-tetrahydro-pyran was subjected to chiral prep-SFC purification to give 85 mg of [cis-EN1] SC-502 and 85 mg of [cis-EN2] SC-503. Preparative SFC Conditions: Column/dimensions: Lux cellulose-2 (250×21) mm; CO2: 75%; Co solvent: 25% MeOH; Total Flow: 100 g/min; Back Pressure: 100 bar; UV: 220 nm.

[cis-EN1] SC-502—analytical SFC: Lux cellulose-2 (250×4.6 mm 5µ), 26° C., 3 g/min, 100 bar, 20% of 0.5% DEA in MeOH, Ret. Time 5.0 min

[cis-EN2] SC-503—analytical SFC: Lux cellulose-2 (250×4.6 mm 5µ), 26° C., 3 g/min, 100 bar, 20% of 0.5% DEA in MeOH, Ret. Time 5.4 min 2-(2-Fluoro-4-methylsulfonyl-phenyl)-4-[(3-isopropyl-phenyl)sulfonyl]-4-methyl-tetrahydro-pyran (Example 78)

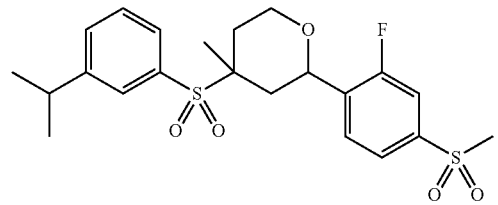 [SMILES: CC(C)c1cccc(S(=O)(=O)C2(C)CCOC(c3ccc(S(C)(=O)=O)cc3F)C2)c1]

The synthesis was carried out in analogy to Example 76 to give [cis rac] 2-(2-fluoro-4-methylsulfonyl-phenyl)-4-[(3-isopropyl-phenyl)sulfonyl]-4-methyl-tetrahydro-pyran [TLC system: EtOAc-PE; 4:6; Rf: 0.62] and [trans rac] 2-(2-fluoro-4-methylsulfonyl-phenyl)-4-[(3-isopropyl-phenyl)sulfonyl]-4-methyl-tetrahydro-pyran SC-505 [TLC system: EtOAc-PE; 4:6; R$_f$: 0.53].

Chiral resolution of [cis-rac] 2-(2-fluoro-4-methyl-sulfonyl-phenyl)-4-[(3-isopropyl-phenyl)sulfonyl]-4-methyl-tetrahydro-pyran

[Cis-rac] 2-(2-fluoro-4-methylsulfonyl-phenyl)-4-[(3-isopropyl-phenyl)sulfonyl]-4-methyl-tetrahydro-pyran was subjected to chiral prep-SFC purification to give 100 mg of [cis-EN1] SC-506 and 105 mg of [cis-EN2] SC-507. Preparative SFC Conditions: Column/dimensions: Chiralpak AD-H (250×30) mm; CO2: 55%; Co solvent: 45% MeOH; Total Flow: 90 g/min; Back Pressure: 100 bar; UV: 222 nm.

[cis-EN1] SC-506—analytical SFC: Chiralpak AD-H (250×4.6 mm 5µ), 26.5° C., 4 g/min, 100 bar, 40% MeOH, Ret. Time 2.17 min

[cis-EN2] SC-507—analytical SFC: Chiralpak AD-H (250×4.6 mm 5µ), 26.4° C., 4 g/min, 100 bar, 40% MeOH, Ret. Time 2.83 min

4-[[3-(Difluoro-methyl)-phenyl]sulfonyl]-2-(2-fluoro-4-methylsulfonyl-phenyl)-4-methyl-tetrahydro-pyran (Example 79)

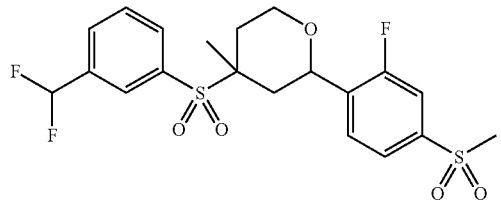 [SMILES: CC1(S(=O)(=O)c2cccc(C(F)F)c2)CCOC(c2ccc(S(C)(=O)=O)cc2F)C1]

The synthesis was carried out in analogy to Example 76 to give [cis rac] 4-[[3-(difluoro-methyl)-phenyl]sulfonyl]-2-(2-fluoro-4-methylsulfonyl-phenyl)-4-methyl-tetrahydro-pyran [TLC system: EtOAc-PE; 5:5; Rf: 0.48] and [trans rac] 4-[[3-(difluoro-methyl)-phenyl]sulfonyl]-2-(2-fluoro-4-methylsulfonyl-phenyl)-4-methyl-tetrahydro-pyran SC-508 [TLC system: EtOAc-PE; 5:5; Rf: 0.45].

Chiral resolution of [cis-rac] 4-[[3-(difluoro-methyl)-phenyl]sulfonyl]-2-(2-fluoro-4-methylsulfonyl-phenyl)-4-methyl-tetrahydro-pyran

[Cis-rac] 4-[[3-(difluoro-methyl)-phenyl]sulfonyl]-2-(2-fluoro-4-methylsulfonyl-phenyl)-4-methyl-tetrahydro-pyran was subjected to chiral prep-SFC purification to give 101 mg of [cis-EN1] SC-509 and 97 mg of [cis-EN2] SC-510. Preparative SFC Conditions: Column/dimensions: Chiralpak IE (250*21) nm; CO2: 67%; Co solvent: 33% MeOH; Total Flow: 60 g/min; Back Pressure: 100 bar; UV: 220 nm.

[cis-EN1] SC-509—analytical SFC: Chiralpak IE (250× 4.6 mm 5µ), 26° C., 3 g/min, 100 bar, 35% of 0.5% DEA in MeOH, Ret. Time 5.70 min

[cis-EN2] SC-510—analytical SFC: Chiralpak IE (250× 4.6 mm 5µ), 26° C., 3 g/min, 100 bar, 35% of 0.5% DEA in MeOH, Ret. Time 6.89 min The starting material 3-(difluoromethyl)benzenethiol was prepared as follows:

(A) A stirred solution of 3-iodobenzaldehyde (25.0 g, 108.2 mmol, 1.0 eq) in DCM (400 ml) was cooled to −78° C. and treated with DAST (57.0 ml, 432.9 mmol, 4.0 eq) in a dropwise manner. The RM was maintained at −78° C. for 2 h, allowed to warm to RT and stirred for 16 h. The RM was quenched with cold water (100 ml), adjusted to a basic pH with sat. aq. NaHCO$_3$ and extracted with DCM (200 ml×3). The combined organic layers were washed with water (300 ml×2) and brine (300 ml), dried (Na$_2$SO$_4$), filtered and concentrated. The residue upon purification by flash chromatography (silica gel; PE-EtOAc; 100:0 to 95:5) afforded 1-(difluoromethyl)-3-iodobenzene (23.0 g, 85%).

(B) To a stirred solution of 1-(difluoromethyl)-3-iodobenzene (6 g, 23.71 mmol, 1.0 eq) in DMF (60 ml) was added sequentially K$_2$CO$_3$ (6.5 g, 47.43 mmol, 2.0 eq), CuI (0.45 g, 2.371 mmol, 0.1 eq) and sulfur powder (2.27 g, 71.1 mmol, 3.0 eq). The resulting RM was heated to 90° C. and stirred for 16 h. The RM was cooled to 0° C. and flushed with an Ar balloon. Triphenylphosphine (9.3 g, 35.5 mmol, 1.5 eq) and con HCl (2.5 ml) were added. The RM was heated to 100° C. and stirred at this temperature for 14 h. The RM was allowed to cool to RT, quenched with cold water (200 ml), adjusted to pH ~2 with 2N HCl and extracted with EtOAc (200 ml×2). The combined organic layers were washed with water (2×200 ml), and brine (500 ml), dried over Na$_2$SO$_4$, filtered and concentrated under reduced pressure to afford 3-(difluoromethyl)benzenethiol (3 g).

2-(2-Fluoro-4-methylsulfonyl-phenyl)-4-[[3-fluoro-5-(trifluoromethyl)-phenyl]sulfonyl]-4-methyl-tetrahydro-pyran (Example 81)

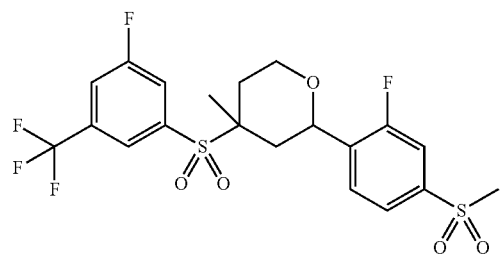 [SMILES: CC1(S(=O)(=O)c2cc(F)cc(C(F)(F)F)c2)CCOC(c2ccc(S(C)(=O)=O)cc2F)C1]

The synthesis was carried out in analogy to Example 76 to give [cis rac] 2-(2-fluoro-4-methylsulfonyl-phenyl)-4-[[3-fluoro-5-(trifluoromethyl)-phenyl]sulfonyl]-4-methyl-tetrahydro-pyran [TLC system: EtOAc-PE; 4:6; Rf: 0.4] and [trans rac] 2-(2-fluoro-4-methylsulfonyl-phenyl)-4-[[3-fluoro-5-(trifluoromethyl)-phenyl]sulfonyl]-4-methyl-tetrahydro-pyran SC-515 [TLC system: EtOAc-PE; 4:6; Rf: 0.40].

Chiral resolution of [cis-rac] 2-(2-fluoro-4-methylsulfonyl-phenyl)-4-[[3-fluoro-5-(trifluoromethyl)-phenyl]sulfonyl]-4-methyl-tetrahydro-pyran

[Cis-rac] 2-(2-fluoro-4-methylsulfonyl-phenyl)-4-[[3-fluoro-5-(trifluoromethyl)-phenyl]sulfonyl]-4-methyl-tetrahydro-pyran was subjected to chiral prep-SFC purification to give 275 mg of [cis-EN1] SC-518 and 345 mg of [cis-EN2] SC-519. Preparative SFC Conditions: Column/dimensions: Chiralpak IE (250*21) nm; CO2: 85%; Co solvent: 15% EtOH; Total Flow: 90 g/min; Back Pressure: 100 bar; UV: 220 nm.

[cis-EN1] SC-518—analytical SFC: Chiralpak IE (250× 4.6 mm 5µ), 25.5° C., 3 g/min, 100 bar, 20% of 0.5% DEA in MeOH, Ret. Time 2.33 min

[cis-EN2] SC-519—analytical SFC: Chiralpak IE (250× 4.6 mm 5µ), 26° C., 3 g/min, 100 bar, 20% of 0.5% DEA in MeOH, Ret. Time 2.67 min

4-[(3-Cyclopropyl-phenyl)sulfonyl]-2-(2-fluoro-4-methylsulfonyl-phenyl)-4-methyl-tetrahydro-pyran (Example 80)

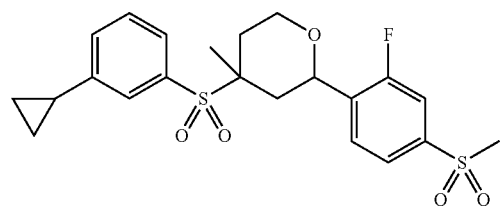 [SMILES: CC1(S(=O)(=O)c2cccc(C3CC3)c2)CCOC(c2ccc(S(C)(=O)=O)cc2F)C1]

Step 1:
2-(4-Bromo-2-fluorophenyl)tetrahydro-2H-pyran-4-ol

Stage 1:
To a solution of 4-bromo-2-fluorobenzaldehyde (60 g, 295.56 mmol, 1 eq) in DCE (500 ml) was added 3-buten-1-ol (30 ml, 354.67 mmol, 1.2 eq) and TFA (440 ml) at 0° C. The RM was stirred at RT for 66 h. The reaction mass was quenched with ice-water (500 ml), basified using 6N NaOH solution to pH=8, and the aq. layer was extracted with DCM (3×500 ml). The combined organic layers were washed with brine (400 ml), dried ($Na_2SO_4$) and upon concentration afforded the desired product (108 g).

Stage 2:
To a solution of the product from stage 1 (108 g, 291.89 mmol, 1 eq) in methanol (500 ml), was added lithium hydroxide (31 g, 758.91 mmol, 2.6 eq) and the RM was stirred for 18 h at RT. MeOH was concentrated under reduced pressure and the residue was diluted with DCM (500 ml). The organic layer was washed with water (500 ml) and brine (500 ml), dried ($Na_2SO_4$) and concentrated in vacuum. Column chromatography (silica gel, 0-20% EtOAc in PE) afforded the title compound (50 g, 61%, over 2 steps).

Step 2:
2-(4-Bromo-2-fluorophenyl)tetrahydro-2H-pyran-4-yl methanesulfonate

Methanesulfonyl chloride (4.2 ml, 54.74 mmol, 1.5 eq) was added to a solution of 2-(4-bromo-2-fluorophenyl)tetrahydro-2H-pyran-4-ol (10 g, 36.49 mmol, 1 eq) and DIPEA (15.7 ml, 91.24 mmol, 2.5 eq) in DCM (150 ml) at 0° C. and the RM was stirred for 3 h at RT. After completion of the reaction, the mixture was diluted with DCM (150 ml), washed with water (2×150 ml) and brine (150 ml), dried ($Na_2SO_4$) and the solvent was distilled off under reduced pressure to afford the desired product (14 g).

Step 3: 3-((-2-(4-Bromo-2-fluorophenyl)tetrahydro-2H-pyran-4-yl)thio)phenol

To a solution of 2-(4-bromo-2-fluorophenyl)tetrahydro-2H-pyran-4-yl methanesulfonate (14 g, 39.66 mmol, 1 eq) in DMF (150 ml) was added $K_2CO_3$ (16.4 g, 118.98 mmol 3 eq) and 3-mercaptophenol (8.1 ml, 79.32 mmol, 2 eq) and the RM was heated to 50° C. and stirred for 18 h. After completion of the reaction, the mixture was diluted with EtOAc (200 ml), washed with water (3×200 ml) and brine (200 ml), dried ($Na_2SO_4$) and concentrated in vacuum to get the crude compound which was purified by CC (silica-gel, 0-15% EtOAc in PE) to afford the desired product (11.0 g, 79%, over 2 steps).

Step 4: 3-((-2-(4-Bromo-2-fluorophenyl)tetrahydro-2H-pyran-4-yl)sulfonyl)phenol Oxone (9.0 g, 31.33 mmol, 3 eq) in water (40 ml) was added to a solution of 3-((-2-(4-bromo-2-fluorophenyl)tetrahydro-2H-pyran-4-yl)thio)phenol (4.0 g, 10.44 mmol, 1 eq) in MeOH (80 ml) at RT and the RM stirred for 18 h. After completion of the reaction MeOH was distilled off under reduced pressure and the residue was diluted with EtOAc (50 ml). This was then washed with water (2×100 ml) and brine (100 ml), dried ($Na_2SO_4$) and concentrated to get the crude product which was purified by flash chromatography to yield the title compound (4.0 g, 92%).

Step 5: (3-((-2-(4-Bromo-2-fluorophenyl)tetrahydro-2H-pyran-4-yl)sulfonyl)phenoxy)(tert-butyl)dimethylsilane To a solution of 3-((-2-(4-bromo-2-fluorophenyl)tetrahydro-2H-pyran-4-yl)sulfonyl)phenol (4 g, 9.63 mmol, 1 eq) in DCM (100 ml) was added imidazole (1.63 g, 24.09 mmol 2.5 eq) and TBDMSCl (2.16 g, 14.45 mmol, 1.5 eq) at 0° C., the RM was stirred at RT for 1 h. After completion of the reaction, the mixture was diluted with EtOAc (100 ml) washed with water (3×100 ml) and brine (210 ml), dried ($Na_2SO_4$) and concentrated in vacuum. The crude compound was purified by flash chromatography to afford the desired product (4.5 g, 90%).

Step 6: 3-((-2-(4-Bromo-2-fluorophenyl)-4-methyltetrahydro-2H-pyran-4-yl)sulfonyl)phenol A solution of 3-((-2-(4-bromo-2-fluorophenyl)tetrahydro-2H-pyran-4-yl)sulfonyl)phenol (5 g, 9.46 mmol, 1 eq) in THF (150 ml) was cooled to −78° C. and potassium tert-butoxide (1M solution in THF) (19 ml, 18.92 mmol, 2 eq) was added dropwise. It was stirred for 30 min and then MeI (0.88 ml, 14.20 mmol, 1.5 eq) was added. The resulting mixture was allowed to warm to RT and stirred for 18 h. The reaction mass was quenched with water (100 ml) and extracted with ethyl acetate (3×150 ml). The combined organic extracts were washed with brine (100 ml), dried ($Na_2SO_4$) and concentrated. The residue upon purification by flash chromatography afforded [cis rac] 3-((-2-(4-bromo-2-fluorophenyl)-4-methyltetrahydro-2H-pyran-4-yl)sulfonyl)phenol (2.1 g, 52%) and [trans rac] 3-((-2-(4-bromo-2-fluorophenyl)-4-methyltetrahydro-2H-pyran-4-yl)sulfonyl)phenol (180 mg).

Step 7: 3-((-2-(2-Fluoro-4-(methylthio)phenyl)-4-methyltetrahydro-2H-pyran-4-yl)sulfonyl)phenol To a solution of [cis rac] 3-((-2-(4-bromo-2-fluorophenyl)-4-methyltetrahydro-2H-pyran-4-yl)sulfonyl)phenol (1.9 g, 4.60 mmol, 1 eq) and DIPEA (2.4 ml, 13.8 mmol, 3 eq) in toluene (40 ml) was added NaSMe (483 mg, 6.90 mmol, 1.5 eq). The mixture was degassed for 10 min and Xantphos (186 mg, 0.322 mmol, 0.07 eq) followed by $Pd_2(dba)_3$ (294 mg, 0.322 mmol, 0.07 eq) was added. The mixture was again degassed for 10 min and heated to 100° C. for 18 h under argon. The reaction mass was filtered through celite and the filtrate concentrated to yield the crude product which upon flash chromatography afforded [cis rac] 3-((-2-(2-fluoro-4-(methylthio)phenyl)-4-methyltetrahydro-2H-pyran-4-yl)sulfonyl)phenol (1.4 g, 76%).

Step 8: 3-((-2-(2-Fluoro-4-(methylthio)phenyl)-4-methyltetrahydro-2H-pyran-4-yl)sulfonyl)phenyl trifluoromethanesulfonate To a solution of [cis rac] 3-((-2-(2-fluoro-4-(methylthio)phenyl)-4-methyltetrahydro-2H-pyran-4-yl)sulfonyl)phenol (1.4 g, 3.53 mmol, 1 eq) in DCM (80 ml) was added pyridine (0.71 mL, 8.83 mmol 2.5 eq) and trifluoroacetic acid anhydride (0.87 mL, 5.30 mmol, 1.5 eq) at 0° C., the RM was stirred at RT for 1 h. The mixture was diluted with DCM (80 ml) washed with sat. $NaHCO_3$ solution (80 ml), water (3×80 ml) and brine (80 ml), dried ($Na_2SO_4$) and concentrated. The crude compound was purified by flash chromatography to afford [cis rac] 3-((-2-(2-fluoro-4-(methylthio)phenyl)-4- methyltetrahydro-2H-pyran-4-yl)sulfonyl)phenyl trifluoromethanesulfonate (1.2 g, 64%).

Step 9: 4-((3-Cyclopropylphenyl)sulfonyl)-2-(2-fluoro-4-(methylthio)phenyl)-4-methyltetrahydro-2H-pyran To a solution of [cis rac] 3-((-2-(2-fluoro-4-(methylthio)phenyl)-4-methyltetrahydro-2H-pyran-4-yl)sulfonyl)phenyl trifluoromethanesulfonate (1.1 g, 2.08 mmol, 1 eq) and cesium carbonate (1.0 g, 3.12 mmol, 1.5 eq) in toluene (60 ml), water (5 mL) and cyclopropyl boronic acid (214 mg, 2.49 mmol, 1.2 eq) was added. It was degassed for 10 min, and Pd(dppf)$_2$Cl$_2$.DCM (135 mg, 0.166 mmol, 0.08 eq) was added and again degassed for 10 min. The resulting mixture was heated to 100° C. and stirred for 16 h under Ar. The RM was filtered through celite and the filtrate concentrated to provide the crude product, which upon flash chromatography afforded compound [cis rac] 4-((3-cyclopropylphenyl)sulfonyl)-2-(2-fluoro-4-(methylthio)phenyl)-4-methyltetrahydro-2H-pyran (640 mg, 73%).

Step 10: 4-[(3-Cyclopropyl-phenyl)sulfonyl]-2-(2-fluoro-4-methylsulfonyl-phenyl)-4-methyl-tetrahydro-pyran Oxone (1.53 g, 4.99 mmol, 3 eq) in water (15 ml) was added to a solution of [cis rac] 4-((3-cyclopropylphenyl)sulfonyl)-2-(2-fluoro-4-(methylthio)phenyl)-4-methyltetrahydro-2H-pyran (700 mg, 1.66 mmol, 1 eq) in methanol (30 ml) at RT and the mixture stirred for 18 h. Methanol was distilled off under reduced pressure, and the residue was diluted with EtOAc (50 ml), washed with water (2×50 ml) and brine (50 ml), dried (Na$_2$SO$_4$) and concentrated. The crude product was purified by flash chromatography to afford [cis rac]4-[(3-cyclopropyl-phenyl)sulfonyl]-2-(2-fluoro-4-methylsulfonyl-phenyl)-4-methyl-tetrahydro-pyran (500 mg, 66%) [TLC system: EtOAc-PE; 4:6; Rf: 0.48].

Chiral resolution of [cis-rac] 4-[(3-cyclopropyl-phenyl)sulfonyl]-2-(2-fluoro-4-methylsulfonyl-phenyl)-4-methyl-tetrahydro-pyran

[Cis-rac] 4-[(3-cyclopropyl-phenyl)sulfonyl]-2-(2-fluoro-4-methylsulfonyl-phenyl)-4-methyl-tetrahydro-pyran was subjected to chiral prep-SFC purification to give 165 mg of [cis-EN1] SC-512 and 175 mg of [cis-EN2] SC-513. Preparative SFC Conditions: Column/dimensions: Chiralpak AD-H (250×30) mm; CO2: 55%; Co solvent: 45% MeOH; Total Flow: 100 g/min; Back Pressure: 100 bar; UV: 222 nm.

[cis-EN1] SC-512-1$^{st}$ eluting enantiomer

[cis-EN2] SC-513-2$^{nd}$ eluting enantiomer

[Trans rac] 4-[(3-cyclopropyl-phenyl)sulfonyl]-2-(2-fluoro-4-methylsulfonyl-phenyl)-4-methyl-tetrahydro-pyran The corresponding [trans rac] isomer was prepared in analogy to steps 7 to 10 starting from [trans rac] 3-((2-(4-bromo-2-fluorophenyl)-4-methyltetrahydro-2H-pyran-4-yl)sulfonyl)phenol (180 mg, see step 6) to yield [trans rac] 4-[(3-cyclopropyl-phenyl)sulfonyl]-2-(2-fluoro-4-methylsulfonyl-phenyl)-4-methyl-tetrahydro-pyran SC-514 (40 mg) [TLC system: EtOAc-PE; 4:6; Rf: 0.55].

4-[[3-(Difluoro-methoxy)-phenyl]sulfonyl]-2-(2-fluoro-4-methylsulfonyl-phenyl)-4-methyl-tetrahydro-pyran (Example 82)

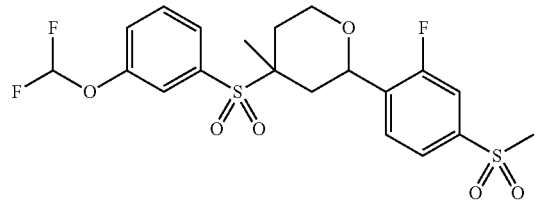 [SMILES: CC1(S(=O)(=O)c2cccc(OC(F)F)c2)CCOC(c2ccc(S(C)(=O)=O)cc2F)C1]

Step 1: 2-(4-Bromo-2-fluorophenyl)-4-((3-(difluoromethoxy)phenyl)thio)tetrahydro-2H-pyran To a solution of 3-((-2-(4-bromo-2-fluorophenyl)tetrahydro-2H-pyran-4-yl)thio)phenol (7.5 g, 19.582 mmol, 1 eq) [see step 3 product, Example 80] in DMF (150 ml), was added K$_2$CO$_3$ (5.4 g, 39.164 mmol, 12 eq). The RM was heated to 90° C. Freon gas was purged into the RM for 4 h. After completion of the reaction, the mixture was diluted with EtOAc (200 ml), washed with water (3×200 ml) and brine (200 ml), dried (Na$_2$SO$_4$) and concentrated in vacuum. The crude compound was purified by CC (silica-gel, 0-15% EtOAc in PE) to afford the title compound (5 g, 59%).

Step 2: 2-(4-Bromo-2-fluorophenyl)-4-((3-(difluoromethoxy)phenyl)sulfonyl)tetrahydro-2H-pyran Oxone (14.2 g, 23.148 mmol, 2 eq) was added to a solution of 2-(4-bromo-2-fluorophenyl)-4-((3-(difluoromethoxy)phenyl)thio)tetrahydro-2H-pyran (5.0 g, 10.44 mmol, 1 eq) in water (40 ml) and MeOH (80 ml) at RT and stirred for 18 h. MeOH was distilled off under reduced pressure and the residue was diluted with EtOAc (100 ml), washed with water (2×100 ml) and brine (100 ml), dried (Na$_2$SO$_4$) and concentrated. The crude product was purified by flash chromatography to afford the title compound (5.0 g, 94%).

Step 3: 2-(4-Bromo-2-fluorophenyl)-4-((3-(difluoromethoxy)phenyl)sulfonyl)-4-methyltetrahydro-2H-pyran To a solution of 2-(4-bromo-2-fluorophenyl)-4-((3-(difluoromethoxy)phenyl)sulfonyl)tetrahydro-2H-pyran (4 g, 8.602 mmol, 1 eq) in THF (150 ml) at −78° C., was added dropwise t-BuOK (1M solution in THF, 17 ml, 17.204 mmol, 2 eq) and the mixture was stirred for 30 min. Methyl iodide (0.88 ml, 12.903 mmol, 1.5 eq) was added and the resulting RM was allowed to warm to RT and stir for 18 h. The reaction mass was quenched with water (100 ml) and extracted with ethyl acetate (3×150 ml). The combined organic extracts were washed with brine (100 ml), dried (Na$_2$SO$_4$) and concentrated. The residue upon purification by flash chromatography afforded [cis rac] 2-(4-bromo-2-fluorophenyl)-4-((3-(difluoromethoxy)phenyl)sulfonyl)-4-methyltetrahydro-2H-pyran (1.3 g, 52%) and [trans rac] 2-(4-bromo-2-fluorophenyl)-4-((3-(difluoromethoxy)phenyl)sulfonyl)-4-methyltetrahydro-2H-pyran (200 mg).

Step 4: 4-((3-(Difluoromethoxy)phenyl)sulfonyl)-2-(2-fluoro-4-(methylthio)phenyl)-4-methyltetrahydro-2H-pyran To a solution of [cis rac] 2-(4-bromo-2-fluorophenyl)-4-((3-(difluoromethoxy)phenyl)sulfonyl)-4-methyltetrahydro- 2H-pyran (1.3 g, 2.719 mmol, 1 eq) and DIPEA (1.4 ml, 8.158 mmol, 3 eq) in toluene (40 ml), was added NaSMe (285 mg, 4.079 mmol, 1.5 eq). The mixture was degassed for 10 min and Xantphos (110 mg, 0.190 mmol, 0.07 eq) followed by Pd$_2$(dba)$_3$ (175 mg, 0.190 mmol, 0.07 eq) was added and it was again degassed for 10 min. The resulting RM was heated to 100° C. for 18 h under Ar. The reaction mass was filtered through celite and the filtrate concentrated to yield the crude product which was purified by flash chromatography to afford [cis rac] 4-((3-(difluoromethoxy)phenyl)sulfonyl)-2-(2-fluoro-4-(methylthio)phenyl)-4-methyltetrahydro-2H-pyran (850 mg, 70%).

Step 5: 4-[[3-(Difluoro-methoxy)-phenyl]sulfonyl]-2-(2-fluoro-4-methylsulfonyl-phenyl)-4-methyl-tetrahydro-pyran Oxone (2.2 g, 3.587 mmol, 2 eq) was added to a solution of [cis rac] 4-((3-(difluoromethoxy)phenyl)sulfonyl)-2-(2-fluoro-4-(methylthio)phenyl)-4-methyltetrahydro-2H-pyran (800 mg, 1.793 mmol, 1 eq) in water (15 ml) and MeOH (30 ml) at RT and the mixture was stirred for 18 h. After completion of the reaction MeOH was distilled off under reduced pressure. The residue was diluted with EtOAc (50 ml), washed with water (2×50 ml) and brine (50 ml), dried (Na$_2$SO$_4$) and concentrated. The crude product was purified by flash chromatography to afford [cis rac] 4-[[3-(difluoro-methoxy)-phenyl]sulfonyl]-2-(2-fluoro-4-methylsulfonyl-phenyl)-4-methyl-tetrahydro-pyran (600 mg, 70%) [TLC system: EtOAc-PE; 4:6; Rf: 0.48].

Chiral resolution of [cis rac] 4-[[3-(difluoro-methoxy)-phenyl]sulfonyl]-2-(2-fluoro-4-methylsulfonyl-phenyl)-4-methyl-tetrahydro-pyran

[Cis-rac] 4-[[3-(difluoro-methoxy)-phenyl]sulfonyl]-2-(2-fluoro-4-methylsulfonyl-phenyl)-4-methyl-tetrahydro-pyran was subjected to chiral prep-SFC purification to give 110 mg of [cis-EN1] SC-516 and 114 mg of [cis-EN2] SC-517. Preparative SFC Conditions: Column/dimensions: Chiralpak AD-H (250×30) mm; CO2: 70%; Co solvent: 30% MeOH; Total Flow: 100 g/min; Back Pressure: 100 bar; UV: 220 nm.

[cis-EN1] SC-516—analytical SFC: Chiralpak AD-H (250×4.6 mm 5µ), 26° C., 4 g/min, 100 bar, 40% of 0.5% DEA in MeOH, Ret. Time 2.33 min

[cis-EN2] SC-517—analytical SFC: Chiralpak AD-H (250×4.6 mm 5µ), 26° C., 4 g/min, 100 bar, 40% of 0.5% DEA in MeOH, Ret. Time 2.67 min

[Trans rac] 4-[[3-(difluoro-methoxy)-phenyl]sulfonyl]-2-(2-fluoro-4-methylsulfonyl-phenyl)-4-methyl-tetrahydro-pyran The corresponding [trans rac] isomer was prepared in analogy to steps 4 & 5 starting from [trans rac] 2-(4-bromo-2-fluorophenyl)-4-((3-(difluoromethoxy)phenyl)sulfonyl)-4-methyltetrahydro-2H-pyran (150 mg, see step 3) to yield [trans rac] 4-[[3-(difluoro-methoxy)-phenyl]sulfonyl]-2-(2-fluoro-4-methylsulfonyl-phenyl)-4-methyl-tetrahydro-pyran SC-520 (70 mg) [TLC system: EtOAc-PE; 4:6; Rf: 0.52].

2-[4-(Cyclopropylsulfonyl)-phenyl]-4-methyl-4-[[3-(trifluoromethyl)phenyl]sulfonyl]-tetrahydro-pyran (Example 83)

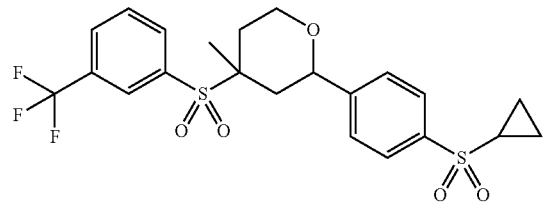 [SMILES: CC1(S(=O)(=O)c2cccc(C(F)(F)F)c2)CCOC(c2ccc(S(=O)(=O)C3CC3)cc2)C1]

Step 1: 2-(4-Bromophenyl)tetrahydro-2H-pyran-4-yl methanesulfonate

A solution of 4-bromobenzaldehyde (5.00 g, 27.0 mmol) in DCM (30 mL) was prepared, followed by applying an ice/water-bath and dropwise addition of MsOH (17.55 mL, 270 mmol). Subsequently, 3-buten-1-ol (2.79 mL, 32.4 mmol) was added dropwise. The RM was stirred at 0° C. for 1.5 h. Sat. aq. Na$_2$CO$_3$ (400 mL) was immersed in an ice/water-bath. The RM was transferred into a separation funnel and added dropwise to the stirred and chilled Na$_2$CO$_3$-solution. The temperature was kept below 15° C. Subsequently, DCM (125 mL) and H$_2$O (100 mL) were added, followed by separation of the phases. The aq. layer was extracted with DCM (2×50 mL). The combination of organic layers was washed with sat. aq. NaHCO$_3$ (50 mL), dried (brine twice & Na$_2$SO$_4$) and concentrated to yield 8.76 g (97%) of the desired product.

Step 2: 2-(4-Bromophenyl)-4-((3-(trifluoromethyl)phenyl)thio)tetrahydro-2H-pyran A solution of 2-(4-bromophenyl)tetrahydro-2H-pyran-4-yl methanesulfonate (8.71 g, 26.0 mmol) in dry MeCN (250 mL) was degassed by N$_2$ bubbling for 1 h. K$_2$CO$_3$ (6.10 g, 44.2 mmol) was added, followed by 3-(trifluoromethyl)benzenethiol (5.87 mL, 44.2 mmol). The RM was stirred at 50° C. overnight. Addition of EtOAc (75 mL) and silica (7 g) was followed by filtration over a cotton plug. The residue was washed with EtOAc (2×75 mL), the combination of filtrates was concentrated. The residue was mixed with DCM (100 mL), silica (40 g) was added, the mixture was concentrated. The residue was eluated with EtOAc (200 mL), followed by concentration. The residue was mixed with DCM (3 mL) and used for flash chromatography (silica, gradient heptane/EtOAc, 1:0 to 96:4) to result in 7.37 g (68%) of the desired product.

Step 3: 2-(4-Bromophenyl)-4-((3-(trifluoromethyl)phenyl)sulfonyl)tetrahydro-2H-pyran 2-(4-Bromophenyl)-4-((3-(trifluoromethyl)phenyl)thio)tetrahydro-2H-pyran (7.34 g, 17.59 mmol) was dissolved in MeOH (180 mL). Oxone (23.79 g, min. 66.9 mmol) was almost completely dissolved in H$_2$O (90 mL), the turbid solution was added portionwise. The RM was stirred vigorously at RT overnight. Addition of MeOH (40 mL) was followed by addition of a solution of oxone (5.41 g, min. 15.2 mmol) in H$_2$O (20 mL). The RM was stirred vigorously at RT for 3 h. The major part of the MeOH was removed from the RM by rotary evaporation at 40° C. H$_2$O (500 mL)

and EtOAc (400 mL) were added to result in a clear two phase system. The layers were separated, the aq. layer was extracted with EtOAc (100 mL). The combination of organic layers was washed with sat. aq. NaHCO$_3$ (100 mL), dried (brine and Na$_2$SO$_4$) and concentrated. The residue was dissolved in DCM (20 mL), followed by addition of MeOH (100 mL) and concentration to around 80 mL. The residual suspension was heated to reflux, addition of MeOH (30 mL) resulted in a solution, cooling to RT started crystallisation. Filtration, washing with MeOH (3×20 mL) and drying by suction provided 4.74 g (60%) of the desired product.

Step 4: 2-(4-Bromophenyl)-4-methyl-4-((3-(trifluoromethyl)phenyl)sulfonyl)tetrahydro-2H-pyran A solution of 2-(4-bromophenyl)-4-((3-(trifluoromethyl)phenyl)sulfonyl)tetrahydro-2H-pyran (1.70 g, 3.78 mmol) in dry THF (20 mL) was prepared, the temperature was lowered to −78° C. A 1.7 M solution of KOt-Bu in THF (3.34 mL, 5.68 mmol) was added dropwise and the RM was stirred for 10 min. Dropwise addition of MeI (0.473 mL, 7.57 mmol) was followed by stirring the RM at −78° C. The flask was left in the cooling bath. Consequently, the temperature was kept at −78° C. for a few hours, followed by slow raise to RT and stirring overnight at RT. The RM was combined with aq. 1 M KHSO$_4$ (100 mL) and EtOAc (120 mL) to result in a two phase system. The layers were separated, the aq. layer was extracted with EtOAc (25 mL). The combination of organic layers was washed with aq. 1 M Na$_2$S$_2$O$_3$ (30 mL), sat. aq. NaHCO$_3$ (50 mL) and dried (brine and Na$_2$SO$_4$), followed by concentration. The residue was dissolved in DCM (5 mL) and added to i-PrOH (50 mL). The solution was concentrated to around 25 mL to result in a suspension. Heating to reflux resulted in a solution, cooling to RT started crystallisation. Filtration and drying by suction provided an impure batch. A second crystallisation from i-PrOH (35 mL) resulted in 1.20 g (68%) of the desired product.

Step 5: 2-[4-(Cyclopropylsulfonyl)-phenyl]-4-methyl-4-[[3-(trifluoromethyl)phenyl]sulfonyl]-tetrahydro-pyran A flask was charged with 2-(4-bromophenyl)-4-methyl-4-((3-(trifluoromethyl)phenyl)sulfonyl)tetrahydro-2H-pyran (1.20 g, 2.59 mmol), sodium cyclopropanesulfinate (0.664 g, 5.18 mmol), 90% (w/w) [CF$_3$SO$_3$Cu]$_2$ benzene (0.724 g, 1.295 mmol), K$_2$CO$_3$ (0.788 g, 5.70 mmol), degassed DMSO (13 mL) and N,N'-dimethylethylenediamine (0.335 mL, 3.11 mmol). The RM was stirred at 100° C. overnight and subsequently combined with H$_2$O (120 mL), aq. 1 M KHSO$_4$ (50 mL) and EtOAc (50 mL). Filtration over a cotton plug provided a clear two phase system. The layers were separated, the aq. layer was extracted with EtOAc (25 mL). The combination of organic layers was washed with H$_2$O (50 mL), aq. 5% (w/w) Na$_4$EDTA (50 mL), sat. aq. NaHCO$_3$, dried (brine and Na$_2$SO$_4$) and concentrated. The residue was dissolved in DCM (2 mL), addition of MeOH (20 mL) was followed by concentration. The residue was dissolved in MeOH (50 mL) at reflux. Cooling to RT started crystallisation. Filtration and drying by suction provided 0.91 g (71%) of [cis-rac] 2-[4-(cyclopropyl-sulfonyl)-phenyl]-4-methyl-4-[[3-(trifluoromethyl)phenyl]sulfonyl]-tetrahydro-pyran SC-349.

$^1$H-NMR (400 MHz, CDCl$_3$) of [cis-rac] 2-[4-(cyclopropyl)sulfonyl)-phenyl]-4-methyl-4-[[3-(trifluoromethyl)phenyl]sulfonyl]-tetrahydro-pyran SC-349: δ 8.13 (s, 1H), 8.05 (d, J=7.9 Hz, 1H), 7.96 (d, J=7.5 Hz, 1H), 7.89 (d, J=8.3 Hz, 2H), 7.75 (t, J=7.8 Hz, 1H), 7.51 (d, J=8.3 Hz, 2H), 4.58-4.50 (m, 1H), 4.21 (dd, J=11.7, 4.8 Hz, 1H), 3.72 (td, J=12.4, 2.0 Hz, 1H), 2.50-2.33 (m, 2H), 2.15 (t, J=12.3 Hz, 1H), 1.86-1.77 (m, 1H), 1.67-1.50 (m, 6H+H$_2$O), 1.40-1.32 (m, 2H), 1.08-0.99 (m, 2H).

Analytical Data:

Material and Methods for LC/MS Analytics:

Hardware: Coupled Agilent 1290 Infinity UHPLC-TOF System; LC-Module: MTP-Handler: Agilent, Model Bench-Cel 2R; Themostatic Control Autoinjector: Agilent, Modell G4226A; Column oven: Agilent, Model G1316C; DAD: Agilent, Model G4212A; Binary Pump: Agilent, Model G4220A; Time Of Flight Mass Spectrometer: Agilent 6224; Ion source: Dual ESI; Column: Supplier: Waters; Type: Acquity UPLC HSS T3 1.8 μm (Part No. 186003538); Dimensions: 2.1×50 mm; Eluents: Eluent A: Water from Millipore Ultrapure water System: Milli-Q Integral 3+0.1% Formic acid; Eluent B: Acetonitrile, Merck KGaA: LiChrosolv Hypergrade for LC-MS (1.00029.9010)+0.1% Formic acid; Formic acid: Merck KGaA: Suprapure 98-100% (1.11670.1000); LC-Method: Flow: 2.5 mL/min; Runtime: 1.2 min; Gradient: Start 2% B, 1 min 100% B, 1.09 min 100% B, 1.11 min 2% B, 1.2 min 2% B Stop; Columntemperature: 80° C.; UV: 190-400 nm; MS-Method: Ion Polarity: Positive; Gas Temperature: 325° C.; Gas Flow: 10 mL/min. The following tables summarize the analytical results.

| Ex. No. | cis/trans | Cpd No. | Target Mass | Target Mass Found | UV$_{254}$-purity |
|---|---|---|---|---|---|
| 1 | cis | SC-100 | 404.046 | Yes | 100 |
| 1 | cis | SC-101 | 404.046 | Yes | 100 |
| 1 | trans | SC-102 | 404.046 | Yes | 100 |
| 1 | trans | SC-103 | 404.046 | Yes | 100 |
| 2 | cis | SC-104 | 419.057 | Yes | 87 |
| 2 | cis | SC-105 | 419.057 | Yes | 100 |
| 2 | trans | SC-106 | 419.057 | Yes | 98 |
| 2 | trans | SC-107 | 419.057 | Yes | 98 |
| 3 | trans | SC-108 | 418.062 | Yes | 100 |
| 3 | trans | SC-109 | 418.062 | Yes | 100 |
| 4 | cis | SC-110 | 432.077 | Yes | 100 |
| 4 | cis | SC-111 | 432.077 | Yes | 100 |
| 5 | cis | SC-112 | 462.078 | Yes | 90 |
| 5 | cis | SC-113 | 462.078 | Yes | 100 |
| 6 | cis | SC-114 | 496.039 | Yes | 100 |
| 6 | cis | SC-115 | 496.039 | Yes | 100 |
| 7 | cis | SC-116 | 418.062 | Yes | 100 |
| 8 | trans | SC-117 | 418.062 | Yes | 91 |
| 9 | cis | SC-118 | 446.093 | Yes | 97 |
| 9 | cis | SC-119 | 446.093 | Yes | 100 |
| 10 | cis | SC-120 | 418.062 | Yes | 94 |
| 10 | trans | SC-121 | 418.062 | Yes | 95 |
| 10 | trans | SC-122 | 418.062 | Yes | 99 |
| 11 | cis | SC-200 | 476.094 | Yes | 100 |
| 11 | cis | SC-201 | 476.094 | Yes | 100 |
| 12 | cis | SC-202 | 530.066 | Yes | 93 |
| 12 | cis | SC-203 | 530.066 | Yes | 100 |
| 13 | cis | SC-204 | 480.069 | Yes | 100 |
| 13 | cis | SC-205 | 480.069 | Yes | 100 |
| 14 | cis | SC-206 | 476.094 | Yes | 100 |
| 14 | cis | SC-207 | 476.094 | Yes | 100 |
| 15 | cis | SC-208 | 480.069 | Yes | 91 |
| 15 | cis | SC-209 | 480.069 | Yes | 96 |
| 16 | cis | SC-210 | 476.094 | Yes | 100 |
| 16 | cis | SC-211 | 476.094 | Yes | 86 |
| 17 | cis | SC-212 | 480.069 | Yes | 92 |
| 17 | cis | SC-213 | 480.069 | Yes | 100 |
| 18 | cis | SC-214 | 461.104 | Yes | 100 |
| 18 | cis | SC-215 | 461.104 | Yes | 100 |
| 19 | cis | SC-216 | 448.072 | Yes | 64 |
| 19 | cis | SC-217 | 448.072 | Yes | 100 |

-continued

| Ex. No. | cis/trans | Cpd No. | Target Mass | Target Mass Found | UV$_{254}$-purity |
|---|---|---|---|---|---|
| 20 | cis | SC-218 | 496.039 | Yes | 98 |
| 20 | cis | SC-219 | 496.039 | Yes | 100 |
| 21 | cis | SC-220 | 462.078 | Yes | 100 |
| 21 | cis | SC-221 | 462.078 | Yes | 100 |
| 22 | cis | SC-222 | 462.078 | Yes | 96 |
| 22 | cis | SC-223 | 462.078 | Yes | 100 |
| 23 | cis | SC-224 | 432.077 | Yes | 91 |
| 23 | cis | SC-225 | 432.077 | Yes | 93 |
| 24 | cis | SC-226 | 448.072 | Yes | 95 |
| 24 | cis | SC-227 | 448.072 | Yes | 99 |
| 25 | cis | SC-228 | 436.052 | Yes | 100 |
| 25 | cis | SC-229 | 436.052 | Yes | 98 |
| 26 | cis | SC-230 | 432.077 | Yes | 89 |
| 26 | cis | SC-231 | 432.077 | Yes | 85 |
| 27 | cis | SC-232 | 530.066 | Yes | 100 |
| 28 | cis | SC-234 | 524.104 | Yes | 100 |
| 29 | cis | SC-235 | 530.066 | Yes | 100 |
| 29 | cis | SC-236 | 530.066 | Yes | 100 |
| 30 | cis | SC-237 | 496.039 | Yes | 100 |
| 30 | cis | SC-238 | 496.039 | Yes | 100 |
| 31 | cis | SC-239 | 496.039 | Yes | 100 |
| 31 | cis | SC-240 | 496.039 | Yes | 100 |
| 32 | cis | SC-241 | 480.069 | Yes | 100 |
| 32 | cis | SC-242 | 480.069 | Yes | 100 |
| 33 | cis | SC-243 | 496.039 | Yes | 100 |
| 33 | cis | SC-244 | 496.039 | Yes | 100 |
| 34 | cis | SC-300 | 446.093 | Yes | 100 |
| 34 | cis | SC-301 | 446.093 | Yes | 98 |
| 34 | trans | SC-302 | 446.093 | Yes | 98 |
| 35 | cis | SC-303 | 436.052 | Yes | 100 |
| 35 | cis | SC-304 | 436.052 | Yes | 100 |
| 35 | trans | SC-305 | 436.052 | Yes | 98 |
| 36 | cis | SC-306 | 362.116 | Yes | 100 |
| 36 | cis | SC-307 | 362.116 | Yes | 100 |
| 36 | trans | SC-308 | 362.116 | Yes | 69 |
| 37 | cis | SC-309 | 418.062 | Yes | 100 |
| 37 | cis | SC-310 | 418.062 | Yes | 98 |
| 37 | trans | SC-311 | 418.062 | Yes | 100 |
| 37 | trans | SC-312 | 418.062 | Yes | 100 |
| 38 | cis | SC-313 | 434.057 | Yes | 100 |
| 38 | cis | SC-314 | 434.057 | Yes | 100 |
| 38 | trans | SC-315 | 434.057 | Yes | 100 |
| 39 | cis | SC-401 | 404.046 | Yes | 99 |
| 39 | trans | SC-402 | 404.046 | Yes | 89 |
| 40 | Cis | SC-127 | 448.072 | Yes | 100 |
| 40 | Cis | SC-128 | 448.072 | Yes | 100 |
| 41 | Cis | SC-130 | 432.077 | Yes | 100 |
| 41 | Cis | SC-131 | 432.077 | Yes | 100 |
| 42 | Cis | SC-132 | 540.056 | Yes | 100 |
| 42 | Cis | SC-133 | 540.056 | Yes | 100 |
| 43 | Cis | SC-134 | 451.118 | Yes | 100 |
| 43 | Cis | SC-135 | 451.118 | Yes | 100 |
| 44 | Cis | SC-136 | 427.086 | Yes | 96 |
| 44 | Cis | SC-137 | 427.086 | Yes | 89 |
| 45 | Cis | SC-138 | 445.097 | Yes | 100 |
| 45 | Cis | SC-139 | 445.097 | Yes | 91 |
| 46 | Trans | SC-140 | 418.062 | Yes | 86 |
| 46 | Trans | SC-141 | 418.062 | Yes | 90 |
| 47 | Cis | SC-142 | 480.069 | Yes | 100 |
| 47 | Cis | SC-143 | 480.069 | Yes | 100 |
| 48 | Cis | SC-144 | 480.069 | Yes | 100 |
| 49 | Cis | SC-148 | 510.079 | Yes | 100 |
| 49 | Cis | SC-149 | 510.079 | Yes | 100 |
| 50 | Cis | SC-150 | 510.079 | Yes | 100 |
| 50 | Cis | SC-151 | 510.079 | Yes | 100 |
| 51 | Cis | SC-245 | 481.064 | Yes | 100 |
| 51 | Cis | SC-246 | 481.064 | Yes | 100 |
| 52 | Cis | SC-247 | 496.039 | Yes | 100 |
| 52 | Cis | SC-248 | 496.039 | Yes | 100 |
| 53 | Cis | SC-249 | 530.066 | Yes | 100 |
| 53 | Cis | SC-250 | 530.066 | Yes | 100 |
| 54 | Cis | SC-251 | 487.073 | Yes | 100 |
| 54 | Cis | SC-252 | 487.073 | Yes | 100 |
| 55 | Cis | SC-253 | 476.094 | Yes | 100 |
| 55 | Cis | SC-254 | 476.094 | Yes | 100 |
| 56 | Cis | SC-255 | 530.066 | Yes | 98 |
| 56 | Cis | SC-256 | 530.066 | Yes | 100 |
| 57 | Cis | SC-257 | 487.073 | Yes | 100 |
| 57 | Cis | SC-258 | 487.073 | Yes | 100 |
| 58 | Cis | SC-259 | 464.072 | Yes | 100 |
| 58 | Cis | SC-260 | 464.072 | Yes | 100 |
| 59 | Cis | SC-261 | 487.073 | Yes | 95 |
| 59 | Cis | SC-262 | 487.073 | Yes | 96 |
| 60 | Cis | SC-263 | 426.111 | Yes | 100 |
| 60 | Cis | SC-264 | 426.111 | Yes | 100 |
| 61 | Cis | SC-265 | 496.064 | Yes | 100 |
| 61 | Cis | SC-266 | 496.064 | Yes | 100 |
| 62 | Cis | SC-267 | 487.073 | Yes | 100 |
| 62 | Cis | SC-268 | 487.073 | Yes | 100 |
| 63 | Cis | SC-269 | 462.078 | Yes | 93 |
| 63 | Cis | SC-270 | 462.078 | Yes | 100 |
| 64 | Cis | SC-271 | 454.128 | Yes | 100 |
| 64 | Cis | SC-272 | 454.128 | Yes | 100 |
| 65 | Cis | SC-273 | 487.073 | Yes | 100 |
| 65 | Cis | SC-274 | 487.073 | Yes | 100 |
| 66 | Cis | SC-275 | 487.073 | Yes | 100 |
| 66 | Cis | SC-276 | 487.073 | Yes | 100 |
| 67 | Cis | SC-277 | 502.110 | Yes | 100 |
| 67 | Cis | SC-278 | 502.110 | Yes | 100 |
| 68 | Cis | SC-279 | 439.106 | Yes | 100 |
| 68 | Cis | SC-280 | 439.106 | Yes | 100 |
| 69 | Cis | SC-281 | 464.074 | Yes | 100 |
| 69 | Cis | SC-282 | 464.074 | Yes | 100 |
| 69 | Cis | SC-283 | 464.074 | Yes | 100 |
| 69 | Cis | SC-284 | 464.074 | Yes | 100 |
| 70 |  | SC-285 | 453.122 | Yes | 100 |
| 71 | Cis | SC-286 | 492.089 | Yes | 100 |
| 71 | Cis | SC-287 | 492.089 | Yes | 100 |
| 72 | Cis | SC-288 | 480.044 | Yes | 100 |
| 72 | Cis | SC-289 | 480.044 | Yes | 100 |
| 72 | Cis | SC-290 | 480.044 | Yes | 100 |
| 72 | Cis | SC-291 | 480.044 | Yes | 100 |
| 73 | Cis | SC-292 | 463.073 | Yes | 93 |
| 73 | Cis | SC-293 | 463.073 | Yes | 100 |
| 74 | Cis | SC-294 | 480.069 | Yes | 100 |
| 74 | Cis | SC-295 | 480.069 | Yes | 100 |
| 75 | Cis | SC-296 | 480.069 | Yes | 100 |
| 75 | Cis | SC-297 | 480.069 | Yes | 100 |
| 76 | Cis | SC-500 | 470.123 | Yes | 100 |
| 76 | Cis | SC-501 | 470.123 | Yes | 100 |
| 77 | Cis | SC-502 | 496.064 | Yes | 98 |
| 77 | Cis | SC-503 | 496.064 | Yes | 100 |
| 77 | Trans | SC-504 | 496.064 | Yes | 97 |
| 78 | Trans | SC-505 | 454.128 | Yes | 100 |
| 78 | Cis | SC-506 | 454.128 | Yes | 100 |
| 78 | Cis | SC-507 | 454.128 | Yes | 100 |
| 79 | Trans | SC-508 | 462.078 | Yes | 98 |
| 79 | Cis | SC-509 | 462.078 | Yes | 100 |
| 79 | Cis | SC-510 | 462.078 | Yes | 97 |
| 76 | Trans | SC-511 | 470.123 | Yes | 100 |
| 80 | Cis | SC-512 | 452.113 | Yes | 100 |
| 80 | Cis | SC-513 | 452.113 | Yes | 100 |
| 80 | Trans | SC-514 | 452.113 | Yes | 100 |
| 81 | Trans | SC-515 | 498.059 | Yes | 100 |
| 82 | Cis | SC-516 | 478.073 | Yes | 100 |
| 82 | Cis | SC-517 | 478.073 | Yes | 100 |
| 81 | Cis | SC-518 | 498.059 | Yes | 100 |
| 81 | Cis | SC-519 | 498.059 | Yes | 100 |
| 82 | Trans | SC-520 | 478.073 | Yes | 100 |
| 83 | cis | SC-349 | 488.094 | Yes | 100 |

2. Assay Descriptions and Biological Data

2.1 Fluorescence Assay for CaV2.2 Channels Using Potassium Depolarization to Induce Channel Opening Human CaV2.2 channels were stably expressed in HEK293 cells together with alpha2-delta and beta subunits of voltage gated calcium channels. In addition, an inwardly rectifying potassium channel (Kir2.3) was stably expressed in these cells to augment control of the cell membrane potential by the concentration of extracellular potassium ions. Raise of the extracellular potassium concentration leads to depolarization of the membrane potential and thus regulates the voltage dependent state of CaV2.2 channels. For preparation, cells were seeded in black poly-D-lysine coated 96-well plates (Becton Dickinson, Biocoat 4640) in 100 μL medium [500 mL DMEM/F-12 plus Glutamax (Invitrogen 31331-093) plus 5.5 mL MEM NEAA 100× (Invitrogen 11140-035) plus 50 mL FBS decomplemented (Invitrogen 10270-106) plus 200 μg/mL Geneticin (Invitrogen 10131-027) plus 50 μg/mL Hygromycin B (Invitrogen 10687-010) plus 2 μg/mL Blasticidin (anti-bl5b Invivo-Gen) plus 0.2 μg/mL Puromycin (A 11138-03)] at a cell density of 30.000 cells per well. Plates were incubated at 37° C. (5% $CO_2$) for 20 to 23 h. On the day of experiment medium was discarded and cells were loaded with Fluo 4 by addition of 100 μL of basic assay buffer (10 mM HEPES, 1 mM KCl, 149 mM NaCl, 0.8 mM $CaCl_2$, 1.7 mM $MgCl_2$, 10 mM Glucose, 0.1% BSA. pH 7.4) containing 2 μM Fluo 4 (Molecular Probes; F-14201), 0.01% pluronic acid (Molecular Probes; P-6866) and 2.5 mM probenecid (Molecular Probes; P36400). Cells were incubated in the dark at 25° C. for 60 min. Then dye containing buffer was discarded and 100 μL basic (1 mM KCl) or alternative (30 mM KCl) assay buffer was added. The alternative assay buffer contained altered concentrations of KCl (30 mM) and NaCl (120 mM) and was used in order to promote the inactivated channel state. After that 25 μL of basic or alternative assay buffer with or without test compound were added and cells were incubated again in the dark at 25° C. for 15 min. Fluorescence intensity was measured on a FLIPR 3 instrument (Molecular Devices Corp., Sunnyvale, Calif.) with excitation at 480 nm and emission at 535 nm. After continuously reading fluorescence for 30 sec, 50 μL of basic assay buffer containing 210 mM KCl (NaCl omitted) were added for depolarization. Peak fluorescent signal intensity was determined and the amplitude of the peak signal, normalized to base line, was used to measure channel inhibition by test compounds.

The following tables summarize the inhibitory activity of exemplified compounds according to the present invention.

| Cpd No. | Activity Category |
|---|---|
| SC-100 | B |
| SC-101 | A |
| SC-102 | B |
| SC-103 | A |
| SC-104 | B |
| SC-105 | A |
| SC-106 | B |
| SC-107 | B |
| SC-108 | B |
| SC-109 | B |
| SC-110 | B |
| SC-111 | C |
| SC-112 | A |
| SC-113 | B |
| SC-114 | B |
| SC-115 | A |
| SC-116 | C |
| SC-117 | A |
| SC-118 | C |
| SC-119 | C |
| SC-120 | B |
| SC-121 | B |
| SC-122 | B |
| SC-127 | A |
| SC-128 | A |
| SC-130 | B |
| SC-131 | B |
| SC-132 | B |
| SC-133 | A |
| SC-134 | B |
| SC-135 | A |
| SC-136 | A |
| SC-137 | A |
| SC-138 | C |
| SC-139 | B |
| SC-140 | B |
| SC-141 | A |
| SC-142 | B |
| SC-143 | B |
| SC-144 | A |
| SC-148 | B |
| SC-149 | A |
| SC-150 | B |
| SC-151 | A |
| SC-200 | B |
| SC-201 | B |
| SC-202 | A |
| SC-203 | A |
| SC-204 | A |

| Cpd No. | Activity Category |
|---|---|
| SC-205 | B |
| SC-206 | A |
| SC-207 | A |
| SC-208 | A |
| SC-209 | B |
| SC-210 | A |
| SC-211 | A |
| SC-212 | A |
| SC-213 | B |
| SC-214 | A |
| SC-215 | C |
| SC-216 | B |
| SC-217 | C |
| SC-218 | A |
| SC-219 | A |
| SC-220 | B |
| SC-221 | B |
| SC-222 | A |
| SC-223 | C |
| SC-224 | B |
| SC-225 | A |
| SC-226 | A |
| SC-227 | A |
| SC-228 | A |
| SC-229 | A |
| SC-230 | A |
| SC-231 | B |
| SC-232 | A |
| SC-235 | A |
| SC-236 | A |
| SC-237 | A |
| SC-238 | A |
| SC-239 | A |
| SC-240 | A |
| SC-241 | A |
| SC-242 | A |
| SC-243 | A |
| SC-244 | A |

| Cpd No. | Activity Category |
|---|---|
| SC-245 | C |
| SC-246 | C |
| SC-247 | A |
| SC-248 | A |
| SC-249 | A |
| SC-250 | A |
| SC-251 | A |
| SC-252 | B |
| SC-253 | B |
| SC-254 | A |
| SC-255 | A |
| SC-256 | A |
| SC-257 | B |
| SC-258 | B |
| SC-259 | A |
| SC-260 | A |
| SC-261 | A |
| SC-262 | B |
| SC-263 | A |
| SC-264 | A |
| SC-265 | B |
| SC-266 | A |
| SC-267 | A |
| SC-268 | B |
| SC-269 | C |
| SC-270 | B |
| SC-271 | A |
| SC-272 | A |
| SC-273 | B |
| SC-274 | B |
| SC-275 | B |
| SC-276 | A |
| SC-277 | A |
| SC-278 | B |
| SC-279 | B |
| SC-280 | A |
| SC-281 | B |
| SC-282 | B |

-continued

| Cpd No. | Activity Category |
|---|---|
| SC-283 | B |
| SC-284 | C |
| SC-285 | B |
| SC-286 | B |
| SC-287 | B |
| SC-288 | B |
| SC-289 | C |
| SC-290 | B |
| SC-291 | A |
| SC-293 | C |
| SC-294 | B |
| SC-295 | B |
| SC-296 | B |
| SC-297 | A |
| SC-300 | A |
| SC-301 | B |
| SC-302 | B |
| SC-303 | B |
| SC-304 | A |
| SC-305 | B |
| SC-306 | C |
| SC-307 | C |
| SC-310 | A |
| SC-311 | A |
| SC-312 | B |
| SC-313 | A |
| SC-314 | A |
| SC-315 | A |
| SC-401 | B |
| SC-402 | A |
| SC-500 | B |
| SC-501 | B |
| SC-502 | A |
| SC-503 | A |
| SC-504 | A |
| SC-505 | A |
| SC-506 | A |
| SC-507 | A |

-continued

| Cpd No. | Activity Category |
|---|---|
| SC-508 | B |
| SC-509 | B |
| SC-510 | A |
| SC-511 | B |
| SC-512 | B |
| SC-513 | A |
| SC-514 | A |
| SC-515 | A |
| SC-516 | C |
| SC-517 | B |
| SC-518 | B |
| SC-519 | A |
| SC-520 | B |
| SC-517 | B |
| SC-518 | B |
| SC-519 | A |
| SC-520 | B |
| SC-517 | B |
| SC-518 | B |
| SC-519 | A |

*%-Inhib (CaV2.2) @3 µM @30 mM KCl: "A": %-Inhibition >95%; "B": %-Inhibition >75% up to ≤95%; "C": %-Inhibition >40% up to ≤75%, "D": %-Inhibition >30% up to ≤40%.

2.2 Electrophysiological Assessment of Calcium Channel Activity

Patch-clamp recordings were performed using HEK293 cells stably expressing human Cav2.2. Cells were plated in T150 flasks and grown a humidified incubator at 37° C. and under 5% $CO_2$ to approximately 50-60% confluency. Cells were maintained at 30° C. for 48 hrs prior to recording. On the day of the experiment, cells were harvested with TrypLE cell detachment solution (Invitrogen) diluted to 25% with phosphate buffered saline and maintained in 50% cell culture media, 50% NaCl based external saline (in mM, 140 NaCl, 4 KCl, 1 $MgCl_2$, 2 $CaCl_2$, 5 Glucose, 10 HEPES, pH 7.4) up to several hours prior to experiment.

Currents were recorded at RT (21-23° C.) using the Patchliner planar array technology (Nanion). Patchliner is a multi-well whole-cell automated patch clamp device that operates asynchronously with fully integrated fluidics. Capacitance and series resistance compensation was automated and no correction for liquid junction potential was employed. Leak was subtracted on-line. Whole-cell patch-clamp recordings were obtained using extracellular saline consisting of (mM): 145 TEA-Cl, 10 $BaCl_2$, 10 HEPES, 10 Glucose. The pH was adjusted to 7.35 with NaOH and the osmolarity was adjusted to 310 mOsm with sucrose. Intracellular solution consisted of (mM): 50 CsCl, 60 CsF, 10

NaCl, 20 EGTA, 5 BAPTA, 10 HEPES. Prior to an experiment, 5 mM MgATP and 0.3 NaGTP were added, the pH was adjusted to 7.2 with CsOH and the osmolarity was adjusted to 290 mOsm with sucrose.

A voltage pulse protocol was utilised to assess compound inhibition. Cells were held at a holding potential of −60 mV and channels were activated using a 10 ms test pulse to +30 mV activated every 10 seconds (0.1 Hz). Increasing concentrations of compound were applied to individual cells with 5 minutes at each test concentration. Compounds were prepared in DMSO as 10 mM stock solutions and subsequent 1:3 serial dilutions performed. Final dilution of 1:1000 in external solution resulted in a final DMSO concentration of 0.1%. For each cell, current responses were normalised to dimethyl sulfoxide vehicle control to generate concentration-response curves. When multiple doses were achieved per cell, IC50 values were calculated from the fits of the Hill equation to the data. The form of the Hill equation used was: Relative current=(100/(1+(IC50/conc)^Slope)). A selection of the foregoing exemplified compounds was tested under these conditions: Several compounds are potent inhibitors (IC50<5 μM) or even very potent inhibitors (IC50<2 μM).

The invention claimed is:

1. A compound of formula (I),

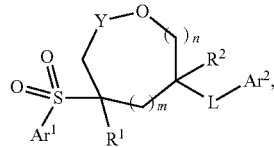

(I)

wherein
m represents 0, 1 or 2;
n denotes 0 or 1;
wherein one of m or n is at least 1;
Y is selected from the group consisting of bond and —C($R^3$)$_2$—;
  wherein each $R^3$ is independently selected from the group consisting of H and $C_{1-6}$-alkyl, or two $R^3$ form together with the C-atom connecting them a $C_{3-10}$-cycloalkyl or a 3 to 7 membered heterocyclyl;
L is —[C($R^4$)$_2$]$_x$—(X)$_y$—[C($R^4$)$_2$]$_z$,
  wherein x is 0, 1 or 2, y is 0 or 1 and z is 0 or 1, with the proviso that x≥y;
  each $R^4$ is independently selected from the group consisting of H and $C_{1-6}$-alkyl,
  or two $R^4$ form together with the C-atom connecting them a $C_{3-10}$-cycloalkyl or a 3 to 7 membered heterocyclyl or two $R^4$ form together with two adjacent C-atoms connecting them a $C_{3-10}$-cycloalkyl or a 3 to 7 membered heterocyclyl,
X is selected from the group consisting of O, S, S(O)$_2$, N(H) or N($C_{1-6}$-alkyl);
$R^1$ is selected from the group consisting of H; F; Cl; CN; $C_{1-6}$-alkyl; $C_{1-6}$-alkyl-O($R^5$) and $C_{1-6}$-alkyl-N($R^5$)$_2$;
  wherein each $R^5$ is independently selected from H or $C_{1-6}$-alkyl or two $R^5$ form together with the N-atom connecting them a 3 to 7 membered heterocyclyl;
$R^2$ is selected from the group consisting of H; F; Cl; CN; $C_{1-6}$-alkyl; $C_{1-6}$-alkyl-O($R^6$) and $C_{1-6}$-alkyl-N($R^6$)$_2$;
  wherein each $R^6$ is independently selected from H or $C_{1-6}$-alkyl or two $R^6$ form together with the N-atom connecting them a 3 to 7 membered heterocyclyl;
$Ar^1$ represents aryl or heteroaryl, wherein said aryl or said heteroaryl is substituted by zero or one or two or three substituents $R^7$,
$Ar^2$ represents aryl or $C_{3-10}$-cycloalkyl, wherein said aryl or said $C_{3-10}$-cycloalkyl is substituted by zero or one or two or three substituents $R^8$,
  wherein each $R^7$ and each $R^8$ is independently selected from the group consisting of F; Cl; Br; I; NO$_2$; CN; $C_{1-6}$-alkyl; CF$_3$; CF$_2$H; CFH$_2$; CF$_2$Cl; CFCl$_2$; C(=O)—H; C(=O)—$C_{1-6}$-alkyl; C(=O)—OH; C(=O)—O—$C_{1-6}$-alkyl; C(=O)—N(H)(OH); C(=O)—NH$_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; OCF$_3$; OCF$_2$H; OCFH$_2$; OCF$_2$Cl; OCFCl$_2$; O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—NH$_2$; O—S(=O)$_2$—N(H)($C_{1-6}$-alkyl); O—S(=O)$_2$—N($C_{1-6}$-alkyl)$_2$; NH$_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—NH$_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—NH$_2$; N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$OH; N(H)—S(=O)$_2$—$C_{1-6}$-alkyl; N(H)—S(=O)$_2$—O—$C_{1-6}$-alkyl; N(H)—S(=O)$_2$—NH$_2$; N(H)—S(=O)$_2$—N(H)($C_{1-6}$-alkyl); N(H)—S(=O)$_2$N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—NH$_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; SCF$_3$; SCF$_2$H; SCFH$_2$; SCF$_2$Cl; SCFCl$_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—NH$_2$; S(=O)$_2$—N(H)($C_{1-6}$-alkyl); S(=O)$_2$—N($C_{1-6}$-alkyl)$_2$; $C_{3-10}$-cycloalkyl; 3 to 7 membered heterocyclyl; aryl; heteroaryl; O—$C_{3-10}$-cycloalkyl; O-(3 to 7 membered heterocyclyl); O-aryl; O-heteroaryl; C(=O)—$C_{3-10}$-cycloalkyl; C(=O)-(3 to 7 membered heterocyclyl); C(=O)-aryl; C(=O)-heteroaryl; S(=O)$_2$—$C_{3-10}$-cycloalkyl; S(=O)$_2$-(3 to 7 membered heterocyclyl); S(=O)$_2$-aryl; S(=O)$_2$-heteroaryl; S(=O)(=NR$^{13}$)—$C_{3-10}$-cycloalkyl; S(=O)(=NR$^{13}$)-(3 to 7 membered heterocyclyl); S(=O)(=NR$^{13}$)-aryl and S(=O)(=NR$^{13}$)-heteroaryl, wherein $R^{13}$ represents H or $C_{1-6}$-alkyl;
wherein in each case said $C_{1-6}$-alkyl may be branched or unbranched; unsubstituted or mono- or polysubstituted; and
wherein in each case said $C_{3-10}$-cycloalkyl, 3 to 7 membered heterocyclyl aryl and heteroaryl may be unsubstituted or mono- or polysubstituted;
optionally in the form of a single stereoisomer or a mixture of stereoisomers, in form of the free compound and/or a physiologically acceptable salt and/or a physiologically acceptable solvate thereof.

2. A compound according to claim, wherein the compound of formula (I) is a compound according to formula (II),

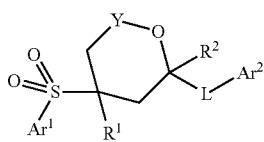

or formula (IIa) or (IIb),

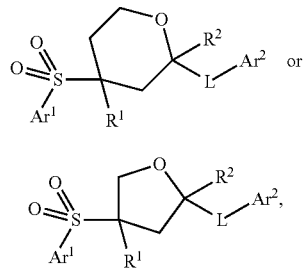

wherein each Ar$^1$, Ar$^2$, R$^1$, R$^2$, Y and L are defined according to claim 1.

3. A compound according to claim 1, wherein the compound of formula (I) is one diastereomer.

4. A compound according to claim 3, wherein the compound of formula (I) is one enantiomer.

5. A compound according to claim 1, wherein
R$^2$ represents H, CH$_3$, C$_2$H$_5$, CH$_2$CH$_2$CH$_3$, CH(CH$_3$)$_2$, CH$_2$OH, CH$_2$OCH$_3$, CH$_2$NH$_2$, CH$_2$N(H)CH$_3$ or CH$_2$N(CH$_3$)$_2$.

6. A compound according to claim 1, wherein
R$^1$ represents H, CH$_3$, C$_2$H$_5$, CH$_2$CH$_2$CH$_3$, CH(CH$_3$)$_2$, CH$_2$OH, CH$_2$OCH$_3$, CH$_2$NH$_2$, CH$_2$N(H)CH$_3$ or CH$_2$N(CH$_3$)$_2$.

7. A compound according to claim 1, wherein Ar$^1$ represents phenyl or pyridinyl, substituted by zero or one or two or three substituents R$^7$,
wherein each R$^7$ is independently selected from the group consisting of F; Cl; CN; C$_{1-6}$-alkyl; CF$_3$; CF$_2$H; CFH$_2$; C(=O)—C$_{1-6}$-alkyl; C(=O)—OH; C(=O)—O—C$_{1-6}$-alkyl; C(=O)—N(H)(OH); C(=O)—NH$_2$; C(=O)—N(H)(C$_{1-6}$-alkyl); C(=O)—N(C$_{1-6}$-alkyl)$_2$; OH; OCF$_3$; OCF$_2$H; OCFH$_2$; OCF$_2$Cl; OCFCl$_2$; O—C$_{1-6}$-alkyl; NH$_2$; N(H)(C$_{1-6}$-alkyl); N(C$_{1-6}$-alkyl)$_2$; N(H)—C(=O)—C$_{1-6}$-alkyl; N(C$_{1-6}$-alkyl)-C(=O)—C$_{1-6}$-alkyl; N(H)—S(=O)$_2$—C$_{1-6}$-alkyl; SCF$_3$; S—C$_{1-6}$-alkyl; S(=O)—C$_{1-6}$-alkyl; S(=O)$_2$—C$_{1-6}$-alkyl; S(=O)$_2$—NH$_2$; S(=O)$_2$—N(H)(C$_{1-6}$-alkyl); S(=O)$_2$—N(C$_{1-6}$-alkyl)$_2$; C$_{3-10}$-cycloalkyl; 3 to 7 membered heterocyclyl; O—C$_{3-10}$-cycloalkyl and O-(3 to 7 membered heterocyclyl).

8. A compound according to claim 1, wherein Ar$^1$ is represented by subformula SF-I

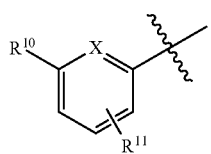

(SF-I)

wherein
X is CH or N,
R$^{10}$ is selected from the group consisting of CF$_3$; CF$_2$H; CFH$_2$; OCF$_3$; OCF$_2$H and OCFH$_2$;
and R$^{11}$ is selected from the group consisting of H; F; Cl; CN; CH$_3$; CH$_2$CH$_3$; CH$_2$CH$_2$CH$_3$; CH(CH$_3$)$_2$; CH(CH$_3$)CH$_2$CH$_3$; CH$_2$CH$_2$CH$_2$CH$_3$; CH$_2$CH(CH$_3$)$_2$; C(CH$_3$)$_3$; CF$_3$; CF$_2$H; CFH$_2$; OCF$_3$; OCH$_3$; OCH$_2$CH$_3$; OCH(CH$_3$)$_2$; S(=O)—CH$_3$ and S(=O)$_2$—CH$_3$.

9. A compound according to claim 1, wherein L is bond, CH$_2$; C(CH$_3$)$_2$; CH(CH$_3$); CH$_2$CH$_2$; CH$_2$C(CH$_3$)$_2$; C(CH$_3$)$_2$CH$_2$; CH$_2$O; C(CH$_3$)$_2$O; CH(CH$_3$)O;

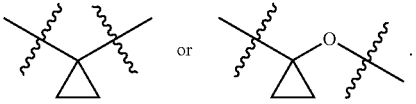 [SMILES: *C1(*)CC1 ; *OC1(*)CC1]

10. A compound according to claim 1, wherein Ar$^2$ represents phenyl, substituted by one or two substituents R$^8$,
wherein each R$^8$ is independently selected from the group consisting of F; Cl; CN; C$_{1-6}$-alkyl; CF$_3$; CF$_2$H; CFH$_2$; OCF$_3$; OCF$_2$H; OCFH$_2$; O—C$_{1-6}$-alkyl; S—C$_{1-6}$-alkyl; S(=O)—C$_{1-6}$-alkyl; S(=O)$_2$—C$_{1-6}$-alkyl; C$_{3-10}$-cycloalkyl; 3 to 7 membered heterocyclyl; aryl; heteroaryl; O—C$_{3-10}$-cycloalkyl; O-(3 to 7 membered heterocyclyl); O-aryl; O-heteroaryl; C(=O)—C$_{3-10}$-cycloalkyl; C(=O)-(3 to 7 membered heterocyclyl); C(=O)-aryl; C(=O)-heteroaryl; S(=O)$_2$—C$_{3-10}$-cycloalkyl; S(=O)$_2$-(3 to 7 membered heterocyclyl); S(=O)$_2$-aryl; S(=O)$_2$-heteroaryl; S(=O)(=NR$^{13}$)—C$_{3-10}$-cycloalkyl; S(=O)(=NR$^{13}$)-(3 to 7 membered heterocyclyl); S(=O)(=NR$^{13}$)-aryl and S(=O)(=NR$^{13}$)-heteroaryl, wherein R$^{13}$ represents H or C$_{1-6}$-alkyl.

11. A compound according to claim 1, wherein Ar$^2$ is represented by subformula SF-II

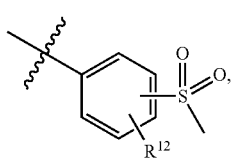

(SF-II)

wherein
R$^{12}$ is selected from the group consisting of H; F; Cl; CN; CH$_3$; CH$_2$CH$_3$; CH$_2$CH$_2$CH$_3$; CH(CH$_3$)$_2$; CF$_3$; CF$_2$H; CFH$_2$; OCF$_3$; OCH$_3$; OCH$_2$CH$_3$; OCH(CH$_3$)$_2$; cyclopropyl and O-cyclopropyl.

12. A pharmaceutical composition comprising at least one compound according to claim 1.

13. A compound selected from the group consisting of:
2-[[2-(4-Chlorophenyl)-4-methyl-tetrahydro-pyran-4-yl]sulfonyl]-6-(trifluoro-methyl)-pyridine;
2-(4-Chlorophenyl)-4-[[2-methyl-5-(trifluoromethyl)-phenyl]sulfonyl]-tetrahydro-pyran;
2-(4-Chlorophenyl)-4-[[2-ethyl-5-(trifluoromethyl)-phenyl]sulfonyl]-tetrahydro-pyran;
4-Methyl-2-(4-methylsulfonyl-phenyl)-4-[[3-(trifluoromethyl)phenyl]sulfonyl]-tetrahydro-pyran;
2-(4-Chloro-2-methylsulfonyl-phenyl)-4-methyl-4-[[3-(trifluoromethyl)phenyl]-sulfonyl]-tetrahydro-pyran;

2-(4-Chlorophenyl)-5-methyl-5-[[3-(trifluoromethyl)phenyl]sulfonyl]-tetrahydro-pyran;
2-(4-Chlorophenyl)-2-methyl-4-[[3-(trifluoromethyl)phenyl]sulfonyl]-tetrahydro-pyran;
2-(4-Chlorophenyl)-4-[[2-isopropyl-5-(trifluoromethyl)-phenyl]sulfonyl]-tetrahydro-pyran;
3-(4-Chlorophenyl)-4-methyl-4-[[3-(trifluoromethyl)phenyl]sulfonyl]-tetrahydro-pyran;
4-Methyl-2-(2-methyl-5-methylsulfonyl-phenyl)-4-[[3-(trifluoromethyl)phenyl]-sulfonyl]-tetrahydro-pyran;
4-Methyl-2-[3-methylsulfonyl-5-(trifluoromethyl)-phenyl]-4-[[3-(trifluoromethyl)-phenyl]sulfonyl]-tetrahydro-pyran;
2-(5-Fluoro-2-methylsulfonyl-phenyl)-4-methyl-4-[[3-(trifluoromethyl)phenyl]-sulfonyl]-tetrahydro-pyran;
4-Methyl-2-(3-methyl-4-methylsulfonyl-phenyl)-4-[[3-(trifluoromethyl)phenyl]sulfonyl]-tetrahydro-pyran;
2-(3-Fluoro-4-methylsulfonyl-phenyl)-4-methyl-4-[[3-(trifluoromethyl)phenyl]sulfonyl]-tetrahydro-pyran;
4-Methyl-2-(4-methyl-3-methylsulfonyl-phenyl)-4-[[3-(trifluoromethyl)phenyl]sulfonyl]-tetrahydro-pyran;
2-(4-Fluoro-3-methylsulfonyl-phenyl)-4-methyl-4-[[3-(trifluoromethyl)phenyl]sulfonyl]-tetrahydro-pyran;
[[2-(4-Chlorophenyl)-4-[[3-(trifluoromethyl)phenyl]sulfonyl]-tetrahydro-pyran-4-yl]-methyl]-dimethyl-amine;
2-(4-Chlorophenyl)-4-(methoxymethyl)-4-[[3-(trifluoromethyl)phenyl]sulfonyl]-tetrahydro-pyran;
2-(2-Chloro-4-methylsulfonyl-phenyl)-4-methyl-4-[[3-(trifluoromethyl)phenyl]sulfonyl]-tetrahydro-pyran;
4-Methyl-2-(3-methylsulfonyl-phenyl)-4-[[3-(trifluoromethyl)phenyl]sulfonyl]-tetrahydro-pyran;
4-Methyl-2-(2-methylsulfonyl-phenyl)-4-[[3-(trifluoromethyl)phenyl]sulfonyl]-tetrahydro-pyran;
2-(4-Chloro-2-methyl-phenyl)-4-methyl-4-[[3-(trifluoromethyl)phenyl]sulfonyl]-tetrahydro-pyran;
2-(4-Chloro-3-methoxy-phenyl)-4-methyl-4-[[3-(trifluoromethyl)phenyl]sulfonyl]-tetrahydro-pyran;
2-(3-Chloro-4-fluoro-phenyl)-4-methyl-4-[[3-(trifluoromethyl)phenyl]sulfonyl]-tetrahydro-pyran;
2-(4-Chlorophenyl)-4-ethyl-4-[[3-(trifluoromethyl)phenyl]sulfonyl]-tetrahydro-pyran;
4-Methyl-2-[2-methylsulfonyl-4-(trifluoromethyl)-phenyl]-4-[[3-(trifluoromethyl)-phenyl]sulfonyl]-tetrahydro-pyran;
2-(4-Chlorophenyl)-4-(phenylmethoxy-methyl)-4-[[3-(trifluoromethyl)phenyl]-sulfonyl]-tetrahydro-pyran;
4-Methyl-2-[4-methylsulfonyl-3-(trifluoromethyl)-phenyl]-4-[[3-(trifluoromethyl)-phenyl]sulfonyl]-tetrahydro-pyran;
2-(4-Chloro-3-methylsulfonyl-phenyl)-4-methyl-4-[[3-(trifluoromethyl)phenyl]-sulfonyl]-tetrahydro-pyran;
2-(3-Chloro-4-methylsulfonyl-phenyl)-4-methyl-4-[[3-(trifluoromethyl)phenyl]sulfonyl]-tetrahydro-pyran;
2-(2-Fluoro-4-methylsulfonyl-phenyl)-4-methyl-4-[[3-(trifluoromethyl)phenyl]sulfonyl]-tetrahydro-pyran;
2-(3-Chloro-5-methylsulfonyl-phenyl)-4-methyl-4-[[3-(trifluoromethyl)phenyl]sulfonyl]-tetrahydro-pyran;
6-(4-Chlorophenyl)-2,2,4-trimethyl-4-[[3-(trifluoromethyl)phenyl]sulfonyl]-tetra-hydro-pyran;
2-(4-Chlorophenyl)-4-[[3-fluoro-5-(trifluoromethyl)-phenyl]sulfonyl]-4-methyl-tetrahydro-pyran;
2-Cyclopropyl-4-ethyl-4-[[3-(trifluoromethyl)phenyl]sulfonyl]-tetrahydro-pyran;
2-(4-Chlorophenyl)-4-methyl-4-[[3-(trifluoromethyl)phenyl]sulfonyl]-tetrahydro-pyran;
2-(4-Chlorophenyl)-4-methyl-4-[[3-(trifluoromethyl-oxy)-phenyl]sulfonyl]-tetra-hydro-pyran;
2-(4-Chlorophenyl)-4-[[3-(trifluoromethyl)phenyl]sulfonyl]-tetrahydro-pyran;
2-[(4-Chloro-phenoxy)-methyl]-4-methyl-4-[[3-(trifluoromethyl)phenyl]sulfonyl]-tetrahydro-pyran;
2-[(4-Chlorophenyl)-methyl]-4-methyl-4-[[3-(trifluoromethyl)phenyl]sulfonyl]-tetrahydro-pyran;
2-[3,4-Bis(methylsulfonyl)-phenyl]-4-methyl-4-[[3-(trifluoromethyl)phenyl]sulfonyl]-tetrahydro-pyran;
1-[4-[4-Methyl-4-[[3-(trifluoromethyl)phenyl]sulfonyl]-tetrahydro-pyran-2-yl]-phenyl]-1H-[1,2,4]triazole;
2-Fluoro-5-[4-methyl-4-[[3-(trifluoromethyl)phenyl]sulfonyl]-tetrahydro-pyran-2-yl]-benzonitrile;
2-Fluoro-5-[4-methyl-4-[[3-(trifluoromethyl)phenyl]sulfonyl]-tetrahydro-pyran-2-yl]-benzamide;
2-(4-Chlorophenyl)-2-methyl-4-[[3-(trifluoromethyl)phenyl]sulfonyl]-tetrahydro-pyran;
4-[[3-Fluoro-5-(trifluoromethyl)-phenyl]sulfonyl]-4-methyl-2-(4-methylsulfonyl-phenyl)-tetrahydro-pyran;
2-(3-Fluoro-4-methylsulfonyl-phenyl)-4-methyl-4-[[3-(trifluoromethyl)phenyl]sulfonyl]-tetrahydro-pyran;
2-[(2-Fluoro-4-methylsulfonyl-phenoxy)-methyl]-4-methyl-4-[[3-(trifluoromethyl)-phenyl]sulfonyl]-tetrahydro-pyran;
2-[(3-Fluoro-4-methylsulfonyl-phenoxy)-methyl]-4-methyl-4-[[3-(trifluoromethyl)-phenyl]sulfonyl]-tetrahydro-pyran;
2-[[2-(3-Fluoro-4-methylsulfonyl-phenyl)-4-methyl-tetrahydro-pyran-4-yl]sulfonyl]-6-(trifluoromethyl)-pyridine;
2-(2-Chloro-5-methylsulfonyl-phenyl)-4-methyl-4-[[3-(trifluoromethyl)phenyl]sulfonyl]-tetrahydro-pyran;
4-Methyl-2-[3-methylsulfonyl-4-(trifluoromethyl)-phenyl]-4-[[3-(trifluoromethyl)phenyl]sulfonyl]-tetra-hydro-pyran;
3-Methylsulfonyl-4-[4-methyl-4-[[3-(trifluoromethyl)phenyl]sulfonyl]-tetrahydro-pyran-2-yl]-benzonitrile;
4-Methyl-2-(2-methyl-4-methylsulfonyl-phenyl)-4-[[3-(trifluoromethyl)phenyl]sulfonyl]-tetrahydro-pyran;
4-Methyl-2-[4-methylsulfonyl-2-(trifluoromethyl)-phenyl]-4-[[3-(trifluoromethyl)phenyl]sulfonyl]-tetra-hydro-pyran;
3-Methylsulfonyl-5-[4-methyl-4-[[3-(trifluoromethyl)phenyl]sulfonyl]-tetrahydro-pyran-2-yl]-benzonitrile;
2,2-Difluoro-5-[4-methyl-4-[[3-(trifluoromethyl)phenyl]sulfonyl]-tetrahydro-pyran-2-yl]-1,3-benzodioxole;
2-Methylsulfonyl-4-[4-methyl-4-[[3-(trifluoromethyl)phenyl]sulfonyl]-tetrahydro-pyran-2-yl]-benzonitrile;
5-[4-Methyl-4-[[3-(trifluoromethyl)phenyl]sulfonyl]-tetrahydro-pyran-2-yl]-2,3-dihydro-benzofuran;
2-(3-Fluoro-4-methylsulfonyl-phenyl)-4-methyl-4-[[3-(trifluoromethyloxy)-phenyl]sulfonyl]-tetrahydro-pyran;
2-Methylsulfonyl-5-[4-methyl-4-[[3-(trifluoromethyl)phenyl]sulfonyl]-tetrahydro-pyran-2-yl]-benzonitrile;
4-[[3-(Difluoro-methyl)-phenyl]sulfonyl]-2-(3-fluoro-4-methylsulfonyl-phenyl)-4-methyl-tetrahydro-pyran;
2-(3-Fluoro-4-methylsulfonyl-phenyl)-4-[(3-isopropyl-phenyl) sulfonyl]-4-methyl-tetrahydro-pyran;
4-Methylsulfonyl-2-[4-methyl-4-[[3-(trifluoromethyl)phenyl]sulfonyl]-tetrahydro-pyran-2-yl]-benzonitrile;
5-Methylsulfonyl-2-[4-methyl-4-[[3-(trifluoromethyl)phenyl]sulfonyl]-tetrahydro-pyran-2-yl]-benzonitrile;
2-(2-Cyclopropyl-5-methylsulfonyl-phenyl)-4-methyl-4-[[3-(trifluoromethyl)phenyl]sulfonyl]-tetrahydro-pyran;

2-Methyl-5-[4-methyl-4-[[3-(trifluoromethyl)phenyl]sulfonyl]-tetrahydro-pyran-2-yl]-benzooxazole;
2-[2-Fluoro-4-(methylsulfinyl)-phenyl]-4-methyl-4-[[3-(trifluoromethyl)phenyl]sulfonyl]-tetrahydro-pyran;
2-Ethyl-5-[4-methyl-4-[[3-(trifluoromethyl)phenyl]sulfonyl]-tetrahydro-pyran-2-yl]-benzooxazole;
2-[[4-[4-Methyl-4-[[3-(trifluoromethyl)phenyl]sulfonyl]-tetrahydro-pyran-2-yl]-phenyl]sulfonyl]-ethanol;
2-[4-Chloro-2-(methylsulfinyl)-phenyl]-4-methyl-4-[[3-(trifluoromethyl)phenyl]sulfonyl]-tetrahydro-pyran;
2-[[4-Methyl-2-(4-methylsulfonyl-phenyl)-tetrahydro-pyran-4-yl]sulfonyl]-6-(trifluoromethyl)-pyridine;
2-(2-Fluoro-5-methylsulfonyl-phenyl)-4-methyl-4-[[3-(trifluoromethyl)phenyl]sulfonyl]-tetrahydro-pyran;
2-(3-Fluoro-5-methylsulfonyl-phenyl)-4-methyl-4-[[3-(trifluoromethyl)phenyl]sulfonyl]-tetrahydro-pyran;
2-(2-Fluoro-4-methylsulfonyl-phenyl)-4-[(3-isopropoxyphenyl) sulfonyl]-4-methyl-tetrahydro-pyran;
2-(2-Fluoro-4-methylsulfonyl-phenyl)-4-methyl-4-[[3-(trifluoromethyloxy)-phenyl]sulfonyl]-tetrahydro-pyran;
4-[[3-(Difluoro-methyl)-phenyl]sulfonyl]-2-(2-fluoro-4-methylsulfonyl-phenyl)-4-methyl-tetrahydro-pyran;
2-(2-Fluoro-4-methylsulfonyl-phenyl)-4-[(3-isopropoxyphenyl) sulfonyl]-4-methyl-tetrahydro-pyran;
4-[(3-Cyclopropyl-phenyl)sulfonyl]-2-(2-fluoro-4-methylsulfonyl-phenyl)-4-methyl-tetrahydro-pyran;
2-(2-Fluoro-4-methylsulfonyl-phenyl)-4-[[3-fluoro-5-(trifluoromethyl)-phenyl]sulfonyl]-4-methyl-tetrahydro-pyran;
4-[[3-(Difluoro-methoxy)-phenyl]sulfonyl]-2-(2-fluoro-4-methylsulfonyl-phenyl)-4-methyl-tetrahydro-pyran; and
2-[4-(Cyclopropylsulfonyl)-phenyl]-4-methyl-4-[[3-(trifluoromethyl)phenyl]sulfonyl]-tetrahydro-pyran;
optionally in the form of a single stereoisomer or a mixture of stereoisomers, in the form of the free compound and/or a physiologically acceptable salt or solvate thereof.

14. A pharmaceutical composition comprising at least one compound according to claim 13.

* * * * *